(12) United States Patent  (10) Patent No.: US 7,498,436 B2
John et al.  (45) Date of Patent: Mar. 3, 2009

(54) SUBSTITUTED HYDROXYETHYLAMINES

(75) Inventors: Varghese John, San Francisco, CA (US); Barbara Jagodzinska, Redwood City, CA (US); Michel Maillard, Redwood Shores, CA (US); James P. Beck, Zionsville, IN (US); Ruth E. TenBrink, Labadie, MO (US); Daniel Getman, Chesterfield, MO (US)

(73) Assignees: Pharmacia & Upjohn Company LLC, Kalamazoo, MI (US); Elan Pharmaceuticals, Inc., S. San Francisco, CA (US)

( * ) Notice: Subject to any disclaimer, the term of this patent is extended or adjusted under 35 U.S.C. 154(b) by 174 days.

(21) Appl. No.: 10/505,947

(22) PCT Filed: Feb. 27, 2003

(86) PCT No.: PCT/US03/07287

§ 371 (c)(1), (2), (4) Date: Sep. 26, 2005

(87) PCT Pub. No.: WO03/072535

PCT Pub. Date: Sep. 4, 2003

(65) Prior Publication Data

US 2006/0106256 A1 May 18, 2006

Related U.S. Application Data

(60) Provisional application No. 60/359,953, filed on Feb. 27, 2002.

(51) Int. Cl.
C07D 295/00 (2006.01)
A61K 31/4965 (2006.01)

(52) U.S. Cl. .............................. 544/391; 544/1; 546/1; 548/100; 548/400; 549/1; 549/200; 560/1; 562/400; 514/255.01

(58) Field of Classification Search ................... None
See application file for complete search history.

(56) References Cited

U.S. PATENT DOCUMENTS 5,142,056 A * 8/1992 Kempe et al. ............... 546/265

* cited by examiner

*Primary Examiner*—Brian J Davis
(74) *Attorney, Agent, or Firm*—McDonnell Boehnen Hulbert & Berghoff LLP

(57) ABSTRACT

This present invention relates to prodrug compounds of the formula (Y) and pharmaceutical salts thereof:

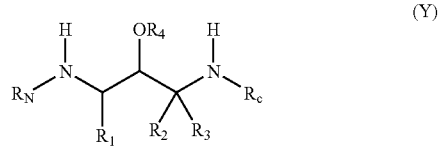

(Y)

where $R_N$, $R_1$, $R_2$, $R_3$ $R_4$ and $R_C$ are defined herein, which are useful in treating Alzheimer's disease and other similar diseases.

7 Claims, No Drawings

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green
```

```
<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
                20                  25                  30

Lys Lys

<210> SEQ ID NO 5
```

```
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green

<400> SEQUENCE: 5

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Ala Cys Lys
            20                  25                  30
Lys

<210> SEQ ID NO 6
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15
Thr Asn Ile Lys Thr Glu Glu Ile Ser Glu Val Asn Leu Asp Ala Glu
            20                  25                  30
Phe

<210> SEQ ID NO 7
<211> LENGTH: 29
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15
Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial sequence
```

```
<220> FEATURE:
<223> OTHER INFORMATION: synthetic peptide

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial sequence
<220> FEATURE:
<223> OTHER INFORMATION: synthetic peptide

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30
```

SUBSTITUTED HYDROXYETHYLAMINES

CROSS REFERENCE TO RELATED APPLICATIONS

This application claims priority from U.S. Provisional Application Ser. No. 60/359,953, filed Feb. 27, 2002, the disclosure of which is incorporated herein by reference in its entirety.

BACKGROUND OF THE INVENTION

1. Field of the Invention

This invention relates to prodrugs of a class of amine compounds which are useful in the treatment of Alzheimer's disease and similar diseases.

2. Description of the Related Art

Alzheimer's disease (AD) is a progressive degenerative disease of the brain primarily associated with aging. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of the disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et.al., 1999, Nature 402:537-554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, Neuron 6:487. Release of A beta from neuronal cells grown in culture and the presence of A beta in cerebrospinal fluid (CSF) of both normal individuals and AD patients has been demonstrated. See, for example, Seubert et al., 1992, Nature 359:325-327.

It has been proposed that A beta peptide accumulates as a result of APP processing by beta secretase, thus inhibition of this enzyme's activity is desirable for the treatement of AD. In vivo processing of APP at the beta-secretase cleavage site is thought to be a rate-limiting step in A beta production, and is thus a therapeutic target for the treatment of AD. See for example, Sabbagh, M., et al., 1997, Alz. Dis. Rev. 3, 1-19.

BACE1 knockout mice fail to produce A beta, and present a normal phenotype. When crossed with transgenic mice that overexpress APP, the progeny show reduced amounts of A beta in brain extracts as compared with control animals (Luo et. al., 2001 Nature Neuroscience 4:231-232). This evidence further supports the proposal that inhibition of beta-secretase activity and reduction of A beta in the brain provides a therapeutic method for the treatment of AD and other beta amyloid disorders.

Published PCT application WO00/47618 entitled "1Beta-Secretase Enzyme Compositions and Methods" identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

The invention provides compounds of formula (Y):

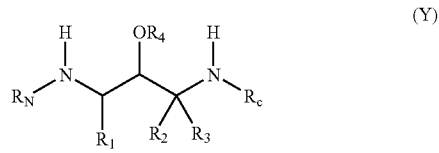

(Y)

and the pharmcaeutically acceptable salts thereof,
where $R_1$ is:
(I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, —OC═O $NR_{1-a}R_{1-b}$ where $R_{1-a}$ and $R_{1-b}$ are as defined above, (II) —$CH_2$—S(O)$_{0-2}$—($C_1$-$C_6$ alkyl), (III) —$CH_2$—$CH_2$—S(O)$_{0-2}$—($C_1$-$C_6$ alkyl), (IV) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (V) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (VI) —$(CH_2)_{n1}$—($R_{1-aryl}$) where $n_1$ is zero or one and where $R_{1-aryl}$ is phenyl, 1-naphthyl, 2-naphthyl and indanyl, indenyl, dihydronaphthayl, tetralinyl optionally substituted with one, two, three or four of the following substituents on the aryl ring:

(A) $C_1$-$C_6$ alkyl optionally substituted with one, two or three substituents selected from the group consisting of $C_1$-$C_3$ alkyl, —F, —Cl, —Br, —I, —OH, —SH, —$NR_{1-a}R_{1-b}$ where $R_{1-a}$ and $R_{1-b}$ are as defined above, —C≡N, —$CF_3$, $C_1$-$C_3$ alkoxy, (B) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (C) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (D) —F, Cl, —Br and —I, (F) —$C_1$-$C_6$ alkoxy optionally substituted with one, two or three —F, (G) —$NR_{N-2}R_{N-3}$ where $R_{N-2}$ and $R_{N-3}$ are as defined below, (H) —OH, (I) —C≡N, (J) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (K) —CO—($C_1$-$C_4$ alkyl), (L) —$SO_2$—$NR_{1-a}R_{1-b}$ where $R_{1-a}$ and $R_{1-b}$ are as defined above, (M) —CO—$NR_{1-a}R_{1-b}$ where $R_{1-a}$ and $R_{1-b}$ are as defined above, (N) —$SO_2$—($C_1$-$C_4$ alkyl), (VII) —$(CH_2)_{n1}$-($R_1$-heteroaryl) where $n_1$ is as defined above and where $R_{1-heteroaryl}$ is selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide tetrahydroquinolinyl dihydroquinolinyl dihydroquinolinonyl dihydroisoquinolinonyl dihydrocoumarinyl dihydroisocoumarinyl isoindolinonyl benzodioxanyl benzoxazolinonyl pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1-heteroaryl}$ group is bonded to —$(CH_2)_{n1}$— by any ring atom of the parent $R_{N-heteroaryl}$ group substituted by hydrogen such that the new bond to the $R_{1-heteroaryl}$ group replaces the hydrogen atom and its bond, where heteroaryl is optionally substituted with one, two, three or four of:

(1) $C_1$-$C_6$ alkyl optionally substituted with one, two or three substituents selected from the group consisting of $C_1$-$C_3$ alkyl, —F, —Cl, —Br, —I, —OH, —SH, —$NR_{1-a}R_{1-b}$ where $R_{1-a}$ and $R_{1-b}$ are as defined above, —C≡N, —$CF_3$, $C_1$-$C_3$ alkoxy, (2) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (3) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl, (4) —F, —Cl, —Br and —I, (6) —$C_1$-$C_6$ alkoxy optionally substituted with one, two, or three —F, (7) —$NR_{N-2}R_{N-3}$ where $R_{N-2}$ and $R_{N-3}$ are as defined below, (8) —OH, (9) —C≡N,

(10) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl,

(11) —CO—($C_1$-$C_4$ alkyl),

(12) —$SO_2$—$NR_{1-a}R_{1-b}$ where $R_{1-a}$ and RI-b are as defined above,

(13) —CO—$NR_{1-a}R_{1-b}$ where $R_{1-a}$ and $R_{1-b}$ are as defined above,

(14) —$SO_2$—($C_1$-$C_4$ alkyl), with the proviso that when $n_1$ is zero $R_{1\text{-}heteroaryl}$ is not bonded to the carbon chain by nitrogen, (VIII) —$(CH_2)_{n1}$—($R_{1\text{-}heterocycle}$) where $n_1$ is as defined above and $R_{1\text{-}heterocycle}$ is selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three or four:
  (1) $C_1$-$C_6$ alkyl optionally substituted with one, two or three substituents selected from the group consisting of $C_1$-$C_3$ alkyl, —F, —Cl, —Br, —I, —OH, —SH, —$NR_{1\text{-}a}R_{1\text{-}b}$ where $R_{1\text{-}a}$ and $R_{1\text{-}b}$ are as defined above, —C≡N, —$CF_3$, $C_1$-$C_3$ alkoxy,
  (2) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl,
  (4) —F, —Cl, —Br and —I,
  (5) $C_1$-$C_6$ alkoxy,
  (6) —$C_1$-$C_6$ alkoxy optionally substituted with one, two, or three —F,
  (7) —$NR_{N\text{-}2}R_{N\text{-}3}$ where $R_{N\text{-}2}$ and $R_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl,
  (11) —CO—($C_1$-$C_4$ alkyl),
  (12) —$SO_2$—$NR_{1\text{-}a}R_{1\text{-}b}$ where $R_{1\text{-}a}$ and $R_{1\text{-}b}$ are as defined above,
  (13) —CO—$NR_{1\text{-}a}R_{1\text{-}b}$ where $R_{1\text{-}a}$ and $R_{1\text{-}b}$ are as defined above,
  (14) —$SO_2$—($C_1$-$C_4$ alkyl),
  (15) =O, with the proviso that when $n_1$ is zero $R_{1\text{-}heterocycle}$ is not bonded to the carbon chain by nitrogen;

where $R_2$ is selected from the group consisting of:
  (I) —H,
  (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are as defined above,
  (III) —$(CH_2)_{0\text{-}4}$—$R_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above;
  (IV) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl,
  (V) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl,
  (VI) —$(CH_2)_{0\text{-}4}$—$C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl, where $R_3$ is selected from the group consisting of:
  (I) —H,
  (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are as defined above,
  (III) —$(CH_2)_{0\text{-}4}$—$R_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above;
  (IV) $C_2$-$C_6$ alkenyl with one or two double bonds,
  (V) $C_2$-$C_6$ alkynyl with one or two triple bonds,
  (VI) —$(CH_2)_{0\text{-}4}$—$C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl, and where $R_2$ and $R_3$ are taken together with the carbon to which they are attached to form a carbocycle of three, four, five, six, and seven carbon atoms, optionally where one carbon atom is replaced by a heteroatom selected from the group consisting of —O—, —S—, —$SO_2$—, —$NR_{N\text{-}2}$—, where $R_{N\text{-}2}$ is as defined below;

where $R_N$ is:
  (I) $R_{N\text{-}1}$—$X_N$— where $X_N$ is selected from the group consisting of:
    (A) —CO—,
    (B) —$SO_2$—,
    (C) —$(CR'R'')_{1\text{-}6}$ where R' and R" are the same or different and are —H and $C_1$-$C_4$ alkyl,
    (D) —CO—$(C'R'')_{1\text{-}6}$—$X_{N\text{-}1}$ where $X_{N\text{-}1}$ is selected from the group consisting of —O—, —S— and —NR'— and where R' and R" are as defined above,
    (E) a single bond;
  where $R_{N\text{-}1}$ is selected from the group consisting of:
    (A) $R_{N\text{-}aryl}$ where $R_{N\text{-}aryl}$ is phenyl, 1-naphthyl, 2-naphthyl, tetralinyl, indanyl, dihydronaphthyl or 6,7,8,9-tetrahydro-5H-benzo[a]cycloheptenyl, optionally substituted with one, two or three of the following substituents which can be the same or different and are:
      (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are as defined above,
      (2) —OH,
      (3) —$NO_2$, (4) —F, —Cl, —Br, —I,
(5) —CO—OH,
(6) —C≡N,
(7) —(CH$_2$)$_{0-4}$—CO—NR$_{N-2}$R$_{N-3}$ where R$_{N-2}$ and R$_{N-3}$ are the same or different and are selected from the group consisting of:
  (a) —H,
  (b) —C$_1$-C$_6$ alkyl optionally substituted with one substitutent selected from the group consisting of:
    (i) —OH,
    (ii) —NH$_2$,
  (c) —C$_1$-C$_6$ alkyl optionally substituted with one to three —F, —Cl, —Br, —I,
  (d) —C$_3$-C$_7$ cycloalkyl,
  (e) —(C$_1$-C$_2$ alkyl)-C$_3$-C$_7$ cycloalkyl),
  (f) —(C$_1$-C$_6$ alkyl)-O—(C$_1$-C$_3$ alkyl),
  (g) —C$_2$-C$_6$ alkenyl with one or two double bonds,
  (h) —C$_2$-C$_6$ alkynyl with one or two triple bonds,
  (i) —C$_1$-C$_6$ alkyl chain with one double bond and one triple bond,
  (j) —R$_{1\text{-}aryl}$ where R$_{1\text{-}aryl}$ is as defined above,
  (k) —R$_{1\text{-}heteroaryl}$ where R$_{1\text{-}heteroaryl}$ is as defined above,
(8) —(CH$_2$)$_{0-4}$—CO—(C$_1$-C$_{12}$ alkyl),
(9) —(CH$_2$)$_{0-4}$—CO—(C$_2$-C$_{12}$ alkenyl with one, two or three double bonds),
(10) —(CH$_2$)$_{0-4}$—CO—(C$_2$-C$_{12}$ alkynyl with one, two or three triple bonds),
(11) —(CH$_2$)$_{0-4}$—CO—(C$_3$-C$_7$ cycloalkyl),
(12) —(CH$_2$)$_{0-4}$—CO—R$_{1\text{-}aryl}$ where R$_{1\text{-}aryl}$ is as defined above,
(13) —(CH$_2$)$_{0-4}$—CO—R$_{1\text{-}heteroaryl}$ where R$_{1\text{-}heteroaryl}$ is as defined above,
(14) —(CH$_2$)$_{0-4}$—CO—R$_{1\text{-}heterocycle}$ where R$_{1\text{-}heterocycle}$ is as defined above,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$-C$_6$ alkyl,
(16) —(CH2)$_{0-4}$—CO—O—R$_{N-5}$ where R$_{N-5}$ is selected from the group consisting of:
  (a) C$_1$-C$_6$ alkyl,
  (b) —(CH$_2$)$_{0-2}$—(R$_{1\text{-}aryl}$) where R$_{1\text{-}aryl}$ is as defined above,
  (c) C$_2$-C$_6$ alkenyl containing one or two double bonds,
  (d) C$_2$-C$_6$ alkynyl containing one or two triple bonds,
  (e) C$_3$-C$_7$ cycloalkyl,
  (f) —(CH$_2$)$_{0-2}$—(R$_{1\text{-}heteroaryl}$) where R$_{1\text{-}heteroaryl}$ is as defined above,
(17) —(CH$_2$)$_{0-4}$—SO$_2$—NR$_{N-2}$R$_{N-3}$ where R$_{N-2}$ and R$_{N-3}$ are as defined above,
(18) —(CH$_2$)$_{0-4}$—SO—(C$_1$-C$_8$ alkyl),
(19) —(CH$_2$)$_{0-4}$—SO$_2$—(C$_1$-C$_{12}$ alkyl)
(20) —(CH$_2$)$_{0-4}$—SO$_2$—(C$_3$-C$_7$ cycloalkyl)
(21) —(CH$_2$)$_{0-4}$—N(H or R$_{N-5}$)—CO—O—R$_{N-5}$ where R$_{N-5}$ can be the same or different and is as defined above,
(22) —(CH$_2$)$_{0-4}$—N(H or R$_{N-5}$)—CO—N(R$_{N-5}$)$_2$, where R$_{N-5}$ can be the same or different and is as defined above,
(23) —(CH$_2$)$_{0-4}$—N—CS—N(R$_{N-5}$)$_2$, where R$_{N-5}$ can be the same or different and is as defined above,
(24) —(CH$_2$)$_{0-4}$—N(—H or R$_{N-5}$)—CO—R$_{N-2}$ where R$_{N-5}$ and R$_{N-2}$ can be the same or different and are as defined above,
(25) —(CH$_2$)$_{0-4}$—NR$_{N-2}$R$_{N-3}$ where R$_{N-2}$ and R$_{N-3}$ can be the same or different and are as defined above,
(26) —(CH$_2$)$_{0-4}$—R$_{N-4}$ where R$_{N-4}$ is as defined above,
(27) —(CH$_2$)$_{0-4}$—O—CO—(C$_1$-C$_6$ alkyl), (28) —(CH$_2$)$_{0-4}$—O—P(O)—(OR$_{N\text{-}aryl\text{-}1}$)$_2$ where R$_{N\text{-}aryl\text{-}1}$ is —H or C$_1$-C$_4$ alkyl,
(29) —(CH$_2$)$_{0-4}$—O—CO—N(R$_{N-5}$)$_2$ where R$_{N-5}$ is as defined above,
(30) —(CH$_2$)$_{0-4}$—O—CS—N(R$_{N-5}$)$_2$ where R$_{N-5}$ is as defined above,
(31) —(CH2)$_{0-4}$—O—(R$_{N-5}$)$_2$ where R$_{N-5}$ is as defined above,
(32) —(CH$_2$)$_{0-4}$—O—(R$_{N-5}$)$_2$—COOH where R$_{N-5}$ is as defined above,
(33) —(CH$_2$)$_{0-4}$—S—(R$_{N-5}$)$_2$ where R$_{N-5}$ is as defined above,
(34) —(CH$_2$)$_{0-4}$—O—(C$_1$-C$_6$ alkyl optionally substituted with one, two, three, four, or five of —F),
(35) C$_3$-C$_7$ cycloalkyl,
(36) C$_2$-C$_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(38) —(CH$_2$)$_{0-4}$—N(—H or R$_{N-5}$)—SO$_2$—R$_{N-2}$ where R$_{N-5}$ and R$_{N-2}$ can be the same or different and are as described above,
(39) —(CH$_2$)$_{0-4}$—C$_3$-C$_7$ cycloalkyl,
(B) —R$_{N\text{-}heteroaryl}$ where R$_{N\text{-}heteroaryl}$ is selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl dihydroquinolinyl dihydroquinolinonyl dihydroisoquinolinonyl dihydrocoumarinyl dihydroisocoumarinyl isoindolinonyl benzodioxanyl benzoxazolinonyl pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{N\text{-}heteroaryl}$ group is bonded by any atom of the parent $R_{N\text{-}heteroaryl}$ group substituted by hydrogen such that the new bond to the $R_{N\text{-}heteroaryl}$ group replaces the hydrogen atom and its bond, where heteroaryl is optionally substituted with one, two, three, or four of:

(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, —NR$_{1\text{-}a}$R$_{1\text{-}b}$ where R$_{1\text{-}a}$ and R$_{1\text{-}b}$ are as defined above,
(2) —OH,
(3) —NO$_2$,
(4) —F, —Cl, —Br, —I,
(5) —CO—OH,
(6) —C≡N,
(7) —(CH$_2$)$_{0\text{-}4}$—CO—NR$_{N\text{-}2}$R$_{N\text{-}3}$ where R$_{N\text{-}2}$ and R$_{N\text{-}3}$ are the same or different and are selected from the group consisting of:
  (a) —H,
  (b) —C$_1$-C$_6$ alkyl optionally substituted with one substitutent selected from the group consisting of:
    (i) —OH,
    (ii) —NH$_2$,
  (c) —C$_1$-C$_6$ alkyl optionally substituted with one to three —F, —Cl, —Br, —I,
  (d) —C$_3$-C$_7$ cycloalkyl,
  (e) —(C$_1$-C$_2$ alkyl)-(C$_3$-C$_7$ cycloalkyl),
  (f) —(C$_1$-C$_6$ alkyl)-O—(C$_1$-C$_3$ alkyl),
  (g) —C$_2$-C$_6$ alkenyl with one or two double bonds,
  (h) —C$_2$-C$_6$ alkynyl with one or two triple bonds,
  (i) —C$_1$-C$_6$ alkyl chain with one double bond and one triple bond,
  (j) —R$_{1\text{-}aryl}$ where R$_{1\text{-}aryl}$ is as defined above,
  (k) —R$_{1\text{-}heteroaryl}$ where R$_{1\text{-}heteroaryl}$ is as defined above,
(8) —(CH$_2$)$_{0\text{-}4}$—CO—(C$_1$-C$_{12}$ alkyl),
(9) —(CH$_2$)$_{0\text{-}4}$—CO—(C$_2$-C$_{12}$ alkenyl with one, two or three double bonds),
(10) —(CH$_2$)$_{0\text{-}4}$—CO—(C$_2$-C$_{12}$ alkynyl with one, two or three triple bonds),
(11) —(CH$_2$)$_{0\text{-}4}$—CO—(C$_3$-C$_7$ cycloalkyl)
(12) —(CH$_2$)$_{0\text{-}4}$—CO—R$_{1\text{-}aryl}$ where R$_{1\text{-}aryl}$ is as defined above,
(13) —(CH$_2$)$_{1\text{-}4}$—CO—R$_{1\text{-}heteroaryl}$ where R$_{1\text{-}heteroaryl}$ is as defined above,
(14) —(CH$_2$)$_{0\text{-}4}$—CO—R$_{1\text{-}heterocycle}$ where R$_{1\text{-}heterocycle}$ is as defined above,
(15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$-C$_6$ alkyl,
(16) —(CH$_2$)$_{0\text{-}4}$—CO—R$_{N\text{-}5}$ where R$_{N\text{-}5}$ is selected from the group consisting of:
  (a) C$_1$-C$_6$ alkyl,
  (b) —(CH$_2$)$_{0\text{-}2}$—(R$_{1\text{-}aryl}$) where R$_{1\text{-}aryl}$ is as defined above,
  (c) C$_2$-C$_6$ alkenyl containing one or two double bonds,
  (d) C$_2$-C$_6$ alkynyl containing one or two triple bonds,
  (e) C$_3$-C$_7$ cycloalkyl,
  (f) —(CH$_2$)$_{0\text{-}2}$—(R$_{1\text{-}heteroaryl}$) where R$_{1\text{-}heteroaryl}$ is as defined above,
(17) —(CH$_2$)$_{0\text{-}4}$—SO$_2$—NR$_{N\text{-}2}$R$_{N\text{-}3}$ where R$_{N\text{-}2}$ and R$_{N\text{-}3}$ are as defined above,
(18) —(CH$_2$)$_{0\text{-}4}$—SO—(C$_1$-C$_8$ alkyl),
(19) —(CH$_2$)$_{0\text{-}4}$—SO$_2$—(C$_1$-C$_{12}$ alkyl)
(20) —(CH$_2$)$_{0\text{-}4}$—SO$_2$—(C$_3$-C$_7$ cycloalkyl)
(21) —(CH$_2$)$_{0\text{-}4}$—N(H or R$_{N\text{-}5}$)—CO—O—R$_{N\text{-}5}$ where R$_{N\text{-}5}$ can be the same or different and is as defined above,
(22) —(CH$_2$)$_{0\text{-}4}$—N(H or R$_{N\text{-}5}$)—CO—N(R$_{N\text{-}5}$)$_2$, where R$_{N\text{-}5}$ can be the same or different and is as defined above,
(23) —(CH$_2$)$_{0\text{-}4}$—N—CS—N(R$_{N\text{-}5}$)$_2$, where R$_{N\text{-}5}$ can be the same or different and is as defined above,
(24) —(CH$_2$)$_{0\text{-}4}$—N(—H or R$_{N\text{-}5}$)—CO—R$_{N\text{-}2}$ where R$_{N\text{-}5}$ and R$_{N\text{-}2}$ can be the same or different and are as defined above,
(25) —(CH$_2$)$_{0\text{-}4}$—NR$_{N\text{-}2}$R$_{N\text{-}3}$ where R$_{N\text{-}2}$ and R$_{N\text{-}3}$ can be the same or different and are as defined above,
(26) —(CH$_2$)$_{0\text{-}4}$—R$_{N\text{-}4}$ where R$_{N\text{-}4}$ is as defined above,
(27) —(CH$_2$)$_{0\text{-}4}$—O—CO—(C$_1$-C$_6$ alkyl)
(28) —(CH$_2$)$_{0\text{-}4}$—O—P(O)—(OR$_{N\text{-}aryl}$)$_2$ where R$_{N\text{-}aryl\text{-}1}$ is —H or C$_1$-C$_4$ alkyl,
(29) —(CH$_2$)$_{0\text{-}4}$—O—CO—N(R$_{N\text{-}5}$)$_2$ where R$_{N\text{-}5}$ is as defined above,
(30) —(CH$_2$)$_{0\text{-}4}$—O—CS—N(R$_{N\text{-}5}$)$_2$ where R$_{N\text{-}5}$ is as defined above,
(31) —(CH$_2$)$_{0\text{-}4}$—O—(R$_{N\text{-}5}$)$_2$ where R$_{N\text{-}5}$ is as defined above,
(32) —(CH$_2$)$_{0\text{-}4}$—O—(R$_{N\text{-}5}$)$_2$—COOH where R$_{N\text{-}5}$ is as defined above,
(33) —(CH$_2$)$_{0\text{-}4}$—S—(R$_{N\text{-}5}$)$_2$ where R$_{N\text{-}5}$ is as defined above,
(34) —(CH$_2$)$_{0\text{-}4}$—O—(C$_1$-C$_6$ alkyl optionally substituted with one, two, three, four, or five of —F),
(35) C$_3$-C$_7$ cycloalkyl,
(36) C$_2$-C$_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(38) —(CH$_2$)$_{0\text{-}4}$—N(—H or R$_{N\text{-}5}$)—SO$_2$—R$_{N\text{-}2}$ where R$_{N\text{-}5}$ and R$_{N\text{-}2}$ can be the same or different and are as described above,
(39) —(CH$_2$)$_{0\text{-}4}$—C$_3$-C$_7$ cycloalkyl,
(C) R$_{N\text{-}aryl}$-W—R$_{N\text{-}aryl}$,
(D) R$_{N\text{-}aryl}$-W—R$_{N\text{-}heteroaryl}$,
(E) R$_{N\text{-}aryl}$-W—R$_{N\text{-}1\text{-}heterocycle}$, where R$_{N\text{-}heterocycle}$ is defined as R$_{1\text{-}heterocycle}$ is defined above,
(F) R$_{N\text{-}heteroaryl}$-W—R$_{N\text{-}aryl}$,
(G) R$_{N\text{-}heteroaryl}$-W—R$_{N\text{-}heteroaryl}$,
(H) R$_{N\text{-}heteroaryl}$-W—R$_{N\text{-}1\text{-}heterocycle}$, where R$_{N\text{-}1\text{-}heterocycle}$ is defined as R$_{1\text{-}heterocycle}$ is defined above,
(I) R$_{N\text{-}heterocycle}$-W—R$_{N\text{-}aryl}$,
(J) R$_{N\text{-}heterocycle}$-W—R$_{N\text{-}heteroaryl}$,
(K) R$_{N\text{-}heterocycle}$-W—R$_{N\text{-}heterocycle}$,
where W is
(1) —(CH$_2$)$_{0\text{-}4}$—,
(2) —O—,
(3) —S(O)$_{0\text{-}2}$—,
(4) —N(R$_{N\text{-}5}$)— where R$_{N\text{-}5}$ is as defined above, or
(5) —CO—;

(II) —CO—($C_1$-$C_{10}$ alkyl) where alkyl is optionally substituted with one two or three substitutents selected from the group consisting of:
  (A) —OH,
  (B) —$C_1$-$C_6$ alkoxy,
  (C) —$C_1$-$C_6$ thioalkoxy,
  (D) —CO—O—$R_{N-8}$ where $R_{N-8}$ is —H, $C_1$-$C_6$ alkyl or —phenyl,
  (E) —CO—$NR_{N-2}R_{N-3}$ where $R_{N-2}$ and $R_{N-3}$ are the same or different and are as defined above,
  (F) —CO—$R_{N-4}$ where $R_{N-4}$ is as defined above,
  (G) —$SO_2$—($C_1$-$C_8$ alkyl),
  (H) —$SO_2$—$NR_{N-2}R_{N-3}$ where $R_{N-2}$ and $R_{N-3}$ are the same or different and are as defined above,
  (I) —NH—CO—($C_1$-$C_6$ alkyl),
  (J) —NH—CO—O—$R_{N-8}$ where $R_{N-8}$ is as defined above,
  (K) —$NR_{N-2}R_{N-3}$ where $R_{N-2}$ and $R_{N-3}$ are the same or different and are as defined above,
  (L) —$R_{N-4}$ where $R_{N-4}$ is as defined above,
  (M) —O—CO—($C_1$-$C_6$ alkyl),
  (N) —O—CO—$NR_{N-8}R_{N-8}$ where $R_{N-8}$ are the same or different and are as defined above,
  (O) —O—($C_1$-$C_5$ alkyl)-COOH,
  (P) —O—($C_1$-$C_6$ alkyl optionally substituted with one, two, or three of —F, —Cl, —Br, —I),
  (Q) —NH—$SO_2$—($C_1$-$C_6$ alkyl),
  (R) —F, —Cl,
(III) —CO—($C_1$-$C_6$ alkyl)-O—($C_1$-$C_6$ alkyl) where alkyl is optionally substituted with one, two, or three substitutents selected from the group consisting of
  (A) —OH,
  (B) —$C_1$-$C_6$ alkoxy,
  (C) —$C_1$-$C_6$ thioalkoxy,
  (D) —CO—O—$R_{N-8}$ where $R_{N-8}$ is —H, $C_1$-$C_6$ alkyl or -phenyl,
  (E) —CO—$NR_{N-2}R_{N-3}$ where $R_{N-2}$ and $R_{N-3}$ are the same or different and are as defined above,
  (F) —CO—$R_{N-4}$ where $R_{N-4}$ is as defined above,
  (G) —$SO_2$—($C_1$-$C_8$ alkyl),
  (H) —$SO_2$—$NR_{N-2}R_{N-3}$ where $R_{N-2}$ and $R_{N-3}$ are the same or different and are as defined above,
  (I) —NH—CO—($C_1$-$C_6$ alkyl),
  (J) —NH—CO—O—$R_{N-8}$ where $R_{N-8}$ is as defined above,
  (K) —$NR_{N-2}R_{N-3}$ where $R_{N-2}$ and $R_{N-3}$ are the same or different and are as defined above,
  (L) —$R_{N-4}$ where $R_{N-4}$ is as defined above,
  (M) —O—CO—($C_1$-$C_6$ alkyl),
  (N) —O—CO—$NR_{N-8}R_{N-8}$ where $R_{N-8}$ are the same or different and are as defined above,
  (O) —O—($C_1$-$C_5$ alkyl)-COOH,
  (P) —O—($C_1$-$C_6$ alkyl optionally substitued with one, two, or three of —F, —Cl, —Br, —I),
  (Q) —NH—$SO_2$—($C_1$-$C_6$ alkyl),
  (R) —F, —Cl,
(IV) —CO—($C_1$-$C_6$ alkyl)-S—($C_1$-$C_6$ alkyl) where alkyl is optionally substituted with one, two, or three of substitutents selected from the group consisting of:
  (A) —OH,
  (B) —$C_1$-$C_6$ alkoxy,
  (C) —$C_1$-$C_6$ thioalkoxy,
  (D) —CO—O—$R_{N-8}$ where $R_{N-8}$ is as defined above,
  (E) —CO—$NR_{N-2}R_{N-3}$ where $R_{N-2}$ and $R_{N-3}$ are the same or different and are as defined above,
  (F) —CO—$R_{N-4}$ where $R_{N-4}$ is as defined above,
  (G) —$SO_2$—($C_1$-$C_8$ alkyl),
  (H) —$SO_2$—$NR_{N-2}R_{N-3}$ where $R_{N-2}$ and $R_{N-3}$ are the same or different and are as defined above,
  (I) —NH—CO—($C_1$-$C_6$ alkyl),
  (J) —NH—CO—O—$R_{N-8}$ where $R_{N-8}$ is as defined above,
  (K) —$NR_{N-2}R_{N-3}$ where $R_{N-2}$ and $R_{N-3}$ are the same or different and are as defined above,
  (L) —$R_{N-4}$ where $R_{N-4}$ is as defined above,
  (M) —O—CO—($C_1$-$C_6$ alkyl),
  (N) —O—CO—$NR_{N-8}R_{N-8}$ where the $R_{N-8}$s are the same or different and are as defined above,
  (O) —O—($C_1$-$C_5$ alkyl)-COOH,
  (P) —O—($C_1$-$C_6$ alkyl optionally substituted with one, two, or three of —F, —Cl, —Br, —I),
  (Q) —NH—$SO_2$—($C_1$-$C_6$ alkyl),
  (R) —F, —Cl,
(V) —CO—CH (—$(CH_2)_{0-2}$—O—$R_{N-10}$)—$(CH_2)_{0-2}$—$R_{N\text{-}aryl}/R_{N\text{-}heteroaryl}$) where $R_{N\text{-}aryl}$ and $R_{N\text{-}heteroaryl}$ are as defined above, where $R_{N-10}$ is selected from the group consisting of:
  (A) —H,
  (B) $C_1$-$C_6$ alkyl,
  (C) $C_3$-$C_7$ cycloalkyl,
  (D) $C_2$-$C_6$ alkenyl with one double bond,
  (E) $C_2$-$C_6$ alkynyl with one triple bond,
  (F) $R_{1\text{-}aryl}$ where $R_{1\text{-}aryl}$ is as defined above,
  (G) $R_{N\text{-}heteroaryl}$ where $R_{N\text{-}heteroaryl}$ is as defined above,
(VI) —CO—($C_3$-$C_8$ cycloalkyl) where cycloalkyl is optionally substituted with one or two substituents selected from the group consisting of:
  (A) —$(CH_2)_{0-4}$—OH,
  (B) —$(CH_2)_{0-4}$-$C_1$-$C_6$ alkoxy,
  (C) —$(CH_2)_{0-4}$-$C_1$-$C_6$ thioalkoxy,
  (D) —$(CH_2)_{0-4}$-CO—O—$R_{N-8}$ where $R_{N-8}$ is —H, $C_1$-$C_6$ alkyl or -phenyl,
  (E) —$(CH_2)_{0-4}$—CO—$NR_{N-2}R_{N-3}$ where $R_{N-2}$ and $R_{N-3}$ are the same or different and are as defined above,
  (F) —$(CH_2)_{0-4}$—CO—$R_{N-4}$ where $R_{N-4}$ is as defined above,
  (G) —$(CH_2)_{0-4}$—$SO_2$—($C_1$-$C_8$ alkyl),
  (H) —$(CH_2)_{0-4}$—$SO_2$—$NR_{N-2}R_{N-3}$ where $R_{N-2}$ and $R_{N-3}$ are the same or different and are as defined above,
  (I) —$(CH_2)_{0-4}$—NH—CO—($C_1$-$C_6$ alkyl),
  (J) —NH—CO—O—$R_{N-8}$ where $R_{N-8}$ is as defined above,
  (K) —$(CH_2)_{0-4}$—$NR_{N-2}R_{N-3}$ where $R_{N-2}$ and $R_{N-3}$ are the same or different and are as defined above,
  (L) —$(CH_2)_{0-4}$—$R_{N-4}$ where $R_{N-4}$ is as defined above,
  (M) —O—CO—($C_1$-$C_6$ alkyl),
  (N) —O—CO—$NR_{N-8}R_{N-8}$ where the $R_{N-8}$s are the same or different and are as defined above,
  (O) —O—($C_1$-$C_5$ alkyl)-COOH,
  (P) —O—($C_1$-$C_6$ alkyl optionally substitued with one, two, or three of —F, —Cl, —Br, —I),
  (Q) —NH—$SO_2$—($C_1$-$C_6$ alkyl),
  (R) —F, —Cl,
where $R_C$ is:
(I) —$C_1$-$C_{10}$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1\text{-}a}R_{1\text{-}b}$ where $R_{1\text{-}a}$ and $R_{1\text{-}b}$ are as defined above, —OC=O $NR_{1\text{-}a}R_{1\text{-}b}$ where $R_{1\text{-}a}$ and $R_{1\text{-}b}$ are as defined above, —S(=O)$_{0-2}$ $R_{1\text{-}a}$ where $R_{1\text{-}a}$ is as defined above, —$NR_{1\text{-}a}$C=O $NR_{1\text{-}a}R_{1\text{-}b}$ where $R_{1\text{-}a}$ and $R_{1\text{-}b}$ are as defined above, —C=O $NR_{1\text{-}a}R_{1\text{-}b}$ where $R_{1\text{-}a}$ and $R_{1\text{-}b}$ are as defined above, and —S(═O)$_2$NR$_{1-a}$R$_{1-b}$ where R$_{1-a}$ and R$_{1-b}$ are as defined above, (II) —(CH$_2$)$_{0-3}$—(C$_3$-C$_8$) cycloalkyl where cycloalkyl can be optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —CO—OH, —CO—O—(C$_1$-C$_4$ alkyl), —NR$_{1-a}$R$_{1-b}$ where R$_{1-a}$ and R$_{1-b}$ are as defined above, (III) —(CR$_{C-x}$R$_{C-y}$)$_{0-4}$—R$_{C-aryl}$ where R$_{C-x}$ and R$_{C-y}$ are
- —H,
- C$_1$-C$_4$ alkyl optionally substituted with one or two —OH,
- C$_1$-C$_4$ alkoxy optionally substituted with one, two, or three of —F,
- —(CH$_2$)$_{0-4}$—C$_3$-C$_7$ cycloalkyl, C$_2$-C$_6$ alkenyl containing one or two double bonds, C$_2$-C$_6$ alkynyl containing one or two triple bonds, phenyl, and where R$_{C-x}$ and R$_{C-y}$ are taken together with the carbon to which they are attached to form a carbocycle of three, four, five, six and seven carbon atoms, optionally where one carbon atom is replaced by a heteroatom selected from the group consisting of —O—, —S—, —SO$_2$—, —NR$_{N-2}$— and R$_{C-aryl}$ is defined as R$_{N-aryl}$ is defined above;

(IV) —(CR$_{C-x}$R$_{C-y}$)$_{0-4}$—R$_{C-heteroaryl}$ where R$_{C-heteroaryl}$ is defined as R$_{N-heteroaryl}$ is defined above and R$_{C-X}$ and R$_{C-y}$ are as defined above, (V) —(CR$_{C-x}$R$_{C-y}$)$_{0-4}$—R$_{C-aryl}$—R$_{C-aryl}$ where R$_{C-aryl}$, R$_{C-x}$ and R$_{C-y}$ are as defined above, (VI) —(CR$_{C-x}$R$_{C-y}$)$_{0-4}$—R$_{C-aryl}$—R$_{C-heteroaryl}$ where R$_{C-aryl}$, R$_{C-heteroaryl}$, R$_{C-x}$ and R$_{C-y}$ are as defined above, (VII) —(CR$_{C-x}$R$_{C-y}$)$_{0-4}$—R$_{C-heteroaryl}$—R$_{C-aryl}$ where R$_{C-heteroaryl}$, R$_{C-aryl}$, R$_{C-x}$ and R$_{C-y}$ are as defined above, (VIII) —(C$_{C-x}$R$_{C-y}$)$_{0-4}$—R$_{C-heteroaryl}$—R$_{C-heteroaryl}$ where R$_{C-heteroaryl}$, R$_{C-x}$ and R$_{C-y}$ are as defined above, (IX) —(CR$_{C-x}$R$_{C-y}$)$_{0-4}$—R$_{C-aryl}$—RC$_{-heterocycle}$ where R$_{C-aryl}$, R$_{C-x}$ and R$_{C-y}$ are as defined above, and R$_{C-heterocycle}$ is defined as R$_{N-heterocycle}$ is defined above, (X) —(CR$_{C-x}$R$_{C-y}$)$_{0-4}$R$_{C-heteroaryl}$—R$_{C-heterocycle}$ where R$_{C-heteroaryl}$, R$_{C-heterocycle}$, R$_{C-x}$ and R$_{C-y}$ are as defined above, (XI) —(CR$_{C-x}$R$_{C-y}$)$_{0-4}$R$_{C-heterocycle}$—R$_{C-aryl}$ where R$_{C-heterocycle}$, R$_{C-aryl}$, R$_{C-x}$ and R$_{C-y}$ are as defined above, (XII) —(CR$_{C-x}$R$_{C-y}$)$_{0-4}$—R$_{C-heterocycle}$—R$_{C-heteroaryl}$ where R$_{C-heterocycle}$, R$_{C-heteroaryl}$, R$_{C-x}$ and R$_{C-y}$ are as defined above, (XIII) —(CR$_{C-x}$R$_{C-y}$)$_{0-4}$—R$_{C-heterocycle}$—R$_{C-heterocycle}$ where R$_{C-heterocycle}$, R$_{C-x}$ and R$_{C-y}$ are as defined above, (XIV) —(CR$_{C-x}$R$_{C-y}$)$_{0-4}$—R$_{C-heterocycle}$ where R$_{C-heterocycle}$, R$_{C-x}$ and R$_{C-y}$ are as defined above, (XV) —[C (R$_{C-1}$) (R$_{C-2}$)]$_{1-3}$—CO—N—(R$_{C-3}$)$_2$ where R$_{C-1}$ and R$_{C-2}$ are the same or different and are selected from the group consisting of:

(A) —H, (B) —C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (C) C$_2$-C$_6$ alkenyl with one or two double bonds, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (D) C$_2$-C$_6$ alkynyl with one or two triple bonds, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (E) —(CH$_2$)$_{1-2}$—S(O)$_{0-2}$—(C$_1$-C$_6$ alkyl)

(F) —(CH$_2$)$_{0-4}$—C$_3$-C$_7$ cycloalkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (G) —(C$_1$-C$_4$ alkyl)-R$_{C'-aryl}$ where R$_{C'-aryl}$ is as defined for R$_{1-aryl}$, (H) —(C$_1$-C$_4$ alkyl)-R$_{C-heteroaryl}$ where R$_{C-heteroaryl}$ is as defined above, (I) —(C$_1$-C$_4$ alkyl)-R$_{C-heterocycle}$ where R$_{C-heterocycle}$ is as defined above, (J) —R$_{C-heteroaryl}$ where R$_{C-heteroaryl}$ is as defined above, (K) —R$_{C-heterocycle}$ where R$_{C-heterocycle}$ is as defined above, (M) —(CH$_2$)$_{1-4}$—R$_{C-4}$—(CH$_2$)$_{0-4}$—R$_{C'-aryl}$ where R$_{C-4}$ is —O—, —S— or —NR$_{C-5}$— where R$_{C-5}$ is C$_1$-C$_6$ alkyl, and where R$_{C'-aryl}$ is defined above, (N) —(CH$_2$)$_{1-4}$—R$_{C-4}$—(CH$_2$)$_{0-4}$—R$_{C-heteroaryl}$ where R$_{C-4}$ and R$_{C-heteroaryl}$ are as defined above, (O) —R$_{C'-aryl}$ where R$_{C'-aryl}$ is as defined above, and where R$_{C-3}$ is the same or different and is:

(A) —H, (B) —C$_1$-C$_6$ alkyl optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (C) C$_2$-C$_6$ alkenyl with one or two double bonds, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (D) C$_2$-C$_6$ alkynyl with one or two triple bonds, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (E) —(CH$_2$)$_{0-4}$—C$_3$-C$_7$ cycloalkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —NR$_{1-a}$R$_{1-b}$ where R$_{1-a}$ and R$_{1-b}$ are as defined above, (F) —R$_{C'-aryl}$ where R$_{C'-aryl}$ is as defined above, (G) —R$_{C-heteroaryl}$ where R$_{C-heteroaryl}$ is as defined above, (H) —R$_{C-heterocycle}$ where R$_{C-heterocycle}$ is as defined above, (I) —(C$_1$-C$_4$ alkyl)-R$_{C'-aryl}$ where R$_{C'-aryl}$ is as defined above, (J) —(C$_1$-C$_4$ alkyl)-R$_{C-heteroaryl}$ where R$_{C-heteroaryl}$ is as defined above, (K) —(C$_1$-C$_4$ alkyl)-R$_{C-heterocycle}$ where R$_{C-heterocycle}$ is as defined above, (XVI) —CH (R$_{C-aryl}$)$_2$ where R$_{C-aryl}$, are the same or different and are as defined above, (XVII) —CH($R_{C\text{-}heteroaryl}$)$_2$ where $R_{C\text{-}heteroaryl}$ are the same or different and are as defined above,
(XVIII) —CH($R_{C\text{-}aryl}$)($R_{C\text{-}heteroaryl}$) where $R_{C\text{-}aryl}$ and $R_{C\text{-}heteroaryl}$ are as defined above,
(XIX) -cyclopentyl, -cyclohexyl, or -cycloheptyl ring fused to $R_{C\text{-}aryl}$ or $R_{C\text{-}heteroaryl}$ or $R_{C\text{-}heterocycle}$ where $R_{C\text{-}aryl}$ or $R_{C\text{-}heteroaryl}$ or $R_{C\text{-}heterocycle}$ are as defined above where one carbon of cyclopentyl, cyclohexyl, or -cycloheptyl is optionally replaced with NH, $NR_{N\text{-}5}$, O, S(=O)$_{0\text{-}2}$, and where cyclopentyl, cyclohexyl, or -cycloheptyl can be optionally substituted with one or two —$C_1$-$C_3$ alkyl, —F, —OH, —SH, —C≡N, —$CF_3$, $C_1$-$C_6$ alkoxy, =O, —$NR_{1\text{-}a}R_{1\text{-}b}$ where $R_{1\text{-}a}$ and $R_{1\text{-}b}$ are as defined above,
(XX) $C_2$-$C_{10}$ alkenyl containing one or two double bonds optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1\text{-}a}R_{1\text{-}b}$ where $R_{1\text{-}a}$ and $R_{1\text{-}b}$ are as defined above,
(XXI) $C_2$-$C_{10}$ alkynyl containing one or two triple bonds optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1\text{-}a}R_{1\text{-}b}$ where $R_{1\text{-}a}$ and $R_{1\text{-}b}$ are as defined above,
(XXI) —(CH$_2$)$_{0\text{-}1}$—CHR$_{C\text{-}6}$—(CH$_2$)$_{0\text{-}1}$—$R_{C\text{-}aryl}$ where $R_{C\text{-}aryl}$ is as defined above and $R_{C\text{-}6}$ is —(CH$_2$)$_{0\text{-}6}$—OH,
(XXII) —(CH$_2$)$_{0\text{-}1}$—CHR$_{C\text{-}6}$—(CH$_2$)$_{0\text{-}1}$—$R_{C\text{-}heteroaryl}$ where $R_{C\text{-}heteroaryl}$ and $R_{C\text{-}6}$ is as defined above,
(XXIII) —CH(—$R_{C\text{-}aryl}$ or $R_{C\text{-}heteroaryl}$)—CO—O($C_1$-$C_4$ alkyl) where $R_{C\text{-}aryl}$ and $R_{C\text{-}heteroaryl}$ are as defined above,
(XXIV) —CH(—CH$_2$—OH)—CH(—OH)-micro-NO$_2$,
(XXV) ($C_1$-$C_6$ alkyl)-O—($C_1$-$C_6$ alkyl)-OH,
(XXVII) —CH$_2$—NH—CH$_2$—CH(—O—CH$_2$—CH$_3$)$_2$,
(XXVIII) —H,
(XXIX) —(CH$_2$)$_{0\text{-}6}$—C(=NR$_{1\text{-}a}$)(NR$_{1\text{-}a}R_{1\text{-}b}$) where $R_{1\text{-}a}$ and $R_{1\text{-}b}$ are as defined above; and
where $R_4$ is:

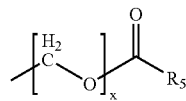

where x is 0 or 1 and $R_5$ is H or is:
(I) $R_{P\text{-}1}$ wherein $R_{P\text{-}1}$ is selected from the group consisting of:
  (A) —Y—$R_{P\text{-}aryl}$ where Y is absent or is oxygen, and $R_{P\text{-}aryl}$ is phenyl, 1-naphthyl, 2-naphthyl, tetralinyl, indanyl, or 6,7,8,9-tetrahydro-5H-benzo[a]cycloheptenyl, optionally substituted with one, two or three of the following substituents which can be the same or different and are:
    (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are independently —H or $C_1$-$C_6$ alkyl,
    (2) —OH,
    (3) —NO$_2$,
    (4) —F, —Cl, —Br, —I,
    (5) —CO—OH,
    (6) —C≡N,
    (7) —(CH$_2$)$_{0\text{-}4}$—CO—NR$_{P\text{-}2}R_{P\text{-}3}$ where $R_{P\text{-}2}$ and $R_{P\text{-}3}$ are the same or different and are selected from the group consisting of:
      (a) —H,
      (b) —$C_1$-$C_6$ alkyl optionally substituted with one substituent selected from the group consisting of:
        (i) —OH,
        (ii) —NH$_2$,
      (c) —$C_1$-$C_6$ alkyl optionally substituted with one to three —F, —Cl, —Br, —I,
      (d) —$C_3$-$C_7$ cycloalkyl,
      (e) —($C_1$-$C_2$ alkyl)-($C_3$-$C_7$ cycloalkyl),
      (f) —($C_1$-$C_6$ alkyl)-O—($C_1$-$C_3$ alkyl)
      (g) —$C_2$-$C_6$ alkenyl with one or two double bonds,
      (h) —$C_2$-$C_6$ alkynyl with one or two triple bonds,
      (i) —$C_1$-$C_6$ alkyl chain with one double bond and one triple bond,
      (j) —$R_{P\text{-}aryl}$ where —$R_{P\text{-}aryl}$ is defined above,
      (k) —$R_{P\text{-}heteroaryl}$ where $R_{P\text{-}heteroaryl}$ is defined below,
      (l) —C(O)$C_1$-$C_6$ alkyl,
    (8) —(CH$_2$)$_{0\text{-}4}$—CO—($C_1$-$C_{12}$ alkyl)
    (9) —(CH$_2$)$_{0\text{-}4}$—CO—($C_2$-$C_{12}$) alkenyl with one, two or three double bonds,
    (10) —(CH$_2$)$_{0\text{-}4}$—CO—($C_2$-$C_{12}$) alkynyl with one, two or three triple bonds,
    (11) —(CH$_2$)$_{0\text{-}4}$—CO—($C_3$-$C_7$ cycloalkyl),
    (12) —(CH$_2$)$_{0\text{-}4}$—CO—$R_{P\text{-}aryl}$ where $R_{P\text{-}aryl}$ is as defined above,
    (13) —(CH$_2$)$_{0\text{-}4}$—CO—$R_{P\text{-}heteroaryl}$ where $R_{P\text{-}heteroaryl}$ is as defined below,
    (14) —(CH$_2$)$_{0\text{-}4}$—CO—$R_{P\text{-}heterocycle}$ where $R_{P\text{-}heterocycle}$ is selected from the group consisting of:
      (A) morpholinyl,
      (B) thiomorpholinyl,
      (C) thiomorpholinyl S-oxide,
      (D) thiomorpholinyl S,S-dioxide,
      (E) piperazinyl,
      (F) homopiperazinyl,
      (G) pyrrolidinyl,
      (H) pyrrolinyl,
      (I) tetrahydropyranyl,
      (J) piperidinyl,
      (K) tetrahydrofuranyl,
      (L) tetrahythiophenyl,
      (M) homopiperidinyl,
      (N) imidazolidine,
      (O) imidazolidine dione, and
      (P) dithiane, where the $R_{P\text{-}heterocycle}$ group is bonded by any atom of the parent $R_{P\text{-}heterocycle}$ group substituted by hydrogen such that the new bond to the $R_{P\text{-}heterocycle}$ group replaces the hydrogen atom and its bond, where heterocycle is optionally substituted with one thru four:
    (1) $C_1$-$C_6$ alkyl optionally substituted with one, two or three substituents selected from the group consisting of $C_1$-$C_3$ alkyl, —F, —Cl, —Br, —I, —OH, —SH, —O—CO—($_1$l-$C_6$ alkyl), and —$NR_{1\text{-}a}R_{1\text{-}b}$ where $R_{1\text{-}a}$ and $R_{1\text{-}b}$ are as defined above, —C≡N, —$CF_3$, $C_1$-$C_6$ alkoxy,
    (2) $C_2$-$C_6$ alkenyl with one or two double bonds,
    (3) $C_2$-$C_6$ alkynyl with one or two triple bonds,
    (4) —F, Cl, —Br and —I,
    (5) $C_1$-$C_6$ alkoxy,
    (6) —O—$C_1$-$C_6$ alkyl optionally substituted with one thru three —F, (7) —NR$_{P-2}$R$_{P-3}$ where R$_{P-2}$ and R$_{P-3}$ are as defined above,
(8) —OH,
(9) —C≡N,
(10) C$_3$-C$_7$ cycloalkyl,
(11) —CO—(C$_1$-C$_4$ alkyl),
(12) —SO$_2$—NR$_{1-a}$R$_{1-b}$ where R$_{1-a}$ and R$_{1-b}$ are as defined above,
(13) —CO—NR$_{1-a}$R$_{1-b}$ where R$_{1-a}$ and R$_{1-b}$ are as defined above,
(14) —SO$_2$—(C$_1$-C$_4$ alkyl);
(15) =O; or
(16) —O—CO—(C$_1$-C$_6$ alkyl);
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: C$_1$-C$_6$ alkyl,
(16) —(CH$_2$)$_{0-4}$—CO—O—R$_{N-5}$ where R$_{N-5}$ is selected from the group consisting of:
(a) C$_1$-C$_6$ alkyl,
(b) —(CH$_2$)$_{0-2}$—(R$_{P-aryl}$) where R$_{P-aryl}$ is as defined above,
(c) C$_2$-C$_6$ alkenyl containing one or two double bonds,
(d) C$_2$-C$_6$ alkynyl containing one or two triple bonds,
(e) C$_3$-C$_7$ cycloalkyl,
(f) —(CH$_2$)$_{0-2}$—(R$_{P-heteroaryl}$) where R$_{P-heteroaryl}$ is as defined below,
(17) —(CH$_2$)$_{0-4}$—SO$_2$—NR$_{P-2}$R$_{P-3}$ where R$_{P-2}$ and R$_{P-3}$ are as defined above,
(18) —(CH$_2$)$_{0-4}$—SO—(C$_1$-C$_8$ alkyl),
(19) —(CH$_2$)$_{0-4}$—SO$_2$—(C$_1$-C$_{12}$ alkyl)
(20) —(CH$_2$)$_{0-4}$—SO$_2$—(C$_3$-C$_7$ cycloalkyl)
(21) —(CH$_2$)$_{0-4}$—N(H or R$_{N-5}$)—CO—O—R$_{N-5}$ where R$_{N-5}$ can be the same or different and is as defined above,
(22) —(CH$_2$)$_{0-4}$—N(H or R$_{N-5}$)—CO—N(R$_{N-5}$)$_2$, where R$_{N-5}$ can be the same or different and is as defined above,
(23) —(CH$_2$)$_{0-4}$—N—CS—N(R$_{N-5}$)$_2$, where R$_{N-5}$ can be the same or different and is as defined above,
(24) —(CH$_2$)$_{0-4}$—N(—H or R$_{N-5}$)—CO—R$_{P-2}$ where R$_{N-5}$ and R$_{P-2}$ can be the same or different and are as defined above,
(25) —(CH$_2$)$_{0-4}$—NR$_{P-2}$R$_{P-3}$ where R$_{P-2}$ and R$_{P-3}$ can be the same or different and are as defined above,
(26) —(CH$_2$)$_{0-4}$—R$_{N-4}$ where R$_{N-4}$ is as defined above,
(27) —(CH$_2$)$_{0-4}$—O—CO—(C$_1$-C$_6$ alkyl),
(28) —(CH$_2$)$_{0-4}$—O—P(O)—(OR$_{N-aryl-1}$)$_2$ where R$_{N-aryl}$ is —H or C$_1$-C$_4$ alkyl,
(29) —(CH$_2$)$_{0-4}$—O—CO—N(R$_{N-5}$)$_2$ where R$_{N-5}$ is as defined above,
(30) —(CH$_2$)$_{0-4}$—O—CS—N(R$_{N-5}$)$_2$ where R$_{N-5}$ is as defined above,
(31) —(CH$_2$)$_{0-4}$—O—(R$_{N-5}$)$_2$ where R$_{N-5}$ is as defined above,
(32) —(CH$_2$)$_{0-4}$—O—(R$_{N-5}$)$_2$—COOH where R$_{N-5}$ is as defined above,
(33) —(CH$_2$)$_{0-4}$—S—(R$_{N-5}$)$_2$ where R$_{N-5}$ is as defined above,
(34) —(CH$_2$)$_{0-4}$—O—(C$_1$-C$_6$ alkyl optionally substituted with one, two, three, four, or five of: —F),
(35) C$_3$-C$_7$ cycloalkyl,
(36) C$_2$-C$_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, —NR$_{1-a}$R$_{1-b}$ where R$_{1-a}$ and R$_{1-b}$ are as defined above,
(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, —NR$_{1-a}$R$_{1-b}$ where R$_{1-a}$ and R$_{1-b}$ are as defined above,
(38) —(CH$_2$)$_{0-4}$—N(—H or R$_{N-5}$)—SO$_2$—R$_{P-2}$ where R$_{N-5}$ and R$_{P-2}$ can be the same of different and are as described above,
(39) —(CH$_2$)$_{0-4}$—C$_3$-C$_7$ cycloalkyl,
(B) —Y—R$_{P-heteroaryl}$ where Y is absent or is oxygen, and R$_{P-heteroaryl}$ is selected from the group consisting of:
(A) pyridinyl,
(B) pyrimidinyl,
(C) quinolinyl,
(F) benzothienyl,
(G) indolyl,
(H) indolinyl,
(I) pryidazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) beta-carbolinyl,
(PP) isochromanyl,
(QQ) chromanyl,
(SS) tetrahydroisoquinolinyl,
(TT) isoindolinyl,
(UU) isobenzotetrahydrofuranyl,
(VV) isobenzotetrahydrothienyl,
(WW) isobenzothienyl,
(XX) benzoxazolyl,
(YY) pyridopyridinyl,
(ZZ) benzotetrahydrofuranyl,
(AAA) benzotetrahydrothienyl,
(BBB) purinyl,
(CCC) benzodioxolyl,
(DDD) triazinyl,
(EEE) phenoxazinyl, (FFF) phenothiazinyl,
(GGG) pteridinyl,
(HHH) benzothiazolyl,
(III) imidazopyridinyl,
(JJJ) imidazothiazolyl,
(KKK) dihydrobenzisoxazinyl,
(LLL) benzisoxazinyl,
(MMM) benzoxazinyl,
(NNN) dihydrobenzisothiazinyl,
(OOO) benzopyranyl,
(PPP) benzothiopyranyl,
(QQQ) coumarinyl,
(RRR) isocoumarinyl,
(SSS) chromonyl,
(TTT) chromanonyl,
(UUU) pyridinyl-N-oxide,
where the $R_{P\text{-}heteroaryl}$ group is bonded by any atom of the parent $R_{p\text{-}heteroaryl}$ group substituted by hydrogen such that the new bond to the Rp-heteroaryl, group replaces the hydrogen atom and its bond, where heteroaryl is optionally substituted with one, two, three, or four of:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, —NR$_{1\text{-}a}$R$_{1\text{-}b}$ where R$_{1\text{-}a}$ and R$_{1\text{-}b}$ are as defined above,
(2) —OH,
(3) —NO$_2$,
(4) —F, —Cl, —Br, —I,
(5) —CO—OH,
(6) —C≡N,
(7) —(CH$_2$)$_{0\text{-}4}$—CO—NR$_{P\text{-}2}$R$_{P\text{-}3}$ where R$_{P\text{-}2}$ and R$_{P\text{-}3}$ are the same or different and are selected from the group consisting of:
  (a) —H,
  (b) —C$_1$-C$_6$ alkyl optionally substituted with one substitutent selected from the group consisting of:
    (i) —OH,
    (ii) —NH$_2$,
  (c) —C$_1$-C$_6$ alkyl optionally substituted with one to three —F, —Cl, —Br, —I,
  (d) —C$_3$-C$_7$ cycloalkyl,
  (e) —(C$_1$-C$_2$alkyl)-(C$_3$-C$_7$ cycloalkyl),
  (f) —(C$_1$-C$_6$ alkyl) —O—(C$_1$-C$_3$ alkyl),
  (g) —C$_2$-C$_6$ alkenyl with one or two double bonds,
  (h) —C$_2$-C$_6$ alkynyl with one or two triple bonds,
  (i) —C$_1$-C$_6$ alkyl chain with one double bond and one triple bond,
  (j) —R$_{P\text{-}aryl}$ where R$_{P\text{-}aryl}$ is as defined above,
  (k) —R$_{P\text{-}heteroaryl}$ where R$_{P\text{-}heteroaryl}$ is as defined above,
(8) —(CH$_2$)$_{0\text{-}4}$—CO—(C$_1$-C$_{12}$ alkyl)
(9) —(CH$_2$)$_{0\text{-}4}$—CO—(C$_2$-C$_{12}$ alkenyl with one, two or three double bonds),
(10) —(CH$_2$)$_{0\text{-}4}$—CO—(C$_2$-C$_{12}$ alkynyl with one, two or three triple bonds),
(11) —(CH$_2$)$_{0\text{-}4}$—CO—(C$_3$-C$_7$ cycloalkyl),
(12) —(CH$_2$)$_{0\text{-}4}$—CO—R$_{P\text{-}aryl}$ where R$_{P\text{-}aryl}$ is as defined above,
(13) —(CH$_2$)$_{0\text{-}4}$—CO—R$_{P\text{-}heteroaryl}$ where R$_{P\text{-}heteroaryl}$ is as defined above,
(14) —(CH$_2$)$_{0\text{-}4}$—CO—R$_{P\text{-}heterocycle}$ where R$_{P\text{-}heterocycle}$ is as defined above,
(15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —(CH$_2$)$_{0\text{-}4}$—CO—O—R$_{N\text{-}5}$ where R$_{N\text{-}5}$ is selected from the group consisting of:
  (a) $C_1$-$C_6$ alkyl,
  (b) —(CH$_2$)$_{0\text{-}2}$—(R$_{P\text{-}aryl}$) where R$_{P\text{-}aryl}$ is as defined above,
  (c) $C_2$-$C_6$ alkenyl containing one or two double bonds,
  (d) $C_2$-$C_6$ alkynyl containing one or two triple bonds,
  (e) $C_3$-$C_7$ cycloalkyl,
  (f) —(CH$_2$)$_{0\text{-}2}$ (R$_{P\text{-}heteroaryl}$) where R$_{P\text{-}heteroaryl}$ is as defined above,
(17) —(CH$_2$)$_{0\text{-}4}$—SO$_2$—NR$_{P\text{-}2}$R$_{P\text{-}3}$ where R$_{P\text{-}2}$ and R$_{P\text{-}3}$ are as defined above,
(18) —(CH$_2$)$_{0\text{-}4}$—SO—(C$_1$-C$_8$ alkyl),
(19) —(CH$_2$)$_{0\text{-}4}$—SO$_2$—(C$_1$-C$_2$ alkyl),
(20) —(CH$_2$)$_{0\text{-}4}$—SO$_2$—(C$_3$-C$_7$ cycloalkyl),
(21) —(CH$_2$)$_{0\text{-}4}$—N(H or R$_{N\text{-}5}$)—CO—O—R$_{N\text{-}5}$ where R$_{N\text{-}5}$ can be the same or different and is as defined above,
(22) —(CH$_2$)$_{0\text{-}4}$—N(H or R$_{N\text{-}5}$)—CO—N(R$_{N\text{-}5}$)$_2$, where R$_{N\text{-}5}$ can be the same or different and is as defined above,
(23) —(CH$_2$)$_{0\text{-}4}$—N—CS—N(R$_{N\text{-}5}$)$_2$, where R$_{N\text{-}5}$ can be the same or different and is as defined above,
(24) —(CH$_2$)$_{0\text{-}4}$—N(—H or R$_{N\text{-}5}$)—CO—R$_{P\text{-}2}$ where R$_{N\text{-}5}$ and R$_{P\text{-}2}$ can be the same or different and are as defined above,
(25) —(CH$_2$)$_{0\text{-}4}$—NR$_{P\text{-}2}$R$_{P\text{-}3}$ where R$_{P\text{-}2}$ and R$_{P\text{-}3}$ can be the same or different and are as defined above,
(26) —(CH$_2$)$_{0\text{-}4}$—R$_{N\text{-}4}$ where R$_{N\text{-}4}$ is as defined above,
(27) —(CH$_2$)$_{0\text{-}4}$—O—CO—(C$_1$-C$_6$ alkyl)
(28) —(CH$_2$)$_{0\text{-}4}$O—P(O)—(OR$_{N\text{-}aryl\text{-}1}$)$_2$ where R$_{N\text{-}aryl\text{-}1}$ is —H or C$_3$-C$_4$ alkyl,
(29) —(CH$_2$)$_{0\text{-}4}$—O—CO—N(R$_{N\text{-}5}$)$_2$ where R$_{N\text{-}5}$ is as defined above,
(30) —(CH$_2$)$_{0\text{-}4}$—O—CS—N(R$_{N\text{-}5}$)$_2$ where R$_{N\text{-}5}$ is as defined above,
(31) —(CH$_2$)$_{0\text{-}4}$—O—(R$_{N\text{-}5}$)$_2$ where R$_{N\text{-}5}$ is as defined above,
(32) —(CH$_2$)$_{0\text{-}4}$—O—(R$_{N\text{-}5}$)$_2$—COOH where R$_{N\text{-}5}$ is as defined above,
(33) —(CH$_2$)$_{0\text{-}4}$—S—(R$_{N\text{-}5}$)$_2$ where R$_{N\text{-}5}$ is as defined above,
(34) —(CH$_2$)$_{0\text{-}4}$—O—(C$_1$-C$_6$ alkyl optionally substituted with one, two, three, four, or five of: —F),
(35) $C_3$-$C_7$ cycloalkyl,
(36) $C_2$-$C_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, —NR$_{1\text{-}a}$R$_{1\text{-}b}$ where R$_{1\text{-}a}$ and R$_{1\text{-}b}$ are as defined above,
(38) —(CH$_2$)$_{0\text{-}4}$—N(—H or R$_{N\text{-}5}$)—SO$_2$—R$_{P\text{-}2}$ where R$_{N\text{-}5}$ and R$_{P\text{-}2}$ can be the same of different and are as described above,
(39) —(CH$_2$)$_{0\text{-}4}$—C$_3$-C$_7$ cycloalkyl,
(C) R$_{P\text{-}aryl}$-W—R$_{P\text{-}aryl}$,
(D) R$_{P\text{-}aryl}$-W—R$_{P\text{-}heteroaryl}$,
(E) R$_{P\text{-}aryl}$-W—R$_{P\text{-}heterocycle}$,
(F) R$_{P\text{-}heteroaryl}$-W—R$_{P\text{-}aryl}$, (G) $R_{P\text{-}heteroaryl}$—W—$R_{P\text{-}heteroaryl}$,
(H) $R_{P\text{-}heteroaryl}$—W—$R_{P\text{-}heterocycle}$,
(I) $R_{P\text{-}heterocycle}$—W—$R_{P\text{-}aryl}$,
(J) $R_{P\text{-}heterocycle}$—W—$R_{P\text{-}heteroaryl}$,
(K) $R_{P\text{-}heterocycle}$—W—$R_{P\text{-}heterocycle}$,
where W is
(1) —$(CH_2)_{0\text{-}4}$—,
(2) —O—,
(3) —$S(O)_{0\text{-}2}$,
(4) —$N(R_{N\text{-}5})$— where $R_{N\text{-}5}$ is as defined above;
(5) —CO—; or
(6) —O—$(CH_2)_{1\text{-}4}$—,
(L) —Y—$R_{P\text{-}heterocycle}$ where Y is absent or is oxygen, and $R_{P\text{-}heterocycle}$ is defined above;

(II) —($C_1$-$C_{10}$-alkyl) where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N\text{-}8}$ where $R_{N\text{-}8}$ is —H, $C_1$-$C_6$ alkyl, phenyl or benzyl,
(E) —CO—$NR_{P\text{-}2}R_{P\text{-}3}$ where $R_{P\text{-}2}$ and $R_{P\text{-}3}$ are the same or different and are as defined above,
(F) —CO—$R_{N\text{-}4}$ where $R_{N\text{-}4}$ is as defined above,
(G) —$SO_2$—($C_1$-$C_8$ alkyl),
(H) —$SO_2$—$NR_{P\text{-}2}R_{P\text{-}3}$ where $R_{P\text{-}2}$ and $R_{P\text{-}3}$ are the same or different and are as defined above,
(I) —NH—CO—($C_1$-$C_6$ alkyl),
(J) —NH—CO—O—$R_{N\text{-}8}$ where $R_{N\text{-}8}$ is as defined above,
(K) —$NR_{P\text{-}2}R_{P\text{-}3}$ where $R_{P\text{-}2}$ and $R_{P\text{-}3}$ are the same or different and are as defined above,
(L) —$R_{N\text{-}4}$ where $R_{N\text{-}4}$ is as defined above,
(M) —O—CO—($C_1$-$C_6$ alkyl),
(N) —O—CO—$NR_{N\text{-}8}R_{N\text{-}8}$ where the $R_{N\text{-}8}$s are the same or different and are as defined above,
(O) —O—($C_1$-$C_5$ alkyl)-COOH,
(P) —O—($C_1$-$C_6$ alkyl) optionally substituted with one, two, or three of —F, —Cl, —Br, —I,
(Q) —NH—$SO_2$—($C_1$-$C_6$ alkyl),
(R) —F, —Cl, (III) —X-T-($C_1$-$C_6$ alkyl) where X is absent or is $C_1$-$C_6$ alkyl, T is oxygen or is $NR_{P\text{-}2}$, and where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N\text{-}8}$ where $R_{N\text{-}8}$ is —H, $C_1$-$C_6$ alkyl, phenyl, or benzyl,
(E) —CO—$NR_{P\text{-}2}R_{P\text{-}3}$ where $R_{P\text{-}2}$ and $R_{P\text{-}3}$ are the same or different and are as defined above,
(F) —CO—$R_{N\text{-}4}$ where $R_{N\text{-}4}$ is as defined above,
(G) —$SO_2$—($C_1$-$C_8$ alkyl),
(H) —$SO_2$—$NR_{P\text{-}2}R_{P\text{-}3}$ where $R_{P\text{-}2}$ and $R_{P\text{-}3}$ are the same or different and are as defined above,
(I) —NH—CO—($C_1$-$C_6$ alkyl),
(J) —NH—CO—O—$R_{N\text{-}8}$ where $R_{N\text{-}8}$ is as defined above,
(K) —$NR_{P\text{-}2}R_{P\text{-}3}$ where $R_{P\text{-}2}$ and $R_{P\text{-}3}$ are the same or different and are as defined above,
(L) —$R_{N\text{-}4}$ where $R_{N\text{-}4}$ is as defined above,
(M) —O—CO—($C_1$-$C_6$ alkyl),
(N) —O—CO—$NR_{N\text{-}8}R_{N\text{-}8}$ where the $R_{N\text{-}8}$s are the same or different and are as defined above,
(O) —O—($C_1$-$C_5$ alkyl)-COOH,
(P) —O—($C_1$-$C_6$) alkyl optionally substituted with one, two, or three of —F, —Cl, —Br, —I,
(Q) —NH—$SO_2$—($C_1$-$C_6$ alkyl),
(R) —F, —Cl,
(S) —O—$R_{p\text{-}aryl}$,
(T) —O—$R_{p\text{-}heteroaryl}$, or
(U) —O—$R_{p\text{-}heterocycle}$, (IV) —($C_1$-$C_6$ alkyl)-Z-($C_1$-$C_6$ alkyl) where Z is S or O, and alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N\text{-}8}$ where $R_{N\text{-}8}$ is as defined above,
(E) —CO—$NR_{P\text{-}2}R_{P\text{-}3}$ where $R_{P\text{-}2}$ and $R_{P\text{-}3}$ are the same or different and are as defined above,
(F) —CO—$R_{N\text{-}4}$ where $R_{N\text{-}4}$ is as defined above,
(G) —$SO_2$—($C_1$-$C_8$ alkyl),
(H) —$SO_2$—$NR_{P\text{-}2}R_{P\text{-}3}$ where $R_{P\text{-}2}$ and $R_{P\text{-}3}$ are the same or different and are as defined above,
(I) —NH—CO—($C_1$-$C_6$ alkyl),
(J) —NH—CO—O—$R_{N\text{-}8}$ where $R_{N\text{-}8}$ is as defined above,
(K) —$NR_{P\text{-}2}R_{P\text{-}3}$ where $R_{P\text{-}2}$ and $R_{P\text{-}3}$ are the same or different and are as defined above,
(L) —$R_{N\text{-}4}$ where $R_{N\text{-}4}$ is as defined above,
(M) —O—CO—($C_1$-$C_6$ alkyl),
(N) —O—CO—$NR_{N\text{-}8}R_{N\text{-}8}$ where the $R_{N\text{-}8}$s are the same or different and are as defined above,
(O) —O—($C_1$-$C_5$ alkyl)-COOH,
(P) —O—($C_1$-$C_6$) alkyl optionally substituted with one, two, or three of —F, —Cl, —Br, —I,
(Q) —NH—$SO_2$—($C_1$-$C_6$ alkyl),
(R) —F, —Cl, (V) —CH(—$(CH_2)_{0\text{-}2}$—O—$R_{N\text{-}1}$)—$(CH_2)_{0\text{-}2}R_{P\text{-}aryl}$/$R_{P\text{-}heteroaryl}$) where $R_{P\text{-}aryl}$ and $R_{P\text{-}heteroaryl}$ are as defined above, where $R_{N\text{-}10}$ is selected from the group consisting of:
(A) —H,
(B) $C_1$-$C_6$ alkyl,
(C) $C_3$-$C_7$ cycloalkyl,
(D) $C_2$-$C_6$ alkenyl with one double bond,
(E) $C_2$-$C_6$ alkynyl with one triple bond,
(F) $R_{P\text{-}aryl}$ where $R_{P\text{-}aryl}$ is as defined above,
(G) $R_{P\text{-}heteroaryl}$ where $R_{P\text{-}heteroaryl}$ is as defined above, (VI) —($C_3$-$C_8$ cycloalkyl) where cycloalkyl is optionally substituted with one or two substituents selected from the group consisting of:
(A) —$(CH_2)_{0\text{-}4}$—OH,
(B) —$(CH_2)_{0\text{-}4}$—$C_1$-$C_6$ alkoxy,
(C) —$(CH_2)_{0\text{-}4}$—$C_1$-$C_6$ thioalkoxy,
(D) —$(CH_2)_{0\text{-}4}$—CO—O—$R_{N\text{-}8}$ where $R_{N\text{-}8}$ is —H, $C_1$-$C_6$ alkyl, phenyl or benzyl,
(E) —$(CH_2)_{0\text{-}4}$—CO—$NR_{P\text{-}2}R_{P\text{-}3}$ where $R_{P\text{-}2}$ and $R_{P\text{-}3}$ are the same or different and are as defined above,
(F) —$(CH_2)_{0\text{-}4}$—CO—$R_{N\text{-}4}$ where $R_{N\text{-}4}$ is as defined above,
(G) —$(CH_2)_{0\text{-}4}$—$SO_2$—($C_1$-$C_8$ alkyl)
(H) —$(CH_2)_{0\text{-}4}$—$SO_2$—$NR_{P\text{-}2}R_{P\text{-}3}$ where $R_{P\text{-}2}$ and $R_{P\text{-}3}$ are the same or different and are as defined above,
(I) —$(CH_2)_{0\text{-}4}$—NH—CO—($C_1$-$C_6$ alkyl),
(J) —NH—CO—O—$R_{N\text{-}8}$ where $R_{N\text{-}8}$ is as defined above,
(K) —$(CH_2)_{0\text{-}4}$—$NR_{P\text{-}2}R_{P\text{-}3}$ where $R_{P\text{-}2}$ and $R_{P\text{-}3}$ are the same or different and are as defined above,
(L) —$(CH_2)_{0\text{-}4}$—$R_{N\text{-}4}$ where $R_{N\text{-}4}$ is as defined above,
(M) —O—CO—($C_1$-$C_6$ alkyl), (N) —O—CO—NR$_{N-8}$R$_{N-8}$ where the R$_{N-8}$s are the same or different and are as defined above,
(O) —O—(C$_1$-C$_5$ alkyl)-COOH,
(P) —O—C$_1$-C$_6$ alkyl optionally substituted with one, two, or three of: —F, —Cl, —Br, —I,
(Q) —NH—SO$_2$—(C$_1$-C$_6$ alkyl),
(R) —F, —Cl;
(VII) —(CR$_{P-x}$R$_{P-y}$)$_{0-4}$—R$_{P-1}$ where R$_{P-1}$ is as defined above and each of R$_{P-x}$ and R$_{P-y}$ are independently any combination of:
(A) —H,
(B) C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, —COOH, —COO (C$_1$-C$_6$ alkyl), —CONR$_{1-a}$R$_{1-b}$ and —NR$_{1-a}$R$_{1-b}$ where R$_{1-a}$ and R$_{1-b}$ are —H or C$_1$-C$_6$ alkyl,
(C) —CH$_2$—S—(C$_1$-C$_6$ alkyl),
(D) —CH$_2$—CH$_2$—S—(C$_1$-C$_6$ alkyl)
(E) C$_2$-C$_6$ alkenyl with one or two double bonds,
(F) C$_2$-C$_6$ alkynyl with one or two triple bonds,
(G) —(CH$_2$)$_{n1}$—(R$_{P-aryl}$) where n$_1$ is zero or one, where R$_{P-aryl}$ is as defined above,
(H) —(CH$_2$)$_{n1}$—(R$_{P-heteroaryl}$) where n$_1$ and R$_{P-heteroaryl}$ are as defined above, or
(I) —(CH$_2$)$_{n1}$—(R$_{P-heterocycle}$) where n$_1$ and R$_{P-heterocycle}$ are as defined above,
(J) —(CH$_2$)$_{0-3}$—(C$_3$-C$_7$) cycloalkyl where cycloalkyl can be optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —CO—OH, —CO—O—(C$_1$-C$_4$ alkyl), and —NR$_{1-a}$R$_{1-b}$ where R$_{1-a}$ and R$_{1-b}$ are as defined above, or
(K) F, Cl, Br or I,
(L) —NR$_{P-2}$;
or R$_{P-x}$ and R$_{P-y}$ are taken together with the carbon to which they are attached to form a carbocycle of three thru seven carbon atoms, optionally where one carbon atom is replaced by a heteroatom selected from the group consisting of —O—, —S—, —SO$_2$—, and —NR$_{P-2}$—;
(VIII) —(C$_1$-C$_6$ alkyl)-Z-(C$_1$-C$_6$ alkyl)-T-(C$_1$-C$_6$ alkyl)- wherein Z is S or O, T is O or NR$_{P-2}$, and alkyl is optionally substituted with one, two, or three substituents selected from the group consisting of:
(A) —OH,
(B) —C$_1$-C$_6$ alkoxy,
(C) —C$_1$-C$_6$ thioalkoxy,
(D) —CO—O—R$_{N-8}$ where R$_{N-8}$ is as defined above,
(E) —CO—NR$_{P-2}$R$_{P-3}$ where R$_{P-2}$ and R$_{P-3}$ are the same or different and are as defined above,
(F) —CO—R$_{N-4}$ where R$_{N-4}$ is as defined above,
(G) —SO$_2$—(C$_1$-C$_8$ alkyl),
(H) —SO$_2$—NR$_{P-2}$R$_{P-3}$ where R$_{P-2}$ and R$_{P-3}$ are the same or different and are as defined above,
(I) —NH—CO—(C$_1$-C$_6$ alkyl),
(J) —NH—CO—O—R$_{N-8}$ where R$_{N-8}$ is as defined above,
(K) —NR$_{P-2}$R$_{P-3}$ where R$_{P-2}$ and R$_{P-3}$ are the same or different and are as defined above,
(L) —R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—(C$_1$-C$_6$ alkyl) optionally substituted with one, two, or three of —F, —Cl, —Br, —I,
(Q) —NH—SO$_2$—(C$_1$-C$_6$ alkyl),
(R) —F, —Cl.

Also-disclosed is a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which comprises administration of a therapeutically effective amount of a compound of formula (Y).

Also disclosed are methods for inhibiting beta-secretase activity, for inhibiting cleavage of amyloid precursor protein (APP), in a reaction mixture, at a site between Met596 and Asp597, numbered for the APP-695 amino acid isotype; or at a corresponding site of an isotype or mutant thereof, for inhibiting production of amyloid beta peptide (A beta) in a cell, for inhibiting the production of beta-amyloid plaque in an animal, and for treating or preventing a disease characterized by beta-amyloid deposits in the brain which comprise administration of a therapeutically effective amount of a compound of formula (Y), and pharmaceutically acceptable salts thereof.

Disclosed is a pharmaceutical composition which comprises a compound of formula (Y), and one or more pharmaceutically acceptable inert carriers.

Disclosed is the use of a compound of formula (Y), and pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The invention also provides methods of preparing the compounds of the invention and the intermediates used in those methods. The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD, and for treating frontotemporal dementias with parkinsonism (FTDP).

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

As noted above, the invention provides compounds of formula Y

Preferred compounds of formula Y include those of formula Y-1, i.e., compounds of formula Y wherein $R_1$ is $R_{1\text{-}aryl}$, $R_{1\text{-}heteroaryl}$, $R_{1\text{-}Heterocycle}$, $-C_1\text{-}C_6$ alkyl-$R_{1\text{-}aryl}$, $-C_1\text{-}C_6$ alkyl-$R_{1\text{-}heteroaryl}$, or $-C_1\text{-}C_6$ alkyl-$R_{1\text{-}heterocycle}$, where the ring portions of each are optionally substituted as indicated above.

More preferred compounds of formula Y-1 include those wherein $R_1$ is $-C_1\text{-}C_6$ alkyl-$R_{1\text{-}aryl}$, $-C_1\text{-}C_6$ alkyl-$R_{1\text{-}heteroaryl}$, or $-C_1\text{-}C_6$ alkyl-$R_{1\text{-}Heterocycle}$, where the ring portions of each are optionally substituted as indicated above. Still more preferred compounds of formula Y-1 include those wherein $R_1$ is $-(CH_2)-R_{1\text{-}aryl}$, $-(CH_2)-R_{1\text{-}heteroaryl}$, or $-(CH_2)-R_{1\text{-}heterocycle}$, where the ring portions of each are optionally substituted as indicated above.

Yet more preferred compounds of formula Y-1 include those wherein $R_1$ is $-CH_2$-phenyl or $-CH_2$-pyridinyl where the ring portions of each are optionally substituted with 1, 2, 3, or 4 groups independently selected from halogen, $C_1\text{-}C_4$ alkoxy, hydroxy, $-NO_2$, and $C_1\text{-}C_4$ alkyl, wherein $C_1\text{-}C_4$ alkyl is optionally substituted with 1, 2, or 3 substituents independently selected from halogen, OH, SH, $NH_2$, $NH(C_1\text{-}C_6$ alkyl), $N-(C_1\text{-}C_6$ alkyl)$(C_1\text{-}C_6$ alkyl), $C\equiv N$, $CF_3$.

Still more preferred compounds of formula Y-1 include those wherein $R_1$ is $-CH_2$-phenyl or $-CH_2$-pyridinyl where the phenyl or pyridinyl rings are each optionally substituted with 1 or 2 groups independently selected from halogen, $C_1\text{-}C_2$ alkyl, $C_1\text{-}C_2$ alkoxy, hydroxy, $-CF_3$, and $-NO_2$.

Preferred compounds of formula Y-1 also include those wherein $R_1$ is $-CH_2$-phenyl or $-CH_2$-pyridinyl where the phenyl or pyridinyl rings are each optionally substituted with 2 groups independently selected from halogen, $C_1\text{-}C_2$ alkyl, $C_1\text{-}C_2$ alkoxy, hydroxy, and $-NO_2$.

Still yet more preferred compounds of formula Y-1 include those wherein $R_1$ is $-CH_2$-pyridinyl, benzyl, 3,5-difluorobenzyl, or 5-Hydroxybenzyl.

Other preferred compounds of formula Y and formula Y-1 include compounds of formula Y-2, i.e., those of formula Y or Y-1 wherein $R_N$ is $-CO-R_{N-1}$, wherein $R_{N-1}$ is as defined above, or $R_N$ is $-CO-(C_1\text{-}C_{10}$ alkyl), wherein $C_1\text{-}C_{10}$ alkyl is optionally substituted as indicated above.

Preferred compounds of formula Y-2 include compounds wherein $R_N$ is $-CO-R_{N-1}$, wherein $R_{N-1}$ is $R_{N\text{-}aryl}$, $R_{N\text{-}heteroaryl}$, or $R_{N\text{-}heterocycle}$, each of which is optionally substituted as indicated above, or $R_N$ is $-CO-(C_3\text{-}C_{10}$ alkyl), wherein $C_1\text{-}C_{10}$ alkyl is optionally substituted as indicated above.

Preferred compounds of formula Y-2 include compounds wherein $R_N$ is $-CO-R_{N-1}$, wherein $R_{N-1}$ is $R_{N\text{-}aryl}$, or $R_{N\text{-}heteroaryl}$, each of which is optionally substituted with 1, 2, or 3 groups independently selected from $-OR$, $-NO_2$, $C_1\text{-}C_6$ alkyl, halogen, $-C\equiv N$, $-OCF_3$, $-CF_3$, $-(CH_2)_{0\text{-}4}-CO-NR_{N\text{-}2}R_{N\text{-}3}$, and $-(CH_2)_{0\text{-}4}-N(R_{N\text{-}2})-SO_2-R_{N\text{-}2}$.

Preferred compounds of formula Y-2 include compounds wherein $R_N$ is $-C(=O)$-phenyl or $-C(=O)$-pyridinyl where each ring is independently optionally substituted with 1 or 2 groups independently selected from $C_1\text{-}C_6$ alkyl, halogen, $-(CH_2)_{0\text{-}4}-CO-N$ $R_{N\text{-}2}R_{N\text{-}3}$, $-(CH_2)_{0\text{-}4}-N(R_{N\text{-}2})-SO_2-R_{N\text{-}2}$.

Preferred compounds of formula Y-2 include compounds wherein $R_N$ is $-C(=O)$-phenyl or $-C(=O)$-pyridinyl where each ring is independently substituted with $-CO-NR_{N\text{-}2}R_{N\text{-}3}$.

Preferred compounds of formula Y-2 include compounds wherein $R_N$ is $-C(=O)$-phenyl or $-C(=O)$-pyridinyl where each ring is independently substituted with $-CO-N(C_1\text{-}C_6$ alkyl) $(C_1\text{-}C_6$ alkyl).

Other preferred compounds of formula Y, formula Y-1 and formula Y-2 include compounds of formula Y-3, i.e., those of formula Y, Y-1 or Y-2 wherein $R_4$ is $-(CH_2-O)-(C=O)-R_5$, or $-(C=O)-R_5$, wherein $R_5$ is as defined above.

Preferred compounds of formula Y-3 include those wherein $R_5$ is:

$-(CR_{P\text{-}x}R_{P\text{-}y})_{0\text{-}4}-R_{P\text{-}1}$, $-(C_1\text{-}C_{10}$ alkyl), $-X\text{-}T\text{-}(C_1\text{-}C_6$ alkyl), $-(C_1\text{-}C_6$ alkyl)$-Z\text{-}(C_1\text{-}C_6$ alkyl), wherein each of these groups is as defined above.

Preferred compounds of formula Y-3 include those wherein $R_4$ is:

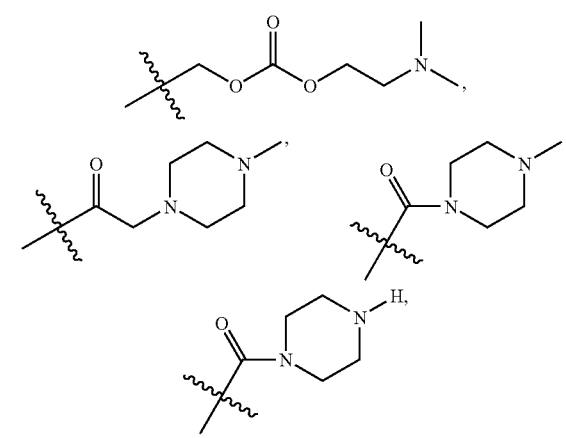

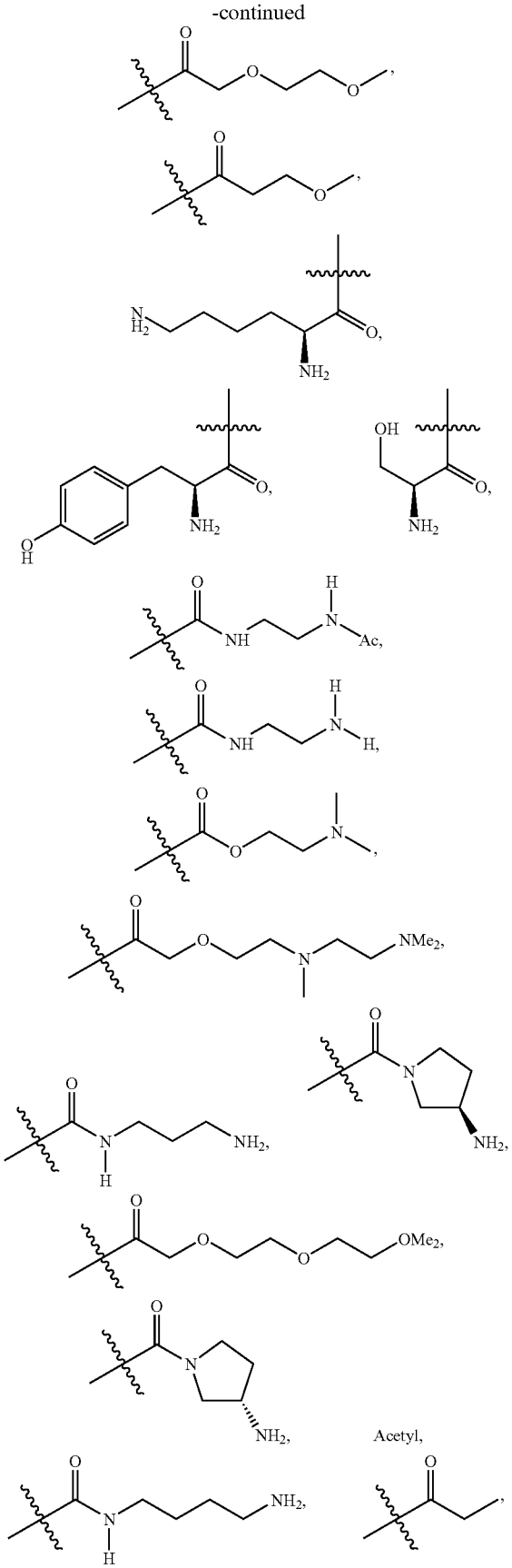
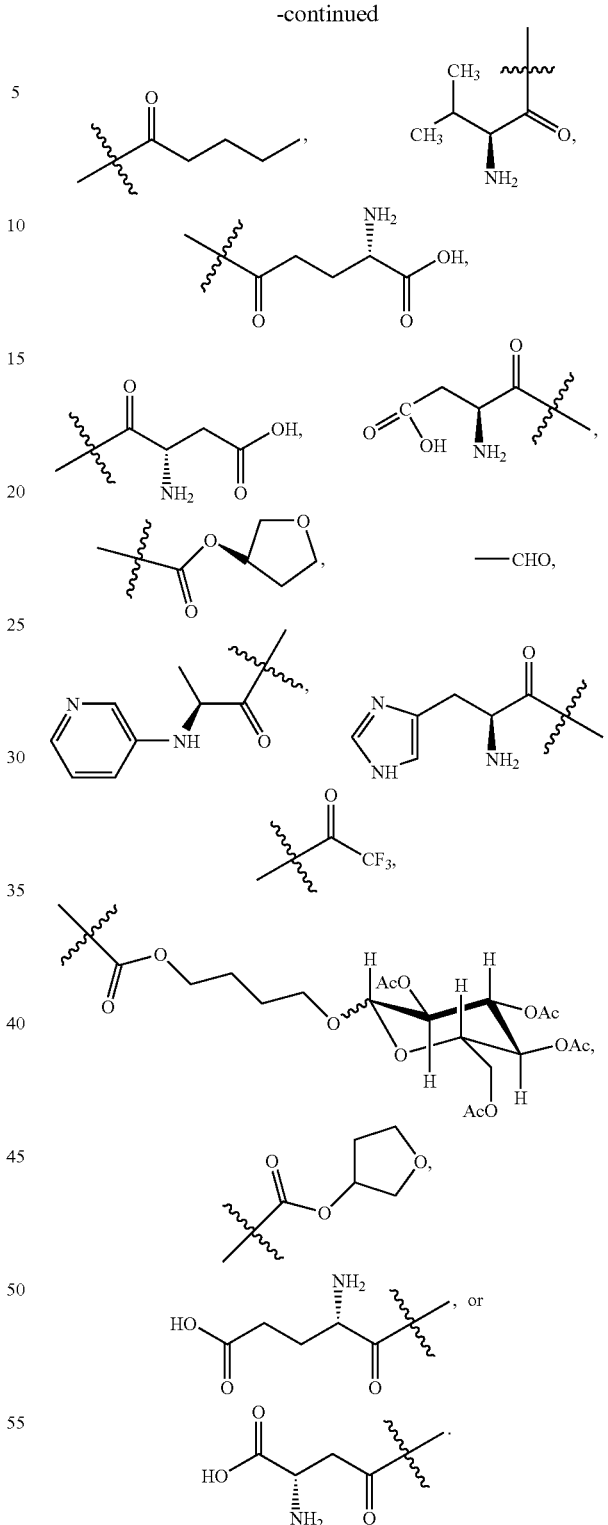
Compounds (Y) of the invention are prodrugs that are useful in treating and preventing Alzheimer's disease. Without being bound by any particular theory, it is believed that the produg compounds (Y) are converted in vivo to the active compounds by hydrolytic or enzymatic cleavage at the $R_4$ position, as shown in equation (I):

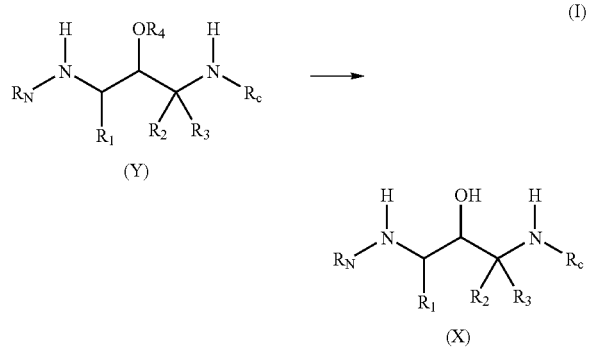

The prodrugs of the invention provide increased aqueous solubility, higher oral bioavailability and facile in vivo generation of the active ingredient.

The prodrug compounds (Y) can be made by methods well known to those skilled in the art from starting compounds known to those skilled in the art. The process chemistry is known to those skilled in the art. The most general process to prepare the compounds (Y) of the present invention is set forth in CHART A. The chemistry is straight forward and in summary involves the steps of N-protecting an amino acid (I) starting material to produce the corresponding protected amino acid (II), reaction of the protected amino acid (II) with diazomethane followed by work-up to add a carbon atom to produce the corresponding protected compound (III), reduction of the protected compound (III) to the corresponding alcohol (IV), formation of the corresponding epoxide (V), opening of the epoxide (V) with a C-terminal amine, $R_C$—$NH_2$ (VI) to produce the corresponding protected alcohol (VII) which then has the nitrogen protecting group removed to produce the corresponding amine (VIII), which is then reacted with an amide forming agent of the formula ($R_{N-1}$—$X_N$)$_2$O or $R_{N-1}X_N$—$X_2$ or $R_{N-1}$—$X_N$—OH (IX) to produce the amine (X). The amine groups of amine (X) are then protected using, for example, t-butoxycarbonyl, to form protected amine (B). Other protecting groups can be used as is known to a person of ordinary skill in the art. Protected amine (B) is converted to compound (C) by methods well known in the art (see EXAMPLES 1260-1275 as illustrative, but non-limiting examples). Compound (C) is deprotected using, for example, trifluoroacetic acid, to provide compounds (Y) of the invention. One skilled in the art will appreciate that these are all well known reactions in organic chemistry. A chemist skilled in the art, knowing the chemical structure of the compounds (Y) of the invention would be able to prepare them by known methods from known starting materials without any additional information. The explanation below therefore is not necessary but is deemed helpful to those skilled in the art who desire to make the compounds of the present invention.

The hydroxyethylamine moiety, —NH—CH(R)—CH (OH)—, of the compounds of the invention, can be readily prepared by methods disclosed in the literature and known to those skilled in the art. For example, *J. Med. Chem.*, 36, 288-291 (1992), *Tetrahedron Letters*, 28, 5569-5572 (1987), *J. Med. Chem.*, 38, 581-584 (1994) and *Tetrahedron Letters*, 38, 619-620 (1997) all disclose processes to prepare hydroxyethylamine type compounds.

CHART A sets forth a general method used in the present invention to prepare the compounds (Y). The anti-Alzheimer compounds (Y) of the present invention are prepared by starting with the corresponding amino acid (I). The amino acids (I) are well known to those skilled in the art or can be readily prepared from known compounds by methods well known to those skilled in the art. The compounds (Y) of the present invention have at least two enantiomeric centers which give four enantiomers. The first of these enantiomeric centers derives from the amino acid starting material (I). It is preferred to commercially obtain or produce the desired enantiomer (S) rather than produce an enantiomerically impure mixture and then have to separate out the desired enantiomer (S). It is preferred to start the process with enantiomerically pure (S)-amino acid (I) of the same configuration as that of the compound (Y) product. For the amino acids (I), $R_1$ is as defined above for compound (Y).

It is further preferred that $R_1$ be —$(CH_2)_{0-1}$—($R_1$-aryl) or —$(CH_2)_{n1}$—($R_{1\text{-}heteroaryl}$). It is more preferred that $R_1$ is —$(CH_2)$—($R_{1\text{-}aryl}$) or —$(CH_2)$—($R_{1\text{-}heteroaryl}$). It is further preferred that $R_1$ is —$(CH_2)$—($R_{1\text{-}aryl}$) where $R_{1\text{-}aryl}$ is phenyl. It is even more preferred that $R_1$ is —$(CH_2)$—($R_{1\text{-}aryl}$) where $R_{1\text{-}aryl}$ is phenyl substituted with two —F. It is additionally preferred that the —F substitution is 3,5-difluorobenzyl.

When $R_1$ is $R_{1\text{-}heteroaryl}$ or $R_{1\text{-}heterocycle}$ the bond from the $R_{1\text{-}heteroaryl}$ or $R_{1\text{-}heterocycle}$ group to the —$(CH_2)_{n1}$— group can be from any ring atom which has an available valence provided that such bond does not result in formation of a charged species or unstable valence. This means that the $R_{1\text{-}heteroaryl}$ or $R_{1\text{-}heterocycle}$ group is bonded to —$(CH_2)_{n1}$— by any ring atom of the parent $R_{1\text{-}heteroaryl}$ or $R_{1\text{-}heterocycle}$ group which was substituted by hydrogen such that the new bond to the $R_{1\text{-}heteroaryl}$ or $R_{1\text{-}heterocycle}$ group replaces the hydrogen atom and its bond.

The first step of the process is to protect the free amino group of the (S)-amino acid (I) with an amino protecting group to produce the (S)-protected amino acid (II) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (I) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art. Suitable amino PROTECTING GROUP is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl) prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH—$CH_2$ and phenyl-C(=N—)—H. It is preferred that the protecting group be t-butoxycarbonyl (BOC) and benzyloxycarbonyl (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

The (S)-protected amino acid (II) is transformed to the corresponding (S)-protected compound (III) by two different methods depending on the nature of $R_2$ and $R_3$. $R_2$ and $R_3$ are as defined above.

It is preferred that $R_2$ and $R_3$ both be —H. If $R_2$ and $R_3$ are not the same, an additional enantiomeric center is added to the molecule. If it is desired that both $R_2$ and $R_3$ are —H, then the (S)-protected amino acid (II) is reacted with diazomethane, as is well known to those skilled in the art, followed by reaction with a compound of the formula H—$X_1$ to produce the (S)-protected compound (III). $X_1$ includes —Cl, —Br, —I, —O-tosylate, —O-mesylate, —O-nosylate.; it is preferred that —$X_1$ be —Br or —Cl. Suitable reaction conditions include running the reaction in inert solvents, such as but not limited to ether, tetrahydrofuran and the like. The reactions from the (S)-protected amino acid (II) to the (S)-protected compound (III) are carried out for a period of time between 10 minutes and 1 day and at temperatures ranging from –78 degrees to 20-25 degrees C. It is preferred to conduct the reactions for a period of time between 1-4 hours and at temperatures between –30 degrees to –10 degrees C. This process adds one methylene group.

Alternatively, the (S)-protected compounds of formula (III) can be prepared by first converting the (S)-protected amino acid (II) to a corresponding methyl or ethyl ester, according to methods well established in the art, followed by treatment with a reagent of formula $X_1$—C($R_2$)($R_3$)—$X_1$ and a strong metal base. The base serves to affect a halogen-metal exchange, where the —$X_1$ undergoing exchange is a halogen selected from chlorine, bromine or iodine. The nucleophilic addition to the ester derivative gives directly the (S)-protected compound (III) Suitable bases include, but are not limited to the alkyllithiums including, for example, sec-butyllithium, n-butyllithium, and t-butyllithium. The reactions are preferably conducted at low temperature., such as –78 degrees C. Suitable reaction conditions include running the reaction in inert solvents, such as but not limited to, ether, tetrahydrofuran and the like. Where $R_2$ and $R_3$ are both hydrogen, then examples of $X_1$—C($R_2$) ($R_3$)—$X_1$ include dibromomethane, diiodomethane, chloroiodomethane, bromoiodomethane and bromochloromethane. One skilled in the art knows the preferred conditions required to conduct this reaction. Furthermore, if $R_2$ and/or $R_3$ are not —H, then by the addition of —C($R_2$) ($R_3$)—$X_1$ to esters of the (S)-protected amino acid (II) to produce the (S)-protected compound (III), an additional chiral center will be incorporated into the product, provided that $R_2$ and $R_3$ are not the same.

The (S)-protected compound (III) is then reduced by means well known to those skilled in the art for reduction of a ketone to the corresponding secondary alcohol affording the corresponding alcohol (IV). The means and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reductions are carried out for a period of time between 1 hour and 3 days at temperatures ranging from –78 degrees C. to elevated temperature up to the reflux point of the solvent employed. It is preferred to conduct the reduction between –78 degrees C. and 0 degrees C. If borane is used, it may be employed as a complex, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989. The reduction of the (S)-protected compound (III) to the corresponding alcohol (IV) produces the second chiral center (third chiral center if $R_2$ and $R_3$ are not the same). The reduction of the (S)-protected compound (III) produces a mixture of enantiomers at the second center, (S, R/S)-alcohol (IV). This enantiomeric mixture is then separated by means known to those skilled in the art such as selective low-temperature recrystallization or chromatographic separation, for example by HPLC, employing commercially available chiral columns. The enantiomer that is used in the remainder of the process of CHART A is the (S,S)-alcohol (IV) since this enantiomer will give the desired biologically active anti-Alzheimer (S,R)-substituted compound (Y).

The (S, S)-alcohol (IV) is transformed to the corresponding epoxide (V) by means known to those skilled in the art. The stereochemistry of the (S)-(IV) center is maintained in forming the epoxide (V). A preferred means is by reaction with base, for example, but not limited to, hydroxide ion generated from sodium hydroxide, potassium hydroxide, lithium hydroxide and the like. Reaction conditions include the use of $C_1$-$C_6$ alcohol solvents; ethanol is preferred. A common co-solvent, such as for example, ethyl acetate may also be employed. Reactions are conducted at temperatures ranging from –45 degrees C. up to the reflux temperature of the alcohol employed; preferred temperature ranges are between –20 degrees C. and 20-25 degrees C.

The epoxide (V) is then reacted with the appropriately substituted C-terminal amine, $R_C$—$NH_2$ (VI) by means known to those skilled in the art that opens the epoxide to produce the desired corresponding enantiomerically pure (S,R)-protected alcohol (VII). The substituted C-terminal amines, $R_C$—$NH_2$ (VI) of this invention are commercially available or can be readily prepared from known compounds using literature procedures. $R_C$ is as defined above.

It is preferred that $R_C$ is:
—$C_1$-$C_8$ alkyl,
—$(CH_2)_{0-3}$—($C_3$-$C_7$) cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to $R_{C-aryl}$ or $R_{C-heteroaryl}$ or
$R_{C-heterocycle}$.

It is more preferred that $R_C$ is:
—$(CH_2)_{0-3}$—($C_3$-$C_7$) cycloalkyl,
—$(CR_{C-x}R_{C-y})_{0-4}$—$R_{C-aryl}$,
—$(CR_{C-x}OR_{C-y})_{0-4}$—$R_{C-heteroaryl}$,
—$(CR_{C-x}R_{C-y})_{0-4}$—$R_{C-heterocycle}$, -cyclopentyl or -cyclohexyl ring fused to a $R_{C\text{-}aryl}$ or $R_{C\text{-}heteroaryl}$ or
$R_{C\text{-}heterocycle}$.

It is even more preferred that $R_C$ is:
—$(CR_{C\text{-}x}R_{C\text{-}y})_{0\text{-}4}$—$R_{C\text{-}aryl}$,
—$(CR_{C\text{-}x}R_{C\text{-}y})_{0\text{-}4}$—$R_{C\text{-}heteroaryl}$,
-cyclopentyl or -cyclohexyl ring fused to a $R_{C\text{-}aryl}$ or $R_{C\text{-}heteroaryl}$ or
$R_{C\text{-}heterocycle}$.

It is still more preferred that $R_C$ is selected from the group consisting of:
—$(CR_{C\text{-}x}R_{C\text{-}y})_{0\text{-}4}$—$R_{C\text{-}aryl}$ where $R_{C\text{-}aryl}$ is phenyl,
—$(CR_{C\text{-}x}R_{C\text{-}y})_{0\text{-}4}$-$R_{C\text{-}heteroaryl}$,
-cyclopentyl or -cyclohexyl ring fused to a $R_{C\text{-}aryl}$ or $R_{C\text{-}heteroaryl}$ or $R_{C\text{-}heterocycle}$. Further, it is preferred that when $R_C$ is phenyl, it is substituted in the 3-position or 3,5-positions.

Suitable reaction conditions for opening the epoxide (V) include running the reaction in a wide range of common and inert solvents. $C_1$-$C_6$ alcohol solvents are preferred and isopropyl alcohol most preferred. The reactions can be run at temperatures ranging from 20-25 degrees C. up to the reflux temperature of the alcohol employed. The preferred temperature range for conducting the reaction is between 50 degrees C. up to the reflux temperature of the alcohol employed. When the substituted C-terminal amine (VI) is a 1-amino-3,5-cis-dimethyl cyclohexyldicarboxylate it is preferrably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI). When the substituted C-terminal amine (VI) is 1-amino-3,5-cis-dimethoxy cyclohexane it is prepared by following the general procedure above and making non-critical variations but starting with 3,5-dimethoxyaniline. When the substituted C-terminal amine (VI) is an aminomethyl group where the substituent on the methyl group is an aryl group, for example $NH_2$—$CH_2$—$R_{C\text{-}aryl}$ and $NH_2$—$CH_2$—$R_C$ aryl is not commercially available it is preferrably prepared as follows. A suitable starting material is the (appropriately substituted) aralkyl compound. The first step is bromination of the alkyl substituent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C\text{-}aryl}$. The suitably functionalized C-terminal amines (VI) may readily be prepared by one skilled in the art via known methods in the literature, making non-significant modifications. Select literature references include 1) Calderwood, et al., *Tet. Lett.*, 1997, 38, 1241, 2) Ciganek, *J. Org. Chem.*, 1992, 57, 4521, 3) Thurkauf, et al., *J. Med. Chem.*, 1990, 33, 1452, 4) Werner, et al., *Org. Syn., Coll. Vol.* 5, 273, 5) *J. Med. Chem.*, 1999, 42, 4193, 6) *Chem. Rev.* 1995, 95, 2457, 7) *J. Am. Chem. Soc.*, 1986, 3150, 8) Felman et al., *J. Med. Chem.*, 1992, 35, 1183, 9) *J. Am. Chem. Soc.* 1970, 92, 3700, 10) *J. Med. Chem.*,1997, 40, 2323.

CHART B discloses an alternative process for production of the enantiomerically pure (S,R)-protected alcohol (VII) from the (S)-protected compound (III). In the alternative process, the (S)-protected compound (III) is first reacted with the appropriately substituted C-terminal amine $R_C$—$NH_2$ (VI) using the preferred conditions described above to produce the corresponding (S)-protected ketone (XI) which is then reduced using the preferred conditions described above to produce the corresponding (S,R)-protected alcohol (VII).

CHART C discloses another alternative process for production of enantiomerically pure (S,R)-protected alcohol (VII) but this time from the epoxide (V). In the process of CHART C, the epoxide (V) is reacted with azide to produce the corresponding enantiomerically pure (S,R)-protected azide (XII). Conditions to conduct the azide mediated epoxide opening are known to those skilled in the art, see for example, J. March, Advanced Organic Chemistry, $3^{rd}$ Edition, John Wiley & Sons Publishers, 1985, p. 380. Next, the (S,R)-protected azide (XII) is reduced to the corresponding protected amine (XIII) by methods known to those skilled in the art. Preferred reducing conditions to reduce the (S,R)-protected azide (XII) in the presence of a t-butoxycarbonyl N-protecting group include catalytic hydrogenation, the conditions for which are known to those skilled in the art. Alternative reducing conditions which may be used to avoid N-deprotection with protecting groups other than t-butoxycarbonyl are known to those skilled in the art, see for example, R. C. Larock in Comprehensive Organic Transformations, VCH Publishers, 1989, p. 409.

The (S,R)-protected alcohol (VII) is deprotected to the corresponding (S,R)-amine (VIII) by means known to those skilled in the art for removal of amine protecting group. Suitable means for removal of the amine protecting group depends on the nature of the protecting group. Those skilled in the art, knowing the nature of a specific protecting group, know which reagent is preferable for its removal. For example, it is preferred to remove the preferred protecting group, BOC, by dissolving the (S,R)-protected alcohol (VII) in a trifluoroacetic acid/dichloromethane mixture. When complete, the solvents are removed under reduced pressure to give the corresponding (S,R)-amine (as the corresponding salt, i.e. trifluoroacetic acid salt) which is used without further purification. However, if desired, the (S,R)-amine can be purified further by means well known to those skilled in the art, such as for example, recrystallization. Further, if the non-salt form is desired that also can be obtained by means known to those skilled in the art, such as for example, preparing the free base amine via treatment of the salt with mild basic conditions. Additional BOC deprotection conditions and deprotection conditions for other protecting groups can be found in T. W. Green and P. G. M. Wuts in "Protective Groups in Organic Chemistry," John Wiley and Sons, 1991, p. 309. Typical chemically suitable salts include trifluoroacetate, and the anion of mineral acids such as chloride, sulfate, phosphate; preferred is trifluoroacetate and chloride.

The (S,R)-amine (VIII) is then reacted with an appropriately substituted amide forming agent (IX) such as anhydride, acyl halide, or acid of the formula $(R_{N\text{-}1}$—$X_N)_2O$ or $R_{N\text{-}1}$—$X_N$—$X_2$ or $R_{N\text{-}1}$—$X_N$—OH (IX) by nitrogen-acylation means known to those skilled in the art to produce the corresponding (S,R)-substituted amine (X). Nitrogen acylation conditions for reaction of the (S,R)-amine (VIII) with an amide forming agent (IX) to produce the corresponding (S,R)-substituted amine (X) are known to those skilled in the art and can be found in R. C. Larock in Comprehensive Organic Transformations, VCH Publishers, 1989, p. 981, 979, and 972. $R_N$ is as defined above. Substituted amine (X) is then converted to prodrug compound (Y) of the invention as shown in CHART A and as discussed above (see also examples 1260-1275 for illustrative but non-limiting examples of the conversion of compound (X) to various compounds (Y) of the invention.

In the compounds of the invention, $R_5$ is preferably —$(CR_{P-x}R_{P-y})_{0-4}$-M, —O-M, or —$NR_{P-2}$-M where M is H, $C_1$-$C_{12}$ alkyl, $C_2$-$C_{12}$ alkenyl, $R_{p-aryl}$, $R_{p-heteroaryl}$ or $R_{P-heterocycle}$, wherein 1-4 of the of the —$CH_2$ radicals of the alkyl or alkenyl group is optionally replaced by a heteroatom selected from O, S, S(O), S(O)$_2$, or $NR_{P-2}$, and wherein $R_{P-x}$, $R_{P-y}$, $R_{P-2}$, $R_{P-aryl}$, $R_{p-heteroaryl}$, and $R_{p-heterocycle}$ are as defined above.

In the compounds of the invention, it is preferred that $R_N$ is selected from the group consisting of:

$R_{N-1}$—$X_N$— where $X_N$ is —CO—, where $R_{N-1}$ is $R_{N-aryl}$ or $R_{N-heteroaryl}$ where $R_{N-aryl}$ is phenyl where the substitution on phenyl is 1,3-, and where $R_{N-aryl}$ or $R_{N-heteroaryl}$, are substituted with one —CO—$NR_{N-2}R_{N-3}$, $R_{N-1}X_N$— where $X_N$ is —CO—, where $R_{N-1}$ is $R_{N-aryl}$ or $R_{N-heteroaryl}$ where $R_{N-aryl}$ is phenyl substituted with one $C_1$ alkyl where the substitution on the phenyl is 1,3,5-, and where $R_{N-aryl}$ or $R_{N-heteroaryl}$ are substituted with one —CO—$NR_{N-2}R_{N-3}$, $R_{N-1}$—$X_N$— where $X_N$ is —CO—, where $R_{N-1}$ is $R_{N-heteroaryl}$ where $R_{N-heteroaryl}$ is substituted with one —CO—$NR_{N-2}R_{N-3}$. It is further preferred that $R_{N-2}$ and $R_{N-3}$ are the same and are $C_3$ alkyl. It is further preferred that:

$R_{N-1}$—$X_N$— where $X_N$ is —CO—, where $R_{N-1}$ is $R_{N-aryl}$ where $R_{N-aryl}$ is phenyl substituted with one —CO—$NR_{N-2}R_{N-3}$ where the substitution on phenyl is 1,3-, $R_{N-1}$—$X_N$— where $X_N$ is —CO—, where $R_{N-1}$ is $R_{N-aryl}$ where $R_{N-aryl}$ is phenyl substituted with one $C_1$ alkyl and with one —CO—$NR_{N-2}R_{N-3}$ where the substitution on the phenyl is 1,3,5-. It is preferred that $X_N$ is (A) —CO— and (B) —$SO_2$—; it is more preferred that $X_N$ be —CO—, $X_2$ includes —Cl, —Br; it is preferred that $X_2$ is —Cl.

The nitrogen-acylation ox primary amines to produce secondary amides is one of the oldest known reactions. The amide forming agents, $(R_{N-1}$—$X_N)_2$O or $R_{N-1}$—$X_N$—$X_2$ or $R_{N-1}$—$X_N$—OH (IX) are known to those skilled in the art and are commercially available or can be readily prepared from known starting materials by methods known in the literature. It is preferred to use an isophthalic acid acylating agent (IX) of the formula $R_{N-2}R_{N-3}$N—CO-phenyl-CO— or a methylisophthalic acid acylating agent (IX) of the formula $R_{N-2}R_{N-3}$N—CO—($CH_3$-)phenyl-CO— where the substitution is 5-methyl-1,3-isophthalic acid. The more preferred 5-methyl-1,3-isophthalic acid is 3-[(N,N-dipropylamino)carbonyl]-5-methylbenzoic acid (IX). These compounds are preferably prepared as follows. An ester, preferably the monomethyl ester of isophthalic acid or methyl 5-methyl-1,3-isophthalate is dissolved in a THF/DMF mixture. 1,1'-carbonyldiimidazole is added at 20-25 degrees C. Next the desired amine (H—$NR_{N-2}R_{N-3}$) is added. After 3-24 hr of stirring at 20 degrees C. to the reflux temperature of the solvent, the reaction mixture is partitioned between saturated aqueous ammonium chloride and a water immiscible organic solvent such as ethyl acetate. The aqueous layer is separated and extracted twice more with the organic solvent (ethyl acetate). The organic extracts are combined and then washed with saturated aqueous solutions of bicarbonate and saline and dried over anhydrous sodium sulfate or magnesium sulfate. Filtration of the drying agent and removal of solvents by reduced pressure gives the methyl ester of the desired $R_{N-2}R_{N-3}$N—CO-phenyl-CO—O—$CH_3$ or a methylisophthalic acid acylating agent (IX) $R_{N-2}R_{N-3}$N—CO—($CH_3$-)phenyl-CO—O—$CH_3$. Purification of the (methyl) ester can be achieved via chromatography on silica gel eluting with ethyl acetate in hexanes. The isophthalate ester or methylisophthalate ester of the mono-alkyl or di-alkyl amide is then treated with an aqueous solution of base such as lithium hydroxide in a minimum amount of THF/methanol/water and stirred 3-24 hours at 20 degrees C. to the reflux temperature of the solvent. The solvents are then removed under reduced pressure and subsequently partitioned between water and a water immiscible solvent such as ethyl acetate, for example. If emulsions prohibit separation of the two phases, a small amount of saline is added to aid in separation. The aqueous phase is separated and extracted once more with a water immiscible solvent such as ethyl acetate, for example. The aqueous phase is then acidified with concentrated acid, preferably hydrochloric until pH$\leq$3. The mixture obtained is then extracted three times with a water immiscible solvent such as ethyl acetate, for example. These combined organic extracts are dried over anhydrous sodium or magnesium sulfate. The drying agent is removed by filtration and the organic solvent is removed under reduced pressure to give product. The mono- or di-alkyl amide isophthalate/methylisophthalate is used as such in the next reaction with the (S,R)-amine (VIII) to produce the (S,R)-substituted amine (X).

When it is desired to produce a primary amide, $R_{N-2}$ and $R_{N-3}$ are both —H, the following procedure is preferred. An ester, preferably the methyl ester of isophthalate or methyl 5-methyl-1,3-isophthalate is dissolved in a THF/DMF mixture. CDI is added at 20-25 degrees C. After five to thirty minutes, ammonia gas is bubbled into the mixture through a syringe needle for 1 hr. The mixture is cooled to 0 degrees C. for the duration of the hour. The reaction is left stirring under a balloon of ammonia overnight at 20-25 degrees C., after which time the reaction mixture is partitioned between saturated aqueous ammonium chloride and a water immiscible solvent such as ethyl acetate, for example. The phases are separated and the aqueous phase is extracted twice more with ethyl acetate. The organic extracts are washed with saturated aqueous solutions of bicarbonate and saline and dried over anhydrous sodium or magnesium sulfate. Filtration of the drying agent and removal of solvents under reduced pressure gives the ester of the desired isophthalic acid or the isophthalic acid acylating agent (IX). Purification of the (methyl) ester can be achieved via chromatography on silica gel eluting with isopropanol/chloroform. The isophthalate ester or methylisophthalate ester of the primary amide is then treated with an aqueous solution of base such as lithium hydroxide in a minimum amount of THF/methanol/water and stirred overnight at 20-25 degrees C. after which time the solvents are removed under reduced pressure and subsequently partitioned between water and a water immiscible solvent such as ethyl acetate, for example. If emulsions prohibit separation of the two phases, a small amount of saline is added to aid in separation. The aqueous phase is separated and extracted once more with a water immiscible solvent such as ethyl acetate, for example. The aqueous phase is then acidified with concentrated acid, preferably hydrochloric until pH$\leq$3. The mixture obtained is then extracted three times with ethyl acetate. These combined organic extracts are dried over anhydrous sodium or magnesium sulfate. The drying agent is removed by filtration and the organic solvent removed under reduced pressure to give product. The amide isophthalic acid is used as such in the next reaction with (VIII) to produce (X).

When it is desired that the amine be cyclized to be a group such as morpholinyl, piperazinyl, piperidinyl and pyrrolidinyl, etc the following procedure is preferably followed. An ester, preferably the methyl ester of isophthalic acid or methyl 5-methyl-1,3-isophthalate is dissolved in dry methylene chloride and three drops of DMF are added. The mixture is cooled to 0 degrees C. and then oxalyl chloride is added. The mixture is stirred at 0 degrees C. for 30 minutes to two hours after which the solvents are removed under reduced pressure. The acid chloride is left under vacuum overnight. The crude acid chloride is dissolved in dry methylene and cooled to 0 degrees C. before the addition of the cyclic amine and a tertiary amine base such as N-methyl piperidine, for example. The reaction mixture is stirred at 0 degrees C. for 1 to 6 hr before the solvents are removed under reduced pressure. The residue is diluted with water and a water immiscible solvent such as ethyl acetate, for example, and the phases are separated. The aqueous phase is extracted twice more with a water immiscible solvent such as ethyl acetate, for example, and the combined organic extracts are washed with saturated aqueous bicarbonate and dried over anhydrous sodium or magnesium sulfate. Filtration of the drying agent and removal of solvents under reduced pressure gives the product cyclic amide. The cyclic amide is then treated with an aqueous base such as lithium hydroxide in a minimum amount of THF/methanol/water and stirred overnight at 20-25 degrees C., after which time the solvents are removed under reduced pressure and the residue is subsequently partitioned between water and a water immiscible solvent such as ethyl acetate, for example. The aqueous phase is extracted once more with ethyl acetate. Removal of water from the aqueous phase under reduced pressure gives the desired cyclic amide product (IX).

When it is desired that $R_{N-1}$ is carbocycle, for example but not limited to, cyclohexane, one may then start with a suitably functionalized dimethyl isophthalate and via methods taught in the literature (Meyers, A. I., Org. Syn., 1971, 51, 103) one may reduce the six-membered ring with reducing agents such as rhodium (5%) on alumina in the presence of acetic acid and methanol under a hydrogen atmosphere to afford the corresponding dimethyl cyclohexane dicarboxylate.

CHART D sets forth an alternative process for production of the (S,R)-substituted amine (X), used in CHART A to produce compound (Y), from the (S,R)-protected azide (XII), which is produced from the corresponding epoxide (V) in CHART C. The amino protecting group is removed to produce the corresponding unprotected azide (XIV) by methods previously described in CHART A for the conversion of (S,R)-protected alcohol (VII) to the corresponding (S,R)-amine (VIII). The (S,R)-unprotected azide (XIV) is then acylated on nitrogen to produce the corresponding (S,R)-azide (XV). Next, the azide functionality is reduced as previously discussed for the conversion of the (S,R)-protected azide (XII) to the corresponding (S,R)-protected amine (XIII) to give the (S,R)-free amine (XVI). Last, the (S,R)-free amine (XVI) is transformed to the corresponding (S,R)-substituted amine (X) by nitrogen alkylation with a compound of the formula $R_C$—$X_3$ to give the corresponding (S,R)-substituted amine (X). $X_3$ is an appropriate leaving group, such as but not limited to, —Cl, —Br, —I, —O-mesylate, —O-tosylate, O-triflate, etc. $X_3$ may also be an aldehyde; the corresponding coupling with (XVI) via the well known reductive amination procedure gives the (S,R)-substituted amine (X).

Carbocyclic amide forming agents (IX) are also provided for by the invention. For example, the carbocyclic amide forming agents of the formula

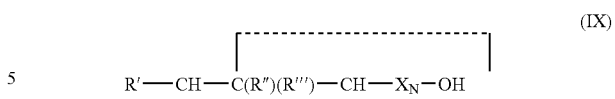

are readily prepared from known starting materials by methods disclosed in the literature and known to those skilled in the art, for example, J. Med. Chem. 1998, 41, 1581, J. Org. Chem. 2000, 65, 1305. It is also understood that instead of the carboxylic acid, one may readily employ an acyl halide, where the halide is preferably choride, or a suitable group to produce a mixed anhydride; these methods are taught by CHART A. For additional guidance on the formation of carbocyles and preferably cyclopropanes, one may consult M. P. Doyle; M. A. McKervery; T. Ye in *Modern Catalytic Methods for Organic Synthesis with Diazo Compounds From Cyclopropanes to Ylides,* Wiley-Interscience, 1998, pp. 163-279.

CHARTs E, F, G, and H disclose various methods to produce the $R_N$ portion of the substituted amine (X) (which is converted to compounds (Y of the invention, as shown in CHART A) where the phenyl ring of the $R_N$ 1,3-disubstituted moiety, —CO-phenyl-CO—, is further substituted in the 5-position with various groups such as amides, nitrites, halides, and amines. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

CHART E discloses alternate processes for the transformation of the aniline (XVII) or acid ester (XVIII) to the corresponding acid (IX-XXIII). One process begins with the commercially available aniline (XVII) where $R_{N-a}$ is preferably —H, $C_1$-$C_4$ alkyl or benzyl. The aniline (XVII) is treated with a diazotizing reagent such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the halo acid ester (XIX) where $R_{N-b}$ is —Cl, —Br or —I. Alternatively, the acid ester (XVIII) is treated with N-halosuccinimide and trifluoromethanesulfonic acid to give the halo acid ester (XIX). The halo acid ester (XIX) is then converted to the ester amide (XXI) using a primary or secondary amine of the formula H-$NR_{Nalpha}R_{Nbeta}$ (AMINE) where $R_{Nalpha}$ and $R_{Nbeta}$ are the same or different or can be cyclized. These groups, $R_{Nalpha}$ and $R_{Nbeta}$, become part of the substituted amine (X) and are included in the definition of $R_N$. $R_N$ includes $R_{N-1}$—$X_N$— where the linker, —$X_N$—, includes —CO— and $R_{N-1}$ includes $R_{N-aryl}$. $R_{N-aryl}$ is defined to include phenyl (-phenyl) optionally substituted with two amides:

—CO—$NR_{N-2}R_{N-3}$ and —CO—$R_{N-4}$. $R_{Nalpha}$ and $R_{Nbeta}$ include both the non-cyclic amides, —CO—$NR_{N-2}R_{N-3}$ and the cyclic amides-CO—$R_{N-4}$ where $R_{N-2}$, $R_{N-3}$ and $R_{N-4}$ are as defined in the claims. Alternatively, the halo acid ester (XIX) is converted to the dihalo ester (XX) by methods known to those skilled in the art. $R_{N-c}$ includes —Cl and —F. The dihalo ester (XX) is treated with a primary or secondary amine of the formula H-NR$_{Nalpha}$R$_{Nbeta}$ (AMINE) to give the ester amide (XXI). The ester amide (XXI) is then reacted with an AMINE in a carbon monoxide atmosphere in the presence of a palladium catalyst using methods such as those reviewed by Heck, (Palladium Reagents in Organic Synthesis, 1985 pp. 342-365) to give the diamide (XXII). Hydrolysis of the ester portion of the diamide (XXII) using methods well known to those skilled in the art gives the diamide acid (XXIII).

In CHART F, an alternate route to intermediate diamide (XXII) is shown starting from commercially available phenol (XXIV). The phenol (XXIV) is treated with a trifluoromethanesulfonating reagent such as trifluoromethanesulfonic anhydride to give triflate (XXV). The triflate (XXV) is reacted under the conditions of palladium catalysis in the presence of carbon monoxide and an amine of the formula H—NR$_{Nalpha}$R$_{Nbeta}$ (AMINE) as for the conversion of the ester amide (XXI) to the corresponding diamide (XXII) in CHART E to give the diester (XXVI). The diester (XXVI) is hydrolyzed using methods known to those skilled in the art to give the monoacid (XXVII). The monoacid (XXVII) is then converted to the diamide (XXII) using conditions such as for the conversion of the halo acid ester (XIX) to the ester amide (XXI) in CHART E.

CHART G discloses another route to prepare the ester amide (XXI). The reaction starts with commercially available nitro compound (XXVIII) which is condensed with an (AMINE) using coupling methods known to those skilled in the art to give the nitro amide (XXX). The nitro amide (XXX) can also be prepared by first treating the nitro compound (XXVIII) with reagents such as thionyl chloride, or DMF and oxalyl chloride, or other methods known to those skilled in the art to give the acid chloride (XXIX), which upon treatment with the (AMINE) gives the nitro amide (XXX). Reduction of the nitro amide (XXX) using methods known to those skilled in the art (see, for example, Smith and March, Advanced Organic Chemistry, 5$^{th}$ ed.) gives amide aniline (XXXI). The amide aniline (XXXI) is then treated with diazotizing reagents such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the ester amide (XXI).

CHART H discloses a process to prepare the diamide acid (IX-XXIII) from the ester amide (XXI), where one of the amides is unsubstituted and is —CO—NH$_2$. This process starts from either the ester or the acid, for example the ester amide (XXI) is treated with copper (I) cyanide (CuCN) in N-methylpyrrolidinone or DMF, preferably N-methylpyrrolidinone, to give the nitrite (XXXII). The nitrite (XXXII) is converted to the primary amide (XXXIII) using urea-hydrogen peroxide complex (see *Synth. Commun.* (1993) 3149) or the methods of Synth. Commun. (1990) 1445, *Synth. Commun.* (1997) 3119, *J. Org. Chem.* (1992) 2521, *Tet. Lett.* (1996) 6555, *Ind. J. Chem., Sect.* B, (1999) 974, *Tet. Lett.* (1995) 3469, *Tet. Lett.* (1998) 3005, or others. When the ester amide (XXI) is in the form of an ester, an additional hydrolysis step using lithium hydroxide, sodium hydroxide, potassium hydroxide, barium hydroxide, or other hydrolysis methods known to those skilled in the art is used to convert the diamide ester (XXXIII) to the diamide acid (IX-XXIII).

CHART I discloses an alternate synthetic route from the protected alcohol (VII) to the substituted amine (X) (used to form compounds (Y)) which uses a diprotected intermediate (XXXIV) whereby the nitrogen atom attached to the R$_C$ substitutent is protected. Using the process of CHART I, the mono protected alcohol (VII) is reacted with a new protecting group to form the orthogonally protected (XXXIV). This is a common strategy employed in traditional peptide chemistry by those skilled in the art, see M. Bodansky, Principles of Peptide Chemistry. When the mono protected alcohol (VII) is protected with CBZ one skilled in the art could react it with either (BOC)$_2$O in methylene chloride or similar organic solvent or FMOC-Cl in methylene chloride or similar organic solvent to prepare orthogonally protected (XXXIV). Then the CBZ group is removed by hydrogenation in the presence of a catalytic amount of palladium on carbon in an alcoholic solvent, such as methanol, or ethyl acetate, or with catalytic palladium on carbon in alcoholic solvents in the presence of ammonium formate as is known to those skilled in the art. This gives the R$_C$—N protected (XXXV). Similarly, when the mono protected alcohol (VII) is protected as a BOC it can be reacted with CBZ-Cl under Schotten-Bauman conditions or CBZ-OSu in THF to prepare the reversed (XXXIV). Then the BOC group can be cleaved with hydrochloric acid (4 N) in methanol, ethanol or dioxane or with trifluoroacetic acid in methylene chloride or by other methods such as those described in The Peptides, Analysis, Synthesis, Biology, Vol. 3, Ed. E. Gross and J. Meienhofer (1981) to liberate the CBZ R$_C$—N protected (XXXV). This functional group manipulation gives various permutations in the sequence (VII) to (XXXIV) to (XXXV) as is apparent to one skilled in the art. When the appropriately R$_C$—N protected compound (XXXV) is reacted with the amide forming agent (IX), in acid form, under standard peptide coupling conditions, for example, EDC/HOBt in methylene chloride or DMF or a previously activated acid, (R$_N$—)$_2$O gives the corresponding R$_N$-substituted R$_C$—N protected (XXXVI). Simple de-protection of the R$_N$-substituted R$_C$—N protected (XXXVI) then gives the desired substituted amine (X). Thus when the R$_N$-substituted R$_C$—N protected (XXXVI) is protected with BOC, treatment with hydrochloric acid (4N) in dioxane or the other reagents discussed above gives the substituted amine (X). When the R$_N$-substituted R$_C$—N protected (XXXVI) is protected with CBZ, treatment with hydrogen from 10-50 psi in alcoholic solvents, such as methanol with a catalytic amount of palladium on carbon will give, after work-up, the desired substituted amine (X). Similarly when the R$_N$-substituted R$_C$—N protected (XXXVI) is protected with FMOC, treatment with a secondary amine, preferably either piperidine (10%) or diethylamine (10%) in an inert solvent such as, for example, methylene chloride will give after work up the desired substituted amine (X).

CHART J discloses a process to prepare compounds where the phenyl ring of the R$_N$ substituent of —CO-phenyl-CO— is substituted with a sulfonamide group in the 5-position. The process starts with the halo amide ester (XXI, CHART E) which is reacted with sodium nitrite, sulfur dioxide, copper chloride (II) and acetic acid by the method disclosed in *J. Med. Chem.*, 42, 3797 (1999) to prepare the sulfonyl chloride (XXXVII). The sulfonyl chloride (XXXVII) is then reacted with AMINE, as defined above, by methods known to those skilled in the art to produce the corresponding sulfonamide (XXXVIII). Last the sulfonamide (XXXVIII) is transformed to the corresponding sulfonamide acid (XXXIX) by methods known to those skilled in the art such as using lithium hydroxide, sodium hydroxide, potassium hydroxide, barium hydroxide, or other hydrolysis methods known to those skilled in the art.

CHART K discloses how to prepare the R$_N$ substituents where R$_N$ is R$_{N-1}$—X$_N$—, where X$_N$ is —CO— and R$_{N-1}$ is R$_{N-aryl}$ where R$_{N-aryl}$ is phenyl substituted with one alkyl group and one —CO—NR$_{N-2}$R$_{N-3}$ or —CO—R$_{N-4}$. See the discussion above for CHART E regarding the amine, H—$NR_{Nalpha}R_{Nbeta}$ (AMINE), used to form the amide $R_N$ substituents. The process starts with the halo amide ester (XXI) which is then reacted with an alkyl boronic acid having the desired alkyl group in the presence of a palladium catalyst such as $Pd(PPh_3)Cl_2$ using the general method described in *J. Med. Chem.*, 4288 (2000). The alkyl boronic acids are commercially available or can be prepared by the process described in *J. Am. Chem. Soc.*, 60, 105 (1938). It is preferred that $R_{N-b}$ is bromo. This step produces the alkyl ester (XL) which is then hydrolyzed by means known to those skilled in the art to produce the desired alkyl acid (XLI).

CHART L discloses a process to prepare the amide forming agent (IX-XLVII) where the $R_N$ substituent is $R_{N-1}$—$X_N$—, where the linker, —$X_N$— is —CO—, where $R_{N-1}$ is $R_{N-aryl}$ and where $R_{N-aryl}$ is phenyl (-phenyl) substituted with groups:

$C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1-a}R_{1-b}$ where $R_{1-a}$ and $R_{1-b}$ are as defined above, and —N(—H and $C_1$-$C_3$ alkyl)-CO—$R_{N-5}$. This specific amide forming agent, (IX-XLVII) is prepared by starting with the phenyl nitro compound (XLII) which is reduced to the corresponding phenyl nitro hydroxy compound (XLIII) using borane-methyl sulfide or borane in THF. The phenyl nitro hydroxy compound (XLIII) is reduced to the corresponding phenyl amino hydroxy compound (XLIV) using hydrogen and palladium catalyst as is known to those skilled in the art. The phenyl amino hydroxy compound (XLIV) is reacted with an aldehyde in the presence of a reducing agent such as sodium cyanoborohydride or sodium triacetoxyborohydride to give the phenyl substituted amino hydroxy compound (XLV). The phenyl substituted amino hydroxy compound (XLV) is acylated with an acid chloride or acid anhydride by methods known to those skilled in the art to give the phenyl disubstituted amino hydroxy compound (XLVI). The phenyl disubstituted amino hydroxy compound (XLVI) is hydrolyzed using an alkali hydroxide, followed by acidification, to give the amide forming agent (IX-XLVII) The amide forming agent (XLVII) is then coupled with amine (VIII) using methods known to those skilled in the art and methods previously discussed, such as with diethyl cyanophosphonate, to give the substituted amine (X). Further treatment of the substituted amine (X) with diethyl cyanophosphonate gives the substituted amine where the hydroxyalkyl substitutent on the phenyl ring has a phosphate substituent.

CHART M discloses a process to prepare amide forming agents (IX-L) where the $R_N$ substituent is $R_{N-1}$—$X_N$—, where the linker, —$X_N$— is —CO—, where $R_{N-1}$ is $R_{N-aryl}$ and where $R_{N-aryl}$ is phenyl (-phenyl) substituted with two groups. The first substituent at what is usually identified as position "5-" can be either:

—$R_{N-aryl}$ or

—$R_{N-heteroaryl}$. The second substituent at what is usually identified as position "3-" can be either:

—CO—$NR_{N-2}R_{N-3}$ or

—CO—$R_{N-4}$.

$R_{Nalpha}$ and $R_{Nbeta}$ include both the non-cyclic amides, —CO—$NR_{N-2}R_{N-3}$ and the cyclic amides-CO—$R_{N-4}$ where $R_{N-2}$, $R_{N-3}$ and $R_{N-4}$ are as defined in the claims. The process starts with the trisubstituted phenyl compound (XLVIII) where $R_{N-d}$ is —Cl, —Br, —I or —O-triflate. Treatment with an aryl or heteroaryl boronic acid or heteroaryl or aryl boronic acid ester such as (aryl or heteroaryl)-B(OH)$_2$ or (aryl or heteroaryl)-B(OR$^a$)(OR$^b$) (where R$^a$ and R$^b$ are lower alkyl, ie. $C_1$-$C_6$, or taken together, R$^a$ and R$^b$ are lower alkylene, ie. $C_2$-$C_{12}$) in the presence of a metal catalyst with or without a base in an inert solvent yields (XLIX). Metal catalysts in these transformations include, but are not limited to, salts or phosphine complexes of Cu, Pd, or Ni (eq. Cu(OAc)$_2$, PdCl$_2$ (PPh$_3$)$_2$, NiCl$_2$(PPh$_3$)$_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979-988 (1994). Intermediate (XLIX) is then hydrolyzed using alkali metal hydroxide, for example lithium, sodium or potassium hydroxide, followed by acidification, to give aryl or heteroaryl coupled acids (IX-L). Alternatively, as described in *Tetrahedron*, 50, 979-988 (1994), one may convert the $R_{N-d}$ to the corresponding boronic acid or boronic acid ester $(OH)_2^B$— or $(OR^a)(OR^b)B$— and obtain the same products set forth above by treating with a suitable aryl or heteroaryl halide or triflate.

CHART N discloses a process to prepare amide forming agents (IX-LII) where the $R_N$ substituent is $R_{N-1}$—$X_N$— where the linker, —$X_N$— is —CO—, where $R_{N-1}$ is $R_{N-aryl}$ and where $R_{N-aryl}$ is phenyl (-phenyl) substituted with two groups. The first substituent at what is usually identified as position "5-" is —C≡C—R. The second substituent at what is usually identified as position "3-" can be either —CO—$NR_{N-2}R_{N-3}$ or —CO—$R_{N-4}$. The halo ester (XXI) is treated with a mixture of PdCl$_2$(Pphenyl$_3$)$_2$ and trimethylsilyl acetylene, using methods known to those skilled in the art, to give acetylene ester (LI). Acetylene ester (LI) is then hydrolyzed using alkali metal hydroxide, followed by acidification, to give acetylene acid (IX-LII).

CHARTs O and O' disclose processes to prepare amide forming agents (IX-LX) and (IX-LXIII) with an extended methylene group where the $R_N$ substituent is $R_{N-1}X_N$— where the linker, —$X_N$— is —CO—, where $R_{N-1}$ is $R_{N-aryl}$ and where $R_{N-aryl}$ is phenyl (-phenyl) substituted with two groups. The substituent at what is usually identified as postion "3-" can be either —CO—$NR_{N-2}R_{N-3}$ or —CO—$R_{N-4}$. In the process of CHART O, the substituent at the 5-position is —CH$_2$CO—NH$_2$ and in the process of CHART O', the substituent at the 5-position is —CH$_2$C≡N. The starting diester acid (LIII) is reduced with borane in solvents such as THF to give the corresponding diester alcohol (LIV). The diester alcohol (LIV) is converted to the corresponding diester bromo compound (LV) using a brominating agent such as PBr$_3$, CBr$_4$, or other halogenating agent such as are known to those skilled in the art. The bromine of the diester bromo compound (LV) is then displaced with cyanide to give the corresponding nitrile (LVI). In CHART O', the nitrile (LVI) is then hydrolyzed to the corresponding cyano ester (LXI). The cyano ester (LXI) is then coupled with H—$NR_{N\alpha}R_{N\beta}$ (AMINE), as previously described using methods known to those skilled in the art to give the corresponding cyano amide (LXII). The cyano amide (LXII) is then hydrolyzed to the corresponding cyano acid (IX-LXIII) which is in turn coupled with amine (VIII) to give the substituted amine (X). Amine (X) is converted to compound (Y) as shown in CHART A. When the substituent on the extended methyl group is —CO—$NH_2$, the process of CHART O is used. There the nitrile (LVI) is converted to the corresponding diester amine (LVII) by methods known to those skilled in the art. The next steps are the same as for CHART O' where the diester amide (LVII) is hydrolyzed to the corresponding ester amine (LVIII) which is then converted to the corresponding diamide ester (LIX) which is hydrolyzed to the corresponding diamide acid (IX-LX). The diamide acid (IX-XL) is then coupled with the appropriate amine (VIII) to produce the desired substituted amine (X). Amine (X) is readily converted to compounds (Y) as shown in CHART A.

CHART P discloses a process to prepare amide forming agents (IX-LXVII) with an extended hydroxymethylene group where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either —CO—$NR_{N-2}R_{N-3}$ or —CO—$R_{N-4}$. The process begins with a halo amide (LXIV), preferably iodo, which is converted to the corresponding aldehyde (LXV) and then to the corresponding alcohol (LXVI) by the method described in *Synth. Commun.* 28, 4270 (1998), optionally with variations known to those skilled in the art. Hydrolysis of the alcohol (LXVI) using alkali hydroxides, followed by acidification, gives the desired hydroxy acid (IX-LXVII). The hydroxy acid (IX-LXVII) is then coupled with the appropriate amine (VIII) to give the desired substituted amine (X) which is converted to compounds (Y) as shown in CHART A.

CHART Q discloses a process to prepare amide forming agents (IX-LXXII) with an alkyl group or a halogen atom or an amino group at the 5-position where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either —CO—$NR_{N-2}R_{N-3}$ or —CO—$R_{N-4}$. The process begins with an appropriately 5-substituted diacid (LXVIII) which is esterified by methods known to those skilled in the art to give the corresponding diester (LXIX). The diester (LXIX) is then hydrolyzed using alkali hydroxides, followed by acidification, to give the corresponding monoacid (LXX). Alternatively, the monoacid (LXX) can be produced directly from the diacid (LXVIII) by known methods. The monoacid (LXX) is then coupled with H-$NR_{Nalpha}R_{Nbeta}$ (AMINE) to give the corresponding amide ester (LXXI). The amide ester (LXXI) is then hydrolyzed using alkali hydroxides, followed by acidification, to give the corresponding acid amide (IX-LXXII).

CHART R discloses a general process to prepare the amide forming agents (IX-LXXVII) which, for example, have an alkyl group at what is known as the 5-position and a ketone at the 3-position. These acids (IX-LXXVII) are formed by starting with the acid (LXXIII) which is converted to the corresponding acid halide (LXXIV) using methods known to those skilled in the art. The acid halide (LXXIV) is preferably the acid chloride. The acid halide (LXXIV) in the presence of copper (I) bromide and tetrahydrofuran and at temperatures ranging from −78 degrees C. to 0 degrees C. is treated with a Grignard reagent (aryl-Mg—X, or alkyl-Mg—X, where X is —Cl or —Br) to give the ketone esters (LXXVI and LXXVI'). Many Grignard reagents are available for purchase; others are prepared by methods known to those skilled in the art. An alternative method for preparing the ketone esters (LXXVI, LXXVI') is to prepare the Weinreb amide (LXXV), either from the acid (LXXIII) directly or by way of acid halide (LXXIV) followed by treatment with N,O-dimethylhydroxylamine to give Weinreb amide (LXXV) and then treating the Weinreb amide (LXXV) with a Grignard reagent, by methods known to those skilled in the art. The ketone esters (LXXVI, LXXVI') are then hydrolyzed using alkali hydroxides, followed by acidification, to give the ketone acids (LXXVII, LXXVII').

CHART S discloses-various methods to modify the RN portion of the substituted amine (X) where the phenyl ring of the RN moiety is further substituted in the 3-position with various groups such as aryl and heteroaryl. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

CHART S sets forth a general method used in the present invention to prepare the substitued amines (X) where $R_N$=$R_{N-aryl}$—$R_{N-aryl}$—$X_N$ or $R_{N-heteroaryl}$—$R_{N-aryl}$—$X_N$. Amines (X) are converted to compounds (Y) of the invention as shown in CHART A.

Treatment of the (S,R)-amine (VIII) with amide forming agents (IX) according to the methods set forth above where for CHART S, $R_{N-1}$ is Br—$R_{N-aryl}$ generates the corresponding (S,R)-substituted amine (X) where $R_N$ is Br—$N_{R-aryl}$—$X_N$. Further treatment with an aryl boronic acid or aryl boronic acid ester such as (aryl or heteroaryl)-$B(OH)_2$ or (aryl or heteroaryl)-$B(OR^a)(OR^b)$ (where $R^a$ and $R^b$ are lower alkyl, ie. $C_1$-$C_6$, or taken together, $R^a$ and $R^b$ are lower alkylene, ie. $C_2$-$C_{12}$) in the presence of a metal catalyst with or without a base in an inert solvent yields the (S,R)-substituted amine (X) where $R_N$ is $N_{R-aryl}$—$N_{R-aryl}$—$X_N$ or $R_{N-heteroaryl}$—$R_{N-aryl}$—$X_N$. Metal catalysts in these transformations include, but are not limited to, salts or phosphine complexes of Cu, Pd, or Ni (eg. $Cu(OAc)_2$, $PdCl_2(PPh_3)_2$, $NiCl_2(PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl) amide), trialkyl amines (preferably diisopropylethylamine or triethylamine) or aromatic amines (preferably pyridine). Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic ydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron,* 50, 979-988 (1994).

Where the above chemistry is incompatible with other functionality present in the (S,R)-substituted amine (X) where $R_N$ is Br—$N_{R\text{-}aryl}$—$X_N$, then one skilled in the art will readily understand that an alternative sequence of coupling steps is required. For example, treatment of an appropriately substituted amide forming agent (IX) $R_{N\text{-}1}$—$X_N$—OH where $R_{N\text{-}1}$ is Br—$R_{N\text{-}aryl}$ with a boronic acid or boronic acid ester under the conditions described above will afford the appropriately substituted amide forming agent (IX) where $R_{N\text{-}1}$ is $N_{R\text{-}aryl}$—$N_{R\text{-}aryl}$ or $R_{N\text{-}heteroaryl}$—$R_{N\text{-}aryl}$. When the amide forming agent (IX) where $R_{N\text{-}1}$ is $N_{R\text{-}aryl}$—$N_{R\text{-}aryl}$ or $R_{N\text{-}heteroaryl}$—$R_{N\text{-}aryl}$ is treated with the (S,R)-amine (VIII), one then obtains the same substituted amines (X) set forth in CHART S.

The above examples for CHART S are not meant to limit the scope of the chemistry. In addition to bromine, a suitable group may include iodine or triflate. Alternatively, as described in *Tetrahedron,* 50, 979-988 (1994), one may convert the Br—$R_{N\text{-}aryl}$ to the corresponding boronic acid or boronic acid ester $(OH)_2B$—$R_{N\text{-}aryl}$ or $(OR^a)(OR^b)B$—$R_{N\text{-}aryl}$ and obtain the same products set forth above by treating with a suitable aryl or heteroaryl halide or triflate. Additionally, each —$R_{N\text{-}aryl}$ and —$R_{N\text{-}heteroaryl}$ are interchangeable at each occurrence in the chemistry described above.

CHART T discloses a process to prepare amide forming agents (IX-LXXIX) where the $R_N$ substituent is $R_{N\text{-}1}$—$X_N$—, where the linker, —$X_N$— is —CO—, where $R_{N\text{-}1}$ is $R_{N\text{-}aryl}$ and where $R_{N\text{-}aryl}$ is phenyl substituted with —CO—$NR_{N alpha}R_{N beta}$ (AMINE) and with an amide of the formulas:

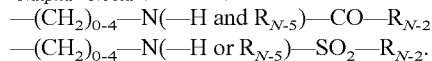

—$(CH_2)_{0\text{-}4}$—N(—H and $R_{N\text{-}5}$)—CO—$R_{N\text{-}2}$
—$(CH_2)_{0\text{-}4}$—N(—H or $R_{N\text{-}5}$)—$SO_2$—$R_{N\text{-}2}$.

The process begins with the amide aniline (XXXI) which is reacted with the corresponding acid halide or sulfonyl halide, or acid anhydride or sulfonyl anhydride to produce the corresponding amide ester (LXXVIII). Suitable solvents include THF or dichloromethane at temperatures ranging from -78 degrees to 100 degrees C. The amide ester (LXXVIII) is then hydrolyzed to the corresponding amide acid (IX-LXXIX) by methods known to those skilled in the art. When the amide forming agent (IX-LXXIX) is reacted with the appropriate amine (VIII), the substituted amine (X) is obtained. Amine (X) is converted to compounds (Y) of the invention as shown in CHART A.

CHART U discloses a general method for preparing various C-terminal amines (VI) as represented by the preparation of C-terminal amine (LXXXIV). Methods to prepare amines of this type are well understood using methods known to those skilled in the art, or one may consult the references: 1) *JACS,* 1970, 92, 3700, and 2) U.S. Pat. No. 4,351,842.

CHART V further discloses general methods for preparing various C-terminal amines (VI) as represented by the preparation of C-terminal amines (LXXXIX). Multiple examples of the heterocyclic carboxylic acids or acid chlorides are commercially available. Optionally, the carboxylic acid (LXXXV) may be converted to the acid chloride (LXXXVI) with reagents such as, but not limited to, thionyl chloride. Displacement with ammonia generates the common intermediate amides (LXXXVII) which are readily reduced to amines (VI-LXXXIX) using a variety of methods detailed previously. Alternatively, other heteroaryls are commercially available as the methyl halide (LXXXVIII) which are treated with ammonia to yield the title C-terminal amines (VI-LXXXVIII).

CHART W discloses general methods for preparing thiazolyl containing C-terminal amines as represented by the preparation of C-terminal amines (LXXXXI). The synthesis of the thiazoles is outlined in CHART W; these procedures are amply taught in the literature and are modified from the procedures outlined in: Mashraqui, S H; Keehn, P M. *J. Am. Chem. Soc.* 1982, 104, 4461-4465. The synthesis of substituted 5-aminomethylthiazoles (XCI) was achieved from 5-hydroxymethylthiazole (XC) by the procedure described in: Alterman et al. *J. Med. Chem.* 1998, 41, 3782-3792. All other thiazole analogs were transformed to the hydroxymethyl derivative using CHART W, and converted to the aminomethyl derivative by the Alterman procedure without notable changes.

CHART X discloses general methods for preparing isoxazolyl containing C-terminal amines as represented by the preparation of C-terminal amines (XCII). The synthesis of isoxazole derivatives was modified from the procedure in: Felman, S W et al. *J. Med. Chem.* 1992, 35, 1183-1190 and is readily understood by those skilled in the art making non-notable changes to achieve the title compounds. The substituted hydroxylamine precursors were synthesized using the procedure taught by Bousquet, E W. *Org. Synth. Coll. Vol II,* 313-315. Commercially available propargylamine may be protected using any number of methods known in the art (see: Greene, T W; Wuts, PGM. *Protective Groups in Organic Synthesis,* 3rd Ed. New York: John Wiley, 1999. Chapter 7.), prefered is a BOC protecting group. Substituted propargyl amines may be obtained by a number of methods commonly known in the art.

CHART Y discloses a general route to prepare hydroxyethylamines where one carbon atom of the peptide backbone, along with $R_2$ and $R_3$ form a ring. It is understood that the present invention also allows for a heteroatom to be incorporated into the ring. In summary, the synthesis of compounds where $R_2$ and $R_3$ may form a ring proceeds from a suitably protected amino acid aldehyde and cycloalkyllithium species, both of which are commercially available or where known procedures for making such compounds are known in the art. The general procedure involved is also precedent in the literature, for example, see Klumpp, et al., *J. Am. Chem. Soc.,* 1979, 101, 7065, and it is intended that making non-critical variations, one may obtain the title compounds provided for by CHART Y. Treatment of a suitably protected amino acid aldehyde and cycloalkyllithium species affords alcohol (XCIII). These reactions are carried out in an inert solvent such as, for example, tetrahydrofuran or diethyl ether. Optimally the reactions are conducted at low temperatures, for example below 0 degrees C. Carbonylation via the Klumpp procedure yields the acid (XCIV) which when exposed to Curtius, or related procedures well known to those skilled in the art, generates the primary amine (XCV). The primary amines (XCV) may be capped C-terminally via the conditions set forth in CHART C & D followed by nitrogen deprotection and capping N-terminally via the conditions set forth in CHART A.

The compounds of the invention may contain geometric or optical isomers as well as tautomers. Thus, the invention includes all tautomers and pure geometric isomers, such as the E and Z geometric isomers, as well as mixtures thereof. Futhermore, the invention includes pure enantiomers and diastereomers as well as mixtures thereof, including racemic mixtures. The individual geometric isomers, enantiomers, or diasteriomers may be prepared or isolated by methods known in the art.

Compounds of the invention with the stereochemistry designated in formula X may be included in mixtures, including racemic mixtures, with other enantiomers, diasteriomers, geometric isomers or tautomers. Compounds of the invention with the stereochemistry designated in formula X are typically present in these mixtures in excess of 50 percent. Preferably, compounds of the invention with the stereochemistry designated in formula X are present in these mixtures in excess of 80 percent. Most preferably, compounds of the invention with the stereochemistry designated in formula X are present in these mixtures in excess of 90 percent.

The compounds (Y) are amines and as such form salts when reacted with acids. Pharmaceutically acceptable salts are preferred over the corresponding compounds (Y) since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201-217 (1986) and *J. Pharm. Sci.*, 66(1), 1, (1977).

The present invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating, humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like.

A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo—IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, Arch. Neurol. 57:454), and other neurotropic agents of the future.

In addition, the compounds of formula (Y) can also be used with inhibitors of P-glycoprotein (P-gp). The use of P-gp inhibitors is known to those skilled in the art. See for example, *Cancer Research*, 53, 4595-4602 (1993), *Clin. Cancer Res.*, 2, 7-12 (1996), *Cancer Research*, 56, 4171-4179 (1996), International Publications WO99/64001 and WO01/10387. The important thing is that the blood level of the P-gp inhibitor be such that it exerts its effect in inhibiting P-gp from decreasing brain blood levels of the compounds of formula (I). To that end the P-gp inhibitor and the compounds of formula (I) can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102, 918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known-to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

The exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et.al., 1999, *Mol. Cell. Neurosci.* 14:419-427; Vassar et.al., 1999, *Science* 286:735-741; Yan et.al., 1999, *Nature* 402: 533-537; Sinha et.al., 1999, *Nature* 40:537-540; and Lin et.al., 2000, *PNAS USA* 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds inhibit about 50% of beta-secretase enzymatic activity at a concentration of less than about 50 micromolar, preferably at a concentration of about 10 micromolar or less, more preferably about 1 micromolar or less, and most preferably about 10 nanomolar or less.

APP Substrate

Assays that demonstrate inhibition of beta-secretase-mediated cleavage of APP can utilize any of the known forms of APP, including the 695 amino acid "normal" isotype described by Kang et.al., 1987, *Nature* 325:733-6, the 770 amino acid isotype described by Kitaguchi et. al., 1981, *Nature* 331:530-532, and variants such as the Swedish Mutation (KM670-1NL) (APP-SW), the London Mutation (V7176F), and others. See, for example, U.S. Pat. No. 5,766, 846 and also Hardy, 1992, *Nature Genet.* 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et.al., 1999, *Neuro. Lett.* 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 1-40. and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612, 486; 5,387,742; 5,720,936; 5,850,003; 5,877,015, and 5,811, 633, and in Ganes et al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

DEFINITIONS AND CONVENTIONS

The definitions and explanations below are for the terms as used throughout this entire document including both the specification and the claims.

I. Conventions for Formulas and Definitions of Variables

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Celsius.
TLC refers to thin-layer chromatography.
psi refers to pounds/in$^2$.
HPLC refers to high pressure liquid chromatography.
THF refers to tetrahydrofuran.
DMF refers to dimethylformamide.
EDC refers to ethyl-1-(3-dimethylaminopropyl) carbodiimide or 1-(3-dimethylaminopropyl)-3-ethylcarbodiimide hydrochloride.
HOBt refers to 1-Hydroxy benzotriazole hydrate.
NMM refers to N-methylmorpholine.
NBS refers to N-bromosuccinimide.
TEA refers to triethylamine.
BOC refers to 1,1-dimethylethoxy carbonyl or t-butoxycarbonyl, —CO—O—C (CH$_3$)$_3$.
CBZ refers to benzyloxycarbonyl, —CO—O—CH$_2$-phenyl.
FMOC refers to 9-fluorenylmethyl carbonate.
TFA refers to trifluoracetic acid, CF$_3$-COOH.
CDI refers to 1,1'-carbonyldiimidazole.
Saline refers to an aqueous saturated sodium chloride solution.
Chromatography (column and flash chromatography) refers to purification/separation of compounds expressed as (support, eluent). It is understood that the appropriate fractions are pooled and concentrated to give the desired compound(s).
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (d) downfield from TMS.
IR refers to infrared spectroscopy.
-phenyl refers to phenyl (C$_6$H$_5$).
MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.
HRMS refers to high resolution mass spectrometry.
Ether refers to diethyl ether.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).
When the solubility of a solid in a solvent is used the ratio of the solid to the solvent is weight/volume (wt/v).
BOP refers to benzotriazol-1-yloxy-tris(dimethylamino) phosphonium hexafluorophosphate.
TBDMSCl refers to t-butyldimethylsilyl chloride.
TBDMSOTf refers to t-butyldimethylsilyl trifluosulfonic acid ester.
Trisomy 21 refers to Down's Syndrome.
The following terms are used (in EXAMPLEs 321 and above) for the amide forming agent (IX):
"PHTH" refers to (CH$_3$—CH$_2$—CH$_2$—)$_2$N—CO-phenyl-CO—OH where the attachment to the—phenyl-ring is 1,3-;
"5-Me-PHTH" refers to (CH$_3$—CH$_2$—CH$_2$—)$_2$N—CO—(CH$_3$—) phenyl —CO—OH where the attachment to the—phenyl-ring is 1,3- for the carbonyl groups and 5- for the methyl group;
"3,5-pyridinyl" refers to (CH$_3$—CH$_2$—CH$_2$—)$_2$N—CO-(pyridinyl)-CO—OH where the attachment to the -pyridinyl-ring is 3,5- for the carbonyl groups;
"—SO$_2$—" refers to (CH$_3$—CH$_2$—CH$_2$—)$_2$CH—SO$_2$-phenyl —CO—OH where the attachment to the—phenyl-ring is 1,3-;
"5—OMe-PHTH" refers to (CH$_3$—CH$_2$—CH$_2$—)$_2$N—CO—(CH$_3$—O—) phenyl —CO—OH where the attachment to the—phenyl-ring is 1,3- for the carbonyl groups and 5- for the methoxy group;
"5-C$_1$-PHTH" refers to (CH$_3$—CH$_2$—CH$_2$—)$_2$N—CO—(Cl-)phenyl-CO—OH where the attachment to the—phenyl-ring is 1,3- for the carbonyl groups and 5- for the chlorine atom;
"5—F-PHTH" refers to (CH$_3$—CH$_2$—CH$_2$—)$_2$N—CO—(F-)phenyl-CO—OH where the attachment to the—phenyl-ring is 1,3- for the carbonyl groups and 5- for the fluorine atom;
"thienyl" refers to (CH$_3$—CH$_2$—CH$_2$—)$_2$N—CO-thienyl-CO—OH where the attachment to the thiophene ring is -2,5;
"2,4-pyridinyl" refers to (CH$_3$—CH$_2$—CH$_2$—)$_2$N—CO-(pyridinyl)-CO—OH where the attachment to the—pyridinyl-ring is 2,4- for the carbonyl groups;
"4,6-pyrimidinyl" refers to (CH$_3$—CH$_2$—CH$_2$—)$_2$N—CO-(pyrimidinyl-)phenyl-CO—OH where the attachment to the -pyrimidiny-1 ring is 4,6- for the carbonyl groups;
"morpholinyl" refers to morpholinyl-CO-phenyl-CO—OH where the attachment to the—phenyl-ring is 1,3 for the carbonyl groups.
APP, amyloid precursor protein, is defined as any APP polypeptide, including APP variants, mutations, and isoforms, for example, as disclosed in U.S. Pat. No. 5,766,846.
A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.
Beta-secretase (BACE1, Asp2, Memapsin 2) is an aspartyl protease that mediates cleavage of APP at the amino-terminal edge of A beta. Human beta-secretase is described, for example, in WO00/17369.
"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-Hexyl, 3-Hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxyl" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-Hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl or di($C_1$-$C_6$)alkylamino ($C_1$-$C_6$) alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$)alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$($C_1$-$C_6$ alkyl), —O—C(=O)($C_1$-$C_6$ alkyl), —NH—C (=O)—($C_1$-$C_6$ alkyl) —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$-($C_1$-$C_6$ alkyl), —NH—C(=O)NH$_2$, —NH—C(=O)N (mono- or di-$C_1$-$C_6$ alkyl), —NH($C_1$-$C_6$ alkyl)-C(=O)—NH$_2$ or —NH($C_1$-$C_6$ alkyl)-C(=O)—N—(mono- or di-$C_1$-$C_6$ alkyl).

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide; tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl, —COOH, —C(=O)O($C_1$-$C_6$ alkyl), —C(=O)NH$_2$, -C(=O)N(mono- or di-$C_1$-$C_6$ alkyl), —S($C_1$-$C_6$ alkyl), —SO$_2$($C_1$-$C_6$ alkyl), —O—C(=O) ($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl) —SO$_2$—($C_1$-$C_6$ alkyl), —NH—C(=O)NH$_2$, —NH—C (=O)N(mono- or di-$C_1$-$C_6$ alkyl), —NH($C_1$-$C_6$ alkyl)-C (=O)—NH$_2$ or —NH($C_1$-$C_6$ alkyl)-C(=O)—N— (mono- or di-$C_1$-$C_6$ alkyl).

By "heterocycle", "heterocycloalkyl" or "heterocyclyl" is meant one or more carbocyclic ring systems of 3-, 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, azepanyl, diazepanyl, tetrahydrothienyl S-oxide, tetrahydrothienyl S,S-dioxide and homothiomorpholinyl S-oxide. The heterocycle groups herein maybe unsubstituted or, as specified, substituted in one or more substitutable positions with various groups. For example, such heterocycle groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl, di($C_1$-$C_6$)alkylamino($C_1$-$C_6$)alkyl or =O.

Structures were named using Name Pro IUPAC Naming Software, version 4.0 or 5.09, available from Advanced Chemical Development, Inc., 90 Adelaide Street West, Toronto, Ontario, M5H 3V9, Canada.

All patents and publications referred to herein are hereby incorporated by reference for all purposes.

The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1 3-Amino-5-(methoxycarbonyl)benzoic acid (XVII)

A suspension of mono-methyl 5-nitro-isophthalate (22.5 g, 100 mmol) and palladium on carbon (5%, 2.00 g) in methanol (100 mL) is shaken in a hydrogenation apparatus under hydrogen (50 psi) for 3 hours. The mixture is then filtered through diatomaceous earth and concentrated to give the title compound, NMR (300 MHz, CDCl$_3$) delta 7.67, 7.41, 7.40 and 3.83; MS (ESI-) for $C_9H_9NO_4$ m/z (M-H)$^-$=194.

PREPARATION 2 3-Bromo-5-(methoxycarbonyl)benzoic acid (XIX)

A mixture of copper (II) bromide (1.85 g, 8.30 mmol), n-butyl nitrite (1.07 g, 10.4 mmol), and acetonitrile (30 mL) is stirred in a round bottomed flask in a water bath to which a few chunks of ice has been added. 3-Amino-5-(methoxycarbonyl)benzoic acid (XVII, PREPARATION 1, 1.35 g, 6.92 mmol) is added as a slurry in warm acetonitrile (70 mL) over 15 min and the mixture is stirred at 20-25 degrees C. for an additional 2 hour, at which time the mixture is partitioned between dichloromethane and hydrochloric acid (3N). The organic phase is separated and dried over sodium sulfate and concentrated to dryness. Chromatography (silica gel, 125 mL; methanol/dichloromethane, 15/85) and concentration of the appropriate fractions gives a solid which is crystallized from methanol to give the title compound in two crops, NMR (DMSO-d$_6$) delta 3.90, 8.26 and 8.65.

PREPARATION 3 Methyl 3-bromo-5-[(dipropylamino)carbonyl]benzoate (XXI)

Carbonyl diimidazole (3.0 g, 18 mmol) is added to a solution of 3-bromo-5-(methoxycarbonyl)benzoic acid (XIX, PREPARATION 2, 3.9 g, 15 mmol) in THF (30 mL). The mixture is stirred for 0.5 hours. Dipropylamine (AMINE, 4.2 mL, 30 mmol) is added to the mixture, which is then stirred for 24 hours. The solvent is then removed under reduced pressure and the mixture is partitioned between ethyl acetate and water. The organic phase is then washed with saline, dried over anhydrous magnesium sulfate, filtered, and concentrated. Column chromatography (silica gel; ethyl acetate/hexanes, 15/85) gives the title compound, IR (diffuse reflectance) 2968, 2958, 1714, 1637, 1479, 1440, 1422, 1321, 1310, 1288, 1273, 1252, 889, 772 and 718 cm$^{-1}$; NMR (300 MHz, CDCl$_3$) δ 8.21, 7.96, 7.70, 3.95, 3.46, 3.15, 1.69, 1.57, 1.00 and 0.78; MS (ESI+) for $C_{15}H_{20}BrNO_3$ m/z (M+H)$^+$=344.1.

PREPARATION 4 3-Bromo-5-[(dipropylamino)carbonyl]benzoic acid

To a solution of methyl 3-bromo-5-[(dipropylamino)carbonyl]benzoate (XXI, PREPARATION 3, 1.4 g, 4.1 mmol) in THF/water/methanol (4/2/2, 8 mL) is added to lithium hydroxide monohydrate (0.17 g, 4.05 mmol). The mixture is stirred at 20 degrees -25 degrees C. for 1 hour and then solvent is removed under reduced pressure. The residue is dissolved in water (50 mL) and hydrochloric acid (1 N) is added to adjust the pH to about 3. The aqueous mixture is extracted with ethyl acetate and the organic phase is separated and dried over magnesium sulfate to give the title compound. Analytical calculated for $C_{14}H_{18}BrNO_3$: C, 51.23; H, 5.53; N, 4.27; Br, 24.35. Found: C, 51.37; H, 5.56; N, 4.28.

PREPARATION 5 Methyl 3-(aminocarbonyl)-5-[(dipropylamino)carbonyl]-benzoate (XXII)

To a mixture of methyl 3-bromo-5-[(dipropylamino)carbonyl]benzoate (XXI, PREPARATION 3, 0.5 g, 1.47 mmol) in dry N-methyl pyrrolidinone under a carbon monoxide atmosphere is added palladium (II) acetate (0.017 9, 0.074 mmol), 1,3-bis(diphenylphosphino)propane (0.045 g, 0.11 mmol), hexamethyldisilazane (1.0 mL, 4.7 mmol), and diisopropylethylamine (0.38 g, 2.94 mmol). The mixture is heated at 100 degrees C. for 24 hours. The mixture is cooled to 20-25 degrees C. and partitioned between water and ethyl acetate. The layers are separated and the aqueous phase is backwashed with ethyl acetate. The organic phases are combined and washed three times with saline, dried over anhydrous magnesium sulfate, filtered and concentrated. Column chromatography (silica gel, 75 mL; methanol/methylene chloride, 2.5/97.5) gives the title compound, NMR (CDCl$_3$) delta 0.77, 1.02, 1.57, 1.71, 3.17, 3.49, 3.98, 5.78, 6.34, 8.07, 8.20 and 8.48.

PREPARATION 6 3-(Aminocarbonyl)-5-[(dipropylamino) carbonyl]benzoic acid (XXIII)

To a mixture of methyl 3-(aminocarbonyl)-5-[(dipropylamino)carbonyl]benzoate (XXII, PREPARATION 5, 0.197 g, 0.64 mmol) in methanol (5.0 mL) is added sodium hydroxide (1N, 3.0 mL). The mixture is stirred at 20-25 degrees C. for 24 hours. The mixture is acidified to about pH 5 with hydrochloric acid (10%). Water (50 mL) is added and the mixture is washed twice with ethyl acetate (2×50 mL). The organic extracts are combined and dried over anhydrous magnesium sulfate and concentrated to give the title compound, NMR (DMSO-d$_6$) delta 0.66, 0.930, 1.48, 1.62, 3.12, 3.35, 7.54, 7.98, 8.22 and 8.51.

PREPARATION 7 3-Cyano-5-[(dipropylamino)carbonyl]benzoic acid (IX/XXXII)

A mixture of 3-bromo-5-[(dipropylamino)carbonyl]benzoic acid (PREPARATION 4, 0.596 9, 1.82 mmol) and copper nitrile (0.325 g, 3.63 mmol) in N-methylpyrrolidinone (1.5 mL) is stirred at 175 degrees C. for 2.5 hour, at which time the mixture is cooled and partitioned between ethyl acetate and hydrochloric acid (3N). The organic layer is washed twice more with hydrochloric acid (3N) and then twice more with saline which had been acidified with a small amount of hydrochloric acid (3N). The organic layer is dried over magnesium sulfate and concentrated under high vacuum to give the title compound, NMR (CDCl$_3$) delta 0.80, 1.02, 1.60, 1.73, 3.17, 3.51, 7.90, 8.31 and 8.41; an aliquot is crystallized from ethyl ether/dichloromethane/hexane-IR (diffuse reflectance) 3017, 2970, 2937, 2898, 2877, 2473, 2432, 2350, 2318, 2236, 1721, 1608, 1588, 1206 and 1196 cm$^{-1}$.

PREPARATION 8 3-(Aminocarbonyl)-5-[(dipropylamino)carbonyl]benzoic acid (XXXIII)

A mixture of 3-cyano-5-[(dipropylamino)carbonyl]benzoic acid (IX/XXXII, PREPARATION 7, 0.602 g, 2.19 mmol), potassium carbonate (0.212 g, 1.53 mmol), and acetone (2.5 mL) is stirred at 20-25 degrees C. Water (2.5 mL) and urea-hydrogen peroxide adduct (0.825 g, 8.78 mmol) are added and the mixture is stirred for 15 hours at 20-25 degrees C., at which time additional urea-hydrogen peroxide adduct (0.204 g) is added; after stirring for another 3 hours, an additional 0.205 g of urea-hydrogen peroxide is added. After a total of 39 hours has elapsed, the acetone is removed under reduced pressure and the residue is acidified with hydrochloric acid (3N) to pH=2-4. The mixture is extracted with dichloromethane, the organic layer is separated and washed with hydrochloric acid (0.5 N), and the organic phase is dried with anhydrous magnesium sulfate to a solid. The solid is crystallized from dichloromethane/hexane/methanol to give the title compound, MS (ESI+) for $C_{15}H_{20}N_2O_4$ m/z (M+H)$^+$=293.2.

PREPARATION 9 Methyl 3-[(dipropylamino)carbonyl]-5-nitrobenzoate (XXX)

Carbonyl diimidazole (3.90 g, 24.0 mmol) is added to a mixture of mono-methyl 5-nitro-isophthalate (XXVIII, 4.50 g, 20.0 mmol) in dry THF (50 mL). The mixture is stirred for 0.5 hours. Dipropylamine (3.28 mL, 24.0 mmol) is added slowly to the mixture. The reaction mixture is then stirred for 4 hours. The solvent is removed under reduced pressure and the mixture is partitioned between ethyl acetate and water. The organic phase is separated and washed with saline, dried over anhydrous sodium sulfate, filtered, and concentrated. Column chromatography (silica gel; ethyl acetate/hexanes, 15/85) gives the title compound, NMR (300 MHz, CDCl$_3$) delta 8.88, 8.41, 8.35, 4.00, 3.48, 3.15, 1.72, 1.57, 1.00 and 0.77; MS (ESI+) for $C_{15}H_{20}N_2O_5$ m/z (M+H)$^+$=309.2.

PREPARATION 10 Methyl 3-amino-5-[(dipropylamino)carbonyl]benzoate (XXXI)

A suspension of methyl 3-[(dipropylamino)carbonyl]-5-nitrobenzoate (XXX, PREPARATION 9, 6.00g, 20.0 mmol) and palladium on carbon (5%, 0.600 g) in methanol (40 mL) is shaken in a hydrogenation apparatus under hydrogen (45 psi) for 3 hours. The mixture is then filtered through diatomaceous earth and concentrated to give the title compound, NMR (300 MHz, CDCl$_3$) delta 7.27, 6.77, 4.10, 3.82, 3.38, 3.10, 1.62, 1.46, 0.91 and 0.68.

PREPARATION 11 Methyl 3-(chlorosulfonyl)-5-[(dipropylamino)carbonyl]-benzoate (XXXVII)

Methyl 3-amino-5-[(dipropylamino)carbonyl]benzoate (XXXI, PREPARATION 10, 1.11 g, 4 mmol) is added to a mixture of water (5 mL) and concentrated hydrochloric acid (1 mL). Sodium nitrite (0.276 g, 4 mmol) is added to the mixture slowly at 0 degrees C. The mixture is then added to an acetic acid solution (5 mL) of CuCl$_2$.2H$_2$O saturated with sulfur dioxide. The mixture is stirred for 0.5 hours and poured into ice water. The mixture is extracted with ethyl acetate. The organic phase is separated and washed with saturated sodium bicarbonate, water, and saline and dried over anhydrous sodium sulfate, filtered, and concentrated to give the title compound, NMR (300 MHz, CDCl$_3$) delta 8.69, 8.38, 8.20, 4.01, 3.49, 3.14, 1.72, 1.59, 1.01 and 0.79; MS (ESI+) for $C_{15}H_{20}ClNO_5S$ m/z (M+H)$^+$=362.2

PREPARATION 12 Methyl 3-(aminosulfonyl)-5-[(dipropylamino)carbonyl]-benzoate (XXXVIII)

To a solution of methyl 3-(chlorosulfonyl)-5-[(dipropylamino)carbonyl]benzoate (XXXVII, PREPARATION 11, 0.100 g, 0.300 mmol) in dry THF (3 mL) is added ammonia (7 N solution in methanol, 0.214 mL, 1.50 mmol). The mixture is stirred for 18 hours and solvent is then removed. The residue is partitioned between ethyl acetate and water. The organic phase is separate and washed with saline, dried over anhydrous sodium sulfate, filtered, and concentrated to give the title compound, NMR (300 MHz, CDCl$_3$) delta 8.45, 8.07, 8.01, 6.05, 3.93, 3.44, 3.09, 1.67, 1.52, 0.96 and 0.73; MS (ESI+) for $C_{12}H_{22}N_2O_5S$ m/z (M+H)$^+$=343.3.

PREPARATION 13 3-(Aminosulfonyl)-5-[(dipropylamino)carbonyl]benzoic acid (XXXVIII)

Lithium hydroxide monohydrate (0.011 g, 0.263 mmol) is added to a solution of methyl 3-(aminosulfonyl)-5-[(dipropylamino)carbonyl]benzoate (XXXVIII, PREPARATION 12, 0.090 9, 0.263 mmol) in a mixture of THF/methanol/water (2/1/1, 2 mL). The mixture is stirred at 20-25 degrees C. for 3 hours. The mixture is then diluted with water and hydrochloric acid (1 N) is added to bring the pH to less than 3. The aqueous solution is extracted with ethyl acetate. The organic phase is separated and washed with saline, dried over anhydrous sodium sulfate, filtered and concentrated to give the title compound. $^1$H NMR (300 MHz, CDCl$_3$) delta 10.36 (s, 1 H), 8.39 (s, 1 H), 8.09 (s, 2 H), 6.06 (s, 2 H), 3.48 (t, J=7 Hz, 2 H), 3.15 (t, J=7 Hz, 2 H), 1.71 (m, 2 H), 1.55 (m, 2 H), 0.97 (t, J=7 Hz, 3 H), 0.74 (t, J=7 Hz, 3 H). MS (ESI+) for $C_{11}H_{20}N_2O_5S$ m/z 329.2 (M+H)$^+$.

PREPARATION 14 Methyl 3-[(dipropylamino)carbonyl]-5-(1-pyrrolidinylsulfonyl)-benzoate (XXXVIII)

Following the general procedure of PREPARATION 12 and making non-critical variations but using pyrrolidine (0.347 mL, 4.16 mmol), the title compound is obtained, MS (ESI+) for $C_{19}H_{28}N_2O_5S$ m/z (M+H)$^+$=397.1.

PREPARATION 15 3-[(Dipropylamino)carbonyl]-5-(1-pyrrolidinylsulfonyl)benzoic acid (XXXIX)

Following the general procedure of PREPARATION 13 and making non-critical variations, the title compound is obtained, MS (ESI+) for $C_{18}H_{26}N_2O_5S$ m/z (M+H)$^+$=383.3.

PREPARATION 16 Methyl 3-[(dipropylamino)carbonyl]-5-[(methylamino)-sulfonyl]benzoate (XXXVIII)

Following the general procedure of PREPARATION 12 and making non-critical variations but using methyl amine (2 N solution in THF, 0.692 mL, 1.38 mmol), the title compound is obtained, MS (ESI+) for $C_{16}H_{24}N_2O_5S$ m/z (M+H)$^+$=357.1.

PREPARATION 17 3-[(Dipropylamino)carbonyl]-5-[(methylamino)-sulfonyl]benzoic acid (XXXIX)

Following the general procedure of PREPARATION 13 and making non-critical variations, the title compound is obtained, MS (ESI+) for $C_{15}H_{22}N_2O_5S$ m/z $(M+H)^+=343.1$.

PREPARATION 18 Methyl 3-[(dimethylamino)sulfonyl]-5-[(dipropylamino)-carbonyl]benzoate (XXXVIII)

Following the general procedure of PREPARATION 12 and making non-critical variations but using dimethylamine (2 N solution in THF, 0.692 mL, 1.38 mmol), the title compound is obtained, MS (ESI+) for $C_{17}H_{26}N_2O_5S$ m/z $(M+H)^+=371.1$.

PREPARATION 19 3-[(Dimethylamino)sulfonyl]-5-[(dipropylamino)carbonyl]-benzoic acid (XXXIX)

Following the general procedure of PREPARATION 13 and making non-critical variations, the title compound is obtained, MS (ESI+) for $C_{16}H_{24}N_2O_5S$ m/z $(M+H)^+=357.1$.

PREPARATION 20 Methyl 3-[(dipropylamino)carbonyl]-5-ethylbenzoate (IX)

Ethylboronic acid (0.800 g, 10.8 mmol), dichlorobis(triphenylphosphine)-palladium(II) (0.252 g, 0.360 mmol), potassium carbonate (2.50 9, 18.0 mmol) and lithium chloride (0.151 g, 3.60 mmol) are added to a mixture of methyl 3-bromo-5-[(dipropylamino)carbonyl]benzoate (1.23 g, 3.60 mmol) in dry DMF (20 mL). The mixture is heated at 100 degrees C. for 18 hours. The mixture is then partitioned between ethyl acetate and water. The phases are separated and the ethyl acetate phase is washed with saline, dried over sodium sulfate and concentrated. The concentrate is column chromatographed (silica gel; ethyl acetate/hexanes, 15/85) to give the title compound, MS (ESI+) for $C_{17}H_{25}NO_3$ m/z $(M+H)^+=292.2$.

PREPARATION 21 3-[(Dipropylamino)carbonyl]-5-ethylbenzoic acid (IX)

Lithium hydroxide monohydrate (0.0680 g, 1.6 mmol) is added to a mixture of methyl 3-[(dipropylamino)carbonyl]-5-ethylbenzoate (PREPARATION 20, 0.450 g, 1.6 mmol) in a mixture of THF/methanol/water (2/1/1, 8 mL). The mixture is stirred at 20-25 degrees C. for 3 hours. The mixture is then diluted with water (20 mL) and hydrochloric acid (1 N) is added to bring the pH to less than 3. The aqueous mixture is extracted with ethyl acetate. The organic phase is separated and washed with saline, dried over anhydrous magnesium sulfate, filtered and concentrated to give the title compound, MS (ESI+) for $C_{16}H_{23}NO_3$ m/z $(M+H)^+=278.2$.

Example 1 tert-Butyl (1S)-3-bromo-1-(3,5-difluorobenzyl)-2-oxopropylcarbamate (III)

N-methyl-morpholine (5.83 Ml, 53 mmole, 1.05 eq.) is added to (2S)-2-[(tert-butoxycarbonyl)amino]-3-(3,5-difluorophenyl)propanoic acid (II, 15 g, 50 mmole) in THF (100 mL) and the reaction is cooled to −78 degrees C. Isobutyl chloroformate (6.87 mL, 53 mmole, 1.05 eq.) is added rapidly. The cold bath is then removed and the mixture stirred for 1 hour. The reaction is monitored by TLC to insure completion of the reaction and the mixture is then filtered and washed with dry THF (50 ml) and kept cold in the filtered flask at −20 degrees C.

In an ice-salt bath is placed a 500 ml graduate cylinder containing ether (200 mL) and aqueous potassium hydroxide (40%, 60 ml). 1-Methyl-3-nitro-1-nitrosoguanidine (5.6 g, 106 mmole, 2.1 eq.) is added slowly with stirring and temperature kept below 0 degrees C. The mixture turned yellow and the bubbling lasted for 10 minutes. The stirring is stopped and without mixing the layers, the top diazomethane ethereal layer is transferred with non-ground tip pipette into the stirred mixed anhydride mixture at −20 degrees C. The reaction is monitored by TLC (ethyl acetate/hexane, 50/50; $R_f=0.69$). After 1 hour nitrogen is then bubbled into the mixture. The solvent is removed under reduced pressure (with heat) and the mixture is partitioned between ether and water. The phases are separated, the organic phase is washed with bicarbonate, saline, dried over anhydrous sodium sulfate and solvent removed under reduced pressure (with heat). The residue is dissolved in ether (100 mL) and hydrobromic acid (48%, 15 mL, 135 mmole, 2.7 eq,) is added at −20 degrees C., the cold bath is removed and the mixture is stirred for another 0.5 hours. The reaction is monitored by TLC (ethyl acetate/hexane, 50/50; $R_f=0.88$). The mixture is partitioned between ether and water, washed with bicarbonate, saline, dried over anhydrous sodium sulfate and the solvent removed. The residue is recrystallized from ethanol to give the title compound, TLC (ethyl acetate/hexane, 50/50) $R_f=0.88$; MS $(MH^+)=379.3$.

Example 2 tert-Butyl (1S, 2S)-3-bromo-1-(3,5-difluorobenzyl)-2-hydroxypropylcarbamate (IV)

Sodium borohydride (1.32 g, 34.9 mmole, 1.1 eq.) is added to tert-Butyl (1S)-3-bromo-1-(3,5-difluorobenzyl)-2-oxopropylcarbamate (III, EXAMPLE 1, 12 g, 31.75 mmole) dissolved in absolute alcohol (500 mL) at −78 degrees C. The reaction mixture is stirred for 0.5 hour and monitored by TLC (ethyl acetate/hexane, 20/80; $R_f=0.2$). The mixture is quenched with water (10 mL) and the solvent removed under reduced pressure with heat (not exceeding 30 degrees C.) to dryness. The solid is partitioned between dichloromethane and water, washed with saline, dried over anhydrous sodium sulfate. The solvent is removed under reduced pressure to give the title compound, TLC (ethyl acetate/hexane, 20/80) $R_f=0.2$; MS $(MH^+)=381.2$.

Example 3 tert-Butyl (1S)-2-(3,5-difluorophenyl)-1-[(2S)-oxiranyl]ethylcarbamate (V)

tert-Butyl (1S, 2S)-3-bromo-1-(3,5-difluorobenzyl)-2-hydroxypropylcarbamate (IV, EXAMPLE 2) is dissolved in absolute alcohol (150 mL) and ethyl acetate (100 mL) and potassium hydroxide (2.3 g, 34.9 mmole, 1.1 eq.) in ethyl alcohol (85%, 5 mL) is added at −20 degrees C. The cold bath is then removed and the mixture stirred for 0.5 hour. The reaction is monitored by TLC (ethyl acetate/hexane, 20/80). When the reaction is complete, it is diluted with dichloromethane and extracted, washed with water, saline, dried over anhydrous sodium sulfate and the solvent removed under reduced pressure. The crude material is purified by flash chromatography on silica gel to give the title compound, TLC (ethyl acetate/hexane, 20/80) $R_f=0.3$; MS $(MH^+)=300.4$.

Example 4 tert-Butyl (1S, 2R)-1-(3,5-difluorobenzyl)-2-hydroxy-3-[(3-methoxybenzyl)amino]propylcarbamate (VII)

tert-Butyl (1S)-2-(3,5-difluorophenyl)-1-[(2S)-oxiranyl] ethylcarbamate (V, EXAMPLE 3, 245 mg, 0.82 mmol) is suspended in isopropyl alcohol (6 mL) and 3-methoxybenzylamine (160 microL, 1.22 mmol) is added with stirring at 20-25 degrees C. This mixture is heated to gentle reflux (bath temp 85 degrees C.) under nitrogen for 2 hours, whereupon the resulting mixture is concentrated under reduced pressure to give the title compound. The title compound is purified by flash chromatography (2-5% methanol/methylene chloride; gradient elution) to give purified title compound.

Example 5

(2R,3S)-3-amino-4-(3,5-difluorophenyl)-1-[(3-methoxybenzyl)amino]-2-butanol trifluoroacetate (VIII)

tert-Butyl (1S, 2R)-1-(3,5-difluorobenzyl)-2-hydroxy-3-[(3-methoxybenzyl)amino]propylcarbamate (VII, EXAMPLE 4, 258 mg, 0.59 mmol) is dissolved in methylene chloride (1 mL) at 20-25 degrees C., and trifluoroacetic acid (1 mL) is added with stirring under nitrogen. The reaction mixture is stirred at 20-25 degrees C. for 1 hour, whereupon the reaction mixture is concentrated under reduced pressure to give the title compound. The title compound is used in the next reaction without further purification.

Example 6

$N^1$-{(1S,2R)-1-(3,5-difluorobenzyl)-2-hydroxy-3-[(3-methoxybenzyl)amino]propyl}-5-methyl-$N^3$,$N^3$-dipropylisophthalamide (X)

(2R,3S)-3-amino-4-(3,5-difluorophenyl)-1-[(3-methoxybenzyl)amino]-2-butanol trifluoroacetate salt (VIII, EXAMPLE 5) is dissolved in anhydrous DMF (3 mL) and cooled to 0 degrees C. Triethylamine (500 microliter, 3.6 mmol) and 5-methyl-N,N-dipropylisophthalamic acid (156 mg, 0.59 mmol) are added with stirring. The mixture is warmed to 20-25 degrees C. briefly to allow for complete dissolution of the carboxylic acid, before recooling to 0 degrees C. 1-Hydroxybenzotriazole (157 mg, 1.2 mmol) is added with stirring, followed by 1-(3-dimethylaminopropyl)-3-ethylcarbodiimide hydrochloride (229 mg, 1.2 mmol). The resulting mixture is stirred at 0 degrees C. for 5 minutes, then warmed to 20-25 degrees C. for 15 hours. The reaction mixture is then quenched with aqueous citric acid (10%), and the mixture extracted three times with ethyl acetate. The combined organic extracts are washed with saturated sodium bicarbonate, saline, dried over sodium sulfate, filtered and concentrated under reduced pressure to give the the title compound in crude form. This material is purified by flash chromatography (2-10% methanol/methylene chloride gradient elution) to give purified title compound, MS (ES) $MH^+$=582.3.

Examples 7-9

Following the general procedure of EXAMPLE 1 and making non critical variations but starting with the protecting group of Column A and using the acid of Column B, the protected compound (III) of Column C is obtained:

| EXAMPLE | Column A | Column B | Column C |
|---|---|---|---|
| 7 | BOC | Hydrochloric | tert-butyl (1S)-3-chloro-1-(3,5-difluorobenzyl)-2-oxopropylcarbamate |
| 8 | CBZ | Hydrobromic | benzyl (1S)-3-bromo-1-(3,5-difluorobenzyl)-2-oxopropylcarbamate |
| 9 | CBZ | Hydrochloric | benzyl (1S)-3-chloro-1-(3,5-difluorobenzyl)-2-oxopropylcarbamate |

Examples 10-12

Following the general procedure of EXAMPLE 2 and making non critical variations but starting with the protected compound (III) of Column A, the alcohol (IV) of Column B is obtained:

| EXAMPLE | Column A | Column B |
|---|---|---|
| 10 | 7 | Tert-butyl (1S,2S)-3-chloro-1-(3,5-difluorobenzyl)-2-hydroxypropylcarbamate |
| 11 | 8 | Benzyl (1S,2S)-3-bromo-1-(3,5-difluorobenzyl)-2-hydroxypropylcarbamate |
| 12 | 9 | Benzyl (1S,2S)-3-chloro-1-(3,5-difluorobenzyl)-2-hydroxypropylcarbamate |

Example 13

Benzyl (1S)-2-(3,5-difluorophenyl)-1-[(2S)-oxiranyl]ethylcarbamate (V)

Following the general procedure of EXAMPLE 3 and making non critical variations but starting with the alcohol (IV) of EXAMPLE 12, the title compound is obtained.

Examples 14-10

Following the general procedure of EXAMPLE 4 and making non-critical variations but reacting tert-butyl (1S,2S)-1-(2-oxiranyl)-2-phenylethylcarbamate (V, commercially available) with the C-terminal amine (VI) of Column A, the protected alcohol (VII) of Column B is obtained.

| EXA | Column A<br>C-terminal amine<br>(VI) | Column B<br>Protected alcohol<br>(VII) |
|---|---|---|
| 14 | $H_2N$—$CH_2CH_3$ | tert-butyl (1S,2R)-1-benzyl-3-(ethylamino)-2-hydroxypropylcarbamate |

-continued

| EXA | Column A<br>C-terminal amine<br>(VI) | Column B<br>Protected alcohol<br>(VII) |
|---|---|---|
| 15 | H₂N—CH₂-phenyl | tert-butyl (1S,2R)-1-benzyl-3-(benzylamino)-2-hydroxypropylcarbamate |
| 16 | H₂N—CH(CH₃)₂ | tert-butyl (1S,2R)-1-benzyl-3-(isopropylamino)-2-hydroxypropylcarbamate |
| 17 | H₂N—CH₂-phenyl-4-CH₃ | tert-butyl (1S,2R)-1-benzyl-2-hydroxy-3-[(4-methylbenzyl)amino]propylcarbamate |
| 18 | H₂N—(CH₂)₂-phenyl-4-OCH₃ | tert-butyl (1S,2R)-1-benzyl-2-hydroxy-3-{[2-(4-methoxyphenyl)ethyl]amino}propylcarbamate |
| 19 | H₂N—CH₂-phenyl-3-OCH₃ | tert-butyl (1S,2R)-1-benzyl-2-hydroxy-3-[(3-methoxybenzyl)amino]propylcarbamate |
| 20 | H₂N—CH(-phenyl)-CO—OC₂H₅ | ethyl ({(2R,3S)-3-[(tert-butoxycarbonyl)amino]-2-hydroxy-4-phenylbutyl}amino)(phenyl)acetate |
| 21 | H₂N—(CH₂)₂-phenyl | tert-butyl (1S,2R)-1-benzyl-2-hydroxy-3-[(2-phenylethyl)amino]propylcarbamate |
| 22 | H₂N—CH(—CH₂OH)—CH(OH)-phenyl-4-NO₂ | tert-butyl (1S,2R)-1-benzyl-2-hydroxy-3-{[(1S)-2-hydroxy-1-(hydroxymethyl)-2-(4-nitrophenyl)ethyl]amino}propylcarbamate |
| 23 | H₂N—CH₂-phenyl-2-Cl | tert-butyl (1S,2R)-1-benzyl-3-[(2-chlorobenzyl)amino]-2-hydroxypropylcarbamate |
| 24 | H₂N—CH₂-phenyl-4-Cl | tert-butyl (1S,2R)-1-benzyl-3-[(4-chlorobenzyl)amino]-2-hydroxypropylcarbamate |
| 25 | H₂N—(CH₂)₂—O—(CH₂)₂—OH | tert-butyl (1S,2R)-1-benzyl-2-hydroxy-3-{[2-(2-hydroxyethoxy)ethyl]amino}propylcarbamate |
| 26 | H₂N-1-indanyl | tert-butyl (1S,2R)-1-benzyl-3-(2,3-dihydro-1H-inden-1-ylamino)-2-hydroxypropylcarbamate |
| 27 | H₂N—CH₂—CH(OH)—CH₃ | tert-butyl (1S,2R)-1-benzyl-2-hydroxy-3-[(2-hydroxypropyl)amino]propylcarbamate |
| 28 | H₂N—CH₂-tetrahydrofuranyl | tert-butyl (1S,2R)-1-benzyl-2-hydroxy-3-[(tetrahydro-2-furanylmethyl)amino]propylcarbamate |
| 29 | H₂N—CH₂—CH(—OCH₂CH₃) | tert-butyl (1S,2R)-1-benzyl-3-[(2,2-diethoxyethyl)amino]-2-hydroxypropylcarbamate |
| 30 | H₂N—(CH₂)₄—CH₃ | tert-butyl (1S,2R)-1-benzyl-2-hydroxy- |

-continued

| EXA | Column A<br>C-terminal amine<br>(VI) | Column B<br>Protected alcohol<br>(VII) |
|---|---|---|
| 31 | H$_2$N-cyclohexyl | 3-(pentylamino)propylcarbamate<br>tert-butyl (1S,2R)-1-benzyl-3-(cyclohexylamino)-2-hydroxypropylcarbamate |
| 32 | H$_2$N—CH$_2$-pyridin-2-yl | tert-butyl (1S,2R)-1-benzyl-2-hydroxy-3-[(2-pyridinylmethyl)amino]propylcarbamate |
| 33 | H$_2$N—CH$_2$-phenyl-2-NH$_2$ | tert-butyl (1S,2R)-3-[(2-aminobenzyl)amino]-1-benzyl-2-hydroxypropylcarbamate |
| 34 | H$_2$N—CH$_2$-pyridin-3-yl | tert-butyl (1S,2R)-1-benzyl-2-hydroxy-3-[(3-pyridinylmethyl)amino]propylcarbamate |
| 35 | H$_2$N—(CH$_2$)$_2$-pyrrolidin-1-yl | tert-butyl (1S,2R)-1-benzyl-2-hydroxy-3-{[2-(1-pyrrolidinyl)ethyl]amino}propylcarbamate |
| 36 | H$_2$N—CH$_2$—CH(OH)-phenyl | tert-butyl (1S,2R)-1-benzyl-2-hydroxy-3-[(2-hydroxy-2-phenylethyl)amino]propylcarbamate |
| 37 | H$_2$N—(CH$_2$)$_3$—O—(CH$_2$)$_3$—CH$_3$ | tert-butyl (1S,2R)-1-benzyl-3-[(3-butoxypropyl)amino]-2-hydroxypropylcarbamate |
| 38 | H$_2$N—(CH$_2$)$_3$—O—CH(CH$_3$)$_2$ | tert-butyl (1S,2R)-1-benzyl-2-hydroxy-3-[(3-isopropoxypropyl)amino]propylcarbamate |
| 39 | H$_2$N—(CH$_2$)$_2$—CH(CH$_3$)$_2$ | tert-butyl (1S,2R)-1-benzyl-2-hydroxy-3-(isopentylamino)propylcarbamate |
| 40 | H$_2$N—(CH$_2$)$_3$-phenyl | tert-butyl (1S,2R)-1-benzyl-2-hydroxy-3-[(3-phenylpropyl)amino]propylcarbamate |
| 41 | H$_2$N—(CH$_2$)$_2$—OCH$_3$ | tert-butyl (1S,2R)-1-benzyl-2-hydroxy-3-[(2-methoxyethyl)amino]propylcarbamate |
| 42 | H$_2$N—(CH$_2$)$_2$—O-phenyl | tert-butyl (1S,2R)-1-benzyl-2-hydroxy-3-[(2-phenoxyethyl)amino]propylcarbamate |
| 43 | H$_2$N—(CH$_2$)$_2$—O—(CH$_2$)$_2$—CH$_3$ | tert-butyl (1S,2R)-1-benzyl-2-hydroxy-3-[(2-propoxyethyl)amino]propylcarbamate |
| 44 | H$_2$N—(CH$_2$)$_2$—C(CH$_3$)$_3$ | tert-butyl (1S,2R)-1-benzyl-3-[(3,3-dimethylbutyl)amino]-2-hydroxypropylcarbamate |
| 45 | H$_2$N—(CH$_2$)$_4$-phenyl | tert-butyl (1S,2R)-1-benzyl-2-hydroxy-3-[(4-phenylbutyl)amino]propylcarbamate |
| 46 | H$_2$N—CH$_2$-phenyl-3-I | tert-butyl (1S,2R)-1-benzyl-2-hydroxy-3-[(3-iodobenzyl)amino]propylcarbamate |
| 47 | H$_2$N—CH$_2$-phenyl-4-NO$_2$ | tert-butyl (1S,2R)-1-benzyl-2-hydroxy- |

-continued

| EXA | Column A<br>C-terminal amine<br>(VI) | Column B<br>Protected alcohol<br>(VII) |
|---|---|---|
| 48 | $H_2N-CH_2$-phenyl-3-Cl | 3-[(4-nitrobenzyl)amino]propylcarbamate tert-butyl (1S,2R)-1-benzyl-3-[(3-chlorobenzyl)amino]-2-hydroxypropylcarbamate |
| 49 | $H_2N-(CH_2)_2$-phenyl-4-Cl | tert-butyl (1S,2R)-1-benzyl-3-{[2-(4-chlorophenyl)ethyl]amino}-2-hydroxypropylcarbamate |
| 50 | $H_2N-(CH_2)_2$-pyridin-2-yl | tert-butyl (1S,2R)-1-benzyl-2-hydroxy-3-{[2-(2-pyridinyl)ethyl]amino}propylcarbamate |
| 51 | $H_2N-CH_2$-pyridin-4-yl | tert-butyl (1S,2R)-1-benzyl-2-hydroxy-3-[(4-pyridinylmethyl)amino]propylcarbamate |
| 52 | $H_2N-(CH_2)_2-$(N-methylpyrrolidin-2-yl) | tert-butyl (1S,2R)-1-benzyl-2-hydroxy-3-{[2-(1-methyl-2-pyrrolidinyl)ethyl]amino}propylcarbamate |
| 53 | $H_2N-CH_2$-phenyl-2,3-dimethyl | tert-butyl (1S,2R)-1-benzyl-3-[(2,3-dimethylbenzyl)amino]-2-hydroxypropylcarbamate |
| 54 | $H_2N-CH_2$-phenyl-2-$OCF_3$ | tert-butyl (1S,2R)-1-benzyl-2-hydroxy-3-{[2-(trifluoromethoxy)benzyl]amino}propylcarbamate |
| 55 | $H_2N-CH_2$-phenyl-2-Cl-6-O-phenyl | tert-butyl (1S,2R)-1-benzyl-3-[(2-chloro-6-phenoxybenzyl)amino]-2-hydroxypropylcarbamate |
| 56 | $H_2N-CH_2$-phenyl-4-$CF_3$ | tert-butyl (1S,2R)-1-benzyl-2-hydroxy-3-{[4-(trifluoromethyl)benzyl]amino}propylcarbamate |
| 57 | $H_2N-CH_2$-phenyl-2,3-dichloro | tert-butyl (1S,2R)-1-benzyl-3-[(2,3-dichlorobenzyl)amino]-2-hydroxypropylcarbamate |
| 58 | $H_2N-CH_2$-phenyl-3,5-dichloro | tert-butyl (1S,2R)-1-benzyl-3-[(3,5-dichlorobenzyl)amino]-2-hydroxypropylcarbamate |
| 59 | $H_2N-CH_2$-phenyl-3,5-difluoro | tert-butyl (1S,2R)-1-benzyl-3-[(3,5-difluorobenzyl)amino]-2-hydroxypropylcarbamate |
| 60 | $H_2N-CH_2$-phenyl-4-$OCF_3$ | tert-butyl (1S,2R)-1-benzyl-2-hydroxy-3-{[4-(trifluoromethoxy)benzyl]amino}propylcarbamate |
| 61 | $H_2N-(CH_2)_2$-phenyl-4-$SO_2-NH_2$ | tert-butyl (1S,2R)-3-{[4-(aminosulfonyl)benzyl]amino}-1-benzyl-2-hydroxypropylcarbamate |
| 62 | $H_2N-CH_2$-phenyl-4-$OCH_3$ | tert-butyl (1S,2R)-1-benzyl-2-hydroxy- |

-continued

| EXA | Column A<br>C-terminal amine<br>(VI) | Column B<br>Protected alcohol<br>(VII) |
|---|---|---|
| 63 | H$_2$N—CH$_2$-phenyl-4-CH$_3$ | tert-butyl (1S,2R)-1-benzyl-2-hydroxy-3-[(4-methoxybenzyl)amino]propylcarbamate |
| 64 | H$_2$N—CH$_2$—Ph-(3,4,5-trimethoxy) | tert-butyl (1S,2R)-1-benzyl-2-hydroxy-3-[(4-methylbenzyl)amino]propylcarbamate |
| 65 | H$_2$N—CH$_2$-phenyl-3-OCF$_3$ | tert-butyl (1S,2R)-1-benzyl-2-hydroxy-3-[(3,4,5-trimethoxybenzyl)amino]propylcarbamate |
| 66 | H$_2$N—CH$_2$-phenyl-3,5-dimethoxy | tert-butyl (1S,2R)-1-benzyl-2-hydroxy-3-{[3-(trifluoromethoxy)benzyl]amino}propylcarbamate |
| 67 | H$_2$N—CH$_2$-phenyl-2,4-dimethoxy | tert-butyl (1S,2R)-1-benzyl-3-[(3,5-dimethoxybenzyl)amino]-2-hydroxypropylcarbamate |
| 68 | H$_2$N—CH$_2$-phenyl-phenyl | tert-butyl (1S,2R)-1-benzyl-3-[(2,4-dimethoxybenzyl)amino]-2-hydroxypropylcarbamate |
| 69 | H$_2$N—CH$_2$-phenyl-3,4-dichloro | tert-butyl (1S,2R)-1-benzyl-3-[([1,1'-biphenyl]-3-ylmethyl)amino]-2-hydroxypropylcarbamate |
| 70 | H$_2$N—CH$_2$-phenyl-4-F | tert-butyl (1S,2R)-1-benzyl-3-[(3,4-dichlorobenzyl)amino]-2-hydroxypropylcarbamate |
| 71 | H$_2$N—CH$_2$-phenyl-3-CF$_3$ | tert-butyl (1S,2R)-1-benzyl-3-[(4-fluorobenzyl)amino]-2-hydroxypropylcarbamate |
| 72 | H$_2$N—CH$_2$-phenyl-2-CH$_3$ | tert-butyl (1S,2R)-1-benzyl-2-hydroxy-3-{[3-(trifluoromethyl)benzyl]amino}propylcarbamate |
| 73 | H$_2$N—CH((R)—CH$_3$)-phenyl | tert-butyl (1S,2R)-1-benzyl-2-hydroxy-3-[(2-methylbenzyl)amino]propylcarbamate |
| 74 | H$_2$N—CH((S)—CH$_3$)-phenyl | tert-butyl (1S,2R)-1-benzyl-2-hydroxy-3-{[(1R)-1-phenylethyl]amino}propylcarbamate |
| 75 | H$_2$N—CH$_2$-phenyl-3,5-(bis)trifluoromethyl | tert-butyl (1S,2R)-1-benzyl-2-hydroxy-3-{[(1S)-1-phenylethyl]amino}propylcarbamate |
| 76 | H$_2$N—CH$_2$-phenyl-2-CF$_3$ | tert-butyl (1S,2R)-1-benzyl-3-{[3,5-bis(trifluoromethyl)benzyl]amino}-2-hydroxypropylcarbamate |
| 77 | H$_2$N—CH((S)—CH$_3$)-(naphth-1-yl) | tert-butyl (1S,2R)-1-benzyl-2-hydroxy-3-{[2-(trifluoromethyl)benzyl]amino}propylcarbamate |
| | | tert-butyl (1S,2R)-1-benzyl-2-hydroxy-3-{[(1S)-1-(1-naphthyl)ethyl]amino}propyl carbamate |

-continued

| EXA | Column A<br>C-terminal amine<br>(VI) | Column B<br>Protected alcohol<br>(VII) |
|---|---|---|
| 78 | —NH$_2$—CH((R)—CH$_3$)-(naphth-1-yl) | tert-butyl (1S,2R)-1-benzyl-2-hydroxy-3-{[(1R)-1-(1-naphthyl)ethyl]amino}propylcarbamate |
| 79 | H$_2$N—CH$_2$-phenyl-3-OCH$_3$-4-OH | tert-butyl (1S,2R)-1-benzyl-2-hydroxy-3-[(4-hydroxy-3-methoxybenzyl)amino]propylcarbamate |
| 80 | H$_2$N—CH$_2$-phenyl-3,4-dihydroxy | tert-butyl (1S,2R)-1-benzyl-3-[(3,4-dihydroxybenzyl)amino]-2-hydroxypropylcarbamate |
| 81 | H$_2$N—(CH$_2$)$_3$—OCH$_3$ | tert-butyl (1S,2R)-1-benzyl-2-hydroxy-3-[(3-methoxypropyl)amino]propylcarbamate |
| 82 | H$_2$N—CH((S)—CH$_3$)—CH$_2$—OH | tert-butyl (1S,2R)-1-benzyl-2-hydroxy-3-{[(1S)-2-hydroxy-1-methylethyl]amino}propylcarbamate |
| 83 | H$_2$N—CH((R)—CH$_3$)—CH$_2$—OH | tert-butyl (1S,2R)-1-benzyl-2-hydroxy-3-{[(1R)-2-hydroxy-1-methylethyl]amino}propylcarbamate |
| 84 | H$_2$N—CH$_2$—C≡CH | tert-butyl (1S,2R)-1-benzyl-2-hydroxy-3-(2-propynylamino)propylcarbamate |
| 85 | H$_2$N—(CH$_2$)$_2$-phenyl-2-F | tert-butyl (1S,2R)-1-benzyl-3-{[2-(2-fluorophenyl)ethyl]amino}-2-hydroxypropylcarbamate |
| 86 | H$_2$N—(CH$_2$)$_2$-phenyl-3-F | tert-butyl (1S,2R)-1-benzyl-3-{[2-(3-fluorophenyl)ethyl]amino}-2-hydroxypropylcarbamate |
| 87 | H$_2$N—(CH$_2$)$_2$-phenyl-4-F | tert-butyl (1S,2R)-1-benzyl-3-{[2-(4-fluorophenyl)ethyl]amino}-2-hydroxypropylcarbamate |
| 88 | H$_2$N—(CH$_2$)$_2$-phenyl-4-Br | tert-butyl (1S,2R)-1-benzyl-3-{[2-(4-bromophenyl)ethyl]amino}-2-hydroxypropylcarbamate |
| 89 | H$_2$N—(CH$_2$)$_2$-phenyl-3-OCH$_3$ | tert-butyl (1S,2R)-1-benzyl-2-hydroxy-3-{[2-(3-methoxyphenyl)ethyl]amino}propylcarbamate |
| 90 | H$_2$N—(CH$_2$)$_2$-phenyl-2,4-dichloro | tert-butyl (1S,2R)-1-benzyl-3-{[2-(2,4-dichlorophenyl)ethyl]amino}-2-hydroxypropylcarbamate |
| 91 | H$_2$N—(CH$_2$)$_2$-phenyl-3-Cl | tert-butyl (1S,2R)-1-benzyl-3-{[2-(3-chlorophenyl)ethyl]amino}-2-hydroxypropylcarbamate |
| 92 | H$_2$N—(CH$_2$)$_2$-phenyl-2,5-dimethoxy | tert-butyl (1S,2R)-1-benzyl-3-{[2-(2,5-dimethoxyphenyl) |

-continued

| EXA | Column A<br>C-terminal amine<br>(VI) | Column B<br>Protected alcohol<br>(VII) |
|---|---|---|
| 93 | $H_2N$—$(CH_2)_2$-phenyl-4-$CH_3$ | ethyl]amino}-2-hydroxypropylcarbamate<br>tert-butyl (1S,2R)-1-benzyl-2-hydroxy-3-{[2-(4-methylphenyl)ethyl]amino}propylcarbamate |
| 94 | $H_2N$—$CH(\text{—}(R)CH_2\text{—}OH)$—$CH_2$-phenyl | tert-butyl (1S,2R)-1-benzyl-3-{[(1R)-1-benzyl-2-hydroxyethyl]amino}-2-hydroxypropylcarbamate |
| 95 | $H_2N$—$(CH_2)_3$-(1-morpholinyl) | tert-butyl (1S,2R)-1-benzyl-2-hydroxy-3-{[3-(4-morpholinyl)propyl]amino}propylcarbamate |
| 96 | $H_2N$—$CH_2$—$C(CH_3)_2$ | tert-butyl (1S,2R)-1-benzyl-3-[(3,3-dimethylbutyl)amino]-2-hydroxypropylcarbamate |
| 97 | $H_2N$—$(CH_2)_2$-(1-morpholinyl) | tert-butyl (1S,2R)-1-benzyl-2-hydroxy-3-{[2-(4-morpholinyl)ethyl]amino}propylcarbamate |
| 98 | $H_2N$—$CH(OH)$—$CH_2$—$CH_3$ | tert-butyl (1S,2R)-1-benzyl-2-hydroxy-3-[(1-hydroxypropyl)amino]propylcarbamate |
| 99 | $H_2N$—$(CH_2)_2$-(thien-2-yl) | tert-butyl (1S,2R)-1-benzyl-2-hydroxy-3-[(2-thienylmethyl)amino]propylcarbamate |
| 100 | $H_2N$—$(CH_2)_4$—OH | tert-butyl (1S,2R)-1-benzyl-2-hydroxy-3-[(4-hydroxybutyl)amino]propylcarbamate |
| 101 | $H_2N$—$CH(\text{—}(S)CH_2\text{—}OH)$-phenyl | tert-butyl (1S,2R)-1-benzyl-2-hydroxy-3-{[(1S)-2-hydroxy-1-phenylethyl]amino}propylcarbamate |
| 102 | $H_2N$—$CH_2$-phenyl-2,4-dichloro | tert-butyl (1S,2R)-1-benzyl-3-[(2,4-dichlorobenzyl)amino]-2-hydroxypropylcarbamate |
| 103 | $H_2N$—$CH(\text{—}(R)CH_2\text{—}OH)$-phenyl | tert-butyl (1S,2R)-1-benzyl-2-hydroxy-3-{[(1R)-2-hydroxy-1-phenylethyl]amino}propylcarbamate |
| 104 | $H_2N$—$CH_2$-phenyl-4-$C(CH_3)_3$ | tert-butyl (1S,2R)-1-benzyl-3-[(4-tert-butylbenzyl)amino]-2-hydroxypropylcarbamate |
| 105 | $H_2N$—$CH(CH_3)$-phenyl | tert-butyl (1S,2R)-1-benzyl-2-hydroxy-3-[(1-phenylethyl)amino]propylcarbamate |
| 106 | $H_2N$—(1R,2S)-2-hydroxyinden-1-yl | tert-butyl (1S,2R)-1-benzyl-2-hydroxy-3-{[(1R,2S)-2-hydroxy-2,3-dihydro-1H-inden-1-yl]amino}propylcarbamate |
| 107 | $H_2N$—$CH_2$-phenyl-3,4-dimethyl | tert-butyl (1S,2R)-1-benzyl-3-[(3,4-dimethylbenzyl)amino]- |

| Column A<br>C-terminal amine<br>EXA (VI) | Column B<br>Protected alcohol<br>(VII) |
|---|---|
| | 2-hydroxypropylcarbamate |

Examples 108–164

Following the general procedure of EXAMPLE 4 and making non-critical variations but reacting tert-butyl (1S)-2-(3,5-difluorophenyl)-1-[(2S)-oxiranyl]ethylcarbamate (V, EXAMPLE 3) with the C-terminal amine (VI) of Column A, the protected alcohol (VII) of Column B is obtained.

| EXA | Column A<br>C-terminal amine<br>(VI) | Column B<br>Protected alcohol<br>(VII) |
|---|---|---|
| 108 | $H_2N-(CH_2)_6-CO-O-CH_3$ | methyl 7-{[(2R,3S)-3-[(tert-butoxycarbonyl)amino]-4-(3,5-difluorophenyl)-2-hydroxybutyl]amino}heptanoate |
| 109 | $H_2N-CH(-CH_3)-CO-NH-CH_2-CH(CH_3)_2$ r/s | tert-butyl (1S,2R)-1-(3,5-difluorobenzyl)-2-hydroxy-3-{[2-(isobutylamino)-1-methyl-2-oxoethyl]amino}propylcarbamate |
| 110 | $H_2N-CH((S)-CH_3)-CO-NH-CH_2-CH(CH_3)_2$ | tert-butyl (1S,2R)-1-(3,5-difluorobenzyl)-2-hydroxy-3-{[(1S)-2-(isobutylamino)-1-methyl-2-oxoethyl]amino}propylcarbamate |
| 111 | $H_2N-C(-CH_3)_2-CO-NH-CH_2-CH(CH_3)_2$ | tert-butyl (1S,2R)-1-(3,5-difluorobenzyl)-2-hydroxy-3-{[2-(isobutylamino)-1,1-dimethyl-2-oxoethyl]amino}propylcarbamate |
| 112 | $H_2N-CH_2-CO-NH-CH_2-CH(CH_3)_2$ | tert-butyl (1S,2R)-1-(3,5-difluorobenzyl)-2-hydroxy-3-{[2-(isobutylamino)-2-oxoethyl]amino}propylcarbamate |
| 113 | $H_2N-CH((S)-CH_2CH_3)-CO-NH-CH_2-CH(CH_3)_2$ | tert-butyl (1S,2R)-1-(3,5-difluorobenzyl)-2-hydroxy-3-({(1S)-1-[(isobutylamino)carbonyl]propyl}amino)propylcarbamate |
| 114 | $H_2N-CH((R)-CH_2CH_3)-CO-NH-CH_2-CH(CH_3)_2$ | tert-butyl (1S,2R)-1-(3,5-difluorobenzyl)-2-hydroxy-3-({(1R)-1-[(isobutylamino)carbonyl]propyl}amino)propylcarbamate |
| 115 | $H_2N-CH_2$-phenyl | tert-butyl (1S,2R)-3-(benzylamino)-1-(3,5-difluorobenzyl)-2-hydroxypropylcarbamate |
| 116 | $H_2N-CH_2-CH_3$ | tert-butyl (1S,2R)-1-(3,5-difluorobenzyl)-3-(ethylamino)-2-ydroxypropylcarbamate |

-continued

| EXA | Column A<br>C-terminal amine<br>(VI) | Column B<br>Protected alcohol<br>(VII) |
|---|---|---|
| 117 | $H_2N—CH_2—CH(CH_3)_2$ | tert-butyl (1S,2R)-1-(3,5-difluorobenzyl)-2-hydroxy-3-(isobutylamino)propylcarbamate |
| 118 | $H_2N—CH_2—CH(CH_3)—CONH—CH_2—CH(CH_3)_2$ | tert-butyl (1S,2R)-1-(3,5-difluorobenzyl)-2-hydroxy-3-{[3-(isobutylamino)-2-methyl-3-oxopropyl]amino}propylcarbamate |
| 119 | $H_2N—CH_2$-phenyl-4-$N(CH_3)_2$ | tert-butyl (1S,2R)-1-(3,5-difluorobenzyl)-3-{[4-(dimethylamino)benzyl]amino}-2-hydroxypropylcarbamate |
| 120 | $H_2N—CH((S))—CH_2$-phenyl)-CO—NH—$CH_2$—$CH(CH_3)_2$ | tert-butyl (1S,2R)-3-{[(1S)-1-(3,5-difluorobenzyl)-2-(isobutylamino)-2-oxoethyl]amino}-1-(3,5-difluorobenzyl)-2-hydroxypropylcarbamate |
| 121 | $H_2N—CH((S)—CH(CH_3)_2)—CO—NH—CH_2—CH(CH_3)_2$ | tert-butyl (1S,2R)-1-(3,5-difluorobenzyl)-2-hydroxy-3-({(1S)-1-[(isobutylamino)carbonyl]-3-methylbutyl}amino)propylcarbamate |
| 122 | $H_2N—CH_2—CH_2—N(CH_3)_2$ | tert-butyl (1S,2R)-1-(3,5-difluorobenzyl)-3-{[2-(dimethylamino)ethyl]amino}-2-hydroxypropylcarbamate |
| 123 | $H_2N—CH_2$-(pyridin-3-yl) | tert-butyl (1S,2R)-1-(3,5-difluorobenzyl)-2-hydroxy-3-[(3-pyridinylmethyl)amino]propylcarbamate |
| 124 | $H_2N—CH((S)—CH_2—O—CH_2$-phenyl)-CO—NH—$CH_2$—$CH(CH_3)_2$ | tert-butyl (1S,2R)-3-{[(1S)-1-[(benzyloxy)methyl]-2-(isobutylamino)-2-oxoethyl]amino}-1-(3,5-difluorobenzyl)-2-hydroxypropylcarbamate |
| 125 | $H_2N—C(—CH_3)_2$-phenyl | tert-butyl (1S,2R)-1-(3,5-difluorobenzyl)-2-hydroxy-3-[(1-methyl-1-phenylethyl)amino]propylcarbamate |
| 126 | $H_2N—CH((R)—CH(CH_3)_2)—CO—NH—CH_2—CH(CH_3)_2$ | tert-butyl (1S,2R)-1-(3,5-difluorobenzyl)-2-hydroxy-3-({(1R)-1-[(isobutylamino)carbonyl]-3-methylbutyl}amino)propylcarbamate |
| 127 | $H_2N—CH((S)—CH_2—CH_2—CH_3)—CO—NH—CH_2—CH(CH_3)_2$ | tert-butyl (1S,2R)-1-(3,5-difluorobenzyl)-2-hydroxy-3-({(1S)-1-[(isobutylamino)carbonyl]butyl}amino)propylcarbamate |

-continued

| EXA | Column A<br>C-terminal amine<br>(VI) | Column B<br>Protected alcohol<br>(VII) |
|---|---|---|
| 128 | H$_2$N—CH((S)—CH$_2$—OH)—CO—NH—CH$_2$—CH(CH$_3$)$_2$ | tert-butyl (1S,2R)-1-(3,5-difluorobenzyl)-2-hydroxy-3-{[(1S)-1-(hydroxymethyl)-2-(isobutylamino)-2-oxoethyl]amino}propylcarbamate |
| 129 | H$_2$N—CH$_2$—CH$_2$-phenyl | tert-butyl (1S,2R)-1-(3,5-difluorobenzyl)-2-hydroxy-3-[(2-phenylethyl)amino]propylcarbamate |
| 130 | H$_2$N—CH((S)—CH$_3$)—CO—NH—CH$_2$-phenyl | tert-butyl (1S,2R)-3-{[2-(benzylamino)-1-methyl-2-oxoethyl]amino}-1-(3,5-difluorobenzyl)-2-hydroxypropylcarbamate |
| 131 | H$_2$N—CH((S)—CH$_2$—CH$_3$)-phenyl | tert-butyl (1S,2R)-1-(3,5-difluorobenzyl)-3-{[(1S)-2-(benzylamino)-1-methyl-2-oxoethyl]amino}-2-hydroxypropylcarbamate |
| 132 | H$_2$N—CH$_2$-phenyl-3-OCH$_3$ | tert-butyl (1S,2R)-1-(3,5-difluorobenzyl)-2-hydroxy-3-[(3-methoxybenzyl)amino]propylcarbamate |
| 133 | H$_2$N—CH((S)-phenyl)CO—NHCH$_2$CH(CH$_3$)$_2$ | tert-butyl (1S,2R)-1-(3,5-difluorobenzyl)-2-hydroxy-3-{[(1S)-2-(isobutylamino)-2-oxo-1-phenylethyl]amino}propylcarbamate |
| 134 | H$_2$N—CH$_2$—CH$_2$—CH(CH$_3$)$_2$ | tert-butyl (1S,2R)-1-(3,5-difluorobenzyl)-2-hydroxy-3-(isopentylamino)propylcarbamate |
| 135 | H$_2$N-cyclohexyl | tert-butyl (1S,2R)-1-(3,5-difluorobenzyl)-3-(cyclohexylamino)-2-hydroxypropylcarbamate |
| 136 | H$_2$N—(CH$_2$)$_3$—CH$_3$ | tert-butyl (1S,2R)-1-(3,5-difluorobenzyl)-3-(butylamino)-2-hydroxypropylcarbamate |
| 137 | H$_2$N—(CH$_2$)$_3$—O—CH$_3$ | tert-butyl (1S,2R)-1-(3,5-difluorobenzyl)-2-hydroxy-3-[(3-methoxypropyl)amino]propylcarbamate |
| 138 | H$_2$N—CH$_2$—CH(OH)-phenyl | tert-butyl (1S,2R)-1-(3,5-difluorobenzyl)-2-hydroxy-3-[(2-hydroxy-2-phenylethyl)amino]propylcarbamate |
| 139 | H$_2$N-cyclohexyl-3,5-dimethoxy | tert-butyl (1S,2R)-1-(3,5-difluorobenzyl)-3-{[(3R,5S)-3,5-dimethoxycyclohexyl]amino}-2-hydroxypropylcarbamate |

-continued

| EXA | Column A<br>C-terminal amine<br>(VI) | Column B<br>Protected alcohol<br>(VII) |
|---|---|---|
| 140 | H₂N-cyclohexyl-3,5-di-(—CO—OCH₃) | dimethyl (1R,3S)-5-({(2R,3S)-3-[(tert-butoxycarbonyl)amino]-2-hydroxy-4-phenylbutyl}amino)-1,3-cyclohexanedicarboxylate |
| 141 | H₂N-cyclohexyl-3,5-di-(—COOH) | (1R,3S)-5-({(2R,3S)-3-[(tert-butoxycarbonyl)amino]-2-hydroxy-4-phenylbutyl}amino)-1,3-cyclohexanedicarboxylic acid |
| 142 | H₂N—CH((R)—CH₂—CH₃)-phenyl | tert-butyl (1S,2R)-1-(3,5-difluorobenzyl)-2-hydroxy-3-{[(1R)-1-phenylpropyl]amino}propylcarbamate |
| 143 | H₂N—CH₂-phenyl-3-Cl | tert-butyl (1S,2R)-1-(3,5-difluorobenzyl)-3-[(3-chlorobenzyl)amino]-2-hydroxypropylcarbamate |
| 144 | H₂N—CH₂-phenyl-3-OCH₃ | tert-butyl (1S,2R)-1-(3,5-difluorobenzyl)-2-hydroxy-3-[(3-methoxybenzyl)amino]propylcarbamate |
| 145 | H₂N—CH₂-phenyl-phenyl | tert-butyl (1S,2R)-1-(3,5-difluorobenzyl)-3-[([1,1'-biphenyl]-3-ylmethyl)amino]-2-hydroxypropylcarbamate |
| 146 | H₂N—CH₂-phenyl-3-I | tert-butyl (1S,2R)-1-(3,5-difluorobenzyl)-2-hydroxy-3-[(3-iodobenzyl)amino]propylcarbamate |
| 147 | H₂N—CH₂-phenyl-3-CH₃ | tert-butyl (1S,2R)-1-(3,5-difluorobenzyl)-2-hydroxy-3-[(3-methylbenzyl)amino]propylcarbamate |
| 148 | H₂N—CH₂—CH(—CH₃)-phenyl | tert-butyl (1S,2R)-1-(3,5-difluorobenzyl)-2-hydroxy-3-[(2-phenylpropyl)amino]propylcarbamate |
| 149 | H₂N—CH₂-(thiazol-5-yl) | tert-butyl (1S,2R)-1-(3,5-difluorobenzyl)-2-hydroxy-3-[(1,3-thiazol-5-ylmethyl)amino]propylcarbamate |
| 150 | H₂N—CH₂-(thien-2-yl) | tert-butyl (1S,2R)-1-(3,5-difluorobenzyl)-2-hydroxy-3-[(2-thienylmethyl)amino]propylcarbamate |
| 151 | H₂N-4-methoxytetralin-1-yl | tert-butyl (1S,2R)-1-(3,5-difluorobenzyl)-2-hydroxy-3-[(5-methoxy-1,2,3,4-tetrahydro-1-naphthalenyl)amino]propylcarbamate |
| 152 | H₂N—CH₂-pyrazin-2-yl | tert-butyl (1S,2R)-1-(3,5- |

-continued

| EXA | Column A<br>C-terminal amine<br>(VI) | Column B<br>Protected alcohol<br>(VII) |
|---|---|---|
| | | difluorobenzyl)-2-hydroxy-3-[(2-pyrazinylmethyl)amino]propylcarbamate |
| 153 | H₂N—CH₂-phenyl-3,5-difluoro | tert-butyl (1S,2R)-1-(3,5-difluorobenzyl)-3-[(3,5-difluorobenzyl)amino]-2-hydroxypropylcarbamate |
| 154 | H₂N—CH₂-phenyl-3,4-methylenedioxy | tert-butyl (1S,2R)-3-[(1,3-benzodioxol-5-ylmethyl)amino]-1-(3,5-difluorobenzyl)-2-hydroxypropylcarbamate |
| 155 | H₂N—CH₂-phenyl-3,5-dimethoxy | tert-butyl (1S,2R)-1-(3,5-difluorobenzyl)-3-[(3,5-dimethoxybenzyl)amino]-2-hydroxypropylcarbamate |
| 156 | H₂N—CH₂-phenyl-3-CF₃ | tert-butyl (1S,2R)-1-(3,5-difluorobenzyl)-2-hydroxy-3-{[3-(trifluoromethyl)benzyl]amino}propylcarbamate |
| 157 | H₂N—CH₂-(furan-2-yl) | tert-butyl (1S,2R)-1-(3,5-difluorobenzyl)-3-[(2-furylmethyl)amino]-2-hydroxypropylcarbamate |
| 158 | H₂N-(7-methoxytetralin-1-yl) | tert-butyl (1S,2R)-1-(3,5-difluorobenzyl)-2-hydroxy-3-[(7-methoxy-1,2,3,4-tetrahydro-1-naphthalenyl)amino]propylcarbamate |
| 159 | H₂N—CH₂-phenyl-3-O—CF₃ | tert-butyl (1S,2R)-1-(3,5-difluorobenzyl)-2-hydroxy-3-{[3-(trifluoromethoxy)benzyl]amino}propylcarbamate |
| 160 | H₂N—CH₂-phenyl-3-F | tert-butyl (1S,2R)-1-(3,5-difluorobenzyl)-3-[(3-fluorobenzyl)amino]-2-hydroxypropylcarbamate |
| 161 | H₂N—CH₂-phenyl-3-O—CH(CH₃)₂ | tert-butyl (1S,2R)-1-(3,5-difluorobenzyl)-2-hydroxy-3-[(3-isopropoxybenzyl)amino]propylcarbamate |
| 162 | H₂N—CH₂-phenyl-3-Br | tert-butyl (1S,2R)-1-(3,5-difluorobenzyl)-3-[(3-bromobenzyl)amino]-2-hydroxypropylcarbamate |
| 163 | H₂N—CH₂-(5-methylfuran-2-yl) | tert-butyl (1S,2R)-1-(3,5-difluorobenzyl)-2-hydroxy-3-{[(5- |

-continued

| | Column A<br>C-terminal amine<br>EXA (VI) | Column B<br>Protected alcohol<br>(VII) |
|---|---|---|
| 164 | H₂N-(5-methoxytetralin-1-yl) | methyl-2-furyl)methyl]amino}propylcarbamate tert-butyl (1S,2R)-1-(3,5-difluorobenzyl)-2-hydroxy-3-[(5-methoxy-1,2,3,4-tetrahydro-1-naphthalenyl)amino]propylcarbamate |

Example 165 tert-Butyl-(1S, 2R)-3-azido-1-(3,5-difluorobenzyl)-2-hydroxypropylcarbamate (XII)

Sodium azide (0.22 g, 4 mmole) and ammonium chloride (2 eq) are added to tert-butyl (1S)-2-(3,5-difluorophenyl)-1-[(2S)-oxiranyl]ethylcarbamate (V, EXAMPLE 3, 0.6 g, 2 mmole). The reaction is heated to 75-80 degrees C. and stirred for 16 hours. The reaction is monitored by TLC to insure completion. The solvent is removed under reduced pressure. The concentrate is partitioned between ethyl acetate and water, the phases are separated and the organic phase is washed with bicarbonate and saline, dried over anhydrous sodium sulfate and concentrated to give the title compound, TLC (ethyl acetate/hexane) $R_f$=0.45; MS (MH⁺)=343.

Example 166

(2R, 3S)-3-amino-1-azido-4-(3,5-difluorophenyl)-2-butanol (XIV)

tert-Butyl-(1S, 2R)-3-azido-1-(3,5-difluorobenzyl)-2-hydroxypropylcarbamate (XII, EXAMPLE 165, 0.48 g, 1.41 mmole) is dissolved in dichloromethane (20 ml) to which trifluoroacetic acid (5 ml) is added. The reaction is stirred at 20-25 degrees C. for 16 hours and the solvent is removed under reduced pressure with heat. Ethyl acetate is added twice and evaporated twice to give the title compound as the trifluoroacetic acid salt which is used in the next reaction without further purification; MS (MH⁺)=242.

Example 167

N¹-[(1S,2R)-3-azido-1-(3,5-difluorobenzyl)-2-hydroxypropyl]5-methyl-N³,N³-dipropylisophthalamide (XV)

To (2R, 3S)-3-amino-1-azido-4-(3,5-difluorophenyl)-2-buta (XIV, EXAMPLE 166, 0.34 g, 1.4 mmole) in dichloromethane (20 ml) is added N,N-dipropylamidoisophthalic acid (IX, 0.53 g, 2 mmole), t-butyl alcohol (0.27 g, 2 mmole) and triethylamine (0.84 ml, 6 mmole) and ethyl-1-(3-dimethylaminopropyl)carbodiimide (0.58 g, 3 mmole). The mixture is stirred at 20-25 degrees C. for 16 hours. The reaction is monitored by TLC (methanol/dichloromethane, 20/80 +ethyl acetate/hexane, 50/50; $R_f$=0.76). When the reaction is complete as measured by TLC, the reaction mixture is partitioned between dichloromethane and water, washed with hydrochloric acid (0.5 N), bicarbonate, saline, dried over anhydrous sodium sulfate and the solvent is removed under reduced pressure with heat to produce a concentrate. The concentrate is column chouromatographed on silica gel to give the title compound; MS (MH⁺)=488.

Example 168

N¹-[(1S,2R)-3-amino-1-(3,5-difluorobenzyl)-2-hydroxypropyl]-5-methyl -N³,N³-dipropylisophthalamide acetic acid salt (XVI)

N¹-[(1S,2R)-3-azido-1-(3,5-difluorobenzyl)-2-hydroxypropyl]5-methyl -N³,N³-dipropylisophthalamide (XV, EXAMPLE 167, 0.3 9, 0.62 mmole) in ethyl acetate (20 ml) and acetic acid (5ml) is placed in a Parr pressure bottle. Palladium on carbon (10%, 5 g) is added and the mixture shaken under hydrogen at 50 psi for 2 hours. The mixture is filtered through a diatomaceous earth and the filtrate is concentrated to give the title compound; MS (MH⁺)=462.

Example 169

N¹-{(1S,2R)-1-(3,5-difluorobenzyl)-3-[(2-furylmethyl)amino]-2-hydroxypropyl}-5-methyl-N³,N³-dipropylisophthalamide (X)

N¹-[(1S,2R)-3-amino-1-(3,5-difluorobenzyl)-2-hydroxypropyl]-5-methyl-N³,N³-dipropylisophthalamide acetic acid salt (XVI, EXAMPLE 168, 76 mg, 0.146 mmol) is dissolved in absolute ethanol (2 mL). 3-Furaldehyde (20 microL, 0.231 mmol) and triethylamine (30 microL, 0.215 mmol) are added via syringe, with stirring at 20-25 degrees C. After 10 minutes, palladium on carbon 122 mg, 5 weight %) is added and the mixture placed under a hydrogen atmosphere (50 psi) and shaken for 20 minutes. The resulting mixture is then filtered through diatomaceous earth, with ethanol washings. The filtrate is purified by flash chromatography (2-10% methanol/methylene chloride) to give purified title compound, MS (MH⁺)=542.2.

Example 169a tert-butyl (1S,2R)-1-(3,5-difluorobenzyl)-3-{[(1S)-2-(ethylamino)-1-methyl-2-oxoethyl]amino}-2-hydroxypropylcarbamate (VII)

Following the general procedure of EXAMPLEs 4 and 14-164 and making non-critical variations and reacting tert-butyl (1S)-2-(3,5-difluorophenyl)-1-[(2S)-oxiranyl]ethylcarbamate (V, EXAMPLE 3) with (2S)-2-amino-N-ethylpropanamide (VI), the title compound is obtained.

Examples 170-320

Following the general procedure of EXAMPLE 5 and making non-critical variations but starting with the protected alcohol (VII) of Column A, the amine (VIII) of Column B is obtained.

| EXA | Column A Protected Alcohol (VII) Compound of EXAMPLE | Column B Amine (VIII) |
|---|---|---|
| 170 | 14 | (2R,3S)-3-amino-1-(ethylamino)-4-phenyl-2-butanol |
| 171 | 15 | (2R,3S)-3-amino-1-(benzylamino)-4-phenyl-2-butanol |
| 172 | 16 | (2R,3S)-3-amino-1-(isopropylamino)-4-phenyl-2-butanol |
| 173 | 17 | (2R,3S)-3-amino-1-[(4-methylbenzyl)amino]-4-phenyl-2-butanol |
| 174 | 18 | (2R,3S)-3-amino-1-{[2-(4-methoxyphenyl)ethyl]amino}-4-phenyl-2-butanol |
| 175 | 19 | (2R,3S)-3-amino-1-[(3-methoxybenzyl)amino]-4-phenyl-2-butanol |
| 176 | 20 | ethyl {[(2R,3S)-3-amino-2-hydroxy-4-phenylbutyl]amino}(phenyl)acetate |
| 177 | 21 | (2R,3S)-3-amino-4-phenyl-1-[(2-phenylethyl)amino]-2-butanol |
| 178 | 22 | (2S)-2-{[(2R,3S)-3-amino-2-hydroxy-4-phenylbutyl]amino}-1-(4-nitorphenyl)-1,3-propanediol |
| 179 | 23 | (2R,3S)-3-amino-1-[(2-chlorobenzyl)amino]-4-phenyl-2-butanol |
| 180 | 24 | (2R,3S)-3-amino-1-[(4-chlorobenzyl)amino]-4-phenyl-2-butanol |
| 181 | 25 | (2R,3S)-3-amino-1-{[2-(2-hydroxyethoxy)ethyl]amino}-4-phenyl-2-butanol |
| 182 | 26 | (2R,3S)-3-amino-1-(2,3-dihydro-1H-inden-1-ylamino)-4-phenyl-2-butanol |
| 183 | 27 | (2R,3S)-3-amino-1-[(2-hydroxypropyl)amino]-4-phenyl-2-butanol |
| 184 | 28 | (2R,3S)-3-amino-4-phenyl-1-[(tetrahydro-2-furanylmethyl)amino]-2-butanol |
| 185 | 29 | (2R,3S)-3-amino-1-[(2,2-diethoxyethyl)amino]-4-phenyl-2-butanol |
| 186 | 30 | (2R,3S)-3-amino-1-(butylamino)-4-phenyl-2-butanol |
| 187 | 31 | (2R,3S)-3-amino-1-(cyclohexylamino)-4-phenyl-2-butanol |
| 188 | 32 | (2R,3S)-3-amino-4-phenyl-1-[(2-pyridinylmethyl)amino]-2-butanol |
| 189 | 33 | (2R,3S)-3-amino-1-[(2-aminobenzyl)amino]-4-phenyl-2-butanol |
| 190 | 34 | (2R,3S)-3-amino-4-phenyl-1-[(3-pyridinylmethyl)amino]-2-butanol |
| 191 | 35 | (2R,3S)-3-amino-4-phenyl-1-{[2-(1-pyrrolidinyl)ethyl]amino}-2-butanol |
| 192 | 36 | (2R,3S)-3-amino-1-[(2-hydroxy-2-phenylethyl)amino]-4-phenyl-2-butanol |
| 193 | 37 | (2R,3S)-3-amino-1-[(3-butoxypropyl)amino]-4-phenyl-2-butanol |
| 194 | 38 | (2R,3S)-3-amino-1-[(3-isopropoxypropyl)amino]-4-phenyl-2-butanol |
| 195 | 39 | (2R,3S)-3-amino-1-(isopentylamino)-4-phenyl-2-butanol |
| 196 | 40 | (2R,3S)-3-amino-4-phenyl-1-[(3-phenylpropyl)amino]-2-butanol |
| 197 | 41 | (2R,3S)-3-amino-1-[(2-methoxyethyl)amino]-4-phenyl-2-butanol |
| 198 | 42 | (2R,3S)-3-amino-1-[(2-phenoxyethyl)amino]-4-phenyl-2-butanol |
| 199 | 43 | (2R,3S)-3-amino-4-phenyl-1-[(2-propoxyethyl)amino]-2-butanol |
| 200 | 44 | (2R,3S)-3-amino-1-[(3,3-dimethylbutyl)amino]-4-phenyl-2-butanol |
| 201 | 45 | (2R,3S)-3-amino-4-phenyl-1-[(4-phenylbutyl)amino]-2-butanol |
| 202 | 46 | (2R,3S)-3-amino-1-[(3-iodobenzyl)amino]-4-phenyl-2-butanol |
| 203 | 47 | (2R,3S)-3-amino-1-[(4-nitrobenzyl)amino]-4-phenyl-2-butanol |
| 204 | 48 | (2R,3S)-3-amino-1-[(3-chlorobenzyl)amino]-4-phenyl-2-butanol |
| 205 | 49 | (2R,3S)-3-amino-1-{[2-(4-chlorophenyl)ethyl]amino}-4-phenyl-2-butanol |
| 206 | 50 | (2R,3S)-3-amino-4-phenyl-1-{[2-(2-pyridinyl)ethyl]amino}-2-butanol |
| 207 | 51 | (2R,3S)-3-amino-4-phenyl-1-[(4-pyidinylmethyl)amino]-2-butanol |
| 208 | 52 | (2R,3S)-3-amino-1-{[2-(1-methyl-2-pyrrolidinyl)ethyl]amino}-4-phenyl-2-butanol |
| 209 | 53 | (2R,3S)-3-amino-1-[(2,3-dimethylbenzyl)amino]-4-phenyl-2-butanol |
| 210 | 54 | (2R,3S)-3-amino-4-phenyl-1-{[2-(trifluoromethoxy)benzyl]amino}-2-butanol |
| 211 | 55 | (2R,3S)-3-amino-1-[(2-chloro-6-phenoxybenzyl)amino]-4-phenyl-2-butanol |
| 212 | 56 | (2R,3S)-3-amino-4-phenyl-1-{[4-(trifluoromethyl)benzyl]amino}-2-butanol |
| 213 | 57 | (2R,3S)-3-amino-1-[(2,3-dichlorobenzyl)amino]-4-phenyl-2-butanol |
| 214 | 58 | (2R,3S)-3-amino-1-[(3,5-dichlorobenzyl)amino]-4-phenyl-2-butanol |
| 215 | 59 | (2R,3S)-3-amino-1-[(3,5-difluorobenzyl)amino]-4-phenyl-2-butanol |

-continued

| EXA | Column A Protected Alcohol (VII) Compound of EXAMPLE | Column B Amine (VIII) |
|---|---|---|
| 216 | 60 | (2R,3S)-3-amino-4-phenyl-1-{[4-(trifluoromethoxy)benzyl]amino}-2-butanol |
| 217 | 61 | 4-({[(2R,3S)-3-amino-2-hydroxy-4-phenylbutyl]amino}methyl)benzenesulfonamide |
| 218 | 62 | (2R,3S)-3-amino-1-[(4-methoxybenzyl)amino]-4-phenyl-2-butanol |
| 219 | 63 | (2R,3S)-3-amino-1-[(4-methylbenzyl)amino]-4-phenyl-2-butanol |
| 220 | 64 | (2R,3S)-3-amino-4-phenyl-1-[(3,4,5-trimethoxybenzyl)amino]-2-butanol |
| 221 | 65 | (2R,3S)-3-amino-4-phenyl-1-{[3-(trifluoromethoxy)benzyl]amino}-2-butanol |
| 222 | 66 | (2R,3S)-3-amino-1-[(3,5-dimethoxybenzyl)amino]-4-phenyl-2-butanol |
| 223 | 67 | (2R,3S)-3-amino-1-[(2,4-dimethoxybenzyl)amino]-4-phenyl-2-butanol |
| 224 | 68 | (2R,3S)-3-amino-1-[([1,1'-biphenyl]-3-ylmethyl)amino]-4-phenyl-2-butanol |
| 225 | 69 | (2R,3S)-3-amino-1-[(3,4-dichlorobenzyl)amino]-4-phenyl-2-butanol |
| 226 | 70 | (2R,3S)-3-amino-1-[(2-fluorobenzyl)amino]-4-phenyl-2-butanol |
| 227 | 71 | (2R,3S)-3-amino-4-phenyl-1-{[3-(trifluoromethyl)benzyl]amino}-2-butanol |
| 228 | 72 | (2R,3S)-3-amino-1-[(2-methylbenzyl)amino]-4-phenyl-2-butanol |
| 229 | 73 | (2R,3S)-3-amino-4-phenyl-1-{[(1R)-1-phenylethyl]amino}-2-butanol |
| 230 | 74 | (2R,3S)-3-amino-4-phenyl-1-{[(1S)-1-phenylethyl]amino}-2-butanol |
| 231 | 75 | (2R,3S)-3-amino-1-{[3,5-bis(trifluoromethyl)benzyl]amino}-4-phenyl-2-butanol |
| 232 | 76 | (2R,3S)-3-amino-4-phenyl-1-{[2-(trifluoromethyl)benzyl]amino}-2-butanol |
| 233 | 77 | (2R,3S)-3-amino-1-{[(1S)-1-(1-naphthyl)ethyl]amino}-4-phenyl-2-butanol |
| 234 | 78 | (2R,3S)-3-amino-1-{[(1R)-1-(1-naphthyl)ethyl]amino}-4-phenyl-2-butanol |
| 235 | 79 | 4-({[(2R,3S)-3-amino-2-hydroxy-4-phenylbutyl]amino}methyl)-2-methoxyphenol |
| 236 | 80 | 4-({[(2R,3S)-3-amino-2-hydroxy-4-phenylbutyl]amino}methyl)-1,2-benzenediol |
| 237 | 81 | (2R,3S)-3-amino-1-[(3-methoxypropyl)amino]-4-phenyl-2-butanol |
| 238 | 82 | (2R,3S)-3-amino-1-{[(1S)-2-hydroxy-1-methylethyl]amino}-4-phenyl-2-butanol |
| 239 | 83 | (2R,3S)-3-amino-1-{[(1R)-2-hydroxy-1-methylethyl]amino}-4-phenyl-2-butanol |
| 240 | 84 | (2R,3S)-3-amino-4-phenyl-1-(2-propynylamino)-2-butanol |
| 241 | 85 | (2R,3S)-3-amino-1-{[2-(2-fluorophenyl)ethyl]amino}-4-phenyl-2-butanol |
| 242 | 86 | (2R,3S)-3-amino-1-{[2-(3-fluorophenyl)ethyl]amino}-4-phenyl-2-butanol |
| 243 | 87 | (2R,3S)-3-amino-1-{[2-(4-fluorophenyl)ethyl]amino}-4-phenyl-2-butanol |
| 244 | 88 | (2R,3S)-3-amino-1-{[2-(4-bromophenyl)ethyl]amino}-4-phenyl-2-butanol |
| 245 | 89 | (2R,3S)-3-amino-1-{[2-(3-methoxyphenyl)ethyl]amino}-4-phenyl-2-butanol |
| 246 | 90 | (2R,3S)-3-amino-1-{[2-(2,4-dichlorophenyl)ethyl]amino}-4-phenyl-2-butanol |
| 247 | 91 | (2R,3S)-3-amino-1-{[2-(3-chlorophenyl)ethyl]amino}-4-phenyl-2-butanol |
| 248 | 92 | (2R,3S)-3-amino-1-{[2-(2,5-dimethoxyphenyl)ethyl]amino}-4-phenyl-2-butanol |
| 249 | 93 | (2R,3S)-3-amino-1-{[2-(4-methylphenyl)ethyl]amino}-4-phenyl-2-butanol |
| 250 | 94 | (2R,3S)-3-amino-1-{[(1R)-1-benzyl-2-hydroxyethyl]amino}-4-phenyl-2-butanol |
| 251 | 95 | (2R,3S)-3-amino-1-{[3-(4-morpholinyl)propyl]amino}-4-phenyl-2-butanol |
| 252 | 96 | (2R,3S)-3-amino-1-(isobutylamino)-4-phenyl-2-butanol |
| 253 | 97 | (2R,3S)-3-amino-1-{[2-(4-morpholinyl)ethyl]amino}-4-phenyl-2-butanol |
| 254 | 98 | (2R,3S)-3-amino-4-phenyl-1-[(2-hydroxybutyl)amino]-2-butanol |
| 255 | 99 | (2R,3S)-3-amino-4-phenyl-1-{[2-(2-thienyl)ethyl]amino}-2-butanol |
| 256 | 100 | 4-{[(2R,3S)-3-amino-2-hydroxy-4-phenylbutyl]amino}-1-butanol |
| 257 | 101 | (2R,3S)-3-amino-1-{[(1S)-2-hydroxy-1-phenylethyl]amino}-4-phenyl-2-butanol |
| 258 | 102 | (2R,3S)-3-amino-1-[(2,4-dichlorobenzyl)amino]-4-phenyl-2-butanol |
| 259 | 103 | (2R,3S)-3-amino-1-{[(1R)-2-hydroxy-1-phenylethyl]amino}-4-phenyl-2-butanol |
| 260 | 104 | (2R,3S)-3-amino-1-[(4-tert-butylbenzyl)amino]-4-phenyl-2-butanol |
| 261 | 105 | (2R,3S)-3-amino-4-phenyl-1-[(1-phenylethyl)amino]-2-butanol |
| 262 | 106 | (1R,2S)-1-{[(2R,3S)-3-amino-2-hydroxy-4-phenylbutyl]amino}-2,3-dihydro-1H-inden-2-ol |
| 263 | 107 | (2R,3S)-3-amino-1-[(3,4-dimethylbenzyl)amino]-4-phenyl-2-butanol |

| EXA | Column A Protected Alcohol (VII) Compound of EXAMPLE | Column B Amine (VIII) |
|---|---|---|
| 264 | 108 | methyl 7-{[(2R,3S)-3-amino-4-(3,5-difluorophenyl)-2-hydroxybutyl]amino}heptanoate |
| 265 | 109 | 2-{[(2R,3S)-3-amino-4-(3,5-difluorophenyl)-2-hydroxybutyl]amino}-N-isobutylpropanamide |
| 266 | 110 | (2S)-2-{[(2R,3S)-3-amino-4-(3,5-difluorophenyl)-2-hydroxybutyl]amino}-N-isobutylpropanamide |
| 267 | 111 | 2-{[(2R,3S)-3-amino-4-(3,5-difluorophenyl)-2-hydroxybutyl]amino}-N-isobutyl-2-methylpropanamide |
| 268 | 112 | 2-{[(2R,3S)-3-amino-4-(3,5-difluorophenyl)-2-hydroxybutyl]amino}-N-isobutylacetamide |
| 269 | 113 | (2S)-2-{[(2R,3S)-3-amino-4-(3,5-difluorophenyl)-2-hydroxybutyl]amino}-N-isobutylbutanamide |
| 270 | 114 | (2R)-2-{[(2R,3S)-3-amino-4-(3,5-difluorophenyl)-2-hydroxybutyl]amino}-N-isobutylbutanamide |
| 271 | 115 | (2R,3S)-3-amino-1-(benzylamino)-4-(3,5-difluorophenyl)-2-butanol |
| 272 | 116 | (2R,3S)-3-amino-4-(3,5-difluorophenyl)-1-(ethylamino)-2-butanol |
| 273 | 117 | (2R,3S)-3-amino-4-(3,5-difluorophenyl)-1-(isobutylamino)-2-butanol |
| 274 | 118 | 3-{[(2R,3S)-3-amino-4-(3,5-difluorophenyl)-2-hydroxybutyl]amino}-N-isobutyl-2-methylpropanamide |
| 275 | 119 | (2R,3S)-3-amino-4-(3,5-difluorophenyl)-1-{[4-(dimethylamino)benzyl]amino}-2-butanol |
| 276 | 120 | (2S)-2-{[(2R,3S)-3-amino-4-(3,5-difluorophenyl)-2-hydroxybutyl]amino}-N-isobutyl-3-phenylpropanamide |
| 277 | 121 | (2S)-2-{[(2R,3S)-3-amino-4-(3,5-difluorophenyl)-2-hydroxybutyl]amino}-N-isobutyl-3-methylbutanamide |
| 278 | 122 | (2R,3S)-3-amino-4-(3,5-difluorophenyl)-1-{[2-(dimethylamino)ethyl]amino}-2-butanol |
| 279 | 123 | (2R,3S)-3-amino-4-(3,5-difluorophenyl)-1-[(3-pyridinylmethyl)amino]-2-butanol |
| 280 | 124 | (2S)-2-{[(2R,3S)-3-amino-4-(3,5-difluorophenyl)-2-hydroxybutyl]amino}-3-(benzyloxy)-N-isobutylpropanamide |
| 281 | 125 | (2R,3S)-3-amino-4-(3,5-difluorophenyl)-1-[(1-methyl-1-phenylethyl)amino]-2-butanol |
| 282 | 126 | (2R)-2-{[(2R,3S)-3-amino-4-(3,5-difluorophenyl)-2-hydroxybutyl]amino}-N-isobutyl-3-methylbutanamide |
| 283 | 127 | (2S)-2-{[(2R,3S)-3-amino-4-(3,5-difluorophenyl)-2-hydroxybutyl]amino}-N-isobutylpentanamide |
| 284 | 128 | (2S)-2-{[(2R,3S)-3-amino-4-(3,5-difluorophenyl)-2-hydroxybutyl]amino}-3-hydroxy-N-isobutylpropanamide |
| 285 | 129 | (2R,3S)-3-amino-4-(3,5-difluorophenyl)-1-[(2-phenylethyl)amino]-2-butanol |
| 286 | 130 | (2S)-2-{[(2R,3S)-3-amino-4-(3,5-difluorophenyl)-2-hydroxybutyl]amino}-N-benzylpropanamide |
| 287 | 131 | (2R,3S)-3-amino-4-(3,5-difluorophenyl)-1-{[(1S)-1-phenylpropyl]amino}-2-butanol |
| 287a | 169a | (2S)-2-{[(2R,3S)-3-amino-4-(3,5-difluorophenyl)-2-hydroxybutyl]amino}-N-ethylpropanamide |
| 288 | 132 | (2R,3S)-3-amino-4-(3,5-difluorophenyl)-1-[(3-methoxybenzyl)amino]-2-butanol |
| 289 | 133 | (2S)-2-{[(2R,3S)-3-amino-4-(3,5-difluorophenyl)-2-hydroxybutyl]amino}-N-isobutyl-2-phenylethanamide |
| 290 | 134 | (2R,3S)-3-amino-4-(3,5-difluorophenyl)-1-(isopentylamino)-2-butanol |
| 291 | 135 | (2R,3S)-3-amino-1-(cyclohexylamino)-4-(3,5-difluorophenyl)-2-butanol |
| 292 | 136 | (2R,3S)-3-amino-1-(butylamino)-4-(3,5-difluorophenyl)-2-butanol |
| 293 | 137 | (2R,3S)-3-amino-4-(3,5-difluorophenyl)-1-[(3-methoxypropyl)amino]-2-butanol |
| 294 | 138 | (2R,3S)-3-amino-4-(3,5-difluorophenyl)-1-[(2-hydroxy-2-phenylethyl)amino]-2-butanol |
| 295 | 139 | (2R,3S)-3-amino-4-(3,5-difluorophenyl)-1-{[(3R,5S)-3,5-dimethoxycyclohexyl]amino}-2-butanol |
| 296 | 140 | dimethyl (1R,3S)-5-{[(2R,3S)-3-amino-4-(3,5-difluorophenyl)-2-hydroxybutyl]amino}-1,3-cyclohexanedicarboxylate |
| 297 | 141 | (1R,3S)-5-{[(2R,3S)-3-amino-4-(3,5-difluorophenyl)-2-hydroxybutyl]amino}-1,3-cyclohexanedicarboxylic acid |
| 298 | 142 | (2R,3S)-3-amino-4-(3,5-difluorophenyl)-1-{[(1R)-1-phenylpropyl]amino}-2-butanol |
| 299 | 143 | (2R,3S)-3-amino-1-[(3-chlorobenzyl)amino]-4-(3,5-difluorophenyl)-2-butanol |
| 300 | 144 | (2R,3S)-3-amino-4-(3,5-difluorophenyl)-1-[(3-methoxybenzyl)amino]-2-butanol |
| 301 | 145 | (2R,3S)-3-amino-1-[([1,1'-biphenyl]-3-ylmethyl)amino]-4-(3,5-difluorophenyl)-2-butanol |
| 302 | 146 | (2R,3S)-3-amino-4-(3,5-difluorophenyl)-1-[(3-iodobenzyl)amino]-2-butanol |

-continued

| EXA | Column A Protected Alcohol (VII) Compound of EXAMPLE | Column B Amine (VIII) |
|---|---|---|
| 303 | 147 | (2R,3S)-3-amino-4-(3,5-difluorophenyl)-1-[(3-methylbenzyl)amino]-2-butanol |
| 304 | 148 | (2R,3S)-3-amino-4-(3,5-difluorophenyl)-1-[(2-phenylpropyl)amino]-2-butanol |
| 305 | 149 | (2R,3S)-3-amino-4-(3,5-difluorophenyl)-1-[(1,3-thiazol-5-ylmethyl)amino]-2-butanol |
| 306 | 150 | (2R,3S)-3-amino-4-(3,5-difluorophenyl)-1-[(2-thienylmethyl)amino]-2-butanol |
| 307 | 151 | (2R,3S)-3-amino-4-(3,5-difluorophenyl)-1-[(5-methoxy-1,2,3,4-tetrahydro-1-naphthalenyl)amino]-2-butanol |
| 308 | 152 | (2R,3S)-3-amino-4-(3,5-difluorophenyl)-1-[(2-pyrazinylmethyl)amino]-2-butanol |
| 309 | 153 | (2R,3S)-3-amino-1-[(3,5-difluorobenzyl)amino]-4-(3,5-difluorophenyl)-2-butanol |
| 310 | 154 | (2R,3S)-3-amino-1-[(1,3-benzodioxol-5-ylmethyl)amino]-4-(3,5-difluorophenyl)-2-butanol |
| 311 | 155 | (2R,3S)-3-amino-4-(3,5-difluorophenyl)-1-[(3,5-dimethoxybenzyl)amino]-2-butanol |
| 312 | 156 | (2R,3S)-3-amino-4-(3,5-difluorophenyl)-1-{[3-(trifluoromethyl)benzyl]amino}-2-butanol |
| 313 | 157 | (2R,3S)-3-amino-4-(3,5-difluorophenyl)-1-[(2-furylmethyl)amino]-2-butanol |
| 314 | 158 | (2R,3S)-3-amino-4-(3,5-difluorophenyl)-1-[(7-methoxy-1,2,3,4-tetrahydro-1-naphthalenyl)amino]-2-butanol |
| 315 | 159 | (2R,3S)-3-amino-4-(3,5-difluorophenyl)-1-{[3-(trifluoromethoxy)benzyl]amino}-2-butanol |
| 316 | 160 | (2R,3S)-3-amino-4-(3,5-difluorophenyl)-1-[(3-fluorobenzyl)amino]-2-butanol |
| 317 | 161 | (2R,3S)-3-amino-4-(3,5-difluorophenyl)-1-[(3-isopropoxybenzyl)amino]-2-butanol |
| 318 | 162 | (2R,3S)-3-amino-1-[(3-bromobenzyl)amino]-4-(3,5-difluorophenyl)-2-butanol |
| 319 | 163 | (2R,3S)-3-amino-4-(3,5-difluorophenyl)-1-[(5-methyl-2-furylmethyl)amino]-2-butanol |
| 320 | 164 | (2R,3S)-3-amino-4-(3,5-difluorophenyl)-1-[(5-methoxy-1,2,3,4-tetrahydro-1-naphthalenyl)amino]-2-butanol |

Examples 321-473

Following the general procedure of EXAMPLE 6 and making non-critical variations but starting with the amine (VIII) of Column A and reacting it with the amide forming agent (IX) of Column B, the substituted amine (X) of Column C is obtained.

| EXA | Column A Amine (VIII) Compound of EXA | Column B Amide Forming Agent (IX) | Column C Substitued amine (X) | Column D Physical Data |
|---|---|---|---|---|
| 321 | 170 | "PHTH" | $N^1$-[(1S,2R)-1-benzyl-3-(ethylamino)-2-hydroxypropyl]-$N^3,N^3$-dipropylisophthalamide | $MH^+$ = 440.7 |
| 322 | 171 | "PHTH" | $N^1$-[(1S,2R)-1-benzyl-3-(benzylamino)-2-hydroxypropyl]-$N^3,N^3$-dipropylisophthalamide | MH+ = 502.7 |
| 323 | 172 | "PHTH" | $N^1$-[(1S,2R)-1-benzyl-2-hydroxy-3-(isopropylamino)propyl]-$N^3,N^3$-dipropylisophthalamide | MH+ = 454.6 |
| 324 | 173 | "PHTH" | $N^1$-[(1S,2R)-1-benzyl-2-hydroxy-3-(4-toluidino)propyl]-$N^3,N^3$-dipropylisophthalamide | MH+ = 502.2 |
| 325 | 174 | "PHTH" | $N^1$-((1S,2R)-1-benzyl-2-hydroxy-3-{2-(4-methoxyphenyl)ethyl]amino}propyl)-$N^3,N^3$-dipropylisophthalamide | MH+ = 546 |

-continued

| EXA | Column A Amine (VIII) Compound of EXA | Column B Amide Forming Agent (IX) | Column C Substitued amine (X) | Column D Physical Data |
|---|---|---|---|---|
| 326 | 175 | "PHTH" | $N^1$-{(1S,2R)-1-benzyl-2-hydroxy-3-[(3-methoxybenzyl)amino]propyl}-$N^3,N^3$-dipropylisophthalamide | MH+ = 532 |
| 327 | 176 | "PHTH" | ethyl {[(3S)-3-({3-[(dipropylamino)carbonyl]benzoyl}amino)-2-hydroxy-4-phenylbutyl]amino}(phenyl)acetate | MH+ = 574 |
| 329 | 178 | "PHTH" | $N^1$-((1S)-1-benzyl-2-hydroxy-3-{[(1S)-2-hydroxy-1-(hydroxymethyl)-2-(4-nitrophenyl)ethyl]amino}propyl)-$N^3,N^3$-dipropylisophthalamide | MH+ = 607 |
| 330 | 179 | "PHTH" | $N^1$-{(1S,2R)-1-benzyl-3-[(2-chlorobenzyl)amino]-2-hydroxypropyl}-$N^3,N^3$-dipropylisophthalamide | MH+ = 537 |
| 331 | 180 | "PHTH" | $N^1$-{(1S,2R)-1-benzyl-3-[(4-chlorobenzyl)amino]-2-hydroxypropyl}-$N^3,N^3$-dipropylisophthalamide | MH+ = 537 |
| 332 | 181 | "PHTH" | $N^1$-((1S,2R)-1-benzyl-2-hydroxy-3-{[2-(2-hydroxyethoxy)ethyl]amino}propyl)-$N^3,N^3$-dipropylisophthalamide | MH+ = 500 |
| 333 | 182 | "PHTH" | $N^1$-[(1S,2R)-1-benzyl-3-(2,3-dihydro-1H-inden-1-ylamino)-2-hydroxypropyl]-$N^3,N^3$-dipropylisophthalamide | MH+ = 528 |
| 334 | 183 | "PHTH" | $N^1$-{(1S,2R)-1-benzyl-2-hydroxy-3-[(2-hydroxypropyl)amino]propyl}-$N^3,N^3$-dipropylisophthalamide | MH+ = 470 |
| 335 | 184 | "PHTH" | $N^1$-{(1S,2R)-1-benzyl-2-hydroxy-3-[(tetrahydro-2-furanylmethyl)amino]propyl}-$N^3,N^3$-dipropylisophthalamide | MH+ = 496 |
| 336 | 185 | "PHTH" | $N^1$-{(1S,2R)-1-benzyl-3-[(2,2-diethoxyethyl)amino]-2-hydroxypropyl}-$N^3,N^3$-dipropylisophthalamide | MH+ = 528 |
| 337 | 186 | "PHTH" | $N^1$-[(1S,2R)-1-benzyl-3-(butylamino)-2-hydroxypropyl]-$N^3,N^3$-dipropylisophthalamide | MH+ = 468 |
| 338 | 187 | "PHTH" | $N^1$-[(1S,2R)-1-benzyl-3-(cyclohexylamino)-2-hydroxypropyl]-$N^3,N^3$-dipropylisophthalamide | MH+ = 494 |
| 339 | 188 | "PHTH" | $N^1$-{(1S,2R)-1-benzyl-2-hydroxy-3-[(2-pyridinylmethyl)amino]propyl}-$N^3,N^3$-dipropylisophthalamide | MH+ = 507 |
| 340 | 189 | "PHTH" | $N^1$-{(1S,2R)-3-[(2-aminobenzyl)amino]-1-benzyl-2-hydroxypropyl}-$N^3,N^3$-dipropylisophthalamide | MH+ = 517 |
| 341 | 190 | "PHTH" | $N^1$-{(1S,2R)-1-benzyl-2-hydroxy-3-[(3-pyridinylmethyl)amino]propyl}- | MH+ = 503 |

| EXA | Column A Amine (VIII) Compound of EXA | Column B Amide Forming Agent (IX) | Column C Substitued amine (X) | Column D Physical Data |
|---|---|---|---|---|
| 342 | 191 | "PHTH" | $N^3,N^3$-dipropylisophthalamide $N^1$-((1S,2R)-1-benzyl-2-hydroxy-3-{[2-(1-pyrrolidinyl)ethyl]amino} propyl)-$N^3,N^3$-dipropylisophthalamide | MH+ = 509 |
| 343 | 192 | "PHTH" | $N^1$-{(1S,2R)-1-benzyl-2-hydroxy-3-[(2-hydroxy-2-phenylethyl)amino]propyl}-$N^3,N^3$-dipropylisophthalamide | MH+ = 532 |
| 344 | 193 | "PHTH" | $N^1$-{(1S,2R)-1-benzyl-3-[(3-butoxypropyl)amino]-2-hydroxypropyl}-$N^3,N^3$-dipropylisophthalamide | MH+ = 526 |
| 345 | 194 | "PHTH" | $N^1$-{(1S,2R)-1-benzyl-2-hydroxy-3-[(3-isopropoxypropyl)amino]propyl}-$N^3,N^3$-dipropylisophthalamide | MH+ = 512 |
| 346 | 195 | "PHTH" | $N^1$-[(1S,2R)-1-benzyl-2-hydroxy-3-(isopentylamino)propyl]-$N^3,N^3$-dipropylisophthalamide | MH+ = 482 |
| 347 | 196 | "PHTH" | $N^1$-{(1S,2R)-1-benzyl-2-hydroxy-3-[(3-phenylpropyl)amino]propyl}-$N^3,N^3$-dipropylisophthalamide | MH+ = 530 |
| 348 | 197 | "PHTH" | $N^1$-{(1S,2R)-1-benzyl-2-hydroxy-3-[(2-methoxyethyl)amino]propyl}-$N^3,N^3$-dipropylisophthalamide | MH+ = 470 |
| 349 | 198 | "PHTH" | $N^1$-{(1S,2R)-1-benzyl-2-hydroxy-3-[(2-phenoxyethyl)amino]propyl}-$N^3,N^3$-dipropylisophthalamide | MH+ = 532 |
| 350 | 199 | "PHTH" | $N^1$-{(1S,2R)-1-benzyl-2-hydroxy-3-[(2-propoxyethyl)amino]propyl}-$N^3,N^3$-dipropylisophthalamide | MH+ = 498 |
| 351 | 200 | "PHTH" | $N^1$-{(1S,2R)-1-benzyl-3-[(3,3-dimethylbutyl)amino]-2-hydroxypropyl}-$N^3,N^3$-dipropylisophthalamide | MH+ = 496 |
| 352 | 201 | "PHTH" | $N^1$-{(1S,2R)-1-benzyl-2-hydroxy-3-[(4-phenylbutyl)amino]propyl}-$N^3,N^3$-dipropylisophthalamide | MH+ = 544 |
| 353 | 202 | "PHTH" | $N^1$-{(1S,2R)-1-benzyl-2-hydroxy-3-[(3-iodobenzyl)amino]propyl}-$N^3,N^3$-dipropylisophthalamide | MH+ = 628 |
| 354 | 203 | "PHTH" | $N^1$-{(1S)-1-benzyl-2-hydroxy-3-[(4-nitrobenzyl)amino]propyl}-$N^3,N^3$-dipropylisophthalamide | MH+ = 547 |
| 355 | 204 | "PHTH" | $N^1$-{(1S,2R)-1-benzyl-3-[(3-chlorobenzyl)amino]-2-hydroxypropyl}-$N^3,N^3$-dipropylisophthalamide | MH+ = 537 |
| 356 | 205 | "PHTH" | $N^1$-((1S,2R)-1-benzyl-3-{[2-(4- | MH+ = 551 |

| EXA | Column A Amine (VIII) Compound of EXA | Column B Amide Forming Agent (IX) | Column C Substitued amine (X) | Column D Physical Data |
|---|---|---|---|---|
| | | | chlorophenyl)ethyl]amino}-2-hydroxypropyl)-N$^3$,N$^3$-dipropylisophthalamide | |
| 357 | 206 | "PHTH" | N$^1$-((1S,2R)-1-benzyl-2-hydroxy-3-{[2-(2-pyridinyl)ethyl]amino}propyl)-N$^3$,N$^3$-dipropylisophthalamide | MH+ = 517 |
| 358 | 207 | "PHTH" | N$^1$-{(1S,2R)-1-benzyl-2-hydroxy-3-[(4-pyridinylmethyl)amino]propyl}-N$^3$,N$^3$-dipropylisophthalamide | MH$^+$ = 503 |
| 359 | 208 | "PHTH" | N$^1$-((1S,2R)-1-benzyl-2-hydroxy-3-{[2-(1-methyl-2-pyrrolidinyl)ethyl]amino}propyl)-N$^3$,N$^3$-dipropylisophthalamide | MH+ = 523 |
| 360 | 209 | "PHTH" | N$^1$-{(1S,2R)-1-benzyl-3-[(2,3-dimethylbenzyl)amino]-2-hydroxypropyl}-N$^3$,N$^3$-dipropylisophthalamide | MH+ = 580 |
| 361 | 210 | "PHTH" | N$^1$-((1S,2R)-1-benzyl-2-hydroxy-3-{[2-(trifluoromethoxy)benzyl]amino}propyl)-N$^3$,N$^3$-dipropylisophthalamide | MH+ = 586 |
| 362 | 211 | "PHTH" | N$^1$-{(1S,2R)-1-benzyl-3-[(2-chloro-6-phenoxybenzyl)amino]-2-hydroxypropyl}-N$^3$,N$^3$-dipropylisophthalamide | MH+ = 629 |
| 363 | 212 | "PHTH" | N$^1$-((1S,2R)-1-benzyl-2-hydroxy-3-{[4-(trifluoromethyl)benzyl]amino}propyl)-N$^3$,N$^3$-dipropylisophthalamide | MH+ = 570 |
| 364 | 213 | "PHTH" | N$^1$-{(1S,2R)-1-benzyl-3-[(2,3-dichlorobenzyl)amino]-2-hydroxypropyl}-N$^3$,N$^3$-dipropylisophthalamide | MH+ = 571 |
| 365 | 214 | "PHTH" | N$^1$-{(1S,2R)-1-benzyl-3-[(3,5-dichlorobenzyl)amino]-2-hydroxypropyl}-N$^3$,N$^3$-dipropylisophthalamide | MH+ = 571 |
| 366 | 215 | "PHTH" | N$^1$-{(1S,2R)-1-benzyl-3-[(3,5-difluorobenzyl)amino]-2-hydroxypropyl}-N$^3$,N$^3$-dipropylisophthalamide | MH+ = 538 |
| 367 | 216 | "PHTH" | N$^1$-((1S,2R)-1-benzyl-2-hydroxy-3-{[4-(trifluoromethoxy)benzyl]amino}propyl)-N$^3$,N$^3$-dipropylisophthalamide | MH+ = 586 |
| 368 | 217 | "PHTH" | N$^1$-[(1S,2R)-3-({2-[4-(aminosulfonyl)phenyl]ethyl}amino)-1-benzyl-2-hydroxypropyl]-N$^3$,N$^3$-dipropylisophthalamide | MH+ = 595 |
| 369 | 218 | "PHTH" | N$^1$-{(1S,2R)-1-benzyl-2-hydroxy-3-[(4-methoxybenzyl)amino]propyl}-N$^3$,N$^3$-dipropylisophthalamide | MH+ = 532 |
| 370 | 219 | "PHTH" | N$^1$-{(1S,2R)-1-benzyl-2-hydroxy-3-[(4- | MH+ = 516 |

-continued

| EXA | Column A Amine (VIII) Compound of EXA | Column B Amide Forming Agent (IX) | Column C Substitued amine (X) | Column D Physical Data |
|---|---|---|---|---|
| 371 | 220 | "PHTH" | N$^1$-{(1S,2R)-1-benzyl-2-hydroxy-3-[(3,4,5-trimethoxybenzyl)amino]propyl}-N$^3$,N$^3$-dipropylisophthalamide methylbenzyl)amino]propyl}-N$^3$,N$^3$-dipropylisophthalamide | MH+ = 592 |
| 372 | 221 | "PHTH" | N$^1$-((1S,2R)-1-benzyl-2-hydroxy-3-{[3-(trifluoromethoxy)benzyl]amino} propyl)-N$^3$,N$^3$-dipropylisophthalamide | MH+ = 586 |
| 373 | 222 | "PHTH" | N$^1$-{(1S,2R)-1-benzyl-3-[(3,5-dimethoxybenzyl)amino]-2-hydroxypropyl}-N$^3$,N$^3$-dipropylisophthalamide | MH+ = 562 |
| 374 | 223 | "PHTH" | N$^1$-{(1S,2R)-1-benzyl-3-[(2,4-dimethoxybenzyl)amino]-2-hydroxypropyl}-N$^3$,N$^3$-dipropylisophthalamide | MH$^+$ = 562 |
| 375 | 224 | "PHTH" | N$^1$-{(1S,2R)-1-benzyl-3-[([1,1'-biphenyl]-3-ylmethyl)amino]-2-hydroxypropyl}-N$^3$,N$^3$-dipropylisophthalamide | MH+ = 578 |
| 376 | 225 | "PHTH" | N$^1$-{(1S,2R)-1-benzyl-3-[(3,4-dichlorobenzyl)amino]-2-hydroxypropyl}-N$^3$,N$^3$-dipropylisophthalamide | MH+ = 571 |
| 377 | 226 | "PHTH" | N$^1$-{(1S,2R)-1-benzyl-3-[(2-fluorobenzyl)amino]-2-hydroxypropyl}-N$^3$,N$^3$-dipropylisophthalamide | MH+ = 520 |
| 378 | 227 | "PHTH" | N$^1$-((1S,2R)-1-benzyl-2-hydroxy-3-{[3-(trifluoromethyl)benzyl]amino} propyl)-N$^3$,N$^3$-dipropylisophthalamide | MH+ = 570 |
| 379 | 228 | "PHTH" | N$^1$-{(1S,2R)-1-benzyl-2-hydroxy-3-[(2-methylbenzyl)amino]propyl}-N$^3$,N$^3$-dipropylisophthalamide | MH+ = 516 |
| 380 | 229 | "PHTH" | N$^1$-((1S,2R)-1-benzyl-2-hydroxy-3-{[(1R)-1-phenylethyl]amino}propyl)-N$^3$,N$^3$-dipropylisophthalamide | MH+ = 516 |
| 381 | 230 | "PHTH" | N$^1$-((1S,2R)-1-benzyl-2-hydroxy-3-{[(1S)-1-phenylethyl]amino}propyl)-N$^3$,N$^3$-dipropylisophthalamide | MH+ = 516 |
| 382 | 231 | "PHTH" | N$^1$-((1S,2R)-1-benzyl-3-{[3,5-bis(trifluoromethyl)benzyl]amino}-2-hydroxypropyl)-N$^3$,N$^3$-dipropylisophthalamide | MH+ = 638 |
| 383 | 232 | "PHTH" | N$^1$-((1S,2R)-1-benzyl-2-hydroxy-3-{[2-(trifluoromethyl)benzyl]amino} propyl)-N$^3$,N$^3$-dipropylisophthalamide | MH+ = 570 |
| 384 | 233 | "PHTH" | N$^1$-((1S,2R)-1-benzyl-2-hydroxy-3-{[(1S)-1-(1-naphthyl)ethyl]amino}propyl)- | MH+ = 566 |

| EXA | Column A Amine (VIII) Compound of EXA | Column B Amide Forming Agent (IX) | Column C Substitued amine (X) | Column D Physical Data |
|---|---|---|---|---|
| 385 | 234 | "PHTH" | N³,N³-dipropylisophthalamide N¹-((1S,2R)-1-benzyl-2-hydroxy-3-{[(1R)-1-(1-naphthyl)ethyl]amino}propyl)- | MH+ = 566 |
| 386 | 235 | "PHTH" | N³,N³-dipropylisophthalamide N¹-{(1S,2R)-1-benzyl-2-hydroxy-3-[(4-hydroxy-3-methoxybenzyl)amino]propyl}- | MH+ = 548 |
| 387 | 236 | "PHTH" | N³,N³-dipropylisophthalamide N¹-{(1S,2R)-1-benzyl-3-[(3,4-dihydroxybenzyl)amino]-2-hydroxypropyl}-N³,N³-dipropylisophthalamide | MH+ = 534 |
| 388 | 237 | "PHTH" | N¹-{(1S)-1-benzyl-2-hydroxy-3-[(3-methoxypropyl)amino]propyl}-N³,N³-dipropylisophthalamide | MH+ = 484 |
| 389 | 238 | "PHTH" | N¹-((1S,2R)-1-benzyl-2-hydroxy-3-{[(1S)-2-hydroxy-1-methylethyl]amino}propyl)-N³,N³-dipropylisophthalamide | MH+ = 470 |
| 390 | 239 | "PHTH" | N¹-((1S,2R)-1-benzyl-2-hydroxy-3-{[(1R)-2-hydroxy-1-methylethyl]amino}propyl)-N³,N³-dipropylisophthalamide | MH+ = 470 |
| 391 | 240 | "PHTH" | N¹-[(1S,2R)-1-benzyl-2-hydroxy-3-(2-propynylamino)propyl]-N³,N³-dipropylisophthalamide | MH+ = 450 |
| 392 | 241 | "PHTH" | N¹-((1S,2R)-1-benzyl-3-{[2-(2-fluorophenyl)ethyl]amino}-2-hydroxypropyl)-N³,N³-dipropylisophthalamide | MH+ = 534 |
| 393 | 242 | "PHTH" | N¹-((1S,2R)-1-benzyl-3-{[2-(3-fluorophenyl)ethyl]amino}-2-hydroxypropyl)-N³,N³-dipropylisophthalamide | MH+ = 534 |
| 394 | 243 | "PHTH" | N¹-(1S,2R)-1-benzyl-3-{[2-(4-fluorophenyl)ethyl]amino}-2-hydroxypropyl)-N³,N³-dipropylisophthalamide | MH+ = 534 |
| 395 | 244 | "PHTH" | N¹-((1S,2R)-1-benzyl-3-{[2-(4-bromophenyl)ethyl]amino}-2-hydroxypropyl)-N³,N³-dipropylisophthalamide | MH+ = 595 |
| 396 | 245 | "PHTH" | N¹-((1S)-1-benzyl-2-hydroxy-3-{[2-(3-methoxyphenyl)ethyl]amino}propyl)-N³,N³-dipropylisophthalamide | MH+ = 546 |
| 397 | 246 | "PHTH" | N¹-((1S,2R)-1-benzyl-3-{[2-(2,4-dichlorophenyl)ethyl]amino}-2-hydroxypropyl)-N³,N³-dipropylisophthalamide | MH+ = 585 |
| 398 | 247 | "PHTH" | N¹-((1S,2R)-1-benzyl-3-{[2-(3-chlorophenyl)ethyl]amino}- | MH+ = 551 |

| EXA | Column A Amine (VIII) Compound of EXA | Column B Amide Forming Agent (IX) | Column C Substitued amine (X) | Column D Physical Data |
|---|---|---|---|---|
| 399 | 248 | "PHTH" | $N^1$-((1S)-1-benzyl-3-{[2-(2,5-dimethoxyphenyl)ethyl]amino}-2-hydroxypropyl)-$N^3$,$N^3$-dipropylisophthalamide | MH+ = 576 |
| 400 | 249 | "PHTH" | $N^1$-((1S,2R)-1-benzyl-2-hydroxy-3-{[2-(4-methylphenyl)ethyl]amino}propyl)-$N^3$,$N^3$-dipropylisophthalamide | MH+ = 530 |
| 401 | 250 | "PHTH" | $N^1$-((1S,2R)-1-benzyl-3-{[(1R)-1-benzyl-2-hydroxyethyl]amino}-2-hydroxypropyl)-$N^3$,$N^3$-dipropylisophthalamide | MH$^+$ = 546 |
| 402 | 251 | "PHTH" | $N^1$-((1S,2R)-1-benzyl-2-hydroxy-3-{[3-(4-morpholinyl)propyl]amino}propyl)-$N^3$,$N^3$-dipropylisophthalamide | MH+ = 539 |
| 403 | 252 | "PHTH" | $N^1$-[(1S,2R)-1-benzyl-2-hydroxy-3-(isobutylamino)propyl]-$N^3$,$N^3$-dipropylisophthalamide | MH+ = 468 |
| 404 | 253 | "PHTH" | $N^1$-((1S,2R)-1-benzyl-2-hydroxy-3-{[2-(4-morpholinyl)ethyl]amino}propyl)-$N^3$,$N^3$-dipropylisophthalamide | MH+ = 525 |
| 405 | 254 | "PHTH" | $N^1$-{(1S,2R)-1-benzyl-2-hydroxy-3-[(2-hydroxybutyl)amino]propyl}-$N^3$,$N^3$-dipropylisophthalamide | MH+ = 484 |
| 406 | 255 | "PHTH" | $N^1$-((1S,2R)-1-benzyl-2-hydroxy-3-{[2-(2-thienyl)ethyl]amino}propyl)-$N^3$,$N^3$-dipropylisophthalamide | MH+ = 522 |
| 407 | 256 | "PHTH" | $N^1$-{(1S,2R)-1-benzyl-2-hydroxy-3-[(4-hydroxybutyl)amino]propyl}-$N^3$,$N^3$-dipropylisophthalamide | MH+ = 484 |
| 408 | 257 | "PHTH" | $N^1$-((1S,2R)-1-benzyl-2-hydroxy-3-{[(1S)-2-hydroxy-1-phenylethyl]amino}propyl)-$N^3$,$N^3$-dipropylisophthalamide | MH+ = 532 |
| 409 | 258 | "PHTH" | $N^1$-{(1S,2R)-1-benzyl-3-[(2,4-dichlorobenzyl)amino]-2-hydroxypropyl}-$N^3$,$N^3$-dipropylisophthalamide | MH+ = 571 |
| 410 | 259 | "PHTH" | $N^1$-((1S,2R)-1-benzyl-2-hydroxy-3-{[(1R)-2-hydroxy-1-phenylethyl]amino}propyl)-$N^3$,$N^3$-dipropylisophthalamide | MH+ = 532 |
| 411 | 260 | "PHTH" | $N^1$-{(1S,2R)-1-benzyl-3-[(4-tert-butylbenzyl)amino]-2-hydroxypropyl}-$N^3$,$N^3$-dipropylisophthalamide | MH$^+$ = 558 |
| 412 | 261 | "PHTH" | $N^1$-{(1S,2R)-1-benzyl-2-hydroxy-3-[(1- | MH$^+$ = 516 |

-continued

| EXA | Column A Amine (VIII) Compound of EXA | Column B Amide Forming Agent (IX) | Column C Substitued amine (X) | Column D Physical Data |
|---|---|---|---|---|
| 413 | 262 | "PHTH" | $N^1$-{(1S,2R)-1-benzyl-3-[(2-phenylethyl)amino]propyl}-$N^3,N^3$-dipropylisophthalamide | $MH^+ = 544$ |
| 414 | 263 | "PHTH" | $N^1$-((1S,2R)-1-benzyl-2-hydroxy-3-{[(1R,2S)-2-hydroxy-2,3-dihydro-1H-inden-1-yl]amino}propyl)-$N^3,N^3$-dipropylisophthalamide | $MH^+ = 530$ |
| 416 | 265 | "PHTH" | $N^1$-{(1S,2R)-1-benzyl-3-[(3,4-dimethylbenzyl)amino]-2-hydroxypropyl}-$N^3,N^3$-dipropylisophthalamide | $MH+ = 575$ |
| 417 | 266 | "PHTH" | $N^1$-((1S,2R)-1-(3,5-difluorobenzyl)-2-hydroxy-3-{[2-(isobutylamino)-1-methyl-2-oxoethyl]amino}propyl)-$N^3,N^3$-dipropylisophthalamide | $MH+ = 575$ |
| 418 | 266 | "3,5-pyridinyl" | $N^1$-((1S,2R)-1-(3,5-difluorobenzyl)-2-hydroxy-3-{[(1S)-2-(isobutylamino)-1-methyl-2-oxoethyl]amino}propyl)-$N^3,N^3$-dipropylisophthalamide | $MH+ = 575$ |
| 419 | 267 | "5-Me-PHTH" | $N^3$-((1S,2R)-1-(3,5-difluorobenzyl)-2-hydroxy-3-{[(1S)-2-(isobutylamino)-1-methyl-2-oxoethyl]amino}propyl)-$N^5,N^5$-dipropyl-3,5-pyridinedicarboxamide | $MH+ = 576$ |
| 420 | 268 | "5-Me-PH" | $N^1$-((1S,2R)-1-(3,5-difluorobenzyl)-2-hydroxy-3-{[2-(isobutylamino)-1,1-dimethyl-2-oxoethyl]amino}propyl)-5-methyl-$N^3,N^3$-dipropylisophthalamide | $MH+ = 603$ |
| 421 | 269 | "5-Me-PHTH" | $N^1$-((1S,2R)-1-(3,5-difluorobenzyl)-2-hydroxy-3-{[2-(isobutylamino)-2-oxoethyl]amino}propyl)-5-methyl-$N^3,N^3$-dipropylisophthalamide | $MH+ = 575.3$ |
| | | | $N^1$-[(1S,2R)-1-(3,5-difluorobenzyl)-2-hydroxy-3-({(1S)-1-[(isobutylamino)carbonyl]propyl}amino)propyl]-5-methyl-$N^3,N^3$-dipropylisophthalamide | $MH+ = 603.8$ |
| 422 | 270 | "5-Me-PHTH" | $N^1$-[(1S,2R)-1-(3,5-difluorobenzyl)-2-hydroxy-3-({(1R)-1-[(isobutylamino)carbonyl]propyl}amino)propyl]-5-methyl-$N^3,N^3$-dipropylisophthalamide | $MH+ = 603.8$ |
| 423 | 271 | "5-Me-PHTH" | $N^1$-[(1S,2R)-3-(benzylamino)-1-(3,5-difluorobenzyl)-2-hydroxypropyl]-5-methyl-$N^3,N^3$-dipropylisophthalamide | $MH+ = 552.3$ |
| 424 | 272 | "5-Me-PHTH" | $N^1$-[(1S,2R)-1-(3,5-difluorobenzyl)-3- | $MH+ = 490.7$ |

| EXA | Column A Amine (VIII) Compound of EXA | Column B Amide Forming Agent (IX) | Column C Substitued amine (X) | Column D Physical Data |
|---|---|---|---|---|
| | | | (ethylamino)-2-hydroxypropyl]-5-methyl-N³,N³-dipropylisophthalamide | |
| 425 | 273 | "5-Me-PHTH" | N¹-[(1S,2R)-1-(3,5-difluorobenzyl)-2-hydroxy-3-(isobutylamino)propyl]-5-methyl-N³,N³-dipropylisophthalamide | MH+ = 518.0 |
| 426 | 274 | "5-Me-PHTH" | N¹-((1S,2R)-1-(3,5-difluorobenzyl)-2-hydroxy-3-{[3-(isobutylamino)-2-methyl-3-oxopropyl]amino}propyl)-5-methyl-N³,N³-dipropylisophthalamide | MH+ = 603 |
| 427 | 275 | "5-Me-PHTH" | N¹-((1S,2R)-1-(3,5-difluorobenzyl)-3-{[4-(dimethylamino)benzyl]amino}-2-hydroxypropyl)-5-methyl-N³,N³-dipropylisophthalamide | MH+ = 595.8 |
| 428 | 276 | "5-Me-PHTH" | N¹-[(1S,2R)-3-{[(1S)-1-benzyl-2-(isobutylamino)-2-oxoethyl]amino}-1-(3,5-difluorobenzyl)-2-hydroxypropyl]-5-methyl-N³,N³-dipropylisophthalamide | MH+ = 665.9 |
| 429 | 277 | "5-Me-PHTH" | N¹-[(1S,2R)-1-(3,5-difluorobenzyl)-2-hydroxy-3-({(1S)-1-[(isobutylamino)carbonyl]-2-methylpropyl}amino)propyl]-5-methyl-N³,N³-dipropylisophthalamide | MH+ = 617.9 |
| 430 | 278 | "5-Me-PHTH" | N¹-((1S,2R)-1-(3,5-difluorobenzyl)-3-{[2-(dimethylamino)ethyl]amino}-2-hydroxypropyl)-5-methyl-N³,N³-dipropylisophthalamide | MH+ = 533.3 |
| 431 | 279 | "5-Me-PHTH" | N¹-{(1S,2R)-1-(3,5-difluorobenzyl)-2-hydroxy-3-[(3-pyridinylmethyl)amino]propyl}-5-methyl-N³,N³-dipropylisophthalamide | MH⁺ = 553 |
| 432 | 280 | "5-Me-PHTH" | N¹-[(1S,2R)-3-{[(1S)-1-[(benzyloxy)methyl]-2-(isobutylamino)-2-oxoethyl]amino}-1-(3,5-difluorobenzyl)-2-hydroxypropyl]-5-methyl-N³,N³-dipropylisophthalamide | MH+ = 695.9 |
| 433 | 281 | "5-Me-PHTH" | N¹-{(1S,2R)-1-(3,5-difluorobenzyl)-2-hydroxy-3-[(1-methyl-1-phenylethyl)amino]propyl}-5-methyl-N³,N³-dipropylisophthalamide | MH+ = 580.8 |
| 434 | 282 | "5-Me-PHTH" | N¹-[(1S,2R)-1-(3,5-difluorobenzyl)-2-hydroxy-3-({(1R)-1-[(isobutylamino)carbonyl]-2-methylpropyl}amino)propyl]- | MH+ = 617.9 |

| EXA | Column A Amine (VIII) Compound of EXA | Column B Amide Forming Agent (IX) | Column C Substitued amine (X) | Column D Physical Data |
|---|---|---|---|---|
| 435 | 283 | "5-Me-PHTH" | 5-methyl-$N^3,N^3$-dipropylisophthalamide $N^1$-[(1S,2R)-1-(3,5-difluorobenzyl)-2-hydroxy-3-({(1S)-1-[(isobutylamino)carbonyl]butyl}amino)propyl]-5-methyl-$N^3,N^3$-dipropylisophthalamide | MH+ = 617.9 |
| 436 | 284 | "5-Me-PHTH" | $N^1$-((1S,2R)-1-(3,5-difluorobenzyl)-2-hydroxy-3-{[(1S)-1-(hydroxymethyl)-2-(isobutylamino)-2-oxoethyl]amino}propyl)-5-methyl-$N^3,N^3$-dipropylisophthalamide | MH+ = 605.8 |
| 437 | 285 | "5-Me-PHTH" | $N^1$-{(1S,2R)-1-(3,5-difluorobenzyl)-2-hydroxy-3-[(2-phenylethyl)amino]propyl}-5-methyl-$N^3,N^3$-dipropylisophthalamide | MH+ = 566.8 |
| 438 | 286 | "5-Me-PHTH" | $N^1$-[(1S,2R)-3-{[(1S)-2-(benzylamino)-1-methyl-2-oxoethyl]amino}-1-(3,5-difluorobenzyl)-2-hydroxypropyl]-5-methyl-$N^3,N^3$-dipropylisophthalamide | MH+ = 623.2 |
| 439 | 287 | "5-Me-PHTH" | $N^1$-((1S,2R)-1-(3,5-difluorobenzyl)-2-hydroxy-3-{[(1S)-1-phenylpropyl]amino}propyl)-5-methyl-$N^3,N^3$-dipropylisophthalamide | MH+ = 580.8 |
| 440 | 287a | "5-Me-PHTH" | $N^1$-((1S,2R)-1-(3,5-difluorobenzyl)-3-{[(1S)-2-(ethylamino)-1-methyl-2-oxoethyl]amino}-2-hydroxypropyl)-5-methyl-$N^3,N^3$-dipropylisophthalamide | MH+ = 561.2 |
| 441 | 289 | "5-Me-PHTH" | $N^1$-((1S,2R)-1-(3,5-difluorobenzyl)-2-hydroxy-3-{[(1S)-2-(isobutylamino)-2-oxo-1-phenylethyl]amino}propyl)-5-methyl-$N^3,N^3$-dipropylisophthalamide | MH+ = 651.9 |
| 442 | 290 | "5-Me-PHTH" | $N^1$-[(1S,2R)-1-(3,5-difluorobenzyl)-2-hydroxy-3-(isopentylamino)propyl]-5-methyl-$N^3,N^3$-dipropylisophthalamide | MH+ = 531.69 |
| 443 | 291 | "5-Me-PHTH" | $N^1$-[(1S,2R)-3-(cyclohexylamino)-1-(3,5-difluorobenzyl)-2-hydroxypropyl]-5-methyl-$N^3,N^3$-dipropylisophthalamide | MH+ = 544.2 |
| 444 | 292 | "5-Me-PHTH" | $N^1$-[(1S,2R)-3-(butylamino)-1-(3,5-difluorobenzyl)-2-hydroxypropyl]-5-methyl-$N^3,N^3$-dipropylisophthalamide | MH+ = 518.2 |
| 445 | 293 | "5-Me-PHTH" | $N^1$-{(1S,2R)-1-(3,5-difluorobenzyl)-2-hydroxy-3-[(3-methoxypropyl)amino]propyl}- | MH+ = 534.2 |

-continued

| EXA | Column A Amine (VIII) Compound of EXA | Column B Amide Forming Agent (IX) | Column C Substitued amine (X) | Column D Physical Data |
|---|---|---|---|---|
| 446 | 294 | "5-Me-PHTH" | 5-methyl-$N^3,N^3$-dipropylisophthalamide $N^1$-{(1S,2R)-1-(3,5-difluorobenzyl)-2-hydroxy-3-[(2-hydroxy-2-phenylethyl)amino]propyl}-5-methyl-$N^3,N^3$-dipropylisophthalamide | MH+ = 582 |
| 447 | 295 | "5-Me-PHTH" | $N^1$-((1S,2R)-1-(3,5-difluorobenzyl)-3-{[(3R,5S)-3,5-dimethoxycyclohexyl]amino}-2-hydroxypropyl)-5-methyl-$N^3,N^3$-dipropylisophthalamide | MH+ = 604.2 |
| 448 | 296 | "5-Me-PHTH" | dimethyl (1R,3S)-5-{[(2R,3S)-4-(3,5-difluorophenyl)-3-({3-[(dipropylamino)carbonyl]-5-methylbenzoyl}amino)-2-hydroxybutyl]amino}-1,3-cyclohexanedicarboxylate | MH+ = 660.2 |
| 449 | 297 | "5-Me-PHTH" | (1R,3S)-5-{[(2R,3S)-4-(3,5-difluorophenyl)-3-({3-[(dipropylamino)carbonyl]-5-methylbenzoyl}amino)-2-hydroxybutyl]amino}-1,3-cyclohexanedicarboxylic acid | MH+ = 632.2 |
| 450 | 298 | "5-Me-PHTH" | $N^1$-((1S,2R)-1-(3,5-difluorobenzyl)-2-hydroxy-3-{[(1R)-1-phenylpropyl]amino}propyl)-5-methyl-$N^3,N^3$-dipropylisophthalamide | MH+ = 580.8 |
| 451 | 299 | "5-Me-PHTH" | $N^1$-[(1S,2R)-3-[(3-chlorobenzyl)amino]-1-(3,5-difluorobenzyl)-2-hydroxypropyl]-5-methyl-$N^3,N^3$-dipropylisophthalamide | MH+ = 586.3 |
| 452 | 300 | "—SO$_2$—" | N-{(1S,2R)-1-(3,5-difluorobenzyl)-2-hydroxy-3-[(3-methoxybenzyl)amino]propyl}-3-[(2-propylpentyl)sulfonyl]benzamide | MH+ = 603.2 |
| 453 | 301 | "5-Me-PHTH" | $N^1$-[(1S,2R)-3-[([1,1'-biphenyl]-3-ylmethyl)amino]-1-(3,5-difluorobenzyl)-2-hydroxypropyl]-5-methyl-$N^3,N^3$-dipropylisophthalamide | MH+ = 628.8 |
| 454 | 302 | "5-Me-PHTH" | $N^1$-{(1S,2R)-1-(3,5-difluorobenzyl)-2-hydroxy-3-[(3-iodobenzyl)amino]propyl}-5-methyl-$N^3,N^3$-dipropylisophthalamide | MH+ = 678 |
| 455 | 303 | "5-Me-PHTH" | $N^1$-{(1S,2R)-1-(3,5-difluorobenzyl)-2-hydroxy-3-[(3-methylbenzyl)amino]propyl}-5-methyl-$N^3,N^3$-dipropylisophthalamide | MH+ = 566.8 |
| 456 | 304 | "5-Me-PHTH" | $N^1$-{(1S,2R)-1-(3,5-difluorobenzyl)-2-hydroxy-3-[(2- | MH+ = 694 |

| EXA | Column A Amine (VIII) Compound of EXA | Column B Amide Forming Agent (IX) | Column C Substitued amine (X) | Column D Physical Data |
|---|---|---|---|---|
| 457 | 305 | "5-Me-PHTH" | phenylpropyl)amino]propyl}-5-methyl-$N^3,N^3$-dipropylisophthalamide $N^1$-{(1S,2R)-1-(3,5-difluorobenzyl)-2-hydroxy-3-[(1,3-thiazol-5-ylmethyl)amino]propyl}-5-methyl-$N^3,N^3$-dipropylisophthalamide | MH+ = 559.5 |
| 458 | 306 | "5-Me-PHTH" | $N^1$-{(1S,2R)-1-(3,5-difluorobenzyl)-2-hydroxy-3-[(2-thienylmethyl)amino]propyl}-5-methyl-$N^3,N^3$-dipropylisophthalamide | MH+ = 558.5 |
| 459 | 307 | "5-Me-PHTH" | $N^1$-{(1S,2R)-1-(3,5-difluorobenzyl)-2-hydroxy-3-[(5-methoxy-1,2,3,4-tetrahydro-1-naphthalenyl)amino]propyl}-5-methyl-$N^3,N^3$-dipropylisophthalamide | MH+ = 814 |
| 460 | 308 | "5-Me-PHTH" | $N^1$-{(1S,2R)-1-(3,5-difluorobenzyl)-2-hydroxy-3-[(2-pyrazinylmethyl)amino]propyl}-5-methyl-$N^3,N^3$-dipropylisophthalamide | MH+ = 554.3 |
| 461 | 309 | "5-Me-PHTH" | $N^1$-{(1S,2R)-1-(3,5-difluorobenzyl)-3-[(3,5-difluorobenzyl)amino]-2-hydroxypropyl}-5-methyl-$N^3,N^3$-dipropylisophthalamide | MH+ = 588.7 |
| 462 | 310 | "PHTH" | $N^1$-{(1S,2R)-3-[(1,3-benzodioxol-5-ylmethyl)amino]-1-benzyl-2-hydroxypropyl}-$N^3,N^3$-dipropylisophthalamide | MH+ = 546 |
| 463 | 311 | "5-Me-PHTH" | $N^1$-{(1S,2R)-1-(3,5-difluorobenzyl)-3-[(3,5-dimethoxybenzyl)amino]-2-hydroxypropyl}-5-methyl-$N^3,N^3$-dipropylisophthalamide | MH+ = 612.4 |
| 464 | 312 | "5-Me-PHTH" | $N^1$-((1S,2R)-1-(3,5-difluorobenzyl)-2-hydroxy-3-{[3-(trifluoromethyl)benzyl]amino}propyl)-5-methyl-$N^3,N^3$-dipropylisophthalamide | MH+ = 620.3 |
| 466 | 314 | "5-Me-PHTH" | Racemic $N^1$-{(1S,2R)-1-(3,5-difluorobenzyl)-2-hydroxy-3-[(7-methoxy-1,2,3,4-tetrahydro-1-naphthalenyl)amino]propyl}-5-methyl-$N^3,N^3$-dipropylisophthalamide | MH+ = 814 |
| 467 | 315 | "5-Me-PHTH" | $N^1$-((1S,2R)-1-(3,5-difluorobenzyl)-2-hydroxy-3-{[3-(trifluoromethoxy)benzyl]amino}propyl)-5-methyl-$N^3,N^3$-dipropylisophthalamide | MH+ = 636.3 |
| 468 | 316 | "5-Me-PHTH" | $N^1$-{(1S,2R)-1-(3,5-difluorobenzyl)-3-[(3-fluorobenzyl)amino]-2-hydroxypropyl}-5-methyl-$N^3,N^3$-dipropylisophthalamide | MH+ = 570.3 |

-continued

| EXA | Column A<br>Amine<br>(VIII)<br>Compound<br>of<br>EXA | Column B<br>Amide<br>Forming<br>Agent (IX) | Column C<br>Substitued amine (X) | Column D<br>Physical<br>Data |
|---|---|---|---|---|
| 469 | 317 | "5-Me-PHTH" | $N^1$-{(1S,2R)-1-(3,5-difluorobenzyl)-2-hydroxy-3-[(3-isopropoxybenzyl)amino]propyl}-5-methyl-$N^3,N^3$-dipropylisophthalamide | MH+ = 610.4 |
| 470 | 318 | "5-Me-PHTH" | $N^1$-[(1S,2R)-3-[(3-bromobenzyl)amino]-1-(3,5-difluorobenzyl)-2-hydroxypropyl]-5-methyl-$N^3,N^3$-dipropylisophthalamide | MH+ = 631.6 |
| 471 | 319 | "5-Me-PHTH" | $N^1$-((1S,2R)-1-(3,5-difluorobenzyl)-2-hydroxy-3-{[(5-methyl-2-furyl)methyl]amino}propyl)-5-methyl-$N^3,N^3$-dipropylisophthalamide | MH+ = 556 |
| 472 | 320 | "5-Me-PHTH" | $N^1$-{(1S,2R)-1-(3,5-difluorobenzyl)-2-hydroxy-3-[(5-methoxy-1,2,3,4-tetrahydro-1-naphthalenyl)amino]propyl}-5-methyl-$N^3,N^3$-dipropylisophthalamide "isomer A" | MH+ = 622 |
| 473 | 320 | "5-Me-PHTH" | $N^1$-{(1S,2R)-1-(3,5-difluorobenzyl)-2-hydroxy-3-[(5-methoxy-1,2,3,4-tetrahydro-1-naphthalenyl)amino]propyl}-5-methyl-$N^3,N^3$-dipropylisophthalamide "isomer B" | $MH^+$ = 622 |

Example 474

$N^1$-[(1S,2R)-1-benzyl-2-hydroxy-3-(1,2,3,4-tetrahydro-1-naphthalenylamino)propyl]-$N^3,N^3$-dipropyl-isophthalamide (X)

Following the general procedures of EXAMPLEs 6 and 321-473 and making non-critical variations but starting with (2R,3S)-3-amino-4-phenyl-1-(1,2,3,4-tetrahydro-1-naphthalenylamino-2-butanol (VIII) and using "PHTH", the title compound is obtained, $MH^+$=542.3.

Examples 475-483

Following the general procedure of EXAMPLE 6 and making non-critical variations but starting with the amine (VIII) of Column A and reacting it with the amide forming agent (IX) of Column B, the substitute amine (X) of Column C is obtained.

| EXA | Column A<br>Amine<br>(VIII)<br>Compound<br>of<br>EXA | Column B<br>Amide<br>Forming<br>Agent (IX) | Column C<br>Substitued amine (X) | Column D<br>Physical<br>Data |
|---|---|---|---|---|
| 475 | 271 | "5-OMe-PHTH" | $N^1$-[(1S,2R)-3-(benzylamino)-1-(3,5-difluorobenzyl)-2-hydroxypropyl]-5-methoxy-$N^3,N^3$-dipropylisophthalamide | $MH^+$ = 568.2 |
| 476 | 271 | "PHTH" | $N^1$-[(1S,2R)-3-(benzylamino)-1-(3,5-difluorobenzyl)-2-hydroxypropyl]-$N^3,N^3$-dipropylisophthalamide | $MH^+$ = 538.2 |

-continued

| EXA | Column A Amine (VIII) Compound of EXA | Column B Amide Forming Agent (IX) | Column C Substitued amine (X) | Column D Physical Data |
|---|---|---|---|---|
| 477 | 271 | "5-Cl-PHTH" | $N^1$-[(1S,2R)-3-(benzylamino)-1-(3,5-difluorobenzyl)-2-hydroxypropyl]-5-chloro-$N^3,N^3$-dipropylisophthalamide | $MH^+$ = 572.1 |
| 478 | 271 | "3,5-pyridinyl" | $N^3$-[(1S,2R)-3-(benzylamino)-1-(3,5-difluorobenzyl)-2-hydroxypropyl]-$N^5,N^5$-dipropyl-3,5-pyridinedicarboxamide | $MH^+$ = 539.5 |
| 479 | 271 | "5-F-PHTH" | $N^1$-[(1S,2R)-3-(benzylamino)-1-(3,5-difluorobenzyl)-2-hydroxypropyl]-5-fluoro-$N^3,N^3$-dipropylisophthalamide | $MH^+$ = 556.3 |
| 480 | 271 | "thienyl" | $N^2$-[(1S,2R)-3-(benzylamino)-1-(3,5-difluorobenzyl)-2-hydroxypropyl]-$N^5,N^5$-dipropyl-2,5-thiophenedicarboxamide | $MH^+$ = 544.2 |
| 481 | 271 | "2,4-pyridinyl" | $N^4$-[(1S,2R)-3-(benzylamino)-1-(3,5-difluorobenzyl)-2-hydroxypropyl]-$N^2,N^2$-dipropyl-2,4-pyridinedicarboxamide | $MH^+$ = 539.3 |
| 482 | 271 | "4,6-pyrimidinyl" | $N^4$-[(1S,2R)-3-(benzylamino)-1-(3,5-difluorobenzyl)-2-hydroxypropyl]-$N^6,N^6$dipropyl-4,6-pyrimidinedicarboxamide | MH+ = 540 |
| 483 | 271 | "morpholinyl" | N-[(1S,2R)-3-(benzylamino)-1-(3,5-difluorobenzyl)-2-hydroxypropyl]-3-(4-morpholinylcarbonyl)benzamide | MH+ = 552 |

Example 484

$N^1$-{ (1S,2R)-1-benzyl-2-hydroxy-3-[(3-methylbenzyl)amino]propyl}-$N^3,N^3$-dipropylisophthalamide (X)

Following the general procedures of EXAMPLEs 4 and 14-107 and making non-critical variations but starting with tert-butyl 1-(2-oxiranyl)-2-phenylethylcarbamate (V, commercially available) and $NH_2$—$CH_2$-phenyl-(3-$CH_3$) (VI), the corresponding protected alcohol (VII) is obtained.

Following the general procedure of EXAMPLEs 5 and 170-320 and making non-critical variations, the corresponding amine (VIII) is obtained.

Following the general procedure of EXAMPLEs 6 and 321-483 and making non-critical variations but using "PHTH" (IX), the title compound is obtained, $MH^+$=516.

Example 485

$N^1$-{(1S,2R)-1-(3,5-difluorobenzyl)-2-hydroxy-3-[(3-methoxybenzyl)amino]propyl}-$N^5,N^5$-dipropylpentanediamide (X)

Following the general procedure of EXAMPLEs 6 and making non-critical variations and using (2R,3S)-3-amino-4-(3,5-difluorophenyl)-1-[(3-methoxybenzyl)amino]-2-butanol (VIII, EXAMPLE 5) with 5-(dipropylamino)-5-oxopentanoic acid (IX), the title compound is obtained, $MH^+$=534.2.

Example 486

$N^1$-[(1S,2R)-3-{[(1R)-1-[(benzyloxy)methyl]-2-(isobutylamino)-2-oxoethyl]amino}-1-(3,5-difluorobenzyl)-2-hydroxypropyl]-5-methyl-$N^3,N^3$-dipropylisophthalamide (X)

Following the general procedures of EXAMPLEs 124, 280 and 432 and making non-critical variations but using the "R" C-terminal amine (VI), the title compound is obtained, $MH^+$=695.

Example 487

N$^1$-((1S,2R)-1-(3,5-difluorobenzyl)-2-hydroxy-3-{[(1R)-1-(hydroxymethyl)-2-(isobutylamino)-2-oxo-ethyl]amino}propyl)-5-methyl-N$^3$,N$^3$-dipropylisophthalamide (X)

Following the general procedures of EXAMPLEs 128, 284 and 436 and making non-critical variations but using the "R" C-terminal amine (VI), the title compound is obtained, MH$^+$=719.

Example 488

N$^1$-[(1S,2R)-1-benzyl-2-hydroxy-3-(pentylamino)propyl]-N$^3$,N$^3$-dipropylisophthalamide (X)

Following the general procedures of EXAMPLEs 96, 252 and 403 and making non-critical variations but using NH$_2$—(CH$_2$)$_4$—CH$_3$ as the C-terminal amine (VI), the title compound is obtained, MH$^+$=481.

Example 489

N$^1$-[(1S)-3-({2-[4-(aminosulfonyl)phenyl]ethyl}amino)-1-benzyl-2-hydroxypropyl]-N$^3$,N$^3$-dipropylisophthalamide (X)

Following the general procedures of EXAMPLEs 61, 217 and 368 and making non-critical variations but using racemic C-terminal amine (VI), the title compound is obtained, MH$^+$=595.

Example 491

N$^3$-{(1S,2R)-1-(3,5-difluorobenzyl)-2-hydroxy-3-[(1,3-thiazol-5-ylmethyl)amino]propyl}-N$^5$,N$^5$-dipropyl-3,5-pyridinedicarboxamide (X)

Following the general procedure of EXAMPLE 457 and making non-critical variations and using (2R,3S)-3-amino-4-(3,5-difluorophenyl)-1-[(1,3-thiazol-5-ylmethyl)amino]-2-butanol (VIII, EXAMPLE 305) with "3,5-pyridinyl" as the amide forming agent (IX), the title compound is obtained.

Example 492

3-Benzoyl-N-{(1S,2R)-1-(3,5-difluorobenzyl)-2-hydroxy-3-[(3-methoxybenzyl)amino]propyl}benzamide (X)

Following the general procedure of EXAMPLE 452 and making non-critical variations and using (2R,3S)-3-amino-4-(3,5-difluorophenyl)-1-[(3-methoxybenzyl)amino]-2-butanol trifluoroacetate (VIII, EXAMPLE 5) and reacting it with phenyl-CO-phenyl-CO—OH (IX) where the attachment to the -phenyl- ring is 1,3- for the carbonyl groups, the title compound is obtained, MH$^+$=545.2

Example 493

N-{(1S,2R)-1-(3,5-difluorobenzyl)-2-hydroxy-3-[(3-methoxybenzyl)amino]propyl}[1,1'-biphenyl]-3-carboxamide (X)

Following the general procedure of EXAMPLE 452 and making non-critical variations and using (2R,3S)-3-amino-4-(3,5-difluorophenyl)-1-[(3-methoxybenzyl)amino]-2-butanol trifluoroacetate (VIII, EXAMPLE 5) and reacting it with phenyl-phenyl-CO—OH (IX) where the attachment to the middle -phenyl- ring is 1,3- for the carbonyl group and other -phenyl, the title compound is obtained, MH$^+$=517.2.

Example 494

N$^1$-{(1S,2R)-1-benzyl-2-hydroxy-3-[(3-methylbenzyl)amino]propyl}-N$^3$,N$^3$-dipropylisophthalamide (X)

Following the general procedure of EXAMPLE 452 and making non-critical variations and using (2R,3S)-3-amino-4-(3,5-difluorophenyl)-1-[(3-methoxybenzyl)amino]-2-butanol trifluoroacetate (VIII, EXAMPLE 5) and reacting it with (CH$_3$—O—CH$_2$—CH$_2$—)$_2$N—CO— —CO—OH (IX) where the attachment to the -phenyl- ring is 1,3- for the carbonyl groups, the title compound is obtained, MH$^+$=570.3.

Example 495

N$^1$[(1S,2R)-3-(benzylamino)-1-(3,5-difluorobenzyl)-2-hydroxypropyl]-N$^3$-(2-methoxyethyl)-N$^3$-propyl-isophthalamide (X)

Following the general procedure of EXAMPLE 452 and making non-critical variations and using (2R,3S)-3-amino-1-(benzylamino)-4-(3,5-difluorophenyl)-2-butanol (VIII, EXAMPLE 271) and reacting it with (CH$_3$—CH$_2$—CH$_2$—)(CH$_3$—O—CH$_2$—CH$_2$—)N—CO-phenyl-CO—OH (IX) where the attachment to the -phenyl- ring is 1,3- for the carbonyl groups, the title compound is obtained, MH$^+$=554.5.

Example 496

N-{(1S,2R)-1-(3,5-difluorobenzyl)-2-hydroxy-3-[(3-methoxybenzyl)amino]propyl}-3-ethoxybenzamide (X)

Following the general procedure of EXAMPLE 452 and making non-critical variations and using (2R,3S)-3-amino-4-(3,5-difluorophenyl)-1-[(3-methoxybenzyl)amino]-2-butanol trifluoroacetate (VIII, EXAMPLE 5) and reacting it with CH$_3$—CH$_2$—O-phenyl-CO—OH (IX) where the attachment to the -phenyl- ring is 1,3- for the carbonyl and ethoxy group, the title compound is obtained, MH$^+$=485

Example 497

N-{(1S,2R)-1-(3,5-difluorobenzyl)-2-hydroxy-3-[(3-methoxybenzyl)amino]propyl}-2-naphthamide (X)

Following the general procedure of EXAMPLE 452 and making non-critical variations and using (2R,3S)-3-amino-4-(3,5-difluorophenyl)-1-[(3-methoxybenzyl)amino]-2-butanol trifluoroacetate (VIII, EXAMPLE 5) and reactinortho position, the title compound is obtained, MH$^+$=491.

Example 498

N$^1$-{(1S,2R)-1-(3,5-difluorobenzyl)-2-hydroxy-3-[(1R)-1,2,3,4-tetrahydro-1-naphthalenylamino]propyl}-5-methyl-N$^3$, N$^3$-dipropylisophthalamide (X)

Following the general procedure of EXAMPLEs 4, 5 and 6 and making non-critical variations but using tert-butyl (1S)-

2-(3,5-difluorophenyl)-1-[(2S)-oxiranyl]ethylcarbamate (V, EXAMPLE 3), 1,2,3,4-tetrahydro-1-naphthalenylamine (VI) and "5-Me-PHTH" (IX), the title compound is obtained, MH$^+$=588.

Example 499

$N^1$-[(1R)-3-{[3,5-bis(trifluoromethyl)benzyl]amino}-1-(3,5-difluorobenzyl)-2-hydroxypropyl]-5-methyl-$N^3$,$N^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), H$_2$N—CH$_2$-phenyl-(3,5-ditrifluoromethyl) (VI) and "5-Me-PHTH" (IX), the title compound is obtained, MH$^+$=688.

Example 500

$N^1$-((1S,2R)-1-benzyl-3-{[2-fluoro-5-(trifluoromethyl)benzyl]amino}-2-hydroxypropyl)-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(2-fluoro-5-trifluoromethyl) (VI) and "PHTH" (IX), the title compound is obtained, MH$^+$=588.

Example 501

$N^1$-{(1S,2R)-1-benzyl-3-[(2,3-difluorobenzyl)amino]-2-hydroxypropyl}-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(2,3-difluoro) (VI) and "PHTH" (IX), the title compound is obtained, MH$^+$=538.

Example 502

$N^1$-((1S,2R)-1-benzyl-3-{[3-fluoro-4-(trifluoromethyl)benzyl]amino}-2-hydroxypropyl)-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-fluoro-4-trifluoromethyl) (VI) and "PHTH" (IX), the title compound is obtained, MH$^+$=588.

Example 503

$N^1$-{(1S,2R)-1-benzyl-3-[(2,5-difluorobenzyl)amino]-2-hydroxypropyl}-$N^3$, $N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(2,5-difluoro) (VI) and "PHTH" (IX), the title compound is obtained, MH$^+$=538.

Example 504

$N^1$-((1S,2R)-1-benzyl-3-{[3-fluoro-5-(trifluoromethyl)benzyl]amino}-2-hydroxypropyl)-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-fluoro-5-trifluoromethyl) (VI) and "PHTH" (IX), the title compound is obtained, MH$^+$=588.

Example 505

$N^1$-{(1S,2R)-1-benzyl-3-[(3,4-difluorobenzyl)amino]-2-hydroxypropyl}-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3,4-difluoro) (VI) and "PHTH" (IX), the title compound is obtained, MH$^+$=538.

Example 506

$N^1$-((1S,2R)-1-benzyl-3-{[4-fluoro-3-(trifluoromethyl)benzyl]amino}-2-hydroxypropyl)-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-trifluoromethyl-4-fluoro) (VI) and "PHTH" (IX), the title compound is obtained, MH$^+$=588.

Example 507

$N^1$-((1S,2R)-1-benzyl-3-{[2-chloro-5-(trifluoromethyl)benzyl]amino}-2-hydroxypropyl)-$N^3$,$N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(2-chloro-5-trifluoromethyl) (VI) and "PHTH" (IX), the title compound is obtained, MH$^+$=605.

Example 508

$N^1$-((1S,2R)-1-benzyl-3-{[4-chloro-3-(trifluoromethyl)benzyl]amino}-2-hydroxypropyl)-$N^3$, $N^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-trifluoromethyl-4-chloro) (VI) and "PHTH" (IX), the title compound is obtained, MH$^+$=605.

Example 509

N$^1$-[(1S,2R)-1-benzyl-3-(2,3-dihydro-1H-inden-2-ylamino)-2-hydroxypropyl]-N$^3$,N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N-(2,3-dihydro-1H-inden-2-yl) and "PHTH" (IX), the title compound is obtained, MH$^+$=528.

Example 510

N$^1$-{(1S)-1-benzyl-2-hydroxy-3-[(3-nitrobenzyl)amino]propyl}-N$^3$, N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-3-nitro (VI) and "PHTH" (IX), the title compound is obtained, MH$^+$=547.

Example 511

N$^1$-((1S,2R)-1-benzyl-3-{[3-(difluoromethoxy)benzyl]amino}-2-hydroxypropyl)-N$^3$,N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-3(—O—CHF$_2$) (VI) and "PHTH" (IX), the title compound is obtained, MH$^+$=538.

Example 512

N$^1$-{(1S,2R)-1-benzyl-3-[(3-ethoxybenzyl)amino]-2-hydroxypropyl}-N$^3$,N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-O—CH$_2$—CH$_3$) (VI) and "PHTH" (IX), the title compound is obtained, MH$^+$=546.

Example 513

N$^1$-((1S,2R)-1-benzyl-2-hydroxy-3-{[(5-methyl-2-pyrazinyl)methyl]amino}propyl)-N$^3$,N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), 5-methyl-2-methylaminoprazine (VI) and "PHTH" (IX), the title compound is obtained, MH$^+$=518.

Example 514

N$^1$-{(1S,2R)-1-benzyl-3-[(3-bromo-4-fluorobenzyl)amino]-2-hydroxypropyl}-N$^3$,N$^3$-dipropylisophthalamide (X)

Following the general procedure of EXAMPLEs 4, 5 and 6 and making non-critical variations but using tert-butyl 1-(2-oxiranyl)-2-phenylethylcarbamate (V), H$_2$N—CH$_2$-phenyl-(3-bromo-4-fluoro) (VI) and "PHTH" (IX), the title compound is obtained, MH$^+$=599.

Example 515

N$^1$-{(1S,2R)-1-(3,5-difluorobenzyl)-3-[(3,5-dimethylbenzyl)amino]-2-hydroxypropyl}-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H$_2$N—CH$_2$-phenyl-(3,5-dimethyl) (VI) and "5-Me-PHTH" (IX), the title compound is obtained, MH$^{30}$=580.

Example 516

N$^1$-{(1S,2R)-1-(3,5-difluorobenzyl)-3-[(3-ethoxybenzyl)amino]-2-hydroxypropyl}-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H$_2$N—CH$_2$-phenyl-(3-ethoxy) (VI) and "5-Me-PHTH" (IX), the title compound is obtained, MH$^+$=596.

Example 517

N$^1$-{(1S,2R)-1-(3,5-difluorobenzyl)-2-hydroxy-3-[(2-phenoxyethyl)amino]propyl}-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H$_2$N—CH$_2$—CH$_2$—O-phenyl (VI) and "5-Me-PHTH" (IX), the title compound is obtained, MH$^+$=582.

Example 518

N$^1$-{(1S,2R)-1-(3,5-difluorobenzyl)-2-hydroxy-3-[(3-isobutoxybenzyl)amino]propyl}-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H$_2$N—CH$_2$-phenyl-O-i-butyl (VI) and "5-Me-PHTH" (IX), the title compound is obtained, MH$^+$=624.

Example 519

N$^1$-((1S,2R)-1-(3,5-difluorobenzyl)-2-hydroxy-3-{[(4-methyl-1,3-thiazol-2-yl)methyl]amino}propyl)-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H$_2$N—CH$_2$-4-methyl-1,3-thiazol-2-yl (VI) and "5-Me-PHTH" (IX), the title compound is obtained, MH$^+$=573.

Example 520

N¹-[(1S,2R)-3-(benzylamino)-1-(3,5-difluorobenzyl)-2-hydroxypropyl]-N³-methyl-N³-propylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H₂N—CH₂-phenyl (VI) and (CH₃—CH₂—CH₂—)(CH₃—)N—CO—(CH₃-)phenyl-CO—OH (IX) where the attachment to the -phenyl- ring for the carbonyls is 1-,3- and 5- for the methyl group, the title compound is obtained, MH⁺=510.

Example 521

N²-[(1S,2R)-3-(benzylamino)-1-(3,5-difluorobenzyl)-2-hydroxypropyl]-N⁵,N⁵-dipropyl-2,5-furandicarboxamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H₂N—CH₂-phenyl (VI) and (CH₃—CH₂—CH₂—)₂N—CO-(2,5-furanyl)-CO— (IX), the title compound is obtained, MH⁺=528.

Example 522

N³-((1S,2R)-1-(3,5-difluorobenzyl)-2-hydroxy-3-{[3-(trifluoromethyl)benzyl]amino}propyl)-N⁵,N⁵-dipropyl-3,5-pyridinedicarboxamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H₂N—CH₂-phenyl-3-trifluoromethyl (VI) and "3,5-pyridinyl" (IX), the title compound is obtained, MH⁺=607.

Example 523

N³-{(1S,2R)-1-(3,5-difluorobenzyl)-2-hydroxy-3-[(1-methyl-1-phenylethyl)amino]propyl}-N⁵,N⁵-dipropyl-3,5-pyridinedicarboxamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), H₂N—C(—CH₃)₂-phenyl (VI) and "3,5-pyridinyl" (IX), the title compound is obtained, MH⁺=567.

Example 524

N¹-[(1S,2R)-3-amino-1-(3,5-difluorobenzyl)-2-hydroxypropyl]-5-methyl-N³,N³-dipropylisophthalamide (X)

Following the general procedure of CHARTs A, C and D and EXAMPLEs 165-168 and making non-critical variations, but using tert-butyl (1S)-2-(3,5-difluorophenyl)-1-[(2S)-oxiranyl]ethylcarbamate (V) and "5-Me-PHTH" (IX), the title compound is obtained, MH⁺=462.

Example 525

N¹-{(1S,2R)-1-(3,5-difluorobenzyl)-3-[(1,2-diphenylethyl)amino]-2-hydroxypropyl}-5-methyl-N³,N³-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), NH₂—CH( )—CH₂-phenyl (VI) and "5-Me-PHTH" (IX), the title compound is obtained, MH⁺=642.

Example 526

N¹-{(1S,2R)-1-(3,5-difluorobenzyl)-2-hydroxy-3-[(7-methoxy-1,2,3,4-tetrahydro-1-naphthalenyl)amino]propyl}-5-methyl-N³,N³-dipropylisophthalamide, isomer A (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 7-methoxy-1,2,3,4-tetrahydro-1-naphthalenylamine (VI) and "5-Me-PHTH" (IX), the title compound is obtained, MH⁺=622.

Example 527

N¹-{(1S,2R)-1-(3,5-difluorobenzyl)-2-hydroxy-3-[(7-methoxy-1,2,3,4-tetrahydro-1-naphthalenyl)amino]propyl}-5-methyl-N³,N³-dipropylisophthalamide, isomer B (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 7-methoxy-1,2,3,4-tetrahydro-1-naphthalenylamine (VI) and "5-Me-PHTH" (IX), the title compound is obtained, MH⁺=622.

Example 528

Benzyl-(1S,2R)-3-azido-1-(3,5-difluorobenzyl)-2-hydroxypropylcarbamate (XII)

Following the general procedure of EXAMPLE 165 and making non-critical variations but starting with benzyl (1S)-2-(3,5-difluorophenyl)-1-[(2S)-oxiranyl]ethylcarbamate (V, EXAMPLE 13), the title compound is obtained.

Example 529

N-{(1S,2R)-1-benzyl-2-hydroxy-3-[(3-methoxybenzyl)amino]propyl}-3-(dimethylamino)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-dimethylaminobenzoic acid (IX), the title compound is obtained, MH⁺=448.

Example 530

N-[(1S,2R)-1-benzyl-2-hydroxy-3-[(3-methoxybenzyl)amino]propyl]-2-methyl-1H-benzimidazole-5-carboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 2-methyl-1H-benzimidazole-5-carboxylic acid (IX), the title compound is obtained, $MH^+=459$.

Example 531

3-(aminosulfonyl)-N-{(1S)-1-benzyl-2-hydroxy-3-[(3-methoxybenzyl)amino]propyl}-4-chlorobenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-(aminosulfonyl)-4-chlorobenzoic acid (IX), the title compound is obtained, $MH^+=519$.

Example 532

N-{(1S,2R)-1-benzyl-2-hydroxy-3-[(3-methoxybenzyl)amino]propyl}-3-cyanobenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-cyanobenzoic acid (IX), the title compound is obtained, $MH^+=430$.

Example 533

N-{(1S,2R)-1-benzyl-2-hydroxy-3-[(3-methoxybenzyl)amino]-propyl}-4-chloro-3-nitrobenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-chloro-3-nitrobenzoic acid (IX), the title compound is obtained, $MH^+=484$.

Example 534

Methyl 3-[({(1S,2R)-1-benzyl-2-hydroxy-3-[(3-methoxybenzyl)amino]propyl}amino)carbonyl]-5-nitrobenzoate (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-nitro-5-(methyl-O—CO-)-phenyl-CO—OH (IX), the title compound is obtained, $MH^+=508$.

Example 535 tert-butyl 3-[({(1S,2R)-1-benzyl-2-hydroxy-3-[(3-methoxybenzyl)amino]propyl}amino)carbonyl]-phenylcarbamate (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-(t-butyl-O—CO—NH)-phenyl-CO—OH (IX), the title compound is obtained, $MH^+=520$.

Example 536

N-[(1S,2R)-1-benzyl-2-hydroxy-3-[(3-methoxybenzyl)amino]propyl]-9,10-dioxo-9,10-dihydro-2-anthourancenylcarboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 9,10-dioxo-9,10-dihydro-2-anthourancenylcarboxylic acid (IX), the title compound is obtained, $MH^+=535$.

Example 537

N-[(1S,2R)-1-benzyl-2-hydroxy-3-[(3-methoxybenzyl)amino]propyl]-1H-1,2,3-benzotriazole-6-carboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 1H-1,2,3-benzotriazolyl-6-carboxylic acid (IX), the title compound is obtained, $MH^+=446$.

Example 538

N-{(1S,2R)-1-benzyl-2-hydroxy-3-[(3-methoxybenzyl)amino]propyl}-4-(3-methyl-5-oxo-4,5-dihydro-1H-pyrazol-1-yl)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-(3-methyl-5-oxo-4,5-dihydro-1H-pyrazol-1-yl)benzoic acid (IX), the title compound is obtained, $MH^+=501$.

Example 539

N-{(1S,2R)-1-benzyl-2-hydroxy-3-[(3-methoxybenzyl)amino]-propyl}-1H-indole-5-carboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and indole-5-carboxylic acid (IX), the title compound is obtained, $MH^+=444$.

Example 540

N-{(1S,2R)-1-benzyl-2-hydroxy-3-[(3-methoxybenzyl)amino]propyl}-3-fluoro-5-(trifluoromethyl)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-fluoro-5-(trifluoromethyl)benzoic acid (IX), the title compound is obtained, $MH^+=491$.

Example 541

N-{(1S,2R)-1-benzyl-2-hydroxy-3-[(3-methoxybenzyl)amino]-propyl}-3-(trifluoromethyl)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-(trifluoromethyl)benzoic acid (IX), the title compound is obtained, $MH^+=473$.

Example 542

N-{(1S,2R)-1-benzyl-2-hydroxy-3-[(3-methoxybenzyl)amino]-propyl}-4-(butylamino)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-(butylamino)benzoic acid (IX), the title compound is obtained, $MH^+=476$.

Example 543

N-{(1S,2R)-1-benzyl-2-hydroxy-3-[(3-methoxybenzyl)amino]-propyl}-3-(trifluoromethoxy)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-(trifluoromethoxy)benzoic acid (IX), the title compound is obtained, $MH^+=489$.

Example 544

N-{(1S,2R)-1-benzyl-2-hydroxy-3-[(3-methoxybenzyl)amino]-propyl}-3,5-dimethoxybenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3,5-dimethoxybenzoic acid (IX), the title compound is obtained, $MH^+=465$.

Example 545

N-{(1S,2R)-1-benzyl-2-hydroxy-3-[(3-methoxybenzyl)amino]-propyl}-3,5-dimethylbenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3,5-dimethylbenzoic acid (IX), the title compound is obtained, $MH^+=433$.

Example 546

N-{(1S,2R)-1-benzyl-2-hydroxy-3-[(3-methoxybenzyl)amino]-propyl}-3,5-difluorobenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3,5-difluorobenzoic acid (IX), the title compound is obtained, $MH^+=441$.

Example 547

N-{(1S,2R)-1-benzyl-2-hydroxy-3-[(3-methoxybenzyl)amino]-propyl}-3,5-dichlorobenzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3,5-dichlorobenzoic acid (IX), the title compound is obtained, $MH^+=474$.

Example 548

N-{(1S,2R)-1-benzyl-2-hydroxy-3-[(3-methoxybenzyl)amino]-propyl}-4-(benzyloxy)benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-(benzyloxy)benzoic acid (IX), the title compound is obtained, $MH^+=511$.

Example 549

N-{(1S,2R)-1-benzyl-2-hydroxy-3-[(3-methoxybenzyl)amino]-propyl}-1,3-benzodioxole-5-carboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 1,3-benzodioxole-5-carboxylic acid (IX), the title compound is obtained, $MH^+=449$.

Example 550

3-(acetylamino)-N-{(1S,2R)-1-benzyl-2-hydroxy-3-[(3-methoxybenzyl)amino]propyl}benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 3-(acetylamino)benzoic acid (IX), the title compound is obtained, $MH^+=462$.

Example 551

4-(acetylamino)-N-{(1S,2R)-1-benzyl-2-hydroxy-3-[(3-methoxybenzyl)amino]propyl}benzamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-(acetylamino)benzoic acid (IX), the title compound is obtained, $MH^+=462$.

Example 552

$N^1$-((1S,2R)-1-(3,5-difluorobenzyl)-3-{[(3,5-dimethyl-4-isoxazolyl)methyl]amino}-2-hydroxypropyl)-5-methyl-$N^3$,$N^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 3,5-dimethyl-4-isoxazolylmethylamine (VI) and "5-Me-PHTH" (IX), the title compound is obtained, $MH^+=571.3$.

Example 553

N[1]-{(1S,2R)-1-(3,5-difluorobenzyl)-2-hydroxy-3-[(3-phenylpropyl)amino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 3-phenylpropyl)amine (VI) and "5-Me-PHTH" (IX), the title compound is obtained, MH$^+$=580.

Example 554

N[1]-{(1S,2R)-1-(3,5-difluorobenzyl)-3-[(3-furylmethyl)amino]-2-hydroxypropyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 3-furylmethylamine (VI) and "5-Me-PHTH" (IX), the title compound is obtained, MH$^+$=542.

Example 555

N[1]-{(1S,2R)-1-(3,5-difluorobenzyl)-2-hydroxy-3-[(tetrahydro-3-furanylmethyl)amino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (tetrahydro-3-furanylmethyl)amine (VI) and "5-Me-PHTH" (IX), the title compound is obtained, MH$^+$=546.

Example 556

N[1]-{(1S,2R)-1-(3,5-difluorobenzyl)-2-hydroxy-3-[(3-propoxybenzyl)amino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (3-propoxybenzyl)amine (VI) and "5-Me-PHTH" (IX), the title compound is obtained, MH$^+$=610.

Example 557

N[1]-{(1S,2R)-1-(3,5-difluorobenzyl)-2-hydroxy-3-[(2-pyridinylmethyl)amino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (2-pyridinylmethyl)amine (VI) and "5-Me-PHTH" (IX), the title compound is obtained, MH$^+$=553.

Example 558

N[1]-[(1S,2R)-3-(benzylamino)-1-(3,5-difluorobenzyl)-2-hydroxypropyl]-5-hydroxy-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), benzylamine (VI) and 5-hydroxy-N,N-dipropylisophthalic acid (IX), the title compound is obtained, MH$^+$=554.

Example 559

N[1]-((1S,2R)-1-(3,5-difluorobenzyl)-2-hydroxy-3-{[1-methyl-1-(3-methylphenyl)ethyl]amino}propyl)-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), [1-methyl-1-(3-methylphenyl)ethyl]amine (VI) and "5-Me-PHTH" (IX), the title compound is obtained, MH$^+$=594.

Example 560

N[1]-{(1S,2R)-1-(3,5-difluorobenzyl)-2-hydroxy-3-[(1S)-1,2,3,4-tetrahydro-1-naphthalenylamino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (1S)-1,2,3,4-tetrahydro-1-naphthalenylamine (VI) and "5-Me-PHTH" (IX), the title compound is obtained, MH$^+$=592.

Example 561

N[1]-{(1S,2R)-1-(3,5-difluorobenzyl)-3-[(2,5-dimethylbenzyl)amino]-2-hydroxypropyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 2,5-dimethylbenzylamine (VI) and "5-Me-PHTH" (IX), the title compound is obtained, MH$^+$=580.

Example 562

N[1]-[(1S,2R)-3-{[2-chloro-5-(trifluoromethyl)benzyl]amino}-1-(3,5-difluorobenzyl)-2-hydroxypropyl]-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 2-chloro-5-trifluorobenzylamine (VI) and "5-Me-PHTH" (IX), the title compound is obtained, MH$^+$=654.

Example 563

N[1]-{(1S,2R)-1-(3,5-difluorobenzyl)-2-hydroxy-3-[(2-hydroxy-5-methylbenzyl)amino]propyl}-5-methyl-N[3],N[3]-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), 2-hydroxy-5-methylbenzylamine (VI) and "5-Me-PHTH" (IX), the title compound is obtained, MH+=582.

Example 564

N¹-((1S,2R)-1-(3,5-difluorobenzyl)-2-hydroxy-3-{[(1S,2R)-2-hydroxy-2,3-dihydro-1H-inden-1-yl]amino}propyl)-5-methyl-N³,N³-dipropylisophthalamide (X)

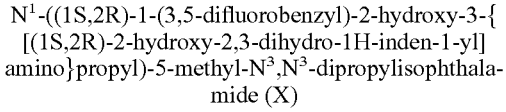

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), [(1S,2R)-2-hydroxy-2,3-dihydro-1H-inden-1-yl]amine (VI) and "5-Me-PHTH" (IX), the title compound is obtained, MH+=594.

Example 565

N¹-{(1S,2R)-1-(3,5-difluorobenzyl)-3-[(1R)-2,3-dihydro-1H-inden-1-ylamino]-2-hydroxypropyl}-5-methyl-N³,N³-dipropylisophthalamide (X)

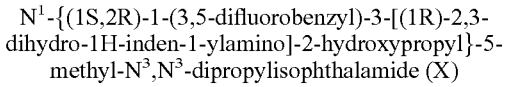

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (1R)-2,3-dihydro-1H-inden-1-ylamine (VI) and "5-Me-PHTH" (IX), the title compound is obtained, MH+=578.

Example 566

5-chloro-N¹-{(1S,2R)-1-(3,5-difluorobenzyl)-2-hydroxy-3-[(1-methyl-1-phenylethyl)amino]propyl}-N³,N³-dipropylisophthalamide (X)

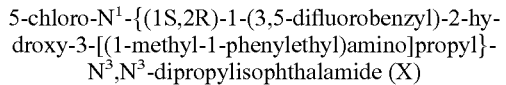

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (1-methyl-1-phenylethyl)amine (VI) and "5-Cl-PHTH" (IX), the title compound is obtained, MH+=601.

Example 567

N¹-[(1S,2R)-3-[(1-benzofuran-2-ylmethyl)amino]-1-(3,5-difluorobenzyl)-2-hydroxypropyl]-5-methyl-N³,N³-dipropylisophthalamide (X)

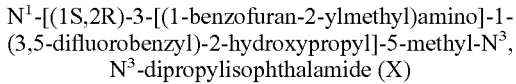

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (1-benzofuran-2-ylmethyl)amine (VI) and "5-Me-PHTH" (IX), the title compound is obtained, MH+=592.

Example 568

N¹-[(1S,2R)-3-{[(1R)-1-(3-bromophenyl)ethyl]amino}-1-(3,5-difluorobenzyl)-2-hydroxypropyl]-5-methyl-N³,N³-dipropylisophthalamide (X)

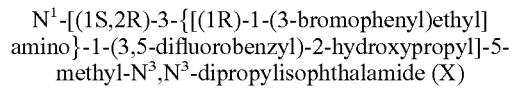

Following the general procedure of EXAMPLEs 4, 5 and 6 and making non-critical variations but using tert-butyl (1S)-2-(3,5-difluorophenyl)-1-[(2S)-oxiranyl]ethylcarbamate (V, EXAMPLE 3), (1R)-1-(3-bromophenyl)ethyl]amine (VI) and "5-Me-PHTH" (IX), the title compound is obtained, MH+=645.

Example 569

N¹-{(1S,2R)-1-(4-fluorobenzyl)-2-hydroxy-3-[(3-iodobenzyl)amino]propyl}-5-methyl-N³,N³-dipropylisophthalamide (X)

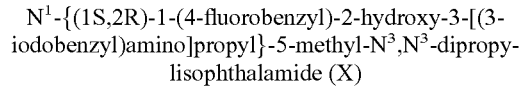

Following the general procedure of EXAMPLEs 4, 5 and 6 and making non-critical variations but using tert-butyl (1S)-2-(4-fluorophenyl)-1-[(2S)-oxiranyl]ethylcarbamate (V), 3-iodobenzylamine (VI) and "5-Me-PHTH" (IX), the title compound is obtained, MH+=660.

Example 570

N-{(1S,2R)-1-benzyl-2-hydroxy-3-[(3-methoxybenzyl)amino]propyl}-3-[butyl(butyryl)amino]-5-methylbenzamide (X)

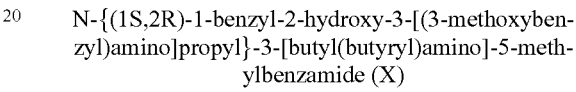

Following the general procedure of EXAMPLES 4, 5 and 6 and making non-critical variations but using tert-butyl 1-(2-oxiranyl)-2-phenylethylcarbamate (V), 3-methoxybenzylamine (VI) and 3-[butyl(butyryl)amino]-5-methylbenzoic acid (IX), the title compound is obtained, MH+=560.

Example 571

N¹-{1-benzyl-2-hydroxy-3-[(3-methox-benzyl)amino]propyl}-4-methyl-N³,N³-dipropylisophthalamide (X)

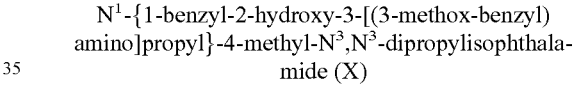

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-methyl-N,N-dipropylisophthalic acid (IX), the title compound is obtained, MH+=546.

Example 572

N³-{1-benzyl-2-hydroxy-3-[(3-methoxybenzyl)amino]propyl}-4-methyl-N¹,N¹-dipropylisophthalamide (X)

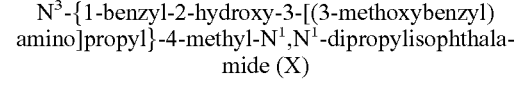

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 4-methyl-N,N-dipropylisophthalic acid (IX), the title compound is obtained, MH+=546.

Example 573

N¹-{(1S,2R)-1-(3,5-difluorobenzyl)-2-hydroxy-3-[(3-methoxybenzyl)amino]propyl}-4-methyl-N³,N³-dipropylisophthalamide (X)

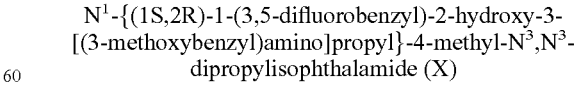

Following the general procedure of EXAMPLEs 4, 5 and 6 and making non-critical variations but. using tert-butyl (1S)-2-(3,5-difluorophenyl)-1-[(2S)-oxiranyl]ethylcarbamate (V), 3-methoxybenzylamine (VI) and 4-methyl-N,N-dipropylisophthalic acid (IX), the title compound is obtained, MH+=582.

Example 574

N-{(1S,2R)-1-benzyl-2-hydroxy-3-[(3-methoxybenzyl)amino]propyl}-1-butyl-1H-indole-6-carboxamide (X)

Following the general procedure of EXAMPLEs 4, 5 and 6 and making non-critical variations but using tert-butyl 1-(2-oxiranyl)-2-phenylethylcarbamate (V), 3-methoxybenzylamine (VI) and 1-butyl-1H-indole-6-carboxylic acid (IX), the title compound is obtained, MH$^+$=500.

Example 575

N$^1$-[(1S,2R)-3-anilino-1-(3,5-difluorobenzyl)-2-hydroxypropyl]-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), aniline (VI) and and "5-Me-PHTH" (IX), the title compound is obtained, MH$^+$=538.

Example 576

5-bromo-N$^1$-[(1S,2R)-3-[(3-bromobenzyl)amino]-1-(3,5-difluorobenzyl)-2-hydroxypropyl]-N$^3$ N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 3-bromobenzylamine (VI) and 5-bromo-N,N-dipropylisophthalic acid (IX), the title compound is obtained, MH$^+$=696.

Example 577

N-{(1S,2R)-1-(3,5-difluorobenzyl)-2-hydroxy-3-[(3-iodobenzyl)amino]propyl}-4-methylpentanamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 3-iodobenzylamine (VI) and 4-methylpentanoic acid (IX), the title compound is obtained, MH$^+$=531.

Example 578

N-{(1S,2R)-1-(3,5-difluorobenzyl)-2-hydroxy-3-[(3-iodobenzyl)amino]propyl}-3-methylpentanamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 3-iodobenzylamine (VI) and CH$_3$—CH$_2$—CH(CH$_3$—)—CH$_2$—CO—OH (IX), the title compound is obtained, MH$^+$=531.

Example 579

N$^1$-{(1S,2R)-1-(3,5-difluorobenzyl)-2-hydroxy-3-[(3-hydroxybenzyl)amino]propyl}-5-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V), 3-hydroxybenzylamine (VI) and "5-Me-PHTH" (IX), the title compound is obtained, MH$^+$=568.

Example 580 tert-butyl (1S)-1-(3,5-difluorobenzyl)-3-[(3-methoxybenzyl)amino]-2-oxopropylcarbamate (XI)

tert-butyl (1S)-3-bromo-1-(3,5-difluorobenzyl)-2-oxopropylcarbamate (III, EXAMPLE 1, 1 equivalent) is dissolved in isopropanol and treated with 3-methoxybenzylamine (VI, 5 equivalents). The reaction is heated at reflux for 2 hours and monitored by TLC for disappearance of the ketone (III). Upon completion, the reaction is concentrated to dryness under reduced pressure and partitioned between equal parts water and ethyl acetate. The organic phase is extracted, washed two additional times with water, then saline, then dried over anhydrous sodium sulfate, filtered and concentrated under reduced pressure. The crude material is purified by column chromatography on silica gel to give the title compound.

Example 581 tert-butyl (1S,2R)-3-amino-1-(3,5-difluorobenzyl)-2-hydroxypropylcarbamate (XIII)

tert-butyl-(1S, 2R)-3-azido-1-(3,5-difluorobenzyl)-2-hydroxypropylcarbamate (XII, EXAMPLE 165, 1 equivalent) is dissolved in methanol and treated with 10% palladium on carbon under hydrogen (50 psi). The reaction is shaken at 20-25 degrees C. for 2 hours, filtered through a diatomaceous earthpad, and concentrated under reduced pressure to dryness. The crude material is purified by column chromatography on silica gel to give the title compound.

Example 582

Benzyl (1S,2R)-1-benzyl-2-hydroxy-3-[(3-methoxybenzyl)amino]propylcarbamate (VII)

A mixture of benzyl (1S)-1-[(2S)-oxiranyl]-2-phenylethylcarbamate (V, 0.22 g, 0.74 mmol), 3-methoxybenzylamine (VI, 0.13 g, 0.92 mmol), and ethanol (2 mL) is stirred at reflux for 2.3 hours and then cooled and concentrated under reduced pressure. The residue is chouromatographed (silica gel; methanol/dichloromethane/ammonium hydroxide, 4/96/trace) to give the title compound, MS m/z at (m+H)$^+$=435.2.

Example 583

Benzyl (1S,2R)-1-benzyl-2-hydroxy-3-(tert-butylcarbamoyl)-3-[(3-methoxybenzyl)amino]propyl-carbamate (XXXIV)

A mixture of benzyl (1S,2R)-1-benzyl-2-hydroxy-3-[(3-methoxybenzyl)amino]propyl-carbamate (VII, EXAMPLE 582, 9.00 g, 21.0 mmol), di-tert-butyl dicarbonate (5.00 g, 23 mmol), sodium carbonate monohydrate (3.12 g, 25 mmol), THF (200 mL), and water (100 mL) is stirred at 20-25 degrees C. for 2 hours. THF is removed under reduced pressure and the residue is partitioned between ethyl acetate and water. The organic layer is then washed with saline, dried over anhydrous sodium sulfate, filtered, and concentrated. Column chromatography (silica gel; methanol/dichloromethane, 1/99) gives the title compound, NMR (300 MHz, CDCl$_3$) delta 7.26, 6.79, 5.00, 4.42, 3.89, 3.78, 3.44, 3.28, 2.91, 1.49; MS (ESI+) for C$_{31}$H$_{38}$N$_2$O$_6$ m/z (M+H)$^+$=535.3.

Example 584 tert-Butyl (2R,3S)-3-amino-2-hydroxy-4-phenylbutyl(3-methoxybenzyl)carbamate (XXXV)

A suspension of benzyl (1S,2R)-1-benzyl-2-hydroxy-3-(tert-butylcarbamoyl)-3-[(3-methoxybenzyl)amino]propylcarbamate (XXXIV, EXAMPLE 583, 10.2 g, 18.6 mmol) and palladium on carbon (5%, 1.00 g) in ethanol (100 mL) is shaken in a hydrogenation apparatus under hydrogen (50 psi) for 2 hours. Then the mixture is filtered through diatomaceous earth and concentrated. The concentrate is chromatographed (silica gel; methanol/dichloromethane, 5/95) to give the title compound, NMR (CDCl$_3$) δ 1.50, 2.46, 2.92, 3.04, 3.42, 3.52, 3.72, 3.82, 4.49, 6.83, 7.19 and 7.28; MS (ESI+) for C$_{23}$H$_{32}$N$_2$O$_4$ m/z (M+H)$^+$=401.3.

Example 585 tert-butyl (2R,3S)-3-({3-cyano-5-[(dipropylamino)carbonyl]benzoyl}amino)-2-hydroxy-4-phenylbutyl (3-methoxybenzyl)carbamate (XXXVI)

To a mixture of 3-cyano-5-[(dipropylamino)carbonyl]benzoic acid (IX/XXXII, PREPARATION 7, 0.086 g, 0.314 mmol) and tert-butyl (2R,3S)-3-amino-2-hydroxy-4-phenylbutyl(3-methoxybenzyl)carbamate (XXXV, EXAMPLE 584, 0.126 g, 0.314 mmol) in dichloromethane (0.3 mL) is added diethylcyanophosphonate (0.062 g, 0.330 mmol) and triethylamine (0.032 g, 0.316 mmol). The mixture is stirred at 20-25 degrees for 65 hours and then partitioned between dichloromethane and saturated aqueous sodium bicarbonate. The organic phase is separated and dried over sodium sulfate and concentrated. The residue is chromatographed (silica gel, 20 mL; methanol/dichloromethane, 5/95) to give several mixed fractions, which are combined and rechromatographed (silica gel; acetone/hexane, 20/80) to give the title compound, MS (ESI+) for C$_{38}$H$_{48}$N$_4$O$_6$ m/z 657.6 (M+H)$^+$=657.6; (M+Na)=679.5 and (M-C$_4$H$_9$O$_2$)=557.5.

Example 586

N$^1$-{(1S,2R)-1-benzyl-2-hydroxy-3-[(3-methoxybenzyl)amino]propyl}-5-cyano-N$^3$,N$^3$-dipropylisophthalamide hydrochloride (X)

A mixture of tert-butyl (2R,3S)-3-({3-cyano-5-[(dipropylamino)carbonyl]benzoyl}amino)-2-hydroxy-4-phenylbutyl (3-methoxybenzyl)carbamate (XXXVI, EXAMPLE 585, 0.080 g, 0.122 mmol), dichloromethane (1 mL), and methanol saturated with hydrochloric acid (1 mL) is stirred for 8 hours, after which time the solvents are removed under reduced pressure. A few drops of methanol, followed by ether, gives the title compound, MS (ESI+) for C$_{33}$H$_{40}$N$_4$O$_4$ m/z (M+H)$^+$=557.5

Example 587

N$^1$-{(1S,2R)-1-Benzyl-2-hydroxy-3-[(3-methoxybenzyl)amino]propyl}-N$^3$,N$^3$-dipropyl-1,3,5-benzenetricarboxamide (X)

To a mixture of 3-(aminocarbonyl)-5-[(dipropylamino)carbonyl]benzoic acid (IX, PREPARATION 6, 0.18 g, 0.616 mmol) in dry DMF (16 mL) is added EDC (0.182 9, 0.9 mmol), HOBT (0.127 g, 0.9 mmol), triethylamine (0.062 g, 0.616 mol), and (2R,3S)-3-amino-1-[(3-methoxybenzyl)amino]-4-phenyl-2-butanol (VIII, EXAMPLE 175, 0.185 g, 0.616 mmol). The mixture is stirred at 20-25 degrees C. for 3 days. The mixture is partitioned between water and ethyl acetate. The phases are separated and the organic phase is washed three times with water. The organic phase is dried over anhydrous magnesium sulfate, filtered and concentrated. Column chromatography (silica gel, 75 mL; methanol/methylene chloride, 10/90) gives the title compound, IR (diffuse reflectance) 3306, 3301, 3270, 2962, 1676, 1667, 1663, 1645, 1638, 1627, 1615, 1550, 1537, 1450 and 1439 cm$^{-1}$; NMR (CDCl$_3$) δ 0.645, 0.968, 1.20, 1.43, 1.67, 2.8, 2.97, 3.38, 3.47, 3.73, 3.87, 4.31, 6.78, 6.91, 7.23, 7.72, 7.87, 8.22 and 8.43.

Example 588

1-tert-butyl (1S,2R)-1-(3,5-difluorobenzyl)-2-hydroxy-3-[(3-iodobenzyl)amino]propylcarbamate (VII)

tert-Butyl (1S)-2-(3,5-difluorophenyl)-1-[(2S)-oxiranyl]ethylcarbamate (V, EXAMPLE 3, 1.75 g, 5.8 mmole) is mixed with isopropanol (30 ml). The reaction flask is charged with 3-iodobenzylamine (VI). The reaction mixture is heated to reflux for 45 minutes, HPLC analysis indicates complete disappearance of the epoxide (V). The reaction mixture is concentrated under reduced pressure and the residue is partitioned between ethyl acetate (150 ml) and aqueous hydrochloric acid (3%, 35 ml). The organic phase is separated and washed with aqueous hydrochloric acid (3%, 20 ml), bicarbonate, saline and dried over sodium sulfate. Concentration under reduced pressure gives the title compound, M+H=535.

Example 589

1-9H-fluoren-9-ylmethyl (2R,3S)-3-(3-t-butyloxycarbonyl)amino-4-(3,5-difluorophenyl)-2-hydroxybutyl(3'-iodobenzyl)carbamate hydrochloride (XXXIV)

1-tert-butyl(1S,2R)-1-(3,5-difluorobenzyl)-2-hydroxy-3-[(3-iodobenzyl)amino]propylcarbamate (VII, EXAMPLE 588, 2.5 g, 4.7 mmole) and triethylamine (0.72 ml, 5.1 mmole) in THF (10 ml) are mixed. The reaction is cooled to 0 degrees and treated with FMOC-Cl (1.2 g, 4.7 mmole) in THF (2 ml) via addition funnel. After 15 minutes HPLC indicates complete disappearance of starting material. The reaction is diluted with ethyl acetate and washed with aqueous potassium bisulfate, saturated aqueous bicarbonate, saline and dried over sodium sulfate. Concentration under reduced pressure gives crude product which is purified by flash chromatography, eluting with ethyl acetate/hexane (20/80) followed by ethyl acetate to give the title compound, M+H=757.

Example 590

1-9H-fluoren-9-ylmethyl(2R,3S)-3-amino-4-(3,5-difluorophenyl)-2-hydroxybutyl(3-iodobenzyl)carbamate hydrochloride (XXXV)

1-9H-fluoren-9-ylmethyl(2R,3S)-3-(3-t-butyloxycarbonyl)amino-4-(3,5-difluorophenyl)-2-hydroxybutyl(3'-iodobenzyl)carbamate hydrochloride (XXXIV, EXAMPLE 589, 2.9 g) in hydrochloric acid/dioxane (4N, 10 ml). The mixture is stirred 1 hour then slowly poured into rapidly stirring ether (200 ml). The product is filtered and dried to give the title compound, M+H=657.

Example 591

1-9H-fluoren-9-ylmethyl(2R,3S)-4-(3,5-difluorophenyl)-2-hydroxy-3-{[5-oxo-5-(1-piperidinyl)pentanoyl]amino}butyl(3-iodobenzyl)carbamate (XXXVI)

HOBt (81 mg, 0.6 mmole) and EDC (105 mg, 0.55 mmole) are added to 1-carboxy-5-piperdinylglutaramide (IX, 100 mg, 0.5 mmole) in DMF (2 ml). The acid is activated 60 minutes then treated with 1-9H-fluoren-9-ylmethyl (2R,3S)-3-amino-4-(3,5-difluorophenyl)-2-hydroxybutyl(3-iodobenzyl)carbamate hydrochloride (XXXV, EXAMPLE 590, 300 mg, 0.43 mmole) and NMM (0.19 ml, 1.72 mmole). The reaction is stirred 3 hours then concentrated under reduced pressure. The residue is partitioned between ethyl acetate and saturated aqueous bicarbonate. The organic phases are washed with aqueous potassium bisulfate, saline, dried over sodium sulfate and finally concentrated under reduced pressure to give crude product. Purification via flash chromatography with ethyl acetate/hexane (50/50) then methanol/ethyl acetate (10/90) gives the title compound, M+H=838.

Example 592

1-N-{(1S,2R)-1-(3,5-difluorobenzyl)-2-hydroxy-3-[(3-iodobenzyl)amino]propyl}-5-oxo-5-(1-piperidinyl)pentanamide trifluroacetate (X)

1-N-{(1S,2R)-1-(3,5-difluorobenzyl)-2-hydroxy-3-[(3-iodobenzyl)amino]propyl}-5-oxo-5-(1-piperidinyl)pentanamide trifluroacetate (XXXVI, EXAMPLE 591, 240 mg, 0.29 mmole is dissolved in diethylamine (10%, 9 ml) in methylene chloride. The reaction is stirred at 20-25 degrees overnight. The next morning the reaction is concentrated under reduced pressure and the residue is redissolved in methylene chloride and purified by preparative reverse phase HPLC. The appropriate fractions are pooled and concentrated under reduced pressure and partitioned between ethyl acetate and saline. The organic phase is separated and dried over sodium sulfate and concentrated to give the title compound, M+H=614.

Example 593

5-(Aminosulfonyl)-$N^1$-{(1S,2R)-1-benzyl-2-hydroxy-3-[(3-methoxybenzyl)amino]propyl}-$N^3$,N-dipropylisophthalamide (X)

O-(7-Azabenzotriazol-1-yl)-N,N,N',N'-tetramethyluronium hexafluorophosphate (HATU, 0.0928 9, 0.244 mmol) is added to a mixture of, 3-(aminosulfonyl)-5-[(dipropylamino)-carbonyl]benzoic acid (XXXIX, PREPARATION 13, 0.0800 g, 0.244 mmol) and (2R,3S)-3-amino-1-[(3-methoxybenzyl)-amino]-4-phenyl-2-butanol (VIII, EXAMPLE 175, 0.0732 g, 0.244 mmol) in dry DMF (3 mL). The mixture is stirred for 18 hours at 20-25 degrees, and then partitioned between ethyl acetate and water. The organic phase is separated and washed with saline, dried over anhydrous sodium sulfate, filtered and concentrated. The concentrate is column chouromatographed (silica gel; methanol/dichloromethane, 5/95) to give the title compound, MS (ESI+) for $C_{32}H_{42}N_4O_6S$ M/z $(M+H)^+$=611.5; HRMS (FAB) calculated for $C_{32}H_{42}N_4O_6S+H_1$=611.2903, found=611.2904.

Example 594

$N^1$-{(1S,2R)-1-benzyl-2-hydroxy-3-[(3-methoxybenzyl)amino]propyl}-$N^3$,$N^3$-dipropyl-5-(1-pyrrolidinylsulfonyl)isophthalamide (X)

Following the general procedure of EXAMPLE 593 and making non-critical variations but using 3-[(dipropylamino)carbonyl]-5-(1-pyrrolidinylsulfonyl)benzoic acid (XXXIX, PREPARATION 15, the title compound is obtained, ES (ESI+) for $C_{36}H_{48}N_4O_6S$ m/z $(M+H)^+$=665.6; HRMS (FAB) calculated for $C_{36}H_{48}N_4O_6S+H_1$=665.3372, found=665.3393.

Example 595

$N^1$-{(1S,2R)-1-benzyl-2-hydroxy-3-[(3-methoxybenzyl)amino]propyl}-5-[(methylamino)sulfonyl]-$N^3$, $N^3$-dipropylisophthalamide (X)

Following the general procedure of EXAMPLE 593 and making non-critical variations but using 3-[(dipropylamino)carbonyl]-5-[(methylamino)-sulfonyl]benzoic acid (XXXIX, PREPARATION 17, the title compound is obtained, MS (ESI+) for $C_{33}H_{44}N_4O_6S$ m/z $(M+H)^+$=625.5.

Example 596

$N^1$-{(1S,2R)-1-benzyl-2-hydroxy-3-[(3-methoxybenzyl)amino]propyl}-5-[(dimethylamino)sulfonyl]-$N^3$, $N^3$-dipropylisophthalamide (X)

Following the general procedure of EXAMPLE 593 and making non-critical variations but using 3-[(dimethylamino)sulfonyl]-5-[(dipropylamino)carbonyl]-benzoic acid (XXXIX, PREPARATION 19), the title compound is obtained, MS (ESI+) for $C_{34}H_{46}N_4O_6S$ m/z $(M+H)^+$=639.5

Examples 597-619

Following the general procedure of EXAMPLEs 589 through 592 but starting with (2R,3S)-3-amino-1-[(3-methoxybenzyl)amino]-4-phenyl-2-butanol (VIII, EXAMPLE 175) and using the amide forming agent (IX) of Column A, the Substituted Amine (X) of Column B is obtained.

| EX # | Column A Amide Forming Agent (IX) | Column B Substituted Amine (X) | MS Data M + H |
|---|---|---|---|
| 597 | 2-methyl-3-(methylsulfonyl)propanoic acid | N-{(1S,2R)-1-benzyl-2-hydroxy-3-[(3-methoxybenzyl)amino]propyl}-2-methyl-3-(methylsulfonyl)propanamide hydrochloride | 449 |
| 598 | 3-(methylsulfonyl)propanoic acid | N-{(1S,2R)-1-benzyl-2-hydroxy-3-[(3-methoxybenzyl)amino]propyl}-3-(methylsulfonyl)propanamide hydrochloride | 435 |
| 599 | 2-amino-1,3-thiazole-4-carboxylic acid hydrochloride | 2-amino-N-{(1S,2R)-1-benzyl-2-hydroxy-3-[(3-methoxybenzyl)amino]propyl}-1,3-thiazole-4-carboxamide dihydrochloride | 427 |
| 600 | 5-(methylsulfonyl)pentanoic acid | N-{(1S,2R)-1-benzyl-2-hydroxy-3-[(3-methoxybenzyl)amino]propyl}-5-(methylsulfonyl)pentanamide hydrochloride | 463 |
| 601 | 4-anilino-4-oxobutanoic acid | $N^1$-{(1S,2R)-1-benzyl-2-hydroxy-3-[(3-methoxybenzyl)amino]propyl}-$N^4$-phenylsuccinamide hydrochloride | 476 |
| 602 | (2R)-4-amino-2,3,3-trimethyl-4-oxobutanoic acid | (3R)-$N^4$-{(1S,2R)-1-benzyl-2-hydroxy-3-[(3-methoxybenzyl)amino]propyl}-2,2,3-trimethylbutanediamide hydrochloride | 442 |
| 603 | 3-[(dipropylamino)sulfonyl]propanoic acid | N-{(1S,2R)-1-benzyl-2-hydroxy-3-[(3-methoxybenzyl)amino]propyl}-3-[(dipropylamino)sulfonyl]-propanamide hydrochloride | 520 |
| 604 | 5-(dipropylamino)-5-oxopentanoic acid | $N^1$-{(1S,2R)-1-benzyl-2-hydroxy-3-[(3-methoxybenzyl)amino]propyl}-$N^5$,$N^5$-dipropylpentanediamide hydrochloride | 498 |
| 605 | 4-oxo-4-(1-piperidinyl)butanoic acid | N-{(1S,2R)-1-benzyl-2-hydroxy-3-[(3-methoxybenzyl)amino]propyl}-4-oxo-4-(1-piperidinyl)butanamide hydrochloride | 468 |
| 606 | 4-(dipropylamino)-4-oxobutanoic acid | N~1~-{(1S,2R)-1-benzyl-2-hydroxy-3-[(3-methoxybenzyl)amino]propyl}-$N^4$,$N^4$-dipropylsuccinamide hydrochloride | 484 |
| 607 | 5-oxo-5-(1-piperidinyl)pentanoic acid | N-{(1S,2R)-1-benzyl-2-hydroxy-3-[(3-methoxybenzyl)amino]propyl}-5-oxo-5-(1-piperidinyl)pentanamide hydrochloride | 482 |
| 608 | 5-anilino-5-oxopentanoic acid | $N^1$-{(1S,2R)-1-benzyl-2-hydroxy-3-[(3-methoxybenzyl)amino]propyl}-$N^5$- | 490 |

|  | -continued | | |
|---|---|---|---|
| EX # | Column A<br>Amide Forming Agent<br>(IX) | Column B<br>Substituted Amine (X) | MS<br>Data<br>M + H |
| 609 | 3,3-dimethyl-4-oxo-4-(1-piperidinyl)butanoic acid | N-{(1S,2R)-1-benzyl-2-hydroxy-3-[(3-methoxybenzyl)amino]propyl}-3,3-dimethyl-4-oxo-4-(1-piperidinyl)butanamide hydrochloride | 496 |
| 610 | 4-(isopentylsulfonyl)butanoic acid | N-{(1S,2R)-1-benzyl-2-hydroxy-3-[(3-methoxybenzyl)amino]propyl}-4-(isopentylsulfonyl)butanamide hydrochloride | 505 |
| 611 | 4-(dipropylamino)-2,2-dimethyl-4-oxobutanoic acid | $N^1$-{(1S,2R)-1-benzyl-2-hydroxy-3-[(3-methoxybenzyl)amino]propyl}-2,2-dimethyl-$N^4$,$N^4$-dipropylsuccinamide hydrochloride | 512 |
| 612 | 4-[(dipropylamino)sulfonyl]butanoic acid | N-{(1S,2R)-1-benzyl-2-hydroxy-3-[(3-methoxybenzyl)amino]propyl}-4-[(dipropylamino)sulfonyl]butanamide hydrochloride | 534 |
| 613 | 4-[(methylanilino)sulfonyl]butanoic acid | N-{(1S,2R)-1-benzyl-2-hydroxy-3-[(3-methoxybenzyl)amino]propyl}-4-[(methylanilino)sulfonyl]butanamide hydrochloride | 540 |
| 614 | 3-[(methylanilino)sulfonyl]propanoic acid | N-{(1S,2R)-1-benzyl-2-hydroxy-3-[(3-methoxybenzyl)amino]propyl}-3-[(methylanilino)sulfonyl]propanamide | 526 |
| 615 | Acetic acid | N-{(1S,2R)-1-benzyl-2-hydroxy-3-[(3-methoxybenzyl)amino]propyl}acetamide hydrochloride | 343 |
| 616 | 3-(isopentylsulfonyl)propanoic acid | N-{(1S,2R)-1-benzyl-2-hydroxy-3-[(3-methoxybenzyl)amino]propyl}-3-(isopentylsulfonyl)propanamide hydrochloride | 491 |
| 617 | 5-oxo-5-(1-piperidinyl)pentanoic acid | N-{(1S,2R)-1-(3,5-difluorobenzyl)-2-hydroxy-3-[(3-iodobenzyl)amino]propyl}-5-oxo-5-(1-piperidinyl)pentanamide trifluoroacetate | 614 |
| 618 | 5-oxo-5-(1-piperidinyl)pentanoic acid | N-{(1S,2R)-1-benzyl-2-hydroxy-3-[(3-iodobenzyl)amino]propyl}-5-oxo-5-(1-piperidinyl)pentanamide trifluoroacetate | 578 |
| 619 | 3-[(dipropylamino)sulfonyl]propanoic | N-{(1S,2R)-1-(3,5-difluorobenzyl)-2-hydroxy-3-[(3- | 652 |

| EX # | Column A<br>Amide Forming Agent<br>(IX) | Column B<br>Substituted Amine (X) | MS<br>Data<br>M + H |
|---|---|---|---|
| | acid | iodobenzyl)amino]propyl}-<br>3-<br>[(dipropylamino)sulfonyl]<br>propanamide | |

Example 620

$N^1$-{(1S,2R)-1-Benzyl-2-hydroxy-3-[(3-methoxy-benzyl)amino]propyl}-5-ethyl-$N^3$,$N^3$-dipropylisoph-thalamide (X)

Diethyl cyanophosphonate (0.132 mL, 0.870 mmol) is added to a mixture of 3-[(dipropylamino)carbonyl]-5-ethyl-benzoic acid (IX, PREPARATION 21, 0.200 g, 0.720 mmol), (2R,3S)-3-amino-1-[(3-methoxybenzyl)amino]-4-phenyl-2-butanol (VIII, EXAMPLE 175, 0.216 mg, 0.720 mmol), and triethylamine (0.121 mL, 0.870 mmol) in dichloromethane (3 mL). The mixture was stirred for 1 hour at 20-25 degrees C. Dichloromethane is then removed under reduced pressure. The residue is partitioned between ethyl acetate and water. The organic phase is separated and is washed with saline, dried over anhydrous sodium sulfate, filtered and concentrated. The concentrate is column chouromatographed (silica gel; methanol/dichloromethane, 5/95) to give the title compound, MS (ESI+) for $C_{34}H_{45}N_3O_4$ m/z (M+H)$^+$=560.4; HOURMS (FAB) calculated for $C_{34}H_{45}NO_4$+H=560.3488, found=560.3487.

Example 621

$N^1$-{(1S,2R)-1-Benzyl-2-hydroxy-3-[(3-methoxy-benzyl)amino]propyl}-5-isobutyl-$N^3$,$N^3$-dipropyl-isophthalamide Following the general procedure of PREPARATIONS 20 and 21 and making non-critical variations but using isobutyl-boronic acid, and following the general procedure of EXAMPLE 620 but using the 5-isobutylisophthalic acid (IX), the title compound is obtained, MS (ESI+) for $C_{36}H_{49}N_3O_4$ m/z (M+H)$^+$=588.6; HRMS (FAB) calculated for $C_{36}H_{49}N_3O_4$+$H_1$=588.3801, found=588.3810.

Example 622

$N^1$-{(1S,2R)-1-Benzyl-2-hydroxy-3-[(3-methoxy-benzyl)amino]propyl}-5-tert-butyl-$N^3$,$N^3$-dipropyl-isophthalamide Following the general procedure of PREPARATIONS 20 and 21 and making non-critical variations but using tert-butylboronic acid, and following the general procedure of EXAMPLE 620 but using the tert-butylphthalic acid (IX), the title compound is obtained, MS (ESI+) for $C_{36}H_{49}N_3O_4$ M/z (M+H)$^+$=588.5; HRMS (FAB) calculated for $C_{36}H_{49}N_3O_4$+$H_1$=588.3801, found=588.3791.

Example 623

$N^1$-{(1S,2R)-1-benzyl-2-hydroxy-3-[(3-methoxyben-zyl)amino]propyl}-5-cyano-$N^3$-propylisophthala-mide (X)

Following the general procedure of EXAMPLE 586 and making non-critical variations, but using tert-butyl (2R,3S)-3-({3-cyano-5-[(propylamino)carbonyl]benzoyl}amino)-2-hydroxy-4-phenylbutyl(3-methoxybenzyl)carbamate (XXXVI) the title compound is obtained, M+H=515.1.

Examples 624-628

Following the general procedure of EXAMPLE 587 and making non-critical variations, but using the appropriate amines (VIII) and amide forming agents (IX), for example PREPARATIONS 6 and 19, the titled compounds are obtained.

| EXAMPLE | Substituted Amine (X) | M + H = |
|---|---|---|
| 624 | $N^1$-{(1S,2R)-1-(3,5-difluorobenzyl)-2-hydroxy-3-[(3-methoxybenzyl)amino]propyl}-$N^3$,$N^3$-dipropyl-1,3,5-benzenetricarboxamide | 611.0 |
| 625 | $N^1$-{(1S,2R)-1-benzyl-2-hydroxy-3-[(3-methoxybenzyl)amino]propyl}-$N^3$,$N^3$-dimethyl-$N^5$,$N^5$-dipropyl-1,3,5-benzenetricarboxamide | 603.0 |
| 626 | $N^1$-[(1S,2R)-3-amino-1-benzyl-2-hydroxypropyl]-$N^3$,$N^3$-dipropyl-1,3,5-benzenetricarboxamide | 455.1 |
| 627 | $N^1$-[(1S,2R)-1-benzyl-2-hydroxy-3-(isopentylamino)propyl]-$N^3$,$N^3$-dipropyl-1,3,5-benzenetricarboxamide | 525.6 |
| 628 | $N^1$-{(1S,2R)-1-benzyl-2-hydroxy-3-[(3-methoxybenzyl)amino]propyl}-$N^3$-propyl-1,3,5-benzenetricarboxamide | 533.1 |

Example 629

N-{(1S,2R)-1-Benzyl-2-hydroxy-3-[(3-methoxyben-zyl)amino]propyl}-3-[butyryl(propyl)amino]-5-me-thylbenzamide (X)

Following the procedure of EXAMPLE 570 and making non-critical variations, diethyl cyanophosphonate (0.0760 mL, 0.550 mmol) is added to a mixture of 3-[butyryl(propyl)amino]-5-methylbenzoic acid (IX, 0.120 g, 0.460 mmol), (2R,3S)-3-amino-1-[(3-methoxybenzyl)amino]-4-phenyl-2-butanol (VIII, 0.137 g, 0.460 mmol), and triethylamine (0.0760 mL, 0.550 mmol) in dichloromethane (5 mL). The mixture is stirred for 1 hour at 20-25 degrees C. Dichloromethane is then removed under reduced pressure. The residue is partitioned between ethyl acetate and water. The organic is separated, is washed with saline, dried over anhydrous sodium sulfate, filtered and concentrated. The concentrate is column chromatographed (silica gel; methanol/dichloromethane, 5/95) to give the title compound, NMR (400 MHz, CDCl$_3$) δ 7.09, 4.15, 3.80, 3.79, 3.60, 3.02, 2.84, 2.36, 1.94, 1.56, 1.49, 0.87 and 0.81;. MS (ESI+) for C$_{33}$H$_{43}$N$_3$O$_4$ m/z (M+H)$^+$=546.3; HRMS (FAB) calculated for C$_{33}$H$_{43}$N$_3$O$_4$+H=546.3331, found=546.3331.

Example 630

N-{(1S,2R)-1-benzyl-2-hydroxy-3-[(3-methoxybenzyl)amino]propyl}-1-propyl-1H-indole-6-carboxamide (X)

Following the general procedure of EXAMPLE 539 and making non-critical variations, the title compound is obtained, IR (diffuse reflectance) 3330, 3314, 2960, 2952, 2931, 2873, 1621, 1599, 1525, 1499, 1467, 1353, 1283, 1253 and 786 cm$^{-1}$.

Example 631

N-{(1S,2R)-1-(3,5-difluorobenzyl)-2-hydroxy-3-[(3-methoxybenzyl)amino]propyl}-1-propyl-1H-indole-6-carboxamide (X)

Following the general procedure of EXAMPLE 539 and making non-critical variations, the title compound is obtained, IR (diffuse reflectance) 3289, 1627, 1621, 1595, 1531, 1525, 1520, 1507, 1466, 1458, 1450, 1349, 1317, 1252 and 1117 cm$^{-1}$.

Examples 633-708

Following the general procedures of CHART A as well as PREPARATIONs 1-13, EXAMPLEs 1-13, 321-48-579, 597-622 and 624-631 and making non-critical variations and using the appropriate reagents, the substituted amines (X) of EXAMPLES 633-708 are obtained.

| EXAMPLE | Substituted Amine (X) | MH$^+$ = |
|---|---|---|
| 633 | N$^1$-{(1S,2R)-1-(3,5-difluorobenzyl)-3-[(3,4-dimethylbenzyl)amino]-2-hydroxypropyl}-5-methyl-N$^3$,N$^3$-dipropylisophthalamide | 580 |
| 634 | N$^1$-[(1S,2R)-3-[(3-aminobenzyl)amino]-1-(3,5-difluorobenzyl)-2-hydroxypropyl]-5-methyl-N$^3$,N$^3$-dipropylisophthalamide | 567 |
| 635 | N-{(1S,2R)-1-(3,5-difluorobenzyl)-2-hydroxy-3-[(3-iodobenzyl)amino]propyl}octanamide | 559 |
| 636 | N$^3$-[(1S,2R)-1-(3,5-difluorobenzyl)-2-hydroxy-3-({1-methyl-1-[3-(trifluoromethyl)phenyl]ethyl}amino)propyl]-N$^5$,N$^5$-dipropyl-3,5-pyridinedicarboxamide | 635 |
| 637 | N$^1$-[(1S,2R)-1-(3,5-difluorobenzyl)-2-hydroxy-3-({1-methyl-1-[3-(trifluoromethyl)phenyl]ethyl}amino)propyl]-5-methyl-N$^3$,N$^3$-dipropylisophthalamide | 648 |
| 638 | N$^1$-((1S,2R)-1-(3,5-difluorobenzyl)-2-hydroxy-3-{[(1R,2S)-2-hydroxy-2,3-dihydro-1H-inden-1-yl]amino}propyl)-5-methyl-N$^3$,N$^3$-dipropylisophthalamide | 594 |
| 639 | N$^1$-{(1S,2R)-1-(3,5-difluorobenzyl)-3-[(1R)-2,3-dihydro-1H-inden-1-ylamino]-2-hydroxypropyl}-5-methyl-N$^3$,N$^3$-dipropylisophthalamide | 578 |
| 640 | N-{(1S,2R)-1-(3,5-difluorobenzyl)-2-hydroxy-3-[(3-iodobenzyl)amino]propyl}-3-methylbenzamide | 551 |
| 641 | N$^1$-[(1S,2R)-1-(3,5-difluorobenzyl)-2-hydroxy-3-(1H-isoindol-3-ylamino)propyl]-5-methyl-N$^3$,N$^3$-dipropylisophthalamide | 577 |
| 642 | N$^1$-((1S,2R)-1-(3,5-difluorobenzyl)-2-hydroxy-3-{[(1R,2S,5R)-2-isopropyl-5-methylcyclohexyl]amino}propyl)-5-methyl-N$^3$,N$^3$-dipropylisophthalamide | 600 |
| 643 | N$^1$,N$^1$-diallyl-5-chloro-N$^3$-{(1S,2R)-1-(3,5-difluorobenzyl)-2-hydroxy-3-[(1-methyl-1-phenylethyl)amino]propyl}isophthalamide | 597 |
| 644 | 5-chloro-N$^1$-{(1S,2R)-1-(3,5-difluorobenzyl)-2-hydroxy-3-[(1-methyl-1-phenylethyl)amino]propyl}-N$^3$,N$^3$-bis(2-methoxyethyl)isophthalamide | 633 |
| 645 | N$^3$-{(1S,2R)-1-(3,5-difluorobenzyl)-2-hydroxy-3-[(1-phenylcyclopentyl)amino]propyl}-N$^5$,N$^5$-dipropyl-3,5-pyridinedicarboxamide | 593 |
| 646 | N$^1$-{(1S,2R)-1-(3,5-difluorobenzyl)-3-[(3-ethylbenzyl)amino]-2-hydroxypropyl}-5-methyl-N$^3$,N$^3$-dipropylisophthalamide | 580 |
| 647 | N$^1$-((1S,2R)-1-(3,5-difluorobenzyl)-3-{[3-(dimethylamino)benzyl]amino}-2-hydroxypropyl)-5-methyl-N$^3$,N$^3$-dipropylisophthalamide | 595 |
| 648 | N$^1$-((1S,2R)-1-(3,5-difluorobenzyl)-3-{[(4,5-dimethyl-2-furyl)methyl]amino}-2-hydroxypropyl)-5-methyl-N$^3$,N$^3$-dipropylisophthalamide | 570 |
| 649 | N$^1$-{(1S,2R)-1-(3,5-difluorobenzyl)-2-hydroxy-3-[(1-phenylcyclopentyl)amino]propyl}-5-methyl-N$^3$,N$^3$-dipropylisophthalamide | 606 |
| 650 | N$^1$-[(1S,2R)-3-(cyclopropylamino)-1-(3,5-difluorobenzyl)-2-hydroxypropyl]-5-methyl-N$^3$,N$^3$-dipropylisophthalamide | 502 |
| 651 | N$^1$-[(1S,2R)-3-[(cyclopropylmethyl)amino]-1-(3,5-difluorobenzyl)-2-hydroxypropyl]-5-methyl-N$^3$,N$^3$-dipropylisophthalamide | 516 |
| 652 | N$^1$-{(1S,2R)-1-(3,5-difluorobenzyl)-2-hydroxy-3-[(3-iodobenzyl)amino]propyl}-N$^5$,N$^5$-dipropylpentanediamide | 630 |
| 653 | N$^3$-{(1S,2R)-1-(3,5-difluorobenzyl)-3-[(2-furylmethyl)amino]-2-hydroxypropyl}-N$^5$,N$^5$-dipropyl-3,5-pyridinedicarboxamide | 529 |
| 654 | N$^1$-{(1S,2R)-1-(3,5-difluorobenzyl)-2-hydroxy-3-[(tetrahydro-2-furanylmethyl)amino]propyl}-5-methyl-N$^3$,N$^3$-dipropylisophthalamide | 546 |
| 655 | N$^3$-{(1S,2R)-1-(3,5-difluorobenzyl)-2-hydroxy-3-[(1-phenylcyclopropyl)amino]propyl}-N$^5$,N$^5$-dipropyl-3,5-pyridinedicarboxamide | 565 |
| 656 | N$^1$-{(1S,2R)-1-(3,5-difluorobenzyl)-2-hydroxy-3-[(2-oxo-3-azepanyl)amino]propyl}-5-methyl-N$^3$,N$^3$-dipropylisophthalamide | 573 |
| 657 | N$^1$-((1S,2R)-1-(3,5-difluorobenzyl)-2-hydroxy-3-{[(3-methyl-2-furyl)methyl]amino}propyl)-5-methyl-N$^3$,N$^3$-dipropylisophthalamide | 556 |
| 658 | N$^1$-((1S,2R)-1-(3,5-difluorobenzyl)-2-hydroxy-3-{[(2S)-tetrahydro-2-furanylmethyl]amino}propyl)-5-methyl-N$^3$,N$^3$-dipropylisophthalamide | 546 |

-continued

| EXAMPLE | Substituted Amine (X) | MH+ = |
|---|---|---|
| 659 | 5-chloro-N$^1$-{(1S,2R)-1-(3,5-difluorobenzyl)-2-hydroxy-3-[(1-methyl-1-phenylethyl)amino]propyl}-N$^3$,N$^3$-di(2-propynyl)isophthalamide | 593 |
| 660 | N$^1$-{(1S,2R)-1-(3,5-difluorobenzyl)-2-hydroxy-3-[(3-isopropenylbenzyl)amino]propyl}-5-methyl-N$^3$,N$^3$-dipropylisophthalamide | 592 |
| 661 | N$^1$-{(1S,2R)-1-(3,5-difluorobenzyl)-2-hydroxy-3-[(2-propoxyethyl)amino]propyl}-5-methyl-N$^3$,N$^3$-dipropylisophthalamide | 548 |
| 662 | N$^1$-[(1S,2R)-1-(3,5-difluorobenzyl)-3-(hexylamino)-2-hydroxypropyl]-5-methyl-N$^3$,N$^3$-dipropylisophthalamide | 546 |
| 663 | N-{(1S,2R)-1-(3,5-difluorobenzyl)-2-hydroxy-3-[(3-iodobenzyl)amino]propyl}-4-(3-methyl-5-oxo-4,5-dihydro-1H-pyrazol-1-yl)benzamide | 633 |
| 664 | methyl 4-({[(2R,3S)-4-(3,5-difluorophenyl)-3-({3-[(dipropylamino)carbonyl]-5-methylbenzoyl}amino)-2-hydroxybutyl]amino}methyl)benzoate | 610 |
| 665 | N$^1$-{(1S,2R)-1-(3,5-difluorobenzyl)-2-hydroxy-3-[(2-methoxyethyl)amino]propyl}-5-methyl-N$^3$,N$^3$-dipropylisophthalamide | 520 |
| 666 | N$^1$-{(1S,2R)-1-(3,5-difluorobenzyl)-2-hydroxy-3-[(5-isoxazolylmethyl)amino]propyl}-5-methyl-N$^3$,N$^3$-dipropylisophthalamide | 543 |
| 667 | (1R,2R)-N$^1$-{(1S,2R)-1-(3,5-difluorobenzyl)-2-hydroxy-3-[(3-iodobenzyl)amino]propyl}-N$^2$,N$^2$-dipropyl-1,2-cyclopropanedicarboxamide | 628 |
| 668 | N$^3$-((1S,2R)-1-(3,5-difluorobenzyl)-2-hydroxy-3-{[(2S)-tetrahydro-2-furanylmethyl]amino}propyl)-N$^5$,N$^5$-dipropyl-3,5-pyridinedicarboxamide | 533 |
| 669 | N$^1$-{(1S,2R)-1-(3,5-difluorobenzyl)-2-hydroxy-3-[(2-methoxybenzyl)amino]propyl}-5-methyl-N$^3$,N$^3$-dipropylisophthalamide | 582 |
| 670 | N$^1$-{(1S,2R)-1-(3,5-difluorobenzyl)-2-hydroxy-3-[(3-isopropylbenzyl)amino]propyl}-5-methyl-N$^3$,N$^3$-dipropylisophthalamide | 594 |
| 671 | 4-(butyrylamino)-N-{(1S,2R)-1-(3,5-difluorobenzyl)-2-hydroxy-3-[(3-iodobenzyl)amino]propyl}benzamide | 622 |
| 672 | N$^1$-[(1S,2R)-3-[(3-amino-3-oxopropyl)amino]-1-(3,5-difluorobenzyl)-2-hydroxypropyl]-5-methyl-N$^3$,N$^3$-dipropylisophthalamide | 533 |
| 673 | N$^3$-[(1S,2R)-3-(benzylamino)-1-(3,5-difluorobenzyl)-2-hydroxypropyl]-N$^5$,N$^5$-dipropyl-3,5-pyridinedicarboxamide 1-oxide | 555 |
| 674 | N$^1$-[(1S,2R)-1-(3,5-difluorobenzyl)-2-hydroxy-3-[(3-iodobenzyl)amino]propyl]-5-ethynyl-N$^3$,N$^3$-dipropylisophthalamide | 688 |
| 675 | N$^1$-{(1S,2R)-1-(3,5-difluorobenzyl)-2-hydroxy-3-[(7-oxabicyclo[2.2.1]hept-2-ylmethyl)amino]propyl}-5-methyl-N$^3$,N$^3$-dipropylisophthalamide | 572 |
| 676 | N$^1$-{(1S,2R)-1-(3,5-difluorobenzyl)-3-[(3-ethynylbenzyl)amino]-2-hydroxypropyl}-5-methyl-N$^3$,N$^3$-dipropylisophthalamide | 576 |
| 677 | N$^1$-((1S,2R)-1-(3,5-difluorobenzyl)-2-hydroxy-3-{[(2-methyl-1,3-thiazol-5-yl)methyl]amino}propyl)-5-methyl-N$^3$,N$^3$-dipropylisophthalamide | 573 |
| 678 | N$^1$-((1S,2R)-1-(3,5-difluorobenzyl)-3-{[(2-ethyl-1,3-thiazol-5-yl)methyl]amino}-2-hydroxypropyl)-5-methyl-N$^3$,N$^3$-dipropylisophthalamide | 587 |
| 679 | N$^1$-((1S,2R)-1-(3,5-difluorobenzyl)-2-hydroxy-3-{[(3R)-2-oxoazepanyl]amino}propyl)-5-methyl-N$^3$,N$^3$-dipropylisophthalamide | 573 |
| 680 | N$^1$-[(1S,2R)-3-(cyclobutylamino)-1-(3,5-difluorobenzyl)-2-hydroxypropyl]-5-methyl-N$^3$,N$^3$-dipropylisophthalamide | 516 |
| 681 | N$^1$-[(1S,2R)-3-(butylamino)-1-(3,5-difluorobenzyl)-2-hydroxypropyl]-5-ethynyl-N$^3$,N$^3$-dipropylisophthalamide | 528 |
| 682 | N$^1$-{(1S,2R)-1-(3,5-difluorobenzyl)-3-[(3-ethylbenzyl)amino]-2-hydroxypropyl}-5-ethynyl-N$^3$,N$^3$-dipropylisophthalamide | 590 |
| 683 | N$^1$-[(1S,2R)-1-(3,5-difluorobenzyl)-3-(5-hexynylamino)-2-hydroxypropyl]-5-methyl-N$^3$,N$^3$-dipropylisophthalamide | 542 |
| 684 | N$^3$-((1S,2R)-1-(3,5-difluorobenzyl)-2-hydroxy-3-{[(5-methyl-2-furyl)methyl]amino}propyl)-N$^5$,N$^5$-dipropyl-3,5-pyridinedicarboxamide | 543 |
| 685 | N$^1$-{(1S,2R)-1-(3,5-difluorobenzyl)-2-hydroxy-3-[(1-methyl-1-phenylethyl)amino]propyl}-N$^5$,N$^5$-dipropylpentanediamide | 532 |
| 686 | N$^1$-((1S,2R)-1-(3,5-difluorobenzyl)-3-{[1-(2-furyl)-1-methylethyl]amino}-2-hydroxypropyl)-5-methyl-N$^3$,N$^3$-dipropylisophthalamide | 570 |
| 687 | N$^1$-((1S,2R)-1-(3,5-difluorobenzyl)-2-hydroxy-3-{[(3-isobutyl-5-isoxazolyl)methyl]amino}propyl)-5-methyl-N$^3$,N$^3$-dipropylisophthalamide | 599 |
| 688 | N$^1$-((1S,2R)-1-(3,5-difluorobenzyl)-2-hydroxy-3-{[(2-isobutyl-1,3-thiazol-5-yl)methyl]amino}propyl)-5-methyl-N$^3$,N$^3$-dipropylisophthalamide | 615 |
| 689 | N-{(1S,2R)-1-(3,5-difluorobenzyl)-3-[(3-ethylbenzyl)amino]-2-hydroxypropyl}-3-[(dipropylamino)sulfonyl]propanamide | 554 |
| 690 | N$^1$-{(1S,2R)-1-benzyl-2-hydroxy-3-[(2-phenylethyl)amino]propyl}-N$^3$,N$^3$-dipropylisophthalamide | 516 |
| 691 | N$^1$-((1S,2R)-1-benzyl-3-{[2-(2-chlorophenyl)ethyl]amino}-2-hydroxypropyl)-N$^3$,N$^3$-dipropylisophthalamide | 551 |
| 692 | N$^1$-((1S,2R)-1-benzyl-2-hydroxy-3-{[3-(2-oxo-1-pyrrolidinyl)propyl]amino}propyl)-N$^3$,N$^3$-dipropylisophthalamide | 537 |
| 693 | N$^1$-{(1S,2R)-1-benzyl-3-[(cyclohexylmethyl)amino]-2-hydroxypropyl}-N$^3$,N$^3$-dipropylisophthalamide | 508 |
| 694 | N$^1$-[(1S,2R)-1-benzyl-3-(cyclopropylamino)-2-hydroxypropyl]-N$^3$,N$^3$-dipropylisophthalamide | 452 |
| 695 | N$^1$-{(1S,2R)-1-benzyl-2-hydroxy-3-[(2-oxo-3-azepanyl)amino]propyl}-N$^3$,N$^3$-dipropylisophthalamide | 523 |
| 696 | N-[(1S,2R)-3-(benzylamino)-1-(3,5-difluorobenzyl)-2-hydroxypropyl]-3-(butylsulfonyl)benzamide | 531 |
| 697 | N$^1$-[(1S,2R)-1-benzyl-3-({2-[(2-ethylhexyl)oxy]ethyl}amino)-2-hydroxypropyl]-N$^3$,N$^3$-dipropylisophthalamide | 568 |
| 698 | N$^1$-[(1S,2R)-1-benzyl-2-hydroxy-3-{[(1S,2R)-2-hydroxy-2,3-dihydro-1H-inden-1-yl]amino}propyl)-N$^3$,N$^3$-dipropylisophthalamide | 544 |

| EXAMPLE | Substituted Amine (X) | MH+ = |
|---|---|---|
| 699 | N¹-((1S,2R)-1-benzyl-2-hydroxy-3-{[1-(4-hydroxyphenyl)ethyl]amino}propyl)-N³,N³-dipropylisophthalamide | 532 |
| 700 | N¹-[(1S,2R)-1-benzyl-3-(cycloheptylamino)-2-hydroxypropyl]-N³,N³-dipropylisophthalamide | 508 |
| 701 | N¹-{(1S,2R)-1-benzyl-3-[([1,1'-biphenyl]-2-ylmethyl)amino]-2-hydroxypropyl}-N³,N³-dipropylisophthalamide | 578 |
| 702 | N¹-{(1S,2R)-1-benzyl-3-[(2-fluorobenzyl)amino]-2-hydroxypropyl}-N³,N³-dipropylisophthalamide | 520 |
| 703 | N-{(1S,2R)-1-(3,5-difluorobenzyl)-2-hydroxy-3-[(3-methoxybenzyl)amino]propyl}-3-(dimethylamino)benzamide | 484 |
| 704 | N-{(1S,2R)-1-(3,5-difluorobenzyl)-2-hydroxy-3-[(3-methoxybenzyl)amino]propyl}-1-naphthamide | 491 |
| 705 | N¹-[(1S,2R)-1-benzyl-3-({2-[({5-[(dimethylamino)methyl]-2-furyl}methyl)sulfanyl]ethyl}amino)-2-hydroxypropyl]-N³,N³-dipropylisophthalamide | 609 |
| 706 | N¹-[(1S,2R)-1-benzyl-3-({2-[(2-chloro-6-fluorobenzyl)sulfanyl]ethyl}amino)-2-hydroxypropyl]-N³,N³-dipropylisophthalamide | 615 |
| 707 | N¹-[(1S,2R)-3-[([1,1'-biphenyl]-4-ylmethyl)amino]-1-(3,5-difluorobenzyl)-2-hydroxypropyl]-5-methyl-N³,N³-dipropylisophthalamide | 628 |
| 708 | N¹-[(1S,2R)-1-(3,5-difluorobenzyl)-2-hydroxy-3-(1-naphthylamino)propyl]-5-methyl-N³,N³-dipropylisophthalamide | 588 |

Examples 709-737

Following the general procedure of CHART D and EXAMPLEs 165-169 and making non-critical variations and using the appropriate reagents, the substituted amines (X) of EXAMPLES 709-737 are obtained.

| EXAMPLE | Substituted Amine (X) | MH+ |
|---|---|---|
| 709 | N¹-{(1S,2R)-1-(3,5-difluorobenzyl)-2-hydroxy-3-[(1H-imidazol-5-ylmethyl)amino]propyl}-5-methyl-N³,N³-dipropylisophthalamide | 542 |
| 710 | N¹-((1S,2R)-1-(3,5-difluorobenzyl)-2-hydroxy-3-{[(2-phenyl-1H-imidazol-5-yl)methyl]amino}propyl)-5-methyl-N³,N³-dipropylisophthalamide | 618 |
| 711 | N¹-((1S,2R)-1-(3,5-difluorobenzyl)-2-hydroxy-3-{[(1-methyl-1H-imidazol-2-yl)methyl]amino}propyl)-5-methyl-N³,N³-dipropylisophthalamide | 556 |
| 712 | N¹-[(1S,2R)-3-{[(2-butyl-4-chloro-1H-imidazol-5-yl)methyl]amino}-1-(3,5-difluorobenzyl)-2-hydroxypropyl]-5-methyl-N³,N³-dipropylisophthalamide | 633 |
| 713 | N¹-[(1S,2R)-3-{[(6-chloroimidazo[2,1-b][1,3]thiazol-5-yl)methyl]amino}-1-(3,5-difluorobenzyl)-2-hydroxypropyl]-5-methyl-N³,N³-dipropylisophthalamide | 633 |
| 714 | N¹-((1S,2R)-1-(3,5-difluorobenzyl)-2-hydroxy-3-{[(1-methyl-1H-benzimidazol-2-yl)methyl]amino}propyl)-5-methyl-N³,N³-dipropylisophthalamide | 606 |
| 715 | N¹-((1S,2R)-1-(3,5-difluorobenzyl)-2-hydroxy-3-{[(2-hydroxy-1-naphthyl)methyl]amino}propyl)-5-methyl-N³,N³-dipropylisophthalamide | 618 |
| 716 | N¹-((1S,2R)-1-(3,5-difluorobenzyl)-2-hydroxy-3-{[(4-oxo-4H-chouromen-3-yl)methyl]amino}propyl)-5-methyl-N³,N³-dipropylisophthalamide | 620 |
| 717 | N¹-((1S,2R)-1-(3,5-difluorobenzyl)-3-{[(1,5-dimethyl-3-oxo-2-phenyl-2,3-dihydro-1H-pyrazol-4-yl)methyl]amino}-2-hydroxypropyl)-5-methyl-N³,N³-dipropylisophthalamide | 662 |
| 718 | N¹-[(1S,2R)-3-({[5-cyano-6-(methylsulfanyl)-2-pyridinyl]methyl}amino)-1-(3,5-difluorobenzyl)-2-hydroxypropyl]-5-methyl-N³,N³-dipropylisophthalamide | 624 |
| 719 | [5-({[(2R,3S)-4-(3,5-difluorophenyl)-3-({3-[(dipropylamino)carbonyl]-5-methylbenzoyl}amino)-2-hydroxybutyl]amino}methyl)-2-furyl]methyl acetate | 614 |
| 720 | N¹-[(1S,2R)-3-[(1-benzofuran-3-ylmethyl)amino]-1-(3,5-difluorobenzyl)-2-hydroxypropyl]-5-methyl-N³,N³-dipropylisophthalamide | 592 |
| 721 | methyl 4-({[(2R,3S)-4-(3,5-difluorophenyl)-3-({3-[(dipropylamino)carbonyl]-5-methylbenzoyl}amino)-2-hydroxybutyl]amino}methyl)-1-methyl-1H-pyrrole-2-carboxylate | 613 |
| 722 | N¹-[(1S,2R)-1-(3,5-difluorobenzyl)-2-hydroxy-3-({[1-(phenylsulfonyl)-1H-pyrrol-2-yl]methyl}amino)propyl]-5-methyl-N³,N³-dipropylisophthalamide | 681 |
| 723 | N¹-((1S,2R)-1-(3,5-difluorobenzyl)-2-hydroxy-3-{[(1-methyl-1H-pyrrol-2-yl)methyl]amino}propyl)-5-methyl-N³,N³-dipropylisophthalamide | 555 |
| 724 | N¹-[(1S,2R)-3-{[(4-chloro-1-methyl-1H-pyrazol-3-yl)methyl]amino}-1-(3,5-difluorobenzyl)-2-hydroxypropyl]-5-methyl-N³,N³-dipropylisophthalamide | 591 |
| 725 | N¹-((1S,2R)-1-(3,5-difluorobenzyl)-3-{[(3,5-dimethyl-1-phenyl-1H-pyrazol-4-yl)methyl]amino}-2-hydroxypropyl)-5-methyl-N³,N³-dipropylisophthalamide | 646 |
| 726 | N¹-[(1S,2R)-3-{[(5-chloro-3-methyl-1-phenyl-1H-pyrazol-4-yl)methyl]amino}-1-(3,5-difluorobenzyl)-2-hydroxypropyl]-5-methyl-N³,N³-dipropylisophthalamide | 667 |
| 727 | N¹-((1S,2R)-1-(3,5-difluorobenzyl)-2-hydroxy-3-{[(3-phenyl-1H-pyrazol-4-yl)methyl]amino}propyl)-5-methyl-N³,N³-dipropylisophthalamide | 618 |
| 728 | N¹-[(1S,2R)-3-{[(5-chloro-2-thienyl)methyl]amino}-1-(3,5-difluorobenzyl)-2-hydroxypropyl]-5-methyl-N³,N³-dipropylisophthalamide | 593 |
| 729 | N¹-((1S,2R)-1-(3,5-difluorobenzyl)-2-hydroxy-3-{[(3-phenoxy-2-thienyl)methyl]amino}propyl)-5-methyl-N³,N³-dipropylisophthalamide | 650 |
| 730 | N¹-{(1S,2R)-1-(3,5-difluorobenzyl)-2-hydroxy-3-[(3-quinolinylmethyl)amino]propyl}-5-methyl-N³,N³-dipropylisophthalamide | 603 |
| 731 | N¹-{(1S,2R)-1-(3,5-difluorobenzyl)-2-hydroxy-3-[(2-quinolinylmethyl)amino]propyl}-5-methyl-N³,N³-dipropylisophthalamide | 603 |
| 732 | N¹-((1S,2R)-1-(3,5-difluorobenzyl)-2-hydroxy-3-{[(1-methyl-1H-indol-2-yl)methyl]amino}propyl)-5-methyl-N³,N³-dipropylisophthalamide | 605 |

-continued

| EXAMPLE | Substituted Amine (X) | MH+ |
|---|---|---|
| 733 | N¹-[(1S,2R)-3-{[(1-benzyl-1H-indol-3-yl)methyl]amino}-1-(3,5-difluorobenzyl)-2-hydroxypropyl]-5-methyl-N³,N³-dipropylisophthalamide | 681 |
| 734 | N¹-((1S,2R)-1-(3,5-difluorobenzyl)-2-hydroxy-3-{[(1-methyl-1H-indol-3-yl)methyl]amino}propyl)-5-methyl-N³,N³-dipropylisophthalamide | 605 |
| 735 | N¹-{(1S,2R)-1-(3,5-difluorobenzyl)-2-hydroxy-3-[({1-[(4-methylphenyl)sulfonyl]-1H-indol-3-yl}methyl)amino]propyl}-5-methyl-N³,N³-dipropylisophthalamide | 745 |
| 736 | N¹-[(1S,2R)-3-{[(2-butyl-1H-imidazol-5-yl)methyl]amino}-1-(3,5-difluorobenzyl)-2-hydroxypropyl]-5-methyl-N³,N³-dipropylisophthalamide | 598 |
| 737 | methyl 3-({[(2R,3S)-4-(3,5-difluorophenyl)-3-({3-[(dipropylamino)carbonyl]-5-methylbenzoyl}amino)-2-hydroxybutyl]amino}methyl)-1H-indole-6-carboxylate | 649 |

Example 738

3-[({(1S,2R)-1-benzyl-2-hydroxy-3-[(3-methoxybenzyl)amino]propyl}amino)carbonyl]-5-[butyl(butyryl)amino]benzyl diethyl phosphate (X)

Following the general procedure of CHART L and EXAMPLE 620 and making non-critical variations, the title compound is obained, HRMS (FAB)=712.3749.

Example 739

$N^1$-{(1S,2R)-1-benzyl-2-hydroxy-3-[(3-methoxybenzyl)amino]propyl}-5-(cyanomethyl)-$N^3$,$N^3$-dipropyl-isophthalamide (X)

Step 1. A mixture of diethyl 1,3,5-benzenetricarboxylate (5.2 g) and borane methylsulfide complex (6.1 g) is stirred in THF (150 mL) at 20-25 degrees C. overnight. The mixture is then treated with methanol, concentrated to dryness, and chouromatographed (silica gel) to give diethyl 5-(hydroxymethyl)isophthalate. Diethyl 5-(hydroxymethyl)isophthalate (3.4 g) is hydroyzed in ethanol and water with lithium hydroxide monohydrate (0.57 g) at 20-25 degrees C. for 3.5 hours at which time the solvents are removed under reduced pressure. Water (100 mL) is added and the mixture is acidified to pH=4 with concentrated hydrochloric acid. The mixture is extracted with ethyl acetate and dried over magnesium sulfate, filtered, and concentrated to give 3-(ethoxycarbonyl)-5-(hydroxymethyl)benzoic acid, high resolution MS MH+=225.0769. 3-(Ethoxycarbonyl)-5-(hydroxymethyl)benzoic acid (2.3 g), EDC (3.0 g), 1-HOBT (2.1 g), diisopropylethylamine (2.7 mL), dipropyl amine (2.8 mL), and DMF (50 mL) are stirred at 20-25 degrees C. overnight. The mixture is then partitioned between ethyl acetate, water, and saline. The organic phase is separated and dried over magnesium sulfate, filtered, and concentrated. Chromatography (silica gel) gives ethyl 3-[(dipropylamino)carbonyl]-5-(hydroxymethyl)benzoate, NMR (CDCl$_3$) δ 0.77, 1.0, 1.4, 1.6, 1.7, 3.2, 3.5, 4.4, 4.8, 7.6, 8.0 and 8.1.

Step 2. A mixture of ethyl 3-[(dipropylamino)carbonyl]-5-(hydroxymethyl)benzoate (1.5 g) and phosphorous tribromide (0.95 mL) is stirred in dichloromethane (10 mL) and heated at 50 degrees C. for 4 hours and then cooled and partitioned between dichloromethane and water. The organic phase is separated and washed with aqueous sodium bicarbonate and then dried over magnesium sulfate and taken to dryness to give ethyl 3-(bromomethyl)-5-[(dipropylamino)carbonyl]benzoate, high resolution MS MH+=370.1020. Ethyl 3-(bromomethyl)-5-[(dipropylamino)carbonyl]benzoate (1.4 g) and sodium cyanide (0.2 g) are stirred in dry DMSO (25 mL) at 20-25 degrees C. for 3.5 hours and the mixture is then partitioned between ethyl acetate, water and saline. The organic layer is separated and dried over magnesium sulfate and taken to dryness under reduced pressure to give ethyl 3-(cyanomethyl)-5-[(dipropylamino)carbonyl] benzoate. Ethyl 3-(cyanomethyl)-5-[(dipropylamino)carbonyl]benzoate (0.6 g) is hydrolyzed with lithium hydroxide monohydrate (0.1 g) in ethanol and water at 20-25 degrees C. overnight and then added to water (50 mL). The pH is adjusted to 4 using concentrated hydrochloric acid and the mixture is partitioned between ethyl acetate, water, and saline. The organic phase is separated and dried over magnesium sulfate and taken to dryness under reduced pressure to give 3-(cyanomethyl)-5-[(dipropylamino)carbonyl]benzoic acid, MS M+H=287.2.

Step 3. A mixture of 3-(cyanomethyl)-5-[(dipropylamino)carbonyl]benzoic acid (IX, 0.13 g), (2R,3S)-3-amino-1-[(3-methoxybenzyl)amino]-4-phenyl-2-butanol (VIII, 0.14 g), HATU (0.17 g), and dichloromethane (10 mL) is stirred at 40 degrees C. overnight. After cooling, the mixture is washed with water and the organic phase is separated and dried over magnesium sulfate and taken to dryness under reduced pressure. Chromatography (silica gel) gives the title compound, M+H=571.2

Example 740

$N^1$-{(1S,2R)-1-benzyl-2-hydroxy-3-[(3-methoxybenzyl)amino]propyl}-5-(hydroxymethyl)-$N^3$,$N^3$-dipropylisophthalamide (X)

Following the procedure of CHART P and EXAMPLE 739 and making non-critical variations but using 3-[(dipropylamino)carbonyl]-5-(hydroxymethyl)benzoic acid (IX) and (2R,3S)-3-amino-1-[(3-methoxybenzyl)amino]-4-phenyl-2-butanol (VIII), the title compound is obtained, HRMS (FAB)= 615.3571.

Example 741

$N^1$-{(1S,2R)-1-benzyl-2-hydroxy-3-[(3-methoxybenzyl)amino]propyl}-5-ethynyl-$N^3$,$N^3$-dipropylisophthalamide (X)

Step 1: A mixture of methyl 3-bromo-5-[(dipropylamino)carbonyl]benzoate (XXI, 200 mg, 0.58 mmol), PdCl$_2$(Ph$_3$P)$_2$ (16 mg, 0.03 mol %) and copper (I) iodide (6 mg, 0.05 mol %) in triethylamine (1.2 mL) is heated to reflux. (Trimethylsilyl) acetylene (100 microliter, 0.7 mmol) is added, and the mixture stirred for 3 hours, cooled to 20-25 degrees, diluted with water (20 mL), and extracted with chloroform (3×15 mL). The combined organic extracts are washed with saline (20 mL), dried over sodium sulfate and concentrated under reduced pressure to give methyl 3-[(dipropylamino)carbonyl]-5-ethynylbenzoate (XXXII, 185.5 mg), NMR (300 MHz, CDCl$_3$): ☐ 7.95, 7.75, 7.43, 3.74, 3.25, 2.95, 1.49, 1.34, 0.79, 0.56 and 0.06.

Step 2: To a stirred mixture of the protected methyl 3-[(dipropylamino)carbonyl]-5-ethynylbenzoate (XXXII, Step 1, 185.3 mg, 0.49 mmol) in methanol (2.5 mL) is added a mixture of potassium hydroxide (2.9 mL of a 1 M mixture in water, 2.9 mmol). The reaction mixture is stirred for 4 hours diluted with chloroform (40 mL), the phases are separated and the organic phase is concentrated under reduced pressure to give 3-[(dipropylamino)carbonyl]-5-ethynylbenzoic acid, NMR (300 MHz, CDCl$_3$): ☐ 8.22, 8.05, 7.71, 3.48, 3.17, 3.16, 1.71, 1.55, 1.00 and 0.78.

Step 3: To a stirred mixture of 3-[(dipropylamino)carbonyl]-5-ethynylbenzoic acid (70 mg, 0.24 mmol) in DMF (2.5 mL) is added (2R,3S)-3-amino-1-[(3-methoxybenzyl)amino]-4-phenyl-2-butanol dihydrochloride (VIII, 81 mg, 0.24 mmol), HOBt (36 mg, 0.26 mmol) and diisopropylethylamine (170 microliter, 0.96 mmol). To this reaction mixture is added EDC (51 mg, 0.26 mmol) and the reaction mixture is stirred overnight. The reaction mixture is diluted with ethyl acetate (30 mL), washed with water (3×50 mL), hydrochloric acid (1 N, 30 mL), saturated sodium bicarbonate (30 mL), saline (30 mL), dried over sodium sulfate and concentrated under reduced pressure. Purification by flash chromatography (silica, ethyl acetate to methanol/chloroform, 1/10) gives the title compound, IR (KBr): 3276, 2956, 2921, 1610, 1450 and 1264 cm$^{-1}$; ESI-MS (m/z) [M+H]$^+$=556.

Example 742

N$^1$-{(1S,2R)-1-benzyl-2-hydroxy-3-[(3-iodobenzyl)amino]propyl}-N$^3$,N$^3$-dipropyl-5-prop-1-ynylisophthalamide (X)

Following the general procedure of EXAMPLE 741 and making non-critical variations but using propyne in place of (trimethylsilyl) acetylene and using (2R,3S)-3-amino-1-[(3-iodobenzyl)amino]-4-phenyl-2-butanol dihydrochloride (VIII) in place of (2R,3S)-3-amino-1-[(3-methoxybenzyl)amino]-4-phenyl-2-butanol dihydrochloride (VIII), the title compound is obtained, IR (ATR): 3305, 2930, 2872, 1613 and 1537 cm$^{-1}$; ESI-MS (m/z) [M+H]$^+$=666.

Example 743

N$^1$-((1S,2R)-1-benzyl-2-hydroxy-3-{[3-(trifluoromethyl)benzyl]amino}propyl)-5-ethynyl-N$^3$,N$^3$-dipropylisophthalamide (X)

Step 1: A mixture of tert-butyl (1S)-1-[(2S)-oxiranyl]-2-phenylethylcarbamate (V, 2.3 g, 8.7 mmol) and 3-(trifluoromethyl)benzylamine (VI, 1.9 mL, 13.1 mmol) in 2-propanol (70 mL) is heated at reflux for 4 hours. The reaction mixture is cooled to 20-25 degrees and concentrated under reduced pressure to give tert-butyl (1S,2R)-1-benzyl-2-hydroxy-3-{[3-(trifluoromethyl)benzyl]amino}propylcarbamate (VII, 3.1 g) as a solid, ESI-MS (m/z) [M+H]$^+$=439.

Step 2: A mixture of tert-butyl (1S,2R)-1-benzyl-2-hydroxy-3-{[3-(trifluoromethyl)benzyl]amino}propylcarbamate (VII, step 1, 2.5 g, 5.7 mmol) and hydrochloric acid (29 mL of a 4.0 M mixture in dioxane, 114 mmol) is stirred at 20-25 degrees. A precipitate forms and is collected by filtration, washed with ether, and dried under reduced pressure to give (2R,3S)-3-amino-4-phenyl-1-{[3-(trifluoromethyl)benzyl]amino}-2-butanol dihydrochloride (VIII, 2.13 g), ESI-MS (M/z) [M+]$^+$=339.

Step 3: A mixture of 3-[(dipropylamino)carbonyl]-5-ethynylbenzoic acid (IX, 231 mg, 0.8 mmol), (2R,3S)-3-amino-4-phenyl-1-{[3-(trifluoromethyl)benzyl]amino}-2-butanol dihydrochloride (VIII, Step 2, 493.5 mg, 1.2 mmol) HOBt (162 mg, 1.2 mmol), and diisopropylethylamine (832 Micro Liter, 4.8 mmol) is stirred in methylene chloride (4 mL) for 15 minutes EDC (206 mg, 1.2 mmol) is added and the reaction mixture is stirred overnight. The reaction mixture is diluted with water, and extracted with methylene chloride (3×25 mL). The organic phase is washed with hydrochloric acid (1N, 25 mL), saturated sodium bicarbonate (25 mL), saline dried over sodium sulfate and concentrated under reduced pressure. Purification by flash column chromatography (silica, 100% ethyl acetate to methanol/chloroform, 1/9) gives title compound, IR (ATR): 3302, 2963, 2932 and 1615 cm$^-$; MS (m/z) [M+H]$^+$=549.

Example 744

N$^1$-{(1S,2R)-1-benzyl-2-hydroxy-3-[(3-iodobenzyl)amino]propyl}-5-ethynyl-N$^3$,N$^3$-dipropylisophthalamide (X)

Following the general procedure of EXAMPLE 744 and making non-critical variations but using 3-iodobenzylamine hydrochloride salt (VI), the title compound is obtained, IR (ATR) 3295, 2960, 2927 and 1616 cm$^{-1}$, APCI-MS (m/z) [M+H]$^+$=652.

Example 745

N$^1$-{(1S,2R)-1-benzyl-3-[(3-fluorobenzyl)amino]-2-hydroxypropyl}-5-ethynyl-N$^3$,N$^3$-dipropylisophthalamide (X)

Following the general procedure of EXAMPLE 744 and making non-critical variations but using 3-fluorobenzylamine (VI), the title compound is obtained, IR (ATR): 3217, 2961, 2918 and 1615 cm$^{-1}$; APCI-MS (m/z) [M+H]$^+$=544.

Example 746

N$^1$-{(1S,2R)-1-benzyl-2-hydroxy-3-[(3-methoxybenzyl)amino]propyl}-N$^3$,N$^3$-dipropyl-5-(8-quinolinyl)isophthalamide (X)

Step 1: A mixture of methyl-3-bromo-5-[(dipropylamino)carbonyl]benzoate (XLVIII, 200 mg, 0.58 mmol), 8-quinolineboronic acid (200.6 mg, 1.2 mmol), sodium carbonate (870 Micro Liter of a 2 M mixture in water, 1.74 mmol) in toluene (6 mL) is degassed under reduced pressure for 15 minutes and purged with argon. Palladium tetrakis(triphenylphosphine) (139 mg, 0.12 mmol) is added and the reaction mixture is degassed under reduced pressure for 15 minutes and purged with argon. The reaction mixture is heated at reflux overnight, cooled to 20-25 degrees C. and diluted with chloroform. The organic phase is separated and washed with water (3×50 mL), and saline, dried over sodium sulfate and concentrated under reduced pressure. Purification by flash column chromatography (silica, ethyl acetate/hexanes, 1.3/1) gives methyl 3-[(dipropylamino)carbonyl]-5-(8-quinolinyl)benzoate (XLIX, 176 mg), NMR (300 MHz, CDCl$_3$): delta 8.91, 8.42, 8.21, 8.09, 7.95, 7.86, 7.77, 7.64, 3.94, 3.49, 3.34, 1.64, 0.99 and 0.84.

Step 2: To a mixture of methyl 3-[(dipropylamino)carbonyl]-5-(8-quinolinyl)benzoate (XLIX, step 1, 175.5 mg, 0.45 mmol) in methanol (2 mL) is added lithium hydroxide (32.3 mg, 1.4 mmol) and water (500 microliter). After stirring overnight, the reaction mixture is partitioned between ethyl acetate (10 mL) and water (10 mL). The aqueous phase is separated and acidified with hydrochloric acid (1N), and extracted with chloroform (3×40 mL). The organic phase is washed with saline, dried (sodium sulfate) and concentrated under reduced pressure to give 3-[(dipropylamino)carbonyl]-5-(8-quinolinyl)benzoic acid (IX-L, L30 mg), NMR (300 MHz, CD$_3$OD) □ 8.84, 8.39, 8.35, 8.05, 7.96, 7.90, 7.87, 7.79, 7.68, 3.50, 3.37, 1.76-1.61, 0.99 and 0.84.

Step 3: A mixture of 3-[(dipropylamino)carbonyl]-5-(8-quinolinyl)benzoic acid (IX-L, Step 2, 130 mg, 0.35 mmol), (2R,3S)-3-amino-1-[(3-methoxybenzyl)amino]-4-phenyl-2-butanol dihydrochloride (VIII, 117 mg, 0.35 mmol), HOBt (70 mg, 0.52 mmol) and diisopropylethylamine (241 microliter, 1.4 mmol) in methylene chloride (2 mL) is stirred for 15 minutes EDC (89 mg, 0.52 mmol) is added and the reaction mixture is stirred overnight. The reaction mixture is diluted with water and extracted with methylene chloride (3×25 mL). The organic phase is washed with hydrochloric acid (1N, 25 mL), saturated sodium bicarbonate (25 mL), saline, dried (sodium sulfate), and concentrated under reduced pressure. Purification by flash column chromatography (silica; methanol/chloroform, 1/9) gives the title compound, IR (NaCl): 3301, 2916, 2365 and 1613 cm$^{-1}$; APCI-MS (m/z) [M+H]$^+$= 659.

Example 747

N$^3$-{(1S,2R)-1-benzyl-2-hydroxy-3-[(3-methoxybenzyl)amino]propyl}-4'-methoxy-N$^5$,N$^5$-dipropyl[1,1'-biphenyl]-3,5-dicarboxamide hydrochloride (X)

Step 1: A mixture of 4-methoxyphenyl boronic acid (463 mg, 3.05 mmol), 3-bromo-5-[(dipropylamino)carbonyl]benzoic acid (XLVIII, 1.02 g, 3.05 mmol), and potassium phosphate (1.29 g, 6.10 mmol) in 1,2-dimethoxyethane (10 mL) and water (5 mL) is degassed with argon for 15 minutes Bis(triphenylphosphine)palladium (II) chloride (21 mg, 0.03 mmol) is added, the reaction mixture is degassed again with argon, and heated at 85 degrees C. overnight. The reaction mixture is cooled to 20-25 degrees C., and passed through a plug of diatomaceous earth.

The filtrate is acidified to pH=4 with hydrochloric acid (1N) and extracted with ethyl acetate. The organic phase is washed with water and saline and dried (magnesium sulfate). The product is purified by flash column chromatography (silica gel; ethyl acetate/acetic acid, 99/1) to give 5-[(dipropylamino)carbonyl]-4'-methoxy[1,1'-biphenyl]-3-carboxylic acid (IX-L, 667 mg), ESI-MS (m/z) [M+H]$^+$=356.

Step 2: A mixture of 5-[(dipropylamino)carbonyl]-4'-methoxy[1,1'-biphenyl]-3-carboxylic acid (IX-L, step 1, 316 mg, 0.89 mmol), (2R,3S)-3-amino-1-[(3-methoxybenzyl)amino]-4-phenyl-2-butanol dihydrochloride (VIII, 332 mg, 0.89 mmol), HOBt (181 mg, 1.34 mmol), and N-methylmorpholine (0.37 g, 3.56 mmol) in methylene chloride (8 mL) and dimethylformamide (2 mL) is stirred at 20-25 degrees for 15 minutes EDC (257 mg, 1.34 mmol) is added and the reaction mixture is stirred for 4.5 hours. The reaction mixture is partitioned between methylene chloride and water. The organic phase is washed with hydrochloric acid (1N), water, and saline, dried (magnesium sulfate), and concentrated. The concentrate is dissolved in a minimum of methanol, treated with hydrochloric acid (3 mL of a 1.0 M mixture in ether, 3 mmol), and stirred for 10 minutes. More ether is added to precipitate the rest of the product. The precipitate is collected by filtration and dried in the vacuum oven at 50 degrees C. to give the title compound, mp=205-209 degrees C.; IR (ATR): 2964 and 1649 cm$^{-1}$; APCI-MS (m/z) [M+H]$^+$=638.

Example 748

N$^3$-{(1S,2R)-1-(3,5-difluorobenzyl)-2-hydroxy-3-[(3-methoxybenzyl)amino]propyl}-N$^5$,N$^5$-dipropyl[1,1'-biphenyl]-3,5-dicarboxamide hydrochloride (X)

Step 1: A mixture of tert-butyl (1S,2R)-2-(3,5-difluorophenyl)-1-[(2S)-oxiranyl]ethylcarbamate (V, 500 mg, 1.67 mmol) and 3-methoxybenzylamine (VI, 0.34g, 2.51 mmol) in 2-propanol (3 mL) is heated at reflux overnight, allowed to cool to 20-25 degrees C., and concentrated under reduced pressure. The residue is crystallized from ethyl acetate/hexanes and collected by filtration to afford tert-butyl (1S,2R)-1-(3,5-difluorobenzyl)-2-hydroxy-3-[(3-methoxybenzyl)amino]propylcarbamate (VII, 575 mg) as a solid: ESI-MS (m/z): 437 [M+H]$^+$.

Step 2: A mixture of tert-butyl (1S,2R)-1-(3,5-difluorobenzyl)-2-hydroxy-3-[(3-methoxybenzyl)amino]propylcarbamate (VII, Step 1, 535 mg, 1.23 mmol) in methanol (2 mL) is treated with hydrochloric acid (3.2 mL of a 1.0 M mixture in ether, 3.2 mmol), and stirred at 20-25 degrees C. for 30 minutes Ether is added until a precipitate formed. The precipitate is collected by filtration is (2R,3S)-3-amino-4-(3,5-difluorophenyl)-1-[(3-methoxybenzyl)amino]-2-butanol dihydrochloride (VIII).

Step 3: A mixture of 5-[(dipropylamino)carbonyl][1,1'-biphenyl]-3-carboxylic acid (IX, 188 mg, 0.56 mmol), (2R,3S)-3-amino-4-(3,5-difluorophenyl)-1-[(3-methoxybenzyl)amino]-2-butanol dihydrochloride (VIII, Step 2, 230 mg, 0.56 mmol), HOBt (114 mg, 0.84 mmol), and N-methylmorpholine (0.23 g, 2.24 mmol) in methylene chloride (6 mL) and dimethylformamide (1 mL) is stirred at 20-25 degrees C. for 15 minutes EDC (161 mg, 0.84 mmol) is added and the reaction mixture is stirred at 20-25 degrees C. overnight. The reaction mixture is washed with water, 1 N hydrochloric acid, water, and saline, dried (sodium sulfate), and concentrated under reduced pressure to give the title compound, mp 230-233degrees C.; IR (ATR): 2965, 1651, 1596 and 1267 cm$^1$; ESI-MS (m/z) [M+H]$^+$=644.

Example 749

N$^3$-{(1S,2R)-1-benzyl-2-hydroxy-3-[(3-methoxybenzyl)amino]propyl}-N$^5$,N$^5$-dipropyl[1,1'-biphenyl]-3,5-dicarboxamide hydrochloride (X)

Following the general procedure of EXAMPLE 748 and making non-critical variations but using (2R,3S)-3-amino-1-[(3-methoxybenzyl)amino]-4-phenyl-2-butanol dihydrochloride (VIII) in place of (2R,3S)-3-amino-4-(3,5-difluorophenyl)-1-[(3-methoxybenzyl)amino]-2-butanol dihydrochloride (VIII), the title compound is obtained, mp=214-219 degrees C.; IR (KBr): 3227, 2961, 1632 and 1605 cm$^{-1}$; ESI-MS (m/z) [M+H]$^+$=608.

Example 750

N$^3$-{(1S,2R)-1-benzyl-2-hydroxy-3-[(3-methoxybenzyl)amino]propyl}-4'-[(dimethylamino)sulfonyl]-N$^5$, N$^5$-dipropyl-1,1'-biphenyl-3,5-dicarboxamide (X)

Step 1: A flask is charged with 1,1'-bis(diphenylphosphino) ferrocene-dichloropalladium 1:1 complex (37 mg, 0.05 mmol), potassium acetate (492 mg, 4.5 mmol) and bis(pinacolato)diboron (408 mg, 1.6 mmol) and is degassed under reduced pressure for 15 min and purged with argon. To this mixture is added a mixture of methyl-3-bromo-5-[(dipropylamino)carbonyl]benzoate (XXI, 500 mg, 1.5 mmol) in anhydrous dimethyl sulfoxide (9 mL) and the reaction mixture is stirred at 80 degrees C. for 4 hours. The reaction mixture is cooled to 20-25 degrees C., diluted with toluene (50 mL), washed with water (3×150 mL), saline, dried (magnesium sulfate), and concentrated under reduced pressure to give methyl 3-[(dipropylamino)carbonyl]-5-(4,4,5,5-tetramethyl-1,3,2-dioxaborolan-2-yl)benzoate, ESI-MS (m/z) [M+H]$^+$= 390.

Step 2: A mixture of methyl 3-[(dipropylamino)carbonyl]-5-(4,4,5,5-tetramethyl-1,3,2-dioxaborolan-2-yl)benzoate (Step 1, 534 mg, 1.4 mmol), 4-bromobenzenedimethyl-sulfonamide (363 mg, 1.4 mmol), and sodium carbonate (2 mL of a 2 M mixture in water, 4.1 mmol) in toluene (10 mL) is degassed under reduced pressure for 15 minutes and then purged with argon. Palladium tetrakis(triphenylphosphine) (40 mg, 0.025 mmol) is added and the reaction mixture is degassed under reduced pressure for 15 minutes and then purged with argon. The reaction mixture is heated at reflux for 4 hours, cooled to 20-25 degrees C., filtered through a plug of diatomaceous earth and sodium sulfate, and the filtrate is concentrated under reduced pressure. Purification by flash column chromatography (silica; ethyl acetate/hexanes, 1/1) gives methyl 4'-[(dimethylamino)sulfonyl]-5-[(dipropylamino)carbonyl][1,1'-biphenyl]-3-carboxylate (XXXVIII), ESI-MS (m/z) [M+H]$^+$=447.

Step 3: A mixture of methyl 4'-[(dimethylamino)sulfonyl]-5-[(dipropylamino)carbonyl][1,1'-biphenyl]-3-carboxylate (XXXVIII, step 2, 555 mg, 1.24 mmol) in methanol (6 mL) and sodium hydroxide (2 mL of a 6.0 M mixture in water, 12 mmol) is stirred at 20-25 degrees C. for 4 hours. The reaction mixture is partitioned between ethyl acetate (40 mL) and water (40 mL). The aqueous phase is acidified to pH=4 with hydrochloric acid (1N), extracted with ether (3×100 mL), and the combined organic phases are concentrated under reduced pressure to give methyl 4'-[(dimethylamino)sulfonyl]-5-[(dipropylamino)carbonyl][1,1'-biphenyl]-3-carboxylic acid (IX-XXXIX), NMR (300 MHz, CDCl$_3$) ☐ 8.37, 8.12, 7.89, 7.80, 3.51, 3.22, 2.76, 1.74, 1.59, 1.02 and 0.79.

Step 4: A mixture of the acid (IX-XXXIX, Step 3, 150 mg, 0.35 mmol), (2R,3S)-3-amino-1-[(3-methoxybenzyl)amino]-4-phenyl-2-butanol dihydrochloride (VIII, 129 mg, 0.35 mmol) HOBt (47 mg, 0.35 mmol), and N-methylmorpholine (122 ☐L, 1.1 mmol) is stirred in methylene chloride (4 mL) for 15 minutes EDC (107 mg, 0.62 mmol) is added and the reaction mixture is stirred overnight. The reaction mixture is diluted with water, and extracted with methylene chloride (3×25 mL). The organic phase is washed with hydrochloric acid (1N, 25 mL), saturated sodium bicarbonate (25 mL), saline, dried (sodium sulfate), and concentrated under reduced pressure. Purification by flash column chromatography (silica; 100% ethyl acetate to methanol/chloroform, 1/9) gives the title compound, IR (ATR) 2932, 2837 and 1593 cm$^{-1}$; APCI-MS (m/z) [M+H]$^+$=715.

Example 751

N$^3$-{(1S,2R)-1-benzyl-2-hydroxy-3-[(3-iodobenzyl) amino]propyl}-4'-[(dimethylamino)sulfonyl]-N$^5$,N$^5$-dipropyl-1,1'-biphenyl-3,5-dicarboxamide (X)

Following the general procedure of EXAMPLE 750 and making non-critical variations but using 2R,3S)-3-amino-1-[(3-iodobenzyl)amino]-4-phenyl-2-butanol dihydrochloride (VIII), the title compound is obtained, IR (ATR): 3303, 2930, 2872 and 1614 cm$^{-1}$; APCI-MS (m/z) [M+H]$^+$=811.

Example 752

N$^1$-{(1S,2R)-1-benzyl-2-hydroxy-3-[(3-methoxybenzyl)amino]propyl}-N$^3$,N$^3$-dipropyl-5-(3-thienyl) isophthalamide hydrochloride (X)

Step 1: To an ice-cold mixture of methyl 3-amino-5-[(dipropylamino)carbonyl]benzoate (XLVIII, 1.0 g, 3.60 mmol) in aqueous hydrogen tetrafluoroborate (48% wt. in H$_2$O, 12.9 mmol) is added a cold mixture of aqueous sodium nitrite (0.25 g, 3.60 mmol) dropwise. The mixture is stirred for 10 min and then extracted with ethyl acetate. The organic phase is washed with water, dried over magnesium sulfate, filtered, and concentrated under reduced pressure to give a diazonium salt which is used without further purification, NMR (500 MHz, CD$_3$OD): ☐ 9.26, 8.86, 8.71, 4.03, 3.50, 3.22, 1.75, 1.60, 1.01 and 0.79.

Step 2: To a mixture of thiophene-3-boronic acid (1.0 g, 7.82 mmol) in methanol is added a concentrated aqueous mixture of potassium hydrogen difluoride (2.01 g, 25.8 mmol) dropwise. The reaction mixture is stirred for 10 minutes and concentrated under reduced pressure. The resulting solid is extracted with acetone and concentrated under reduced pressure gives crude material, which is recrystallized from acetone/ether to give potassium trifluoro(3-thienyl)borate salt, ESI-MS (m/z) [M+H]$^+$=151.

Step 3: A mixture of potassium trifluoro(3-thienyl)borate salt (step 2, 0.69 g, 1.82 mmol), diazonium salt from (XLVIII, step 1, 0.42 g, 2.19 mmol), and lead acetate (0.02 g, 0.09 mmol) in the dark is purged with argon for 15 minutes. Dioxane (8 mL) is added and the reaction mixture is degassed with argon and stirred at 20-25 degrees C. overnight. The reaction mixture is diluted with ether, washed with saline, dried over magnesium sulfate and concentrated under reduced pressure to give methyl 3-[(dipropylamino)carbonyl]-5-(3-thienyl) benzoate (XLIX) which is purified by flash chromatography (silica; ethyl acetate/hexanes, 1/1), ESI-MS (m/z) [M+H]$^+$= 346.

Step 4: A mixture of methyl 3-[(dipropylamino)carbonyl]-5-(3-thienyl)benzoate (XLIX, step 3, 0.31 g, 0.88 mmol) in THF/methanol/sodium hydroxide (3/1/1, 5 mL) is stirred at 40 degrees C. for 2 hours. The reaction is cooled to 20-25 degrees C., diluted with water and extracted with ethyl acetate. The aqueous phase is acidified to pH=4 and extracted with ethyl acetate. The organic phase is washed with water and saline, dried over magnesium sulfate and concentrated under reduced pressure to give 3-[(dipropylamino)carbonyl]-5-(3-thienyl)benzoic acid (IX-L), ESI-MS (m/z) [M+H]$^+$= 332.

Step 5: A mixture of 3-[(dipropylamino)carbonyl]-5-(3-thienyl)benzoic acid (IX-L, step 4, 0.26 g, 0.79 mmol), (2R, 3S)-3-amino-1-[(3-methoxybenzyl)amino]-4-phenyl-2-butanol dihydrochloride (VIII, 0.26 g, 0.71 mmol), HOBt (0.16 g, 1.18 mmol), and triethylamine (0.44 mL, 3.15 mmol) in DMF (4 mL) is stirred at 20-25 degrees C. for 10 minutes EDC (0.23 g, 1.18 mmol) is added and the reaction mixture is stirred for 4 hours. The reaction mixture is diluted with water and extracted with ethyl acetate. The organic phase is washed with hydrochloric acid (1 N), water, and saline, dried over magnesium sulfate and concentrated under reduced pressure. Recrystallization (methylene chloride/hexanes, 1/1) gives the title compound, mp=199-201 degrees C.; IR (KBr): 3278, 2961, 2874 and 2837 cm$^{-1}$; ESI-MS (m/z) [M+H]$^+$=614.

Example 753

N-{(1R,2R)-1-(3,5-difluorobenzyl)-2-hydroxy-3-[(3-methoxybenzyl)amino]propyl}-3-methyl-5-pentanoylbenzamide (X)

Step 1: To an ice-cold, stirred mixture of oxalyl chloride (733 mg, 5.77 mmol) in methylene chloroide (5 mL) is added 3 drops of dimethylformamide. After 10 minutes 3-(methoxycarbonyl)-5-methylbenzoic acid (LXXIII, 560 mg, 2.89 mmol) is added. The reaction mixture is stirred for 1 hour and concentrated under reduced pressure to provide an acid chloride (LXXIV), which is used without further purification.

Step 2: To a −78 degrees C., stirred mixture of acid halide (LXXIV, step 1, 612 mg, 2.89 mmol) and copper (I) bromide (415 mg, 2.89 mmol) in tetrahydrofuran (5 mL) is added butyl magnesium chloride (1.44 mL of a 2.0 M mixture in tetrahydrofuran, 2.89 mmol). The reaction mixture is warmed to 20-25 degrees C., quenched by addition of saturated ammonium chloride, and diluted with ether. The organic phase is separated, washed with saline, dried (sodium sulfate), filtered, and concentrated under reduced pressure. Purification by flash column chromatography (silica; hexanes/ethyl acetate, 6.5/1) gives methyl 3-methyl-5-pentanoylbenzoate (LXXVI), NMR (300 MHz, $CD_3OD$): □ 8.43, 8.05, 3.96, 3.01, 1.77, 1.55 and 1.22.

Step 3: A mixture of methyl 3-methyl-5-pentanoylbenzoate (LXXVI, step 2. 133 mg, 0.605 mmol) in methanol (1 mL) is stirred with tetrahydrofuran/methanol/sodium hydroxide (2 N) (3/1/1, 3 mL) for 3 days. The reaction mixture is diluted with ethyl acetate and washed with water. The aqueous phase is separated and acidified with hydrochloric acid (1 N) and extracted with methylene chloride. The organic phase is dried (sodium sulfate), filtered, and concentrated under reduced pressure to give 3-methyl-5-pentanoylbenzoic acid (IX-LXXVII), NMR (300 MHz, $CD_3OD$): □ 8.44, 8.03, 3.10, 2.33, 1.78, 1.64 and 1.34.

Step 4: To a mixture of 3-methyl-5-pentanoylbenzoic acid (IX-LXXVII, 112 mg, 0.589 mmol), (2R,3S)-3-amino-4-(3,5-difluorophenyl)-1-[(3-methoxybenzyl)amino]-2-butanol dihydrochloride (VIII, 239 mg, 0.589 mmol), HOBt (80 mg, 0.589 mmol), and N-methylmorpholine (250 mg, 2.47 mmol) in methylene chloride (3 mL) is added EDC (203 mg, 1.06 mmol). The reaction mixture is stirred overnight and then partitioned between ethyl acetate and water. The organic phase is washed with hydrochloric acid (1 N), saturated sodium bicarbonate, saline, dried (sodium sulfate), filtered, and concentrated under reduced pressure. Purification by flash column chromatography (silica; methylene chloride/methanol, 12/1) gives the title compound, IR (ATR): 3297, 2957, 1687 and 1628 $cm^{-1}$; APCI-MS (m/z) $[M+H]^+$=539.

Example 754

$N^1$-(4-hydroxybutyl)-$N^3$-{(1S)-2-hydroxy-1-(4-hydroxybenzyl)-3-[(3-methoxybenzyl)amino]propyl}-5-methyl-$N^1$-propylisophthalamide (X)

Step 1: To a mixture of methyl (2S)-3-[4-(benzyloxy)phenyl]-2-(tert-butoxycarbonyl)aminopropanoate (1.79 g, 4.65 mmol) in a THF/methanol/water (1/2/1, 16 ml) is added lithium hydroxide (340 mg, 13.9 mmol) and the mixture stirred at 20-25 degrees C. for 12 hours. The mixture is quenched with citric acid (10%). The resulting mixture is extracted with ethyl acetate (3×15 ml). The combined organic extracts are washed three times with water, dried over sodium sulfate, filtered, and concentrated under reduced pressure to give (2S)-3-[4-(benzyloxy)phenyl]-2-[(tert-butoxycarbonyl)amino]propanoic acid which is carried on without purification. To a −78 degrees C., stirred mixture of (2S)-3-[4-(benzyloxy)phenyl]-2-[(tert-butoxycarbonyl)amino]propanoic acid (10.0 g, 27.0 mmol) in THF (200 mL) is added NMM (3.20 mL, 29.0 mmol) and isobutyl chloroformate (3.8 mL, 29.0 mmol). The cold bath is removed, the reaction mixture is stirred for 1 hour, and then filtered. The filtrate is kept cold and used in the next step. To an ice-cold, stirred mixture of ether (110 mL) and potassium hydroxide (40%, 35 mL) is slowly added 1-methyl-3-nitro-1-nitrosoguanidine (8.40 g, 57.0 mmol). The reaction mixture is stirred until gas evolution ends. The organic phase is separated and slowly added to an ice-cold, stirred mixture of the mixed anhydride filtrate from step 2. After the reaction mixture is stirred for 1 hour, nitrogen is bubbled into the mixture for 10 minutes The resulting mixture is concentrated under reduced pressure, diluted with ethyl acetate (200 mL), and washed with water (100 mL). The organic phase is washed with saturated sodium bicarbonate and saline, dried over sodium sulfate, filtered, and concentrated under reduced pressure to give the diazoketone, which is carried on without purification or characterization. To an ice-cold, stirred mixture of diazoketone in ether (100 mL) is added hydrobromous acid (48%, 4 mL, 73 mmol). The cold bath is removed, the reaction mixture stirred for 30 minutes, and partitioned between ether and water. The organic phase separated and washed with saturated sodium bicarbonate and saline, dried over sodium sulfate, filtered, and concentrated under reduced pressure to give tert-butyl (1S)-1-[4-(benzyloxy)benzyl]-3-bromo-2-oxopropylcarbamate (IV) which is used without further purification or characterization. To a −78 degrees C., stirred mixture of tert-butyl (1S)-1-[4-(benzyloxy)benzyl]-3-bromo-2-oxopropylcarbamate (IV) in a isopropanol/THF (2/1, 150 mL) is slowly added sodium borohydride (1.15 g, 30.0 mmol). The reaction mixture is stirred for 30 minutes followed by the addition of water (30 mL). The resulting mixture is warmed to 20-25 degrees C. and concentrated under reduced pressure in a water bath not exceeding 30 degrees C. The crude residue is dissolved in ethyl acetate and washed with water and saline. The organic phase is dried over magnesium sulfate, filtered and concentrated under reduced pressure to give the bromohydrin as a solid. To an ice-cold, stirred mixture of bromohydrin in ethanol (150 mL) and ethyl acetate (100 ml) is added a potassium hydroxide (1 N) ethanol mixture (36 mL, 36 mmol). The cold bath is removed and the reaction mixture is stirred for 30 minutes. The resulting mixture is partitioned between ethyl acetate and water. The organic phase is separated and washed with saline, dried over magnesium sulfate, filtered, and concentrated under reduced pressure Purification by flash chromatography (silica; hexanes/ethyl acetate, 5/1) gives tert-butyl (1S)-2-[4-(benzyloxy)phenyl]-1-[(2S)-oxiranyl]ethylcarbamate (V, as a 8/1 mixture of diastereomers), NMR (500 MHz, $CDCl_3$) □ 7.44-7.32, 7.14, 6.93, 5.07, 4.45, 3.61, 3.00-2.60 and 1.39.

Step 2: A mixture of 4-benzyloxybutyric acid (2.69 g, 13.8 mmol), propylamine (0.82 g, 13.8 mmol), HOBt (2.05 g, 15.2 mmol), N-methylmorpholine (1.68 g, 16.6 mmol) and EDC (2.91 g, 15.2 mmol) in DMF (6 mL) is stirred at 20-25 degrees C. for 18 hours. The mixture is diluted with ethyl acetate (40 mL) and washed with water (10 mL), hydrochloric acid (1 N, 10 mL), saturated sodium bicarbonate (10 mL), and saline (10 mL). The organic phase is separated, dried over magnesium sulfate, filtered, and concentrated under reduced pressure to provide 4-(benzyloxy)-N-propylbutanamide (2.59 g), APCI-MS (m/z) $[M+H]^+$=236.

Step 3: To an ice-cold, stirred mixture of 4-(benzyloxy)-N-propylbutanamide (2.59 g, 11.0 mmol) in THF (8 mL) is added lithium aluminum hydride (0.54 g, 14.3 mmol). The reaction mixture is heated to 40-50 degrees C. for 5 hours. The cooled reaction mixture is quenched with water (0.5 mL), sodium hydroxide (2 N, 1.0 mL), and saline (0.5 mL) then diluted with ether (30 mL). The precipitate that formed is filtered off, and the ether phase dried over magnesium sulfate, filtered, and concentrated under reduced pressure to give N-[4-(benzyloxy)butyl]-N-propylamine (2.41 g), APCI-MS (m/z): 222 [M+H]$^+$.

Step 4: A mixture of N-[4-(benzyloxy)butyl]-N-propylamine (2.31 g, 10.44 mmol), 3-(ethoxycarbonyl)-5-methylbenzoic acid (2.18 g, 10.44 mmol), HOBt (1.56 g, 11.49 mmol), N-methylmorpholine (1.37 mL, 12.52 mmol), and EDC (2.20 g, 11.49 mmol) in DMF (12 mL) is stirred at 20-25 degrees C. for 18 hours. The reaction mixture is diluted with ethyl acetate (80 mL) and washed with water (2×20 mL), hydrochloric acid (1 N, 20 mL), saturated sodium bicarbonate (20 mL) and saline (20 mL), dried over magnesium sulfate, filtered, and concentrated under reduced pressure. Purification by flash chromatography (silica; hexanes/ethyl acetate, 1/1) gives ethyl 3-{[[4-(benzyloxy)butyl](propyl)amino]carbonyl}-5-methylbenzoate (1.79 g), NMR (500 MHz, DMSO-d$_6$): delta7.80, 7.64, 7.40, 7.38-7.16, 4.50-4.43, 4.34-4.29, 3.53-3.30, 3.20-3.06, 2.41-2.36, 1.70-1.40, 1.36-1.29, 0.94-0.84 and 0.82-0.72; APCI-MS (m/z) [M+H]$^+$=412.

Step 5: To a mixture of ethyl 3-{[[4-(benzyloxy)butyl](propyl)-amino]carbonyl}-5-methylbenzoate (1.75 g, 4.25 mmol) in THF/ethanol/water (1/2/1, 30 mL) is added lithium hydroxide (0.31 g, 12.76 mmol). The reaction mixture is stirred for 2 h and then acidified to pH=3 with concentrated hydrochloric acid (0.5 mL). The reaction mixture is extracted with ethyl acetate (2×30 mL), dried over magnesium sulfate, filtered, and concentrated under reduced pressure to give 3-{[[4-(benzyloxy)butyl](propyl)amino]carbonyl}-5-methylbenzoic acid (IX, 1.63 g), ESI-MS (m/z) [M+H]$^+$=384.

Step 6: A mixture of tert-butyl (1S)-2-[4-(benzyloxy)phenyl]-1-[(2S)-oxiranyl]ethylcarbamate (V, 1.58 g, 4.28 mmol) and 3-methoxybenzylamine (VI, 825 microliter, 6.42 mmol) in isopropanol (45 mL) is heated to 90 degrees C. for 4 hours. Upon cooling to 20-25 degrees C., the reaction mixture is concentrated under reduced pressure. Purification by flash chromatography (silica; methylene chloride/methanol/ammonium hydroxide 98/1/1 to 95/:4/1) gives tert-butyl (1S, 2R)-1-[4-(benzyloxy)benzyl]-2-hydroxy-3-[(3-methoxybenzyl)amino]propylcarbamate (VII, 1.97 9), NMR (300 MHz, MeOH-d$_4$): ☐ 7.41-6.79, 5.05, 4.33-3.33, 3.74, 3.54, 3.03-2.46 and 1.29; ESI-MS (m/z) [M+H]$^+$=507.

Step 7: tert-Butyl (1S,2R)-1-[4-(benzyloxy)benzyl]-2-hydroxy-3-[(3-methoxybenzyl)amino]propylcarbamate (VII, step 6, 2.34 g, 4.62 mmol) in dioxane (10 mL) is treated with hydrochloric acid (12 mL of a 4.0 M mixture in dioxane, 48 mmol) for 2 hours. The precipitate that forms is collected by filtration, washed with ether, and dried under reduced pressure overnight to give (2R,3S)-3-amino-4-[4-(benzyloxy)phenyl]-1-[(3-methoxybenzyl)amino]-2-butanol hydrochloride (VIII), NMR (300 MHz, MeOH-d$_4$): ☐ 7.44-6.96, 5.05, 4.21, 3.83, 3.65) and 3.21-2.77; ESI-MS (m/z) [M+H]$^+$=407.

Step 8: To an ice-cold, stirred mixture of 3-{[[4-benzyloxy)butyl](propyl)amino]carbonyl}-5-methylbenzoic acid (IX, 310 mg, 0.809 mmol), (2R,3S)-3-amino-4-[4-(benzyloxy)phenyl]-1-[(3-methoxybenzyl)amino]-2-butanol hydrochloride (VIII, 359 mg, 0.809 mmol), and bromotripyrrolidinophosphonium hexafluorophosphate (415 mg, 0.890 mmol) in methylene chloride (10 mL) is added diisopropylethylamine (285 microL, 1.62 mmol) dropwise. The resulting mixture is stirred at 0 degrees C. for 30 minutes and then warmed to 20-25 degrees C. After 4 hours, the reaction is concentrated under reduced pressure and is partitioned between ethyl acetate and water. The aqueous phase is separated and extracted with ethyl acetate (3×15 ml), the combined organic phases are dried over magnesium sulfate, and concentrated under reduced pressure. The concentrate is purified by flash chromatography (silica; methylene chloride/methanol/ammonium hydroxide 96/3/0.5) to give N$^1$-{(1S,2R)-1-[4-(benzyloxy)benzyl]-2-hydroxy-3-[(3-methoxybenzyl)amino]propyl}-N$^3$-[4-(benzyloxy)butyl]-5-methyl-N$^3$-propylisophthalamide (X) NMR (300 MHz, Acetone-d$_6$): delta7.99-6.74), 5.01 4.51-4.29, 4.36, 4.01, 3.80, 3.55-3.16, 2.98-2.82, 2.65-2.62, 2.36, 1.85-1.29, 1.01 and 0.68; ESI-MS (m/z) [M+H]$^+$=772.

Step 9. A mixture of N$^1$-{(1S,2R)-1-[4-(benzyloxy)benzyl]-2-hydroxy-3-[(3-methoxybenzyl)amino]propyl}-N$^3$-[4-(benzyloxy)butyl]-5-methyl-N$^3$-propylisophthalamide (X, 100 mg, 0.130 mmol) and palladium on carbon (10%, 100 mg) in absolute glacial acetic acid (5 mL) is shaken under an atmosphere of hydrogen at 35 psi for 5 hours. The resulting mixture is filtered through diatomaceous earth and washed with methanol. The combined filtrates are concentrated under reduced pressure. The concentrate is purified by flash column chromatography (silica; gradent of dichloromethane/methanol/ammonium hydroxide 97/3/0.05 to 93/7/0.05) to give the title compound: NMR (300 MHz, CD$_3$OD): ☐ 7.55-6.64, 4.19, 3.99-3.72, 3.63-3.36, 3.21-3.09, 2.79-2.69, 2.39, 1.90-1.40, 1.29 and 1.02-0.6; ESI-MS (m/z) [M+H]$^+$=592.

Example 755

N$^1$-{(1S,2R)-2-hydroxy-1-(4-hydroxybenzyl)-3-[(3-methoxybenzyl)amino]propyl}-N$^3$-(3-hydroxypropyl)-5-methyl-N$^3$-propylisophthalamide (X)

Following the general procedure of EXAMPLE 754 and making non-critical variations, but using 3-{[[3-(benzyloxy)propyl](propyl)amino]carbonyl}-5-methylbenzoic acid (IX) in place of 3-{[[4-(benzyloxy)butyl](propyl)amino]-carbonyl}-5-methylbenzoic acid (IX), the title compound is obtained, ESI-MS (m/z) [M+H]$^+$=578.

Example 756

N$^1$-{(1S,2R)-2-hydroxy-1-(4-hydroxybenzyl)-3-[(3-methoxybenzyl)amino]propyl}-5-methyl-N$^3$,N$^3$-dipropylisopthalamide (X)

Step 1. To a stirred mixture of 3-[(dipropylamino)carbonyl]-5-methylbenzoic acid (IX, 150 mg, 0.570 mmol), (2R, 3S)-3-amino-4-[4-(benzyloxy)phenyl]-1-[(3-methoxybenzyl)amino]-2-butanol hydrochloride (VIII, 274 mg, 0.571 mmol), N, N-diisopropylethylamine (400 microliter, 2.28 mmol), and HOBt (116 mg, 0.857 mmol) in dichloromethane (10 mL) is added EDC (165 mg, 0.857 mmol). The resulting mixture is stirred at 20-25 degrees C. for 16 hours. The reaction mixture is partitioned between dichloromethane and water. The aqueous phase is separated and extracted with dichloromethane (3×15 mL). The combined organic phases are washed with water, dried (magnesium sulfate), and concentrated under reduced pressure. Purification by flash column chromatography (silica; dichloromethane/methanol/ammonium hydroxide, 97/3/0.05) gives N$^1$-{(1S,2R)-1-[4-(benzyloxy)benzyl]-2-hydroxy-3-[(3-methoxybenzyl)amino]propyl}-5-methyl-N$^3$ ,N$^3$-dipropylisophthalamide, ESI-MS (m/z) [M+H]$^+$=652.

Step 2. A mixture of N$^1$-{(1S,2R)-1-[4-(benzyloxy)benzyl]-2-hydroxy-3-[(3-methoxybenzyl)amino]propyl}-5-methyl-N³,N³-dipropylisophthalamide (140 mg, 0.215 mmol) and palladium on carbon (10%, 140 mg) in absolute glacial acetic acid (5 mL) is shaken under an atmosphere of hydrogen at 35 psi for 5 hours The resulting mixture is filtered through diatomaceous earth and washed with methanol. The combined filtrates are concentrated under reduced pressure. The concentrate is purified by flash column chromatography (silica; methylene chloride/methanol/ammonium hydroxide gradient from 97/3/0.05 to 93/7/0.05) to give the title compound, IR (KEBr) 2962, 2931, 1611, 1594 and 1263 cm⁻¹, ESI-MS (m/z) [M+H]⁺=562.

Example 757

N¹-((1S,2R)-1-benzyl-3-{[3-(2,4-dimethylphenyl) propyl]amino}-2-hydroxypropyl)-5-methyl-N³,N³-dipropylisophthalamide (X)

Step 1: A stirred mixture of tert-butyl (1S)-1-[(2S)-oxiranyl]-2-phenylethylcarbamate (V, 247 mg, 0.939 mmol), sodium carbonate (299 mg, 2.82 mmol), and 3-(2,4-dimethylphenyl)propylamine (VI, 628 mg, 2.82 mmol) is heated at reflux overnight. The reaction mixture is cooled to 20-25 degrees C. and concentrated under reduced pressure. Purification by flash column chromatography (silica; methylene chloride/methanol/ammonium hydroxide, 98/2/1) gives tert-butyl (1S,2R)-1-benzyl-3-{[3-(2,4-dimethylphenyl)propyl]amino}-2-hydroxypropylcarbamate (VII), NMR (300 MHz, CD₃OD): delta 7.22-7.16, 3.81, 3.18, 2.77, 2.54, 2.15, 2.13, 1.89 and 1.23.

Step 2: To a stirred mixture of tert-butyl (1S,2R)-1-benzyl-3-{[3-(2,4-dimethylphenyl)propyl]amino}-2-hydroxypropylcarbamate (VII, 180 mg, 0.423 mmol) in dioxane (2 mL) is added hydrochloric acid (0.32 mL of a 4 N mixture in dioxane, 1.27 mmol). The reaction mixture is stirred overnight and concentrated under reduced pressure to give (2R,3S)-3-amino-1-{[3-(2,4-dimethylphenyl)propyl]amino}-4-phenyl-2-butanol hydrochloride (VIII), NMR (300 MHz, CDCl₃): delta 7.14, 3.73, 2.70, 2.32 and 1.86.

Step 3: To a stirred mixture of (2R,3S)-3-amino-1-{[3-(2,4-dimethylphenyl)propyl]amino}-4-phenyl-2-butanol hydrochloride (VIII, 163 mg, 0.411 mmol), 3-[(dipropylamino)carbonyl]-5-methylbenzoic acid (IX, 108 mg, 0.411 mmol), HOBt (55 mg, 0.411 mmol), and N-methylmorpholine (133 mg, 1.32 mmol) in methylene chloride (5 mL) is added EDC (142 mg, 0.740 mmol). The reaction mixture is stirred overnight and then partitioned between ethyl acetate and water. The organic phase is washed with hydrochloric acid (1 N), saturated sodium bicarbonate, saline, dried (sodium sulfate), filtered, and concentrated under reduced pressure. Purification by flash column chromatography (silica; methylene chloride/methanol/ammonium hydroxide, 95/5/1) gives the title compound, IR (ATR): 3299, 2930 and 1614 cm⁻¹; APCI-MS (m/z) [M+H]⁺=572.

Example 758

N¹-((1s,2R)-1-benzyl-2-hydroxy-3-{[3-(4-methylphenyl)propyl]amino}propyl)-5-methyl-N³,N³-dipropylisophthalamide hydrochloride (X)

Following the general procedure of EXAMPLE 757 and making non-critical variations, but using 3-(4-methylphenyl)propylamine in place of 3-(2,4-dimethylphenyl)propylamine, the title compound is obtained, IR (ATR): 3282, 2929 and 1594 cm⁻¹; APCI-MS (m/z) [M+H]⁺=558.

Example 759

N¹-{(1S,2R)-1-benzyl-2-hydroxy-3-[(3-methoxybenzyl)amino]propyl}-5-methyl-N³,N³-dipropylisophthalamide (X)

Following the general procedure of EXAMPLEs 4, 5, and 6 and making non-critical variations but using tert-butyl (1S)-1-[(2S)-oxiranyl]-2-phenylethylcarbamate (V) and 3-methoxybenzylamine (VI) and "5-Me-PHTH" (IX), the title compound is obtained, MS [M+H]⁺=546.3.

Example 760

N-{(1S,2R)-1-benzyl-2-hydroxy-3-[(3-methoxybenzyl)amino]propyl}-1,3-dioxo-2-propyl-5-isoindolinecarboxamide (X)

Following the general procedure of EXAMPLEs 4, 5, and 6 and making non-critical variations but using tert-butyl (1S)-1-[(2S)-oxiranyl]-2-phenylethylcarbamate (V) and 3-methoxybenzylamine (VI) and 1,3-dioxo-2-propylisoindoline-5-carboxylic acid (IX), the title compound is obtained, MS [M+H]⁺=516.2.

Example 761

N-{(1R,2R)-1-benzyl-2-hydroxy-3-[(3-methoxybenzyl)amino]propyl}-3-bromo-5-methylbenzamide (X)

Following the general procedure of EXAMPLEs 4, 5 and 6 and making non-critical variations but using benzyl (1S)-1-[(2S)-oxiranyl]-2-phenylethylcarbamate (V) and 3-methoxybenzylamine (VI) and 3-bromo-5-methylbenzoic acid (IX), the title compound is obtained, MS [M+H]⁺=497.1, 499.1.

Example 762

3-bromo-N-{(1S,2R)-1-(3,5-difluorobenzyl)-2-hydroxy-3-[(3-methoxybenzyl)amino]propyl}-5-methylbenzamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V) and 3-methoxybenzylamine (VI) and 3-bromo-5-methylbenzoic acid (IX), the title compound is obtained, MS [M+H]⁺=533.3, 535.3.

Example 763

N¹-{(1S,2R)-1-benzyl-2-hydroxy-3-[(3-methoxybenzyl)amino]propyl}-4-methyl-N³,N³-dipropylisophthalamide (X)

Following the general procedure of EXAMPLEs 4, 5 and 6 and making non-critical variations but using benzyl (1S)-1-[(2S)-oxiranyl]-2-phenylethylcarbamate (V) and 3-methoxybenzylamine (VI) and 3-[(dipropylamino)carbonyl]-4-methylbenzoic acid (IX), the title compound is obtained, MS [M+H]⁺=546.4.

Example 764

N$^1$-{(1S,2R)-1-(3,5-difluorobenzyl)-2-hydroxy-3-[(3-methoxybenzyl)amino]propyl}-4-methyl-N$^3$,N$^3$-dipropylisophthalamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V) and 3-methoxybenzylamine (VI) and 3-[(dipropylamino)carbonyl]-4-methylbenzoic acid (IX), the title compound is obtained, MS [M+H]$^+$=582.3.

Example 765

N$^3$-{(1S,2R)-1-benzyl-2-hydroxy-3-[(3-methoxybenzyl)amino]propyl}-4-methyl-N$^1$,N$^1$-dipropylisophthalamide (X)

3-Bromo-4-methylbenzoic acid (10.94 g, 43.25 mmol), copper (I) cyanide (7.75 9, 86.5 mmol) and 1-methyl-2-pyrrolidinone (75 ml) are heated to 160 degrees C. overnight. The mixture is cooled and vacuum distilled to give a residue which is stirred in hydrochloric acid (6N, 60 ml) for 10 minutes. The resulting solid is collected by filtration, washed with water, ether, and dried. The solid is heated to 90 degrees C. in sodium hydroxide (2N, 250 ml) for 3 hours and the mixture is then cooled and stirred overnight at 20-25 degrees C. The reaction is acidified to about pH 3 with concentrated hydrochloric acid which gives a precipitate. The solids are collected by filtration and washed with water, then triturated in boiling water, filtered and dried in a vacuum oven at 60 degrees C. The solid is dissolved in methanol (75 ml) and concentrated hydrochloric acid (5 ml) is added and the mixture is refluxed overnight. The mixture then is cooled and concentrated under reduced pressure. Chromatography (silica gel; methanol/methylene chloride, 8/92) gives 5-(methoxycarbonyl)-2-methylbenzoic acid.

To 5-(methoxycarbonyl)-2-methylbenzoic acid (250 mg, 1.3 mmol) and triethylamine (0.72 ml, 5.2 mmol) in methylene chloride (14 ml) is added diethylcyanopyrocarbonate (90%, 0.24 ml, 1.4 mmol) with stirring. After 1 minute, (2R, 3S)-3-amino-1-[(3-methoxybenzyl)amino]-4-phenyl-2-butanol dihydrochloride (VIII, 485 mg, 1.3 mmol) is added and the reaction is stirred 10 overnight. The mixture is concentrated followed by chromatography (silica gel; methanol/methylene chloride 8/92) to afford 3-[({(1S,2R)-1-benzyl-2-hydroxy-3-[(3-methoxybenzyl)amino]propyl}amino)carbonyl]-4-methylbenzoate.

3-[({(1S,2R)-1-benzyl-2-hydroxy-3-[(3-methoxybenzyl)amino]propyl}amino) carbonyl]-4-methylbenzoate (200 mg, 0.42 mmol) is treated with lithium hydroxide (39 mg, 0.96 mmol) in tetrahydrofuran/methanol/water (2/1/1, 2 ml), and the mixture stirred overnight at 20-25 degrees C. The mixture is decanted and the supernatant concentrated to give 3-[({(1S,2R)-1-benzyl-2-hydroxy-3-[(3-methoxybenzyl)amino]propyl}amino)carbonyl]-4-methylbenzoic acid.

3-[({(1S,2R)-1-benzyl-2-hydroxy-3-[(3-methoxybenzyl)amino]propyl}amino) carbonyl]-4-methylbenzoic acid (124 mg, 0.27 mmol) is dissolved in triethylamine (0.07 ml, 0.54 mmol) and methylene chloride (3 ml) and treated with diethylcyanopyrocarbonate (90%, 0.06 ml, 0.32 mmol) with stirring for 2 minutes. Dipropylamine (0.04 ml, 0.32 mmol) is added and stirring continued overnight. The organic phase is diluted with methylene chloride and washed with saturated sodium bicarbonate (2×50 ml) and saline (50 ml) then dried over anhydrous sodium sulfate, filtered and concentrated. Chromatography (silica gel; methanol/methylene chloride, 8/92) gives the title compound, MS [M+H]$^+$=546.3

Example 766

N-{(1S,2R)-1-benzyl-2-hydroxy-3-[(3-methoxybenzyl)amino]propyl}-3-(2-furyl)-5-methylbenzamide (X)

N-{(1R,2R)-1-benzyl-2-hydroxy-3-[(3-methoxybenzyl)amino]propyl}-3-bromo-5-methylbenzamide (X, EXAMLE 761, 295 mg, 0.59 mmol), 2-furanylboronic acid (133 mg, 1.19 mmol) and sodium carbonate (366 mg, 2.95 mmol) are combined in dimethylformamide (5 ml) and sparged under a flow of nitrogen for 15 minutes. Tetrakis(triphenylphosphino)palladium (136 mg, 0.12 mmol) is added and the mixture heated to 100 degrees C. overnight. The mixture is cooled to 20-25 degrees C., diluted with chloroform (50 ml) and extracted with water (3×100 ml). The organic phase is separated and washed with saturated sodium bicarbonate (2×100 ml) and saline (100 ml), dried over anhydrous sodium sulfate, filtered, and concentrated under reduced pressue. The residue is chouromatographed (silica gel; methanol/methylene chloride, 8/92) to give the title compound, MS [M+H]$^+$=485.3.

Example 767

N-{(1S,2R)-1-benzyl-2-hydroxy-3-[(3-methoxybenzyl)amino]propyl}-3',5,5'-trimethyl-1,1'-biphenyl-3-carboxamide (X)

Following the general procedure of EXAMPLE 766 and making non-critical variations but using 3,5-dimethylphenylboronic acid, the title compound is obtained, MS [M+H]$^+$=523.3.

Example 768

3'-Acetyl-N-{(1S,2R)-1-benzyl-2-hydroxy-3-[(3-methoxybenzyl)amino]propyl}-5-methyl [1,1'-biphenyl]-3-carboxamide (X)

Following the general procedure of EXAMPLE 766 and making non-critical variations but using 3-acetylphenylboronic acid, the title compound is obtained, MS [M+H]$^+$=537.3.

Example 769

N-{(1S,2R)-1-benzyl-2-hydroxy-3-[(3-methoxybenzyl)amino]propyl}-3'-methoxy-5-methyl[1,1'-biphenyl]-3-carboxamide (X)

Following the general procedure of EXAMPLE 766 and making non-critical variations but using 3-methoxyphenylboronic acid, the title compound is obtained, MS [M+H]$^+$=525.3.

Example 770

N-{(1S,2R)-1-benzyl-2-hydroxy-3-[(3-methoxybenzyl)amino]propyl}-5-methyl[1,1'-biphenyl]-3-carboxamide (X)

Following the general procedure of EXAMPLE 766 and making non-critical variations but using phenylboronic acid, the title compound is obtained, MS [M+H]$^+$=495.3.

Example 771

3-Methyl-5-(3-thienyl)benzoic acid (IX)

Following the general procedure of EXAMPLE 766 and making non-critical variations but using 2-thiopheneboronic acid and methyl 3-bromo-5-methylbenzoate, methyl 3-methyl-5-(3-thienyl)benzoate is obtained.

Methyl 3-methyl-5-(3-thienyl)benzoate (257 mg, 1.1 mmol) is treated with lithium hydroxide (186 mg, 4.4 mmol) in tetrahydrofuran/methanol/water (8 ml, 2:1:1) and the mixture is stirred for 2 hours at 20-25 degrees C. The mixture is acidified and concentrated to give the title compound, MS $[M+H]^+=217.0$.

Example 772

N-{(1S,2R)-1-benzyl-2-hydroxy-3-[(3-methoxybenzyl)amino]propyl}-3-methyl-5-(3-thienyl)benzamide (X)

Following the general procedure of EXAMPLEs 4, 5 and 6 and making non-critical variations but using benzyl (1S)-1-[(2S)-oxiranyl]-2-phenylethylcarbamate (V) and 3-methoxybenzylamine (VI) and 3-methyl-5-(3-thienyl)benzoic acid (IX), the title compound is obtained, MS $[M+H]^+=501.2$.

Example 773

N-{(1S,2R)-1-benzyl-2-hydroxy-3-[(3-methoxybenzyl)amino]propyl}-3-methyl-5-(2-thienyl)benzamide (X)

Following the general procedure of EXAMPLEs 4, 5 and 6 and making non-critical variations but using benzyl (1S)-1-[(2S)-oxiranyl]-2-phenylethylcarbamate (V) and 3-methoxybenzylamine (VI) and 3-methyl-5-(2-thienyl)benzoic acid, the title compound is obtained, MS $[M+H]^+=501.2$.

Example 774

N-{(1S,2R)-1-(3,5-difluorobenzyl)-2-hydroxy-3-[(3-methoxybenzyl)amino]propyl}-3-methyl-5-(3-thienyl)benzamide (X)

Following the general procedure of EXAMPLEs 4, 5 and 6 and making non-critical variations but using tert-butyl (1S)-2-(3,5-difluorophenyl)-1-[(2s)-oxiranyl]ethylcarbamate (V) and 3-methoxybenzylamine (VI) and 3-methyl-5-(3-thienyl)benzoic acid (IX), the title compound is obtained, MS $[M+H]^+=537.2$.

Example 775

N-{(1S,2R)-1-(3,5-difluorobenzyl)-2-hydroxy-3-[(3-iodobenzyl)amino]propyl}-3-methyl-5-(3-thienyl)benzamide (X)

Following the general procedure of EXAMPLEs 4, 5 and 6 and making non-critical variations but using tert-butyl (1S)-2-(3,5-difluorophenyl)-1-[(2S)-oxiranyl]ethylcarbamate (V) and 3-iodobenzylamine (VI) and 3-methyl-5-(3-thienyl)benzoic acid (IX), the title compound is obtained, MS $[M+H]^+=633.1$.

Example 776

N-{(1S,2R)-1-benzyl-2-hydroxy-3-[(3-methoxybenzyl)amino]propyl}-4-methyl-3-(3-thienyl)benzamide (X)

Following the general procedure of EXAMPLEs 4, 5, 6 and 766 and making non-critical variations but using benzyl (1S)-1-[(2S)-oxiranyl]-2-phenylethylcarbamate (V) and 3-methoxybenzylamine (VI) and 3-bromo-4-methylbenzoic acid (IX) and 3-thiopheneboronic acid, the title compound is obtained, MS $[M+H]^+=501.2$.

Example 777

$N^1$-{(1S,2R)-1-Benzyl-2-hydroxy-3-[(3-methoxybenzyl)amino]propyl}-$N^3,N^3,N^5,N^5$-tetrapropylbenzene-1,3,5-tricarboxamide hydrochloride (X)

Following the general procedures of CHART A as well as PREPARATIONS 1-13, EXAMPLES 1-13, 321-48-579, 597-622 and 624-631 and making non-critical variations and using the appropriate reagents, the title compound is obtained, HRMS (FAB)=659.4155.

Example 778

$N^1$-{(1S,2R)-1-(3,5-Difluorobenzyl)-3-[(3-ethylbenzyl)amino]-2-hydroxypropyl}-$N^3,N^3$-dipropylbenzene-1,3,5-tricarboxamide (X)

Following the general procedures of CHART A as well as PREPARATIONs 1-13, EXAMPLEs 1-13, 321-48-579, 597-622 and 624-631 and making non-critical variations and using the appropriate reagents, the title compound is obtained, MS $(M+H)^+=609.2$.

Example 779

Ethyl-3-[({(1S,2R)-1-benzyl-2-hydroxy-3-[(3-methoxybenzyl)amino]propyl}amino)carbonyl]-5-[(dipropylamino)carbonyl]benzoate hydrochloride (X)

Following the general procedures of CHART A as well as PREPARATIONs 1-13, EXAMPLEs 1-13, 321-48-579, 597-622 and 624-631 and making non-critical variations and using the appropriate reagents, the title compound is obtained, HRMS (FAB)=604.3392.

Example 780

$N^1$-{(1S,2R)-2-Hydroxy-1-(4-hydroxybenzyl)-3-[(3-methoxybenzyl)amino]propyl}-$N^3,N^3$-dipropylbenzene-1,3,5-tricarboxamide (X)

Following the general procedures of CHART A as well as PREPARATIONs 1-13, EXAMPLEs 1-13, 321-48-579, 597-622 and 624-631 and making non-critical variations and using the appropriate reagents, MS $(M+H)^+=591.0$.

Example 781

N$^1$-{(1S,2R)-1-Benzyl-2-hydroxy-3-[(3-methoxy-benzyl)amino]propyl}-N$^3$,N$^3$-dipropyl-5-{[(trifluoromethyl)sulfonyl]amino}isophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=679.2.

Example 782

5-Amino-N$^1$-{(1S,2R)-1-benzyl-2-hydroxy-3-[(3-methoxybenzyl)amino]propyl}-N$^3$,N$^3$-dipropyl-isophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=547.3.

Example 783

N$^1$-{(1S,2R)-1-Benzyl-2-hydroxy-3-[(3-methoxy-benzyl)amino]propyl}-N$^3$,N$^3$-dipropyl-5-[(trifluoro-acetyl)amino]isophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=643.2

Example 784

N$^1$-{(1S,2R)-1-Benzyl-2-hydroxy-3-[(3-methoxy-benzyl)amino]propyl}-5-[(methylsulfonyl)amino]-N$^3$,N$^3$-dipropylisophthalamide hydrochloride (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=625.0

Example 785

N$^1$-{(1S,2R)-1-Benzyl-2-hydroxy-3-[(3-methoxy-benzyl)amino]propyl}-N$^3$,N$^3$-dipropyl-5-[(thien-2-ylsulfonyl)amino]isophthalamide hydrochloride (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=693.1

Example 786

N$^1$-{(1S,2R)-1-Benzyl-2-hydroxy-3-[(3-methoxy-benzyl)amino]propyl}-N$^3$,N$^3$-dipropyl-5-[(thien-2-ylcarbonyl)amino]isophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=657.2.

Example 787

N$^1$-{(1S,2R)-1-Benzyl-2-hydroxy-3-[(3-methoxy-benzyl)amino]propyl}-5-(methacryloylamino)-N$^3$,N$^3$-dipropylisophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=615.1.

Example 788

N$^1$-{(1S,2R)-1-Benzyl-2-hydroxy-3-[(3-methoxy-benzyl)amino]propyl}-5-[(2,2-dimethylpropanoyl)amino]-N$^3$,N$^3$-dipropylisophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=631.3.

Example 789

N$^1$-{(1S,2R)-1-Benzyl-2-hydroxy-3-[(3-methoxy-benzyl)amino]propyl}-5-[(phenylsulfonyl)amino]-N$^3$,N$^3$-dipropylisophthalamide (X)

Following the general procedures of CHART A and CHART T as well as PREPARATIONs 1-13, EXAMPLEs 1-13, 321-48-579, 597-622 and 624-631 and making non-critical variations and using the appropriate reagents, the title compound is obtained, MS (M+H)$^+$=687.2.

Example 790

N-{(1S,2R)-1-benzyl-2-hydroxy-3-[(3-methoxyben-zyl)amino]propyl}-5-(methylthio)pentanamide Following the general procedure of EXAMPLEs 588-592 and 597-619 and using the appropriate starting materials the title compound is obtained, HRMS m/z calculated for C$_{24}$H$_{35}$N$_2$O$_3$S (M+H)=431.2363, found=431.2397.

Example 791 tert-butyl(2R,3S)-3-({3-[(dipropylamino)sulfonyl]-propanoyl}amino)-2-hydroxy-4-phenylbutyl(3-methoxybenzyl)carbamate Following the general procedure of EXAMPLEs 588-592 and 597-619 and using the appropriate starting materials the title compound is obtained, HRMS calculated for M+H is 620.3369, observed=620.3379.

Example 792

Butylcyclopropylamine hydrochloride (VI)

A solution of triethylphosphonoacetate (22.4 g, 0.1 mol) in 13 mL of diglyme is added to a mixture of 13 mL of diglyme and sodium hydride (60%, 5.7 g, 0.12 mol) in mineral oil. When hydrogen evolution ceased, 1,2-epoxyhexane (12 g, 0.12 mol) in diglyme (12 mL) is added. The mixture is stirred for 1 day at 25 degrees C. and 3 hours at 140 degrees C. A mixture of sodium hydroxide (15 g in 25 mL of water) is added in the cold. The mixture is refluxed 15 hours, diluted with cold water (100 mL), and washed with ether (3×50 mL). Acidification to pH=2 with sulfuric acid (25%), extraction with ether (5×25 mL), drying the ether over anhydrous sodium sulfate, filtration and concentration gives 2-butylcyclopropanecarboxylic acid. The acid (5.0 g, 0.035 mmol) in dichloromethane (15 mL) is heated with thionyl chloride (5.1 g, 3.1 mL) for 15 hours at 60 degrees C. The reaction mixture is distilled (76 degrees C.-80 degrees C.) to give the acid chloride which is dissolved in acetone (15 mL), cooled to −10 degrees C. and treated with sodium azide (2.2 g, 33.8 mmol) in water (5 mL). The reaction mixture is stirred at −10 degrees C. for another 1 hour and then poured onto ice/water, extracted with ether (3×10 mL), dried, and cautiously evaporated to dryness at 20-25 degrees C. under reduced pressure. The residue is dissolved in toluene (15 mL) and carefully warmed to 100 degrees C. while vigorously stirring for 1 hour. Concentrated hydrochloric acid (7 mL) is added and the reaction mixture is refluxed for 15 minutes. The acidic layer is evaporated to dryness to give the title compound, MH$^+$=114.2.

Example 793

2-Aminomethyl-3-methylfuran (VI)

3-Methylfuroic acid (4.0 g, 32 mmol) is dissolved in DMF (10 mL) at 20-25 degrees C., and 1,1-carbonyldiimidazole (5.7 g, 35 mmol) is added. After 15 minutes, ammonia is bubbled into the mixture for approximately 2 minutes. This mixture is stirred at 20-25 degrees C. for 2 hours then the mixture is concentrated under reduced pressure. The residue is partitioned between ethyl acetate and 10% aqueous citric acid. The layers are separated, and the aqueous layer extracted with additional ethyl acetate (2×). The combined organic phases are washed with saturated sodium bicarbonate, then saline and dried over magnesium sulfate, filtered and concentrated. Crystals formed upon standing, which are isolated by filtration and washing with a small amount of ethyl acetate/hexanes (80/20), MS(ESI): MH+: 126.1. 3-Methylfuroic amide (317 mg, 2.5 mmol) is dissolved in dry THF (5 mL). Lithium aluminum hydride (230 mg, 6.0 mmol) is added in one portion, and the mixture heated to reflux overnight. The mixture is cooled to 0 degrees C., and quenched by addition of THF/water (50/50). The mixture is then diluted with THF, and filtered through diatomaceous earth. The filtrate is concentrated to give the title compound, MS(ESI): (M−H)+: 109.1.

Example 794

4-Aminomethyl-3,5-dimethylisoxazole (VI)

4-Chloromethyl-3,5-dimethylisoxazole (700 mg, 4.8 mmol) is suspended in concentrated aqueous ammonia at 20-25 degrees C., and vigorously stirred overnight. The reaction mixture is extracted with isopropyl alcohol/chloroform (10/90, 2×). The combined organic phases are concentrated under nitrogen flow. The residue is purified by flash chromatography methanol/methylene chloride (5-20%, 1% triethylamine) to give the title compound, MR (CDCl$_3$, 300 MHz) delta 3.62, 2.37, 2.29, and 1.44.

Example 795

5-Hydroxymethyl-2-(2-methylpropyl)thiazole (VI)

Isovalerothioamide is synthesized according to the procedure in *J. Med. Chem.* 41, 602-617 (1998). Isovaleramide (10 g, 9.9 mmol) is suspended in dry ether (400 mL), then phosphorous (V) sulfide (4.4 g, 0.99 mmol) is added in portions. This is vigorously stirred at 20-25 degrees C. for 2 hours, then filtered. The filtrate is concentrated under reduced pressure and the residue used without further purification: MS(ESI): MH+: 118.1.

Isovalerothioamide (6.0 g, 51 mmol) and ethyl formylchloroacetate (*Heterocycles* 32 (4), 693-701, (1991), 5.0 g, 33 mmol) are dissolved in dry DMF (20 mL), and heated to 95 degrees C. for 4 hours. The reaction is subsequently cooled to 0 degrees C., and cold water (50 mL) is added. The mixture is basified to pH=8 with solid sodium bicarbonate, then extracted with ether (3×35 mL). The combined organic extracts are washed with water, then saline and dried over magnesium sulfate, filtered, and concentrated. The residue is purified by flash chromatography (ethyl acetate/hexanes 4-10% elution) to give the desired product. NMR (CDCl$_3$, 300 MHz) δ 8.27, 4.45-4.30, 3.70-3.50, 3.00-2.80, 2.30-2.10, 1.40-1.20, and 1.10-0.90.

A solution of ethyl 2-(2-methylpropyl)thiazole-5-carboxylate (2.05 g, 9.6 mmol) in THF (10 mL) is added dropwise with stirring to a suspension of lithium aluminum hydride (730 mg, 19 mmol) in dry THF (50 mL) at 0 degrees C. Upon complete addition, the reaction mixture is allowed to stir at 20-25 degrees C. The reaction mixture is cooled to 0 degrees C., and water (0.75 mL), aqueous sodium hydroxide (15%, 0.75 mL), and water (2.25 mL) is added in succession. This mixture is stirred at 0 degrees C. for 1 hour, then filtered through diatomaceous earth, (THF and chloroform). The filtrate is concentrated to give 5-hydroxymethyl-2-(2-methylpropyl)thiazole, MS(ESI): MH+: 172.1.

Example 796

3-(2-Methylpropyl)-5-aminomethylisoxazole (VI)

Isovaleraldehyde (5.4 mL, 50 mmol) and hydroxylamine hydrochloride (3.5 g, 50.4 mmol) are vigorously stirred in water (6 mL). To this is added a solution of sodium carbonate (2.65 g, 25 mmol) in water (15 mL). This is vigorously stirred overnight. The mixture is extracted with ether. The organic layer is washed with water, then dried over sodium sulfate, filtered and concentrated. This is used in subsequent reactions without further purification: MS(ESI): MH+: 102.1.

Propargylamine (8.0 mL, 117 mmol) is dissolved in methylene chloride (60 mL), and di-tert-butyl dicarbonate (25 g, 114 mmol) is added. This is stirred overnight, and concentrated to provide the BOC-protected propargylamine, which is used without further purification: MS(ESI): MNa+: 178.0.

BOC-propargylamine (6.2 g, 39.7 mmol) and isovaleroxime (3.97 g, 39.3 mmol) is dissolved in methylene chloride (60 mL), and triethylamine (0.55 mL, 3.95 mmol) is added. This is cooled to 0 degrees C., and bleach (5% aqueous solution, 59.1 g) is added dropwise with vigorous stirring. After addition is complete, the mixture is allowed to warm to 20-25 degrees C. over 22 hours. The layers are separated, and the aqueous layer is extracted with methylene chloride (2×). The combined organic extracts are washed with saline, dried over magnesium sulfate, filtered and concentrated. The residue is purified by chromatography (silica gel, ethyl acetate/hexanes 5-10%) to give the BOC-protected title compound, MS(ESI): MH+: 255.3.

BOC-protected 3-(2-methylpropyl)-5-aminomethylisoxazole (2.4 g, 9.3 mmol) is dissolved in methylene chloride (10 mL) and treated with trifluoroacetic acid (10 mL) at 20-25 degrees C. This is stirred at 20-25 degrees C. for 70 minutes, then concentrated. The product is dissolved in methylene chloride, and washed with aqueous potassium carbonate (1 M) until basic (pH=11). The organic layer is isolated, dried over sodium sulfate, filtered and concentrated to give the title compound: MS(ESI): MH+: 155.2.

Example 797 tert-butyl(3R)-2-oxo-1-propylazepanylcarbamate (VI)

To N-t-Boc-D-Lys-OH (10 g, 41.4 mmole) in DMF (4 liters) is added benzotriazol-lyloxytripyrrolidino-phosphonium hexafluorophosphate (BOP, 18.3 g, 41.4 mmole) and sodium bicarbonate (17.4 g, 206.8 mmole); the reaction is stirred at 20-25 degrees C. for 12 hours. The reaction is then concentrated to 50 ml volume and diluted with ethyl acetate and washed with sodium bicarbonate 3×, water, 1M potassium bisulfate and brine, dried and concentrated. Purification by chromatography on silica gel afforded 5.05 g of the tert-butyl (3R)-2-oxoazepanylcarbamate as a solid; the procedure employed is similar to that described in *J. Med. Chem.* 1999, 4193. M+H−(t-Boc) (m/e=129.2), M+Na (m/e=251.1).

To the above lactam (2 g, 8.77 mmole) in dry THF (20 ml) is added n-butyllithium/hexane (2.5 M, 5.3 ml, 13.2 mmole) at −78 degrees C., the reaction is stirred for 1 hour and 1-bromopropane (3.2 ml, 35.1 mmole) is added. The reaction is stirred for 1 hour and the cold bath removed and stirring continued for another 16 hours. Tetrabutylammonium iodide (0.49 g, 2.63 mmole) is added and the reaction stirred for another 16 hours. The reaction is partitioned between ethyl acetate/hydrochloric acid+ice+water, the mixture is washed with water and saline and concentrated. Purification by chromatography on silica gel afforded the title compound, MS (M+Na+) 293.3.

Example 798

$N^1$-{(1S,2R)-1-(3,5-difluorobenzyl)-3-[(3-ethynylbenzyl)amino]-2-hydroxypropyl}-5-methyl-$N^3,N^3$-dipropylisophthalamide (X)

Following the procedure described in *J. Am. Chem. Soc.* 1986, 3150, the trifluoroacetic acid salt of $N^1$-{(1S,2R)-1-(3,5-difluorobenzyl)-2-hydroxy-3-[(3-iodobenzyl)amino]propyl}-5-methyl-$N^3,N^3$-dipropylisophthalamide (92.9 mg, 0.117 mmol) is dissolved in triethylamine (0.2 M, 0.6 mL) before the addition of $PdCl_2(PPh_3)_2$ (3.3 mg, 0.005 mmol), and copper (I) iodide (1.1 mg, 0.006 mmol). The reaction is heated to reflux. While the reaction is refluxing, trimethylsilylacetylene (0.02 ml, 0.14 mmol) is added via syringe. The reaction is refluxed for 3 hour under $N_2$ (g), and the reaction cooled to 20-25 degrees C. before partitioning between aqueous sodium bicarbonate and ethyl acetate. The product is extracted with ethyl acetate (3×), washed with saline, dried over sodium sulfate$_4$, and filtered before the removal of solvent under reduced pressure.

The TMS protected acetylene (0.117 mmol) is dissolved in methanol (0.2 M, 0.5 mL) before the addition of potassium hydroxide (1M, 0.7 mL, 0.7 mmol). The reaction is stirred at 20-25 degrees C. for 6 hours, at which point the mixture is partitioned between sodium bicarbonate and ethyl acetate. The product is extracted with ethyl acetate (3×), washed with saline, dried over sodium sulfate, and filtered before the removal of solvent under reduced pressure. Column chromatography (silica gel; 1.5-2% isopropanol/chloroform under basic conditions; a few drops of ammonium hydroxide per 100 mL of elution solvent) gives the title compound, MS m/z $(M+H)^+$=576.3.

Example 799

1-phenylcyclopropylamine (VI)

Following the procedure described in N. W. Werner et.al., *J. Org. Syn.* Coll. Vol. 5, 273-276, sodium azide (0.915 g, 14.1 mmol) is slowly added to a solution of 1-phenyl-cyclopropanecarboxlic acid (1.0 g, 6.1 mmol) in concentrated sulfuric acid (5 ml) and dichloromethane (10 ml). The sodium sulfate precipitated out of solution. The reaction mixture is heated to 50 degrees C. for 17 hours and then cooled to 0 degrees C. The mixture is basified to pH=11 with sodium hydroxide (1N) and extracted with dichloromethane (2×). The organic layers are combined, dried over sodium sulfate, filtered and concentrated. The residue is purified by chromatography (silica gel; isopropyl alcohol/chloroform/ammonium hydroxide 4/95/1) to give the title compound, MS (ESI+) for $C_9H_{11}N$ m/z $(M+H)^+$=134.

Example 800

7-methoxy-1,2,3,4-tetrahydro-1-naphthalenamine (VI)

7-Methoxy-1-tetralone (2.0 g, 11.3 mmol), hydroxylamine hydrochloride (1.56 g, 22.6 mmol) and sodium acetate (1.8 g, 22.6 mmol) are suspended in ethanol/water (3/1, 40 mL). The mixture is heated for 45 min. at 100 degrees C. The mixture is allowed to cool overnight and the precipitate obtained is filtered and washed with water to yield an intermediate oxime, MS (ES) (M+H): 192.1. The oxime is dissolved in glacial acetic acid (25 ml) and palladium/carbon (500 mg) is added and the mixture hydrogenated under 50 psi at 20-25 degrees C. overnight. The catalyst is filtered over diatomaceous earth and washed with methanol. The combined filtrates are concentrated. The concentrate is triturated with ether to give the title compound, MS (CI) (MH+): 178.2.

Example 801

3-Amino-N-{(1S,2R)-1-benzyl-2-hydroxy-3-[(3-methoxybenzyl)amino]propyl}-2-methylbutanamide dihydrochloride Following the general procedure of EXAMPLE 6 and making non-critical variations but starting with (2R,3S)-3-amino-1-[(3-methoxybenzyl)amino]-4-phenyl-2-butanol (VIII) and reacting it with 3-[(tert-butoxycarbonyl)amino]-2-methylbutanoic acid (IX), and then treatment with HCl, the title compound is obtained, HRMS calculated=400.2600, observed=400.2596.

Example 802

N-{(1S,2R)-1-Benzyl-2-hydroxy-3-[(3-methoxybenzyl)amino]propyl}-2-ethylhexanamide hydrochloride Following the general procedure of EXAMPLE 6 and making non-critical variations but starting with (2R,3S)-3-amino-1-[(3-methoxybenzyl)amino]-4-phenyl-2-butanol (VIII) and reacting it with 2-ethylhexanoic acid (IX), the title compound is obtained, HRMS calculated=427.2961, observed=427.2961.

Example 803

N-{(1S,2R)-1-benzyl-2-hydroxy-3-[(3-iodobenzyl)amino]propyl}-3-[(isobutylsulfonyl)amino]propanamide trifluoroacetate Following the general procedure of CHART I and making non-critical variations but starting with (2R,3S)-3-amino-1-[(3-iodobenzyl)amino]-4-phenyl-2-butanol (VIII) and reacting it with N-(isobutylsulfonyl)-beta-alanine (IX), the title compound is obtained, HRMS calculated=588.1393, observed=588.1379.

Example 804

$N^1$-{(1S,2R)-1-(3,5-difluorobenzyl)-2-hydroxy-3-[(3-iodobenzyl)amino]propyl}-$N^3$-(isobutylsulfonyl)-beta-alaninamide trifluoroacetate Following the general procedure of CHART I and making non-critical variations but starting with (2R,3S)-3-amino-4-(3,5-difluorophenyl)-1-[(3-iodobenzyl)amino]-2-butanol (VIII) and reacting it with N-(isobutylsulfonyl)-beta-alanine (IX), the title compound is obtained, M+H=624.

Example 805

5-bromo-$N^1$-{(1S,2R)-1-(3,5-difluorobenzyl)-2-hydroxy-3-[(3-iodobenzyl)amino]propyl}-$N^3$,$N^3$-dipropylisophthalamide hydrochloride Following the general procedure of EXAMPLE 6 and making non-critical variations but starting with (2R,3S)-3-amino-4-(3,5-difluorophenyl)-1-[(3-iodobenzyl)amino]-2-butanol (VIII) and reacting it with 3-bromo-5-[(dipropylamino)carbonyl]benzoic acid (IX), the title compound is obtained, M+H=745.

Example 806

$N^1$-{(1S,2R)-1-(3,5-difluorobenzyl)-2-hydroxy-3-[(1-phenylcyclopropyl)amino]propyl}-5-methyl-$N^3$,$N^3$-dipropylisophthalamide Following the general procedure of EXAMPLE 6 and making non-critical variations but starting with (2R,3S)-3-amino-4-(3,5-difluorophenyl)-1-[(1-phenylcyclopropyl)amino]-2-butanol (VIII) and reacting it with 3-[(dipropylamino)carbonyl]-5-methylbenzoic acid (IX), the substituted amine (X) is obtained. MH+=578.

Example 806.1

5-bromo-$N^1$-[(1S,2R)-3-[(3-bromobenzyl)amino]-1-(3,5-difluorobenzyl)-2-hydroxypropyl]-$N^3$,$N^3$-dipropylisophthalamide Following the general procedure of EXAMPLE 6 and making non-critical variations but starting with (2R,3S)-3-amino-1-[(3-bromobenzyl)amino]-4-(3,5-difluorophenyl)-2-butanol hydrochloride (VIII) and reacting it with 3-bromo-5-[(dipropylamino)carbonyl]benzoic acid (IX), the title compound is obtained, NMR (500 MHz, CD$_3$OD): ☐ 7.85, 7.72, 7.69, 7.67, 7.52, 7.51, 6.88, 6.86, 6.74, 4.39-4.13, 3.95-3.88, 3.53-2.96, 2.82, 1.70, 1.50, 0.99 and 0.71.

Examples 807-1,064

Following the general procedure of CHART A and EXAMPLES 4-6, 321-327, 329-464; 466-527, 529-579, 597-619 and 633-708 and making non-critical variations, and using the appropriate amines (VIII) and amide forming agents (IX), the following compounds are obtained.

| EXAMPLE | Substituted Amine (X) |
|---|---|
| 807 | N-{(1S,2R)-1-benzyl-2-hydroxy-3-[(3-methoxybenzyl)amino]propyl}-3-methyl-5-(2-propylpentanoyl)benzamide |
| 808 | N-{(1S,2R)-1-(3,5-difluorobenzyl)-3-[(3-ethylbenzyl)amino]-2-hydroxypropyl}-3-(2-ethylpentanoyl)-5-methylbenzamide |
| 809 | N-{(1S,2R)-1-benzyl-3-[(3-ethylbenzyl)amino]-2-hydroxypropyl}-3-methyl-5-(2-propylpentanoyl)benzamide |
| 810 | N-{(1S,2R)-1-benzyl-3-[(3-ethynylbenzyl)amino]-2-hydroxypropyl}-3-methyl-5-(2-propylpentanoyl)benzamide |
| 811 | N-{(1S,2R)-1-(3,5-difluorobenzyl)-3-[(3-ethylbenzyl)amino]-2-hydroxypropyl}-3-(2-ethylbutanoyl)-5-methylbenzamide |
| 812 | $N^1$-{(1S,2R)-1-benzyl-3-[(3-ethylbenzyl)amino]-2-hydroxypropyl}-5-(2-propylpentanoyl)isophthalamide |
| 813 | N-{(1S,2R)-1-benzyl-3-[(3-ethylbenzyl)amino]-2-hydroxypropyl}-3-(2-ethylpentanoyl)-5-methylbenzamide |
| 814 | $N^1$-{(1S,2R)-1-(3,5-difluorobenzyl)-3-[(3-ethylbenzyl)amino]-2-hydroxypropyl}-5-(2-propylpentanoyl)isophthalamide |
| 815 | $N^1$-{(1S,2R)-1-(3,5-difluorobenzyl)-2-hydroxy-3-[(3-methoxybenzyl)amino]propyl}-5-(2-propylpentanoyl)isophthalamide |
| 816 | N-[(1S,2R)-3-[(3-ethylbenzyl)amino]-2-hydroxy-1-(4-hydroxybenzyl)propyl]-3-methyl-5-(2-propylpentanoyl)benzamide |
| 817 | N-{(1S,2R)-1-(3,5-difluorobenzyl)-2-hydroxy-3-[(3-methoxybenzyl)amino]propyl}-3-methyl-5-(2-propylpentanoyl)benzamide |
| 818 | N-{(1S,2R)-1-(3,5-difluorobenzyl)-3-[(3-ethylbenzyl)amino]-2-hydroxypropyl}-3-methyl-5-(2-propylpentanoyl)benzamide |
| 819 | $N^1$-((1S,2R)-1-(3,5-difluorobenzyl)-2-hydroxy-3-{[3-(3-pyridinyl)benzyl]amino}propyl)-5-methyl-$N^3$,$N^3$-dipropylisophthalamide |
| 820 | $N^1$-((1S,2R)-1-(3,5-difluorobenzyl)-2-hydroxy-3-{[3-(4-pyridinyl)benzyl]amino}propyl)-5-methyl-$N^3$,$N^3$-dipropylisophthalamide |
| 821 | $N^1$-{(1S,2R)-1-(3,5-difluorobenzyl)-2-hydroxy-3-[(3- |

| EXAMPLE | Substituted Amine (X) |
|---|---|
| | methoxybenzyl)amino]propyl}-N³,N³-dipropyl-5-(1-propynyl)isophthalamide |
| 822 | N¹-{(1S,2R)-1-(3,5-difluorobenzyl)-3-[(3-ethylbenzyl)amino]-2-hydroxypropyl}-N³,N³-dipropyl-5-(1-propynyl)isophthalamide |
| 823 | N¹-{(1S,2R)-1-(3,5-difluorobenzyl)-3-[(3-ethylbenzyl)amino]-2-hydroxypropyl}-N³,N³-dipropyl-5-(2-propynyl)isophthalamide |
| 824 | N¹-{(1S,2R)-1-(3,5-difluorobenzyl)-2-hydroxy-3-[(3-methoxybenzyl)amino]propyl}-N³,N³-dipropyl-5-(2-propynyl)isophthalamide |
| 825 | N¹-{(1S,2R)-1-(cyclohexylmethyl)-2-hydroxy-3-[(3-methoxybenzyl)amino]propyl}-5-methyl-N³,N³-dipropylisophthalamide |
| 826 | N¹-[(1S,2R)-3-(benzylamino)-2-hydroxy-1-(3-thienylmethyl)propyl]-5-methyl-N³,N³-dipropylisophthalamide |
| 827 | N¹-{(1S,2R)-2-hydroxy-3-[(3-methoxybenzyl)amino]-1-(2-thienylmethyl)propyl]-5-methyl-N³,N³-dipropylisophthalamide |
| 828 | N¹-{(1S)-1-[(1R)-2-(benzylamino)-1-hydroxyethyl]-3-butynyl]-N³,N³-dipropyl-1,3,5-benzenetricarboxamide |
| 829 | N¹-[(1S,2R)-2-hydroxy-3-[(3-methoxybenzyl)amino]-1-(3-thienylmethyl)propyl]-5-methyl-N³,N³-dipropylisophthalamide |
| 830 | N¹-[(1S,2R)-3-(benzylamino)-2-hydroxy-1-(2-thienylmethyl)propyl]-5-methyl-N³,N³-dipropylisophthalamide |
| 831 | N¹-{(1S,2R)-1-(3-furylmethyl)-2-hydroxy-3-[(3-methoxybenzyl)amino]propyl}-5-methyl-N³,N³-dipropylisophthalamide |
| 832 | N¹-{(1S,2R)-3-(benzylamino)-1-[4-(benzyloxy)benzyl]-2-hydroxypropyl}-N³,N³-dipropyl-1,3,5-benzenetricarboxamide |
| 833 | N¹-{(1S,2R)-1-(2-furylmethyl)-2-hydroxy-3-[(3-methoxybenzyl)amino]propyl}-5-methyl-N³,N³-dipropylisophthalamide |
| 834 | N¹-[(1S,2R)-3-(benzylamino)-1-(cyclohexylmethyl)-2-hydroxypropyl]-5-methyl-N³,N³-dipropylisophthalamide |
| 835 | N¹-{(1S,2R)-2-hydroxy-1-(4-hydroxybenzyl)-3-[(3-methoxybenzyl)amino]propyl}-5-methyl-N³,N³-dipropylisophthalamide |
| 836 | N¹-[(1S,2R)-3-(benzylamino)-2-hydroxy-1-(1-naphthylmethyl)propyl]-N³,N³-dipropyl-1,3,5-benzenetricarboxamide |
| 837 | 2,3,5-trideoxy-3-({3-[(dipropylamino)carbonyl]-5-methylbenzoyl}amino)-5-[(3-methoxybenzyl)amino]-1-S-phenyl-1-thio-D-erythrouro-pentitol |
| 838 | N¹-[(1S,2R)-3-(benzylamino)-1-(3-furylmethyl)-2-hydroxypropyl]-5-methyl-N³,N³-dipropylisophthalamide |
| 839 | N¹-((1S)-1-{(1R)-1-hydroxy-2-[(3-methoxybenzyl)amino]ethyl}-3-methylbutyl)-5-methyl-N³,N³-dipropylisophthalamide |
| 840 | N¹-[(1S,2R)-3-(benzylamino)-1-(4-fluorobenzyl)-2-hydroxypropyl]-N³,N³-dipropyl-1,3,5-benzenetricarboxamide |
| 841 | N¹-{(1S,2R)-1-(4-fluorobenzyl)-2-hydroxy-3-[(3-methoxybenzyl)amino]propyl}-5-methyl-N³,N³-dipropylisophthalamide |
| 842 | N¹-[(1S,2R)-3-(benzylamino)-1-(2-furylmethyl)-2-hydroxypropyl]-5-methyl-N³,N³-dipropylisophthalamide |
| 843 | N¹-[(1S,2R)-2-hydroxy-3-[(3-methoxybenzyl)amino]-1-(1-naphthylmethyl)propyl]-5-methyl-N³,N³-dipropylisophthalamide |
| 844 | N¹-{(1S)-1-[(1R)-2-(benzylamino)-1-hydroxyethyl]-3-methylbutyl}-N³,N³-dipropyl-1,3,5-benzenetricarboxamide |
| 845 | N¹-{(1S,2R)-1-[4-(benzyloxy)benzyl]-2-hydroxy-3-[(3-methoxybenzyl)amino]propyl}-5-methyl-N³,N³-dipropylisophthalamide |
| 846 | N¹-[(1S,2R)-3-(benzylamino)-2-hydroxy-1-(4-hydroxybenzyl)propyl]-5-methyl-N³,N³-dipropylisophthalamide |
| 847 | N¹-((1S)-1-{(1R)-1-hydroxy-2-[(3-methoxybenzyl)amino]ethyl}-3-butynyl)-5-methyl-N³,N³-dipropylisophthalamide |
| 848 | N¹-((1S)-1-{(1R)-1-hydroxy-2-[(3-methoxybenzyl)amino]ethyl}-3-butynyl)-N³,N³-dipropyl-1,3,5-benzenetricarboxamide |
| 849 | 5-(benzylamino)-2,3,5-trideoxy-3-({3-[(dipropylamino)carbonyl]-5-methylbenzoyl}amino)-1-S-phenyl-1-thio-D-erythrouro-pentitol |
| 850 | N¹-{(1S,2R)-1-[4-(benzyloxy)benzyl]-2-hydroxy-3-[(3-methoxybenzyl)amino]propyl}-N³,N³-dipropyl-1,3,5-benzenetricarboxamide |
| 851 | N¹-[(1S,2R)-3-(benzylamino)-2-hydroxy-1-(4-hydroxybenzyl)propyl]-N³,N³-dipropyl-1,3,5-benzenetricarboxamide |
| 852 | N¹-[(1S,2R)-2-hydroxy-3-[(3-methoxybenzyl)amino]-1-(1-naphthylmethyl)propyl]-N³,N³-dipropyl-1,3,5-benzenetricarboxamide |
| 853 | N¹-{(1S)-1-[(1R)-2-(benzylamino)-1-hydroxyethyl]-3-methylbutyl}-5-methyl-N³,N³-dipropylisophthalamide |
| 854 | N¹-{(1S,2R)-1-(4-fluorobenzyl)-2-hydroxy-3-[(3-methoxybenzyl)amino]propyl}-N³,N³-dipropyl-1,3,5-benzenetricarboxamide |
| 855 | *N¹-[(1S,2R)-3-(benzylamino)-1-(3-furylmethyl)-2-hydroxypropyl]-N³,N³-dipropyl-1,3,5-benzenetricarboxamide |
| 856 | N¹-((1S)-1-{(1R)-1-hydroxy-2-[(3-methoxybenzyl)amino]ethyl}-3-methylbutyl)-N³,N³-dipropyl-1,3,5-benzenetricarboxamide |
| 857 | N¹-[(1S,2R)-3-(benzylamino)-1-(4-fluorobenzyl)-2-hydroxypropyl]-5-methyl-N³,N³-dipropylisophthalamide |
| 858 | N¹-[(1S,2R)-3-(benzylamino)-1-(2-furylmethyl)-2-hydroxypropyl]-N³,N³-dipropyl-1,3,5-benzenetricarboxamide |
| 859 | N¹-{(1S,2R)-2-hydroxy-1-(4-hydroxybenzyl)-3-[(3-methoxybenzyl)amino]propyl}-N³,N³-dipropyl-1,3,5-benzenetricarboxamide |
| 860 | N¹-[(1S,2R)-3-(benzylamino)-2-hydroxy-1-(1-naphthylmethyl)propyl]-5-methyl-N³,N³-dipropylisophthalamide |
| 861 | N¹-{(1S,2R)-1-(cyclohexylmethyl)-2-hydroxy-3-[(3-methoxybenzyl)amino]propyl}-N³,N³-dipropyl-1,3,5-benzenetricarboxamide |
| 862 | N¹-[(1S,2R)-3-(benzylamino)-2-hydroxy-1-(2-thienylmethyl)propyl]-N³,N³-dipropyl-1,3,5-benzenetricarboxamide |
| 863 | N¹-{(1S,2R)-1-(3-furylmethyl)-2-hydroxy-3-[(3-methoxybenzyl)amino]propyl}-N³,N³-dipropyl-1,3,5-benzenetricarboxamide |
| 864 | N¹-{(1S,2R)-3-(benzylamino)-1-[4-(benzyloxy)benzyl]-2-hydroxypropyl}-5-methyl-N³,N³-dipropylisophthalamide |

| EXAMPLE | Substituted Amine (X) |
|---|---|
| 865 | N$^1$-{(1S,2R)-1-(2-furylmethyl)-2-hydroxy-3-[(3-methoxybenzyl)amino]propyl}-N$^3$,N$^3$-dipropyl-1,3,5-benzenetricarboxamide |
| 866 | N$^1$-[(1S,2R)-3-(benzylamino)-2-hydroxy-1-(3-thienylmethyl)propyl]-N$^3$,N$^3$-dipropyl-1,3,5-benzenetricarboxamide |
| 867 | N$^1$-[(1S,2R)-2-hydroxy-3-[(3-methoxybenzyl)amino]-1-(2-thienylmethyl)propyl]-N$^3$,N$^3$-dipropyl-1,3,5-benzenetricarboxamide |
| 868 | N$^1$-{(1S)-1-[(1R)-2-(benzylamino)-1-hydroxyethyl]-3-butynyl}-5-methyl-N$^3$,N$^3$-dipropylisophthalamide |
| 869 | N$^1$-[(1S,2R)-2-hydroxy-3-[(3-methoxybenzyl)amino]-1-(3-thienylmethyl)propyl]-N$^3$,N$^3$-dipropyl-1,3,5-benzenetricarboxamide |
| 870 | N$^1$-{(1S,2R)-1-(cyclohexylmethyl)-2-hydroxy-3-[(3-methoxybenzyl)amino]propyl}-N$^3$,N$^3$-dipropyl-1,3,5-benzenetricarboxamide |
| 871 | N$^1$-[(1S,2R)-2-hydroxy-3-[(3-methoxybenzyl)amino]-1-(3-thienylmethyl)propyl]-N$^3$,N$^3$-dipropyl-1,3,5-benzenetricarboxamide |
| 872 | N$^1$-[(1S,2R)-2-hydroxy-3-[(3-methoxybenzyl)amino]-1-(2-thienylmethyl)propyl]-N$^3$,N$^3$-dipropyl-1,3,5-benzenetricarboxamide |
| 873 | N$^1$-{(1S,2R)-1-(2-furylmethyl)-2-hydroxy-3-[(3-methoxybenzyl)amino]propyl}-N$^3$,N$^3$-dipropyl-1,3,5-benzenetricarboxamide |
| 874 | N$^1$-{(1S,2R)-1-(3-furylmethyl)-2-hydroxy-3-[(3-methoxybenzyl)amino]propyl}-N$^3$,N$^3$-dipropyl-1,3,5-benzenetricarboxamide |
| 875 | N$^1$-{(1S,2R)-2-hydroxy-1-(4-hydroxybenzyl)-3-[(3-methoxybenzyl)amino]propyl}-N$^3$,N$^3$-dipropyl-1,3,5-benzenetricarboxamide |
| 876 | N$^1$-((1S)-1-{(1R)-1-hydroxy-2-[(3-methoxybenzyl)amino]ethyl}-3-methylbutyl)-N$^3$,N$^3$-dipropyl-1,3,5-benzenetricarboxamide |
| 877 | N$^1$-{(1S,2R)-1-(4-fluorobenzyl)-2-hydroxy-3-[(3-methoxybenzyl)amino]propyl}-N$^3$,N$^3$-dipropyl-1,3,5-benzenetricarboxamide |
| 878 | N$^1$-[(1S,2R)-2-hydroxy-3-[(3-methoxybenzyl)amino]-1-(1-naphthylmethyl)propyl]-N$^3$,N$^3$-dipropyl-1,3,5-benzenetricarboxamide |
| 879 | N$^1$-{(1S,2R)-1-[4-(benzyloxy)benzyl]-2-hydroxy-3-[(3-methoxybenzyl)amino]propyl}-N$^3$,N$^3$-dipropyl-1,3,5-benzenetricarboxamide |
| 880 | N$^1$-{(1S,2R)-2-hydroxy-1-[3-(hydroxymethyl)benzyl]-3-[(3-methoxybenzyl)amino]propyl}-5-methyl-N$^3$,N$^3$-dipropylisophthalamide |
| 881 | N$^1$-{(1S,2R)-3-[(3-ethylbenzyl)amino]-2-hydroxy-1-[3-(hydroxymethyl)benzyl]propyl}-5-methyl-N$^3$,N$^3$-dipropylisophthalamide |
| 882 | N$^1$-{(1S,2R)-2-hydroxy-1-[3-(hydroxymethyl)benzyl]-3-[(3-iodobenzyl)amino]propyl}-5-methyl-N$^3$,N$^3$-dipropylisophthalamide |
| 883 | N$^1$-{(1S,2R)-2-hydroxy-1-[4-(hydroxymethyl)benzyl]-3-[(3-iodobenzyl)amino]propyl}-5-methyl-N$^3$,N$^3$-dipropylisophthalamide |
| 884 | N$^1$-{(1S,2R)-3-[(3-ethylbenzyl)amino]-2-hydroxy-1-[4-(hydroxymethyl)benzyl]propyl}-5-methyl-N$^3$,N$^3$-dipropylisophthalamide |
| 885 | N$^1$-{(1S,2R)-2-hydroxy-1-[4-(hydroxymethyl)benzyl]-3-[(3-methoxybenzyl)amino]propyl}-5-methyl-N$^3$,N$^3$-dipropylisophthalamide |
| 886 | N$^1$-{(1S,2R)-1-(3-fluoro-5-hydroxybenzyl)-2-hydroxy-3-[(3-methoxybenzyl)amino]propyl}-5-methyl-N$^3$,N$^3$-dipropylisophthalamide |
| 887 | N$^1$-[(1S,2R)-3-[(3-ethylbenzyl)amino]-1-(3-fluoro-5-hydroxybenzyl)-2-hydroxypropyl]-5-methyl-N$^3$,N$^3$-dipropylisophthalamide |
| 888 | N$^1$-{(1S,2R)-1-(3-fluoro-5-hydroxybenzyl)-2-hydroxy-3-[(3-iodobenzyl)amino]propyl}-5-methyl-N$^3$,N$^3$-dipropylisophthalamide |
| 889 | N$^1$-{(1S,2R)-1-[3-(benzyloxy)-5-fluorobenzyl]-2-hydroxy-3-[(3-iodobenzyl)amino]propyl}-5-methyl-N$^3$,N$^3$-dipropylisophthalamide |
| 890 | N$^1$-{(1S,2R)-1-[3-(benzyloxy)-5-fluorobenzyl]-2-hydroxy-3-[(3-methoxybenzyl)amino]propyl}-5-methyl-N$^3$,N$^3$-dipropylisophthalamide |
| 891 | N-{(1S,2R)-1-[4-(benzyloxy)benzyl]-2-hydroxy-3-[(3-methoxybenzyl)amino]propyl}-3-[(dipropylamino)sulfonyl]propanamide |
| 892 | N$^1$-{(1S,2R)-1-[4-(benzyloxy)benzyl]-2-hydroxy-3-[(3-methoxybenzyl)amino]propyl}-N$^5$,N$^5$-dipropylpentanediamide |
| 893 | 3-[(dipropylamino)sulfonyl]-N-[(1S,2R)-2-hydroxy-3-[(3-methoxybenzyl)amino]-1-(1-naphthylmethyl)propyl]propanamide |
| 894 | N$^1$-[(1S,2R)-2-hydroxy-3-[(3-methoxybenzyl)amino]-1-(1-naphthylmethyl)propyl]-N$^5$,N$^5$-dipropylpentanediamide |
| 895 | 3-[(dipropylamino)sulfonyl]-N-{(1S,2R)-1-(4-fluorobenzyl)-2-hydroxy-3-[(3-methoxybenzyl)amino]propyl}propanamide |
| 896 | N$^1$-{(1S,2R)-1-(4-fluorobenzyl)-2-hydroxy-3-[(3-methoxybenzyl)amino]propyl}-N$^5$,N$^5$-dipropylpentanediamide |
| 897 | 3-[(dipropylamino)sulfonyl]-N-{(1S,2R)-2-hydroxy-1-(4-hydroxybenzyl)-3-[(3-methoxybenzyl)amino]propyl}propanamide |
| 898 | N$^1$-{(1S,2R)-2-hydroxy-1-(4-hydroxybenzyl)-3-[(3-methoxybenzyl)amino]propyl}-N$^5$,N$^5$-dipropylpentanediamide |
| 899 | 3-[(dipropylamino)sulfonyl]-N-{(1S,2R)-1-(3-furylmethyl)-2-hydroxy-3-[(3-methoxybenzyl)amino]propyl}propanamide |
| 900 | N$^1$-{(1S,2R)-1-(2-furylmethyl)-2-hydroxy-3-[(3-methoxybenzyl)amino]propyl}-N$^5$,N$^5$-dipropylpentanediamide |
| 901 | 3-[(dipropylamino)sulfonyl]-N-{(1S,2R)-1-(2-furylmethyl)-2-hydroxy-3-[(3-methoxybenzyl)amino]propyl}propanamide |
| 902 | N$^1$-{(1S,2R)-1-(3-furylmethy)-2-hydroxy-3-[(3-methoxybenzyl)amino]propyl}-N$^5$,N$^5$-dipropylpentanediamide |
| 903 | 3-[(dipropylamino)sulfonyl]-N-[(1S,2R)-2-hydroxy-3-[(3-methoxybenzyl)amino]-1-(2-thienylmethyl)propyl]propanamide |
| 904 | N$^1$-[(1S,2R)-2-hydroxy-3-[(3-methoxybenzyl)amino]-1-(3-thienylmethyl)propyl]-N$^5$,N$^5$-dipropylpentanediamide |
| 905 | 3-[(dipropylamino)sulfonyl]-N-[(1S,2R)-2-hydroxy-3-[(3-methoxybenzyl)amino]-1-(3-thienylmethyl)propyl]propanamide |
| 906 | N$^1$-[(1S,2R)-2-hydroxy-3-[(3-methoxybenzyl)amino]-1-(2-thienylmethyl)propyl]-N$^5$,N$^5$-dipropylpentanediamide |

-continued

| EXAMPLE | Substituted Amine (X) |
|---|---|
| 907 | N-{(1S,2R)-1-(3,5-difluorobenzyl)-2-hydroxy-3-[(3-methoxybenzyl)amino]propyl}-3-{[(2R)-1-ethylpyrrolidinyl]carbonyl}-5-methylbenzamide |
| 908 | N-{(1S,2R)-1-(3,5-difluorobenzyl)-2-hydroxy-3-[(3-methoxybenzyl)amino]propyl}-3-{[(2S)-1-ethylpyrrolidinyl]carbonyl}-5-methylbenzamide |
| 909 | N-{(1S,2R)-1-(3,5-difluorobenzyl)-2-hydroxy-3-[(3-methoxybenzyl)amino]propyl}-3-[(1-ethyl-1H-imidazol-2-yl)carbonyl]-5-methylbenzamide |
| 910 | N-{(1S,2R)-1-(3,5-difluorobenzyl)-2-hydroxy-3-[(3-methoxybenzyl)amino]propyl}-3-[(1-ethyl-4-methyl-1H-imidazol-5-yl)carbonyl]-5-methylbenzamide |
| 911 | $N^1$-((1S,2S)-1-(3,5-difluorobenzyl)-2-hydroxy-2-{1-[(3-methoxybenzyl)amino]cyclopropyl}ethyl)-5-methyl-$N^3$,$N^3$-dipropylisophthalamide |
| 912 | $N^1$-((1S,2S)-1-(3,5-difluorobenzyl)-2-{1-[(3-ethylbenzyl)amino]cyclopropyl}-2-hydroxyethyl)-5-methyl-$N^3$,$N^3$-dipropylisophthalamide |
| 913 | (1R,2R,3R)-$N^1$-{(1S,2R)-1-(3,5-difluorobenzyl)-2-hydroxy-3-[(3-methoxybenzyl)amino]propyl}-$N^2$,$N^2$-dipropyl-1,2,3-cyclopropanetricarboxamide |
| 914 | (1R,2R,3R)-$N^1$-{(1S,2R)-1-(3,5-difluorobenzyl)-2-hydroxy-3-[(3-methoxybenzyl)amino]propyl}-3-phenyl-$N^2$,$N^2$-dipropyl-1,2-cyclopropanedicarboxamide |
| 915 | (1R,2R,3R)-$N^1$-{(1S,2R)-1-(3,5-difluorobenzyl)-2-hydroxy-3-[(3-methoxybenzyl)amino]propyl}-3-methyl-$N^2$,$N^2$-dipropyl-1,2-cyclopropanedicarboxamide |
| 916 | (1R,2R,3S)-$N^1$-{(1S,2R)-1-(3,5-difluorobenzyl)-2-hydroxy-3-[(3-methoxybenzyl)amino]propyl}-3-methyl-$N^2$,$N^2$-dipropyl-1,2-cyclopropanedicarboxamide |
| 917 | (1R,2R,3S)-$N^1$-{(1S,2R)-1-(3,5-difluorobenzyl)-2-hydroxy-3-[(3-methoxybenzyl)amino]propyl}-3-phenyl-$N^2$,$N^2$-dipropyl-1,2-cyclopropanedicarboxamide |
| 918 | (1R,2R,3S)-$N^1$-{(1S,2R)-1-(3,5-difluorobenzyl)-2-hydroxy-3-[(3-methoxybenzyl)amino]propyl}-$N^2$,$N^2$-dipropyl-1,2,3-cyclopropanetricarboxamide |
| 919 | (1R,2R,3S)-3-(2-amino-2-oxoethyl)-$N^1$-{(1S,2R)-1-(3,5-difluorobenzyl)-2-hydroxy-3-[(3-methoxybenzyl)amino]propyl}-$N^2$,$N^2$-dipropyl-1,2-cyclopropanedicarboxamide |
| 920 | (1R,2R,3R)-3-(2-amino-2-oxoethyl)-$N^1$-{(1S,2R)-1-(3,5-difluorobenzyl)-2-hydroxy-3-[(3-methoxybenzyl)amino]propyl}-$N^2$,$N^2$-dipropyl-1,2-cyclopropanedicarboxamide |
| 921 | (1R,2R,3S)-N-{(1S,2R)-1-(3,5-difluorobenzyl)-2-hydroxy-3-[(3-methoxybenzyl)amino]propyl}-2-[2-(dipropylamino)-2-oxoethyl]-3-methylcyclopropanecarboxamide |
| 922 | (1R,2R,3R)-N-{(1S,2R)-1-(3,5-difluorobenzyl)-2-hydroxy-3-[(3-methoxybenzyl)amino]propyl}-2-[2-(dipropylamino)-2-oxoethyl]-3-methylcyclopropanecarboxamide |
| 923 | (1S,2R,3R)-N-{(1S,2R)-1-(3,5-difluorobenzyl)-2-hydroxy-3-[(3-methoxybenzyl)amino]propyl}-2-[2-(dipropylamino)-2-oxoethyl]-3-phenylcyclopropanecarboxamide |
| 924 | (1S,2R,3S)-N-{(1S,2R)-1-(3,5-difluorobenzyl)-2-hydroxy-3-[(3-methoxybenzyl)amino]propyl}-2-[2-(dipropylamino)-2-oxoethyl]-3-phenylcyclopropanecarboxamide |
| 925 | (1S,2R,3R)-$N^1$-{(1S,2R)-1-(3,5-difluorobenzyl)-2-hydroxy-3-[(3-methoxybenzyl)amino]propyl}-3-[2-(dipropylamino)-2-oxoethyl]-1,2-cyclopropanedicarboxamide |
| 926 | (1S,2R,3S)-$N^1$-{(1S,2R)-1-(3,5-difluorobenzyl)-2-hydroxy-3-[(3-methoxybenzyl)amino]propyl}-3-[2-(dipropylamino)-2-oxoethyl]-1,2-cyclopropanedicarboxamide |
| 927 | $N^1$-{(1S,2R)-1-(3,5-difluorobenzyl)-2-hydroxy-3-[(3-methoxybenzyl)amino]propyl}-$N^3$,$N^3$-dipropyl-5-{[(trifluoromethyl)sulfonyl]amino}isophthalamide |
| 928 | $N^1$-{(1S,2R)-1-(3,5-difluorobenzyl)-3-[(3-ethylbenzyl)amino]-2-hydroxypropyl}-$N^3$,$N^3$-dipropyl-5-{[(trifluoromethyl)sulfonyl]amino}isophthalamide |
| 929 | $N^1$-{(1S,2R)-1-benzyl-3-[(3-ethylbenzyl)amino]-2-hydroxypropyl}-$N^3$,$N^3$-dipropyl-5-{[(trifluoromethyl)sulfonyl]amino}isophthalamide |
| 930 | $N^1$-{(1S,2R)-1-(3,5-difluorobenzyl)-3-[(3-ethylbenzyl)amino]-2-hydroxypropyl}-5-{methyl[(trifluoromethyl)sulfonyl]amino}-$N^3$,$N^3$-dipropylisophthalamide |
| 931 | $N^1$-{(1S,2R)-1-(3,5-difluorobenzyl)-2-hydroxy-3-[(3-methoxybenzyl)amino]propyl}-5-{methyl[(trifluoromethyl)sulfonyl]amino}-$N^3$,$N^3$-dipropylisophthalamide |
| 932 | $N^1$-{(1S,2R)-1-(3,5-difluorobenzyl)-2-hydroxy-3-[(3-methoxybenzyl)amino]propyl}-$N^3$,$N^3$-dipropyl-5-{propyl[(trifluoromethyl)sulfonyl]amino}isophthalamide |
| 933 | $N^1$-{(1S,2R)-1-(3,5-difluorobenzyl)-2-hydroxy-3-[(3-methoxybenzyl)amino]propyl}-5-[(methylsulfonyl)amino]-$N^3$,$N^3$-dipropylisophthalamide |
| 934 | $N^1$-{(1S,2R)-1-(3,5-difluorobenzyl)-2-hydroxy-3-[(3-methoxybenzyl)amino]propyl}-5-[(phenylsulfonyl)amino]-$N^3$,$N^3$-dipropylisophthalamide |
| 935 | N-{(1S,2R)-1-(3,5-difluorobenzyl)-2-hydroxy-3-[(3-isopropylbenzyl)amino]propyl}-3-[(dipropylamino)sulfonyl]propanamide |
| 936 | N-{(1S,2R)-1-(3,5-difluorobenzyl)-3-[(3-ethynylbenzyl)amino]-2-hydroxypropyl}-3-[(dipropylamino)sulfonyl]propanamide |
| 937 | N-((1S,2R)-1-(3,5-difluorobenzyl)-3-{[3-(dimethylamino)benzyl]amino}-2-hydroxypropyl)-3-[(dipropylamino)sulfonyl]propanamide |
| 938 | N-((1S,2R)-1-(3,5-difluorobenzyl)-3-{[(2-ethyl-1,3-thiazol-5-yl)methyl]amino}-2-hydroxypropyl)-3-[(dipropylamino)sulfonyl]propanamide |
| 939 | N-((1S,2R)-1-(3,5-difluorobenzyl)-2-hydroxy-3-{[(2-isobutyl-1,3-thiazol-5-yl)methyl]amino}propyl)-3-[(dipropylamino)sulfonyl]propanamide |

-continued

| EXAMPLE | Substituted Amine (X) |
|---|---|
| 940 | N-((1S,2R)-1-(3,5-difluorobenzyl)-2-hydroxy-3-{[(3-isobutyl-5-isoxazolyl)methyl]amino}propyl)-3-[(dipropylamino)sulfonyl]propanamide |
| 941 | N-[(1S,2R)-3-[(3-cyclopropylbenzyl)amino]-1-(3,5-difluorobenzyl)-2-hydroxypropyl]-3-[(dipropylamino)sulfonyl]propanamide |
| 942 | $N^1$-[(1S,2R)-3-[(3-cyclopropylbenzyl)amino]-1-(3,5-difluorobenzyl)-2-hydroxypropyl]-5-methyl-$N^3,N^3$-dipropylisophthalamide |
| 943 | $N^1$-((1S,2R)-1-(3,5-difluorobenzyl)-2-hydroxy-3-{[3-(1,3-thiazol-2-yl)benzyl]amino}propyl)-5-methyl-$N^3,N^3$-dipropylisophthalamide |
| 944 | $N^1$-((1S,2R)-1-(3,5-difluorobenzyl)-2-hydroxy-3-{[3-(1,3-oxazol-2-yl)benzyl]amino}propyl)-5-methyl-$N^3,N^3$-dipropylisophthalamide |
| 945 | $N^1$-[(1S,2R)-3-[(3-acetylbenzyl)amino]-1-(3,5-difluorobenzyl)-2-hydroxypropyl]-5-methyl-$N^3,N^3$-dipropylisophthalamide |
| 946 | $N^1$-[(1S,2R)-3-[(3-acetylbenzyl)amino]-1-(3,5-difluorobenzyl)-2-hydroxypropyl]-$N^3,N^3$-dipropyl-1,3,5-benzenetricarboxamide |
| 947 | $N^1$-[(1S,2R)-3-[(3-acetylbenzyl)amino]-1-(3,5-difluorobenzyl)-2-hydroxypropyl]-5-(aminosulfonyl)-$N^3,N^3$-dipropylisophthalamide |
| 948 | $N^1$-[(1S,2R)-3-[(3-acetylbenzyl)amino]-1-(3,5-difluorobenzyl)-2-hydroxypropyl]-5-(methylsulfonyl)-$N^3,N^3$-dipropylisophthalamide |
| 949 | $N^1$-[(1S,2R)-3-{[3-(diethylamino)benzyl]amino}-1-(3,5-difluorobenzyl)-2-hydroxypropyl]-5-methyl-$N^3,N^3$-dipropylisophthalamide |
| 950 | $N^1$-((1S,2R)-1-(3,5-difluorobenzyl)-2-hydroxy-3-{[3-(4-morpholinyl)benzyl]amino}propyl)-5-methyl-$N^3,N^3$-dipropylisophthalamide |
| 951 | $N^1$-((1S,2R)-1-(3,5-difluorobenzyl)-2-hydroxy-3-{[3-(1-piperazinyl)benzyl]amino}propyl)-5-methyl-$N^3,N^3$-dipropylisophthalamide |
| 952 | $N^1$-[(1S,2R)-3-{[3-(aminosulfonyl)benzyl]amino}-1-(3,5-difluorobenzyl)-2-hydroxypropyl]-5-methyl-$N^3,N^3$-dipropylisophthalamide |
| 953 | $N^1$-[(1S,2R)-1-(3,5-difluorobenzyl)-3-({3-[(dimethylamino)sulfonyl]benzyl}amino)-2-hydroxypropyl]-5-methyl-$N^3,N^3$-dipropylisophthalamide |
| 954 | $N^1$-((1S,2R)-1-(3,5-difluorobenzyl)-2-hydroxy-3-{[3-(1-piperidinylsulfonyl)benzyl]amino}propyl)-5-methyl-$N^3,N^3$-dipropylisophthalamide |
| 955 | $N^1$-((1S,2R)-1-(3,5-difluorobenzyl)-2-hydroxy-3-{[3-(methylsulfonyl)benzyl]amino}propyl)-5-methyl-$N^3,N^3$-dipropylisophthalamide |
| 956 | $N^1$-((1S,2R)-1-(3,5-difluorobenzyl)-2-hydroxy-3-{[3-(isopropylsulfonyl)benzyl]amino}propyl)-5-methyl-$N^3,N^3$-dipropylisophthalamide |
| 957 | $N^1$-[(1S,2R)-3-{[3-(aminocarbonyl)benzyl]amino}-1-(3,5-difluorobenzyl)-2-hydroxypropyl]-5-methyl-$N^3,N^3$-dipropylisophthalamide |
| 958 | $N^1$-[(1S,2R)-1-(3,5-difluorobenzyl)-3-({3-[(dimethylamino)carbonyl]benzyl}amino)-2-hydroxypropyl]-5-methyl-$N^3,N^3$-dipropylisophthalamide |
| 959 | $N^1$-[(1S,2R)-3-[(3-cyanobenzyl)amino]-1-(3,5-difluorobenzyl)-2-hydroxypropyl]-5-methyl-$N^3,N^3$-dipropylisophthalamide |
| 960 | 3-({[(2R,3S)-4-(3,5-difluorophenyl)-3-({3-[(dipropylamino)carbonyl]-5-methylbenzoyl}amino)-2-hydroxybutyl]amino}methyl)phenylcarbamate |
| 961 | 3-({[(2R,3S)-4-(3,5-difluorophenyl)-3-({3-[(dipropylamino)carbonyl]-5-methylbenzoyl}amino)-2-hydroxybutyl]amino}methyl)phenyl dimethylcarbamate |
| 962 | $N^1$-((1S,2R)-1-(3,5-difluorobenzyl)-2-hydroxy-3-{[3-(1-propynyl)benzyl]amino}propyl)-5-methyl-$N^3,N^3$-dipropylisophthalamide |
| 963 | $N^1$-((1S,2R)-1-(3,5-difluorobenzyl)-2-hydroxy-3-{[3-(3-methyl-1-butynyl)benzyl]amino}propyl)-5-methyl-$N^3,N^3$-dipropylisophthalamide |
| 964 | $N^1$-((1S,2R)-1-(3,5-difluorobenzyl)-2-hydroxy-3-{[3-(2-propynyl)benzyl]amino}propyl)-5-methyl-$N^3,N^3$-dipropylisophthalamide |
| 965 | $N^1$-((1S,2R)-1-(3,5-difluorobenzyl)-2-hydroxy-3-{[3-(5-isobutyl-1,3,4-oxadiazol-2-yl)methyl]amino}propyl)-5-methyl-$N^3,N^3$-dipropylisophthalamide |
| 966 | $N^1$-((1S,2R)-1-(3,5-difluorobenzyl)-3-{[3-(5-ethyl-1,3,4-oxadiazol-2-yl)methyl]amino}-2-hydroxypropyl)-5-methyl-$N^3,N^3$-dipropylisophthalamide |
| 967 | $N^1$-((1S,2R)-1-(3,5-difluorobenzyl)-3-{[3-(5-ethyl-1,3,4-thiadiazol-2-yl)methyl]amino}-2-hydroxypropyl)-5-methyl-$N^3,N^3$-dipropylisophthalamide |
| 968 | $N^1$-((1S,2R)-1-(3,5-difluorobenzyl)-2-hydroxy-3-{[3-(5-isobutyl-1,3,4-thiadiazol-2-yl) methyl]amino}propyl)-5-methyl-$N^3,N^3$-dipropylisophthalamide |
| 969 | $N^1$-((1S,2R)-1-(3,5-difluorobenzyl)-3-{[3-(3-ethyl-1,2,4-thiadiazol-5-yl)methyl]amino}-2-hydroxypropyl)-5-methyl-$N^3,N^3$-dipropylisophthalamide |
| 970 | $N^1$-((1S,2R)-1-(3,5-difluorobenzyl)-2-hydroxy-3-{[3-(3-isobutyl-1,2,4-thiadiazol-5-yl) methyl]amino}propyl)-5-methyl-$N^3,N^3$-dipropylisophthalamide |
| 971 | $N^1$-((1S,2R)-1-(3,5-difluorobenzyl)-2-hydroxy-3-{[3-(3-isobutyl-1,2,4-oxadiazol-5-yl) methyl]amino}propyl)-5-methyl-$N^3,N^3$-dipropylisophthalamide |
| 972 | $N^1$-((1S,2R)-1-(3,5-difluorobenzyl)-3-{[3-(3-ethyl-1,2,4-oxadiazol-5-yl) methyl]amino}-2-hydroxypropyl)-5-methyl-$N^3,N^3$-dipropylisophthalamide |
| 973 | $N^1$-((1S,2R)-1-(3,5-difluorobenzyl)-3-{[(2-ethyl-1,3-oxazol-5-yl)methyl]amino}-2-hydroxypropyl)-5-methyl-$N^3,N^3$-dipropylisophthalamide |
| 974 | $N^1$-((1S,2R)-1-(3,5-difluorobenzyl)-2-hydroxy-3-{[(2-isobutyl-1,3-oxazol-5-yl)methyl]amino}propyl)-5-methyl-$N^3,N^3$-dipropylisophthalamide |
| 975 | $N^1$-((1S,2R)-1-(3,5-difluorobenzyl)-2-hydroxy-3-{[(5-isobutyl-1,3,4-oxadiazol-2-yl)methyl]amino}propyl)-5-methyl-$N^3,N^3$-dipropylisophthalamide |
| 976 | $N^1$-((1S,2R)-1-(3,5-difluorobenzyl)-2-hydroxy-3-{[(5-isobutyl-1,3,4-thiadiazol-2-yl)methyl]amino}propyl)-5-methyl-$N^3,N^3$-dipropylisophthalamide |
| 977 | $N^1$-((1S,2R)-1-(3,5-difluorobenzyl)-3-{[(5-ethyl-1,3,4-thiadiazol-2-yl)methyl]amino}-2-hydroxypropyl)-5-methyl-$N^3,N^3$-dipropylisophthalamide |

-continued

| EXAMPLE | Substituted Amine (X) |
|---|---|
| 978 | $N^1$-((1S,2R)-1-(3,5-difluorobenzyl)-3-{[(5-ethyl-1,3,4-oxadiazol-5-yl)methyl]amino}-2-hydroxypropyl)-5-methyl-$N^3,N^3$-dipropylisophthalamide |
| 979 | $N^1$-((1S,2R)-1-(3,5-difluorobenzyl)-3-{[(3-ethyl-1,2,4-oxadiazol-5-yl)methyl]amino}-2-hydroxypropyl)-5-methyl-$N^3,N^3$-dipropylisophthalamide |
| 980 | $N^1$-((1S,2R)-1-(3,5-difluorobenzyl)-3-{[(3-ethyl-1,2,4-thiadiazol-5-yl)methyl]amino}-2-hydroxypropyl)-5-methyl-$N^3,N^3$-dipropylisophthalamide |
| 981 | $N^1$-((1S,2R)-1-(3,5-difluorobenzyl)-2-hydroxy-3-{[(3-isobutyl-1,2,4-thiadiazol-5-yl)methyl]amino}propyl)-5-methyl-$N^3,N^3$-dipropylisophthalamide |
| 982 | $N^1$-((1S,2R)-1-(3,5-difluorobenzyl)-2-hydroxy-3-{[(3-isobutyl-1,2,4-oxadiazol-5-yl)methyl]amino}propyl)-5-methyl-$N^3,N^3$-dipropylisophthalamide |
| 983 | $N^1$-((1S,2R)-1-(3,5-difluorobenzyl)-3-{[(2-ethyl-2H-tetraazol-5-yl)methyl]amino}-2-hydroxypropyl)-5-methyl-$N^3,N^3$-dipropylisophthalamide |
| 984 | $N^1$-((1S,2R)-1-(3,5-difluorobenzyl)-2-hydroxy-3-{[(2-isobutyl-2H-tetraazol-5-yl)methyl]amino}propyl)-5-methyl-$N^3,N^3$-dipropylisophthalamide |
| 985 | $N^1$-((1S,2R)-1-(3,5-difluorobenzyl)-3-{[(2-ethyl-4-pyrimidinyl)methyl]amino}-2-hydroxypropyl)-5-methyl-$N^3,N^3$-dipropylisophthalamide |
| 986 | $N^1$-((1S,2R)-1-(3,5-difluorobenzyl)-2-hydroxy-3-{[(2-isopropyl-4-pyrimidinyl)methyl]amino}propyl)-5-methyl-$N^3,N^3$-dipropylisophthalamide |
| 987 | $N^1$-((1S,2R)-1-(3,5-difluorobenzyl)-3-{[(2-ethynyl-4-pyrimidinyl)methyl]amino}-2-hydroxypropyl)-5-methyl-$N^3,N^3$-dipropylisophthalamide |
| 988 | $N^1$-((1S,2R)-1-(3,5-difluorobenzyl)-2-hydroxy-3-{[(6-isopropyl-4-pyrimidinyl)methyl]amino}propyl)-5-methyl-$N^3,N^3$-dipropylisophthalamide |
| 989 | $N^1$-[(1S,2R)-1-(3,5-difluorobenzyl)-3-({[6-(dimethylamino)-4-pyrimidinyl]methyl}amino)-2-hydroxypropyl]-5-methyl-$N^3,N^3$-dipropylisophthalamide |
| 990 | $N^1$-[(1S,2R)-1-(3,5-difluorobenzyl)-3-({[2-(dimethylamino)-4-pyrimidinyl]methyl}amino)-2-hydroxypropyl]-5-methyl-$N^3,N^3$-dipropylisophthalamide |
| 991 | $N^1$-[(1S,2R)-1-(3,5-difluorobenzyl)-3-({[4-(dimethylamino)-2-pyrimidinyl]methyl}amino)-2-hydroxypropyl]-5-methyl-$N^3,N^3$-dipropylisophthalamide |
| 992 | $N^1$-((1S,2R)-1-(3,5-difluorobenzyl)-3-{[(4-isopropyl-2-pyrimidinyl)methyl]amino}propyl)-5-methyl-$N^3,N^3$-dipropylisophthalamide |
| 993 | $N^1$-((1S,2R)-1-(3,5-difluorobenzyl)-3-{[(4-ethyl-2-pyrimidinyl)methyl]amino}-2-hydroxypropyl)-5-methyl-$N^3,N^3$-dipropylisophthalamide |
| 994 | $N^1$-((1S,2R)-1-(3,5-difluorobenzyl)-3-{[(5-ethyl-3-pyridazinyl)methyl]amino}-2-hydroxypropyl)-5-methyl-$N^3,N^3$-dipropylisophthalamide |
| 995 | $N^3$-((1S,2R)-1-(3,5-difluorobenzyl)-3-{[3-(dimethylamino)benzyl]amino}-2-hydroxypropyl)-$N^5,N^5$-dipropyl-3,5-pyridinedicarboxamide |
| 996 | $N^1$-((1S,2R)-1-(3,5-difluorobenzyl)-2-hydroxy-3-{[(5-isopropyl-3-pyridazinyl)methyl]amino}propyl)-5-methyl-$N^3,N^3$-dipropylisophthalamide |
| 997 | $N^3$-((1S,2R)-1-(3,5-difluorobenzyl)-2-hydroxy-3-{[3-(1-propynyl)benzyl]amino}propyl)-$N^5,N^5$-dipropyl-3,5-pyridinedicarboxamide |
| 998 | $N^1$-((1S,2R)-1-(3,5-difluorobenzyl)-2-hydroxy-3-{[(6-isopropyl-4-pyridazinyl)methyl]amino}propyl)-5-methyl-$N^3,N^3$-dipropylisophthalamide |
| 999 | $N^3$-{(1S,2R)-1-(3,5-difluorobenzyl)-3-[(3-ethynylbenzyl)amino]-2-hydroxypropyl}-$N^5,N^5$-dipropyl-3,5-pyridinedicarboxamide |
| 1000 | $N^1$-((1S,2R)-1-(3,5-difluorobenzyl)-3-{[(6-ethyl-4-pyridazinyl)methyl]amino}-2-hydroxypropyl)-5-methyl-$N^3,N^3$-dipropylisophthalamide |
| 1001 | $N^3$-{(1S,2R)-1-(3,5-difluorobenzyl)-2-hydroxy-3-[(3-isopropylbenzyl)amino]propyl}-$N^5,N^5$-dipropyl-3,5-pyridinedicarboxamide |
| 1002 | $N^1$-((1S,2R)-1-(3,5-difluorobenzyl)-3-{[(6-ethyl-2-pyrazinyl)methyl]amino}-2-hydroxypropyl)-5-methyl-$N^3,N^3$-dipropylisophthalamide |
| 1003 | $N^3$-{(1S,2R)-1-(3,5-difluorobenzyl)-3-[(3-ethylbenzyl)amino]-2-hydroxypropyl}-$N^5,N^5$-dipropyl-3,5-pyridinedicarboxamide |
| 1004 | $N^1$-((1S,2R)-1-(3,5-difluorobenzyl)-2-hydroxy-3-{[(6-isopropyl-2-pyrazinyl)methyl]amino}propyl)-5-methyl-$N^3,N^3$-dipropylisophthalamide |
| 1005 | $N^1$-[(1S,2R)-2-hydroxy-3-[(3-methoxybenzyl)amino]-1-(3,4,5-trifluorobenzyl)propyl]-5-methyl-$N^3,N^3$-dipropylisophthalamide |
| 1006 | $N^1$-((1S,2R)-2-hydroxy-1-(3,4,5-trifluorobenzyl)-3-{[3-(trifluoromethyl)benzyl]amino}propyl)-5-methyl-$N^3,N^3$-dipropylisophthalamide |
| 1007 | $N^1$-((1S,2R)-2-hydroxy-1-(2,3,5,6-tetrafluorobenzyl)-3-{[3-(trifluoromethyl)benzyl]amino}propyl)-5-methyl-$N^3,N^3$-dipropylisophthalamide |
| 1008 | $N^1$-[(1S,2R)-2-hydroxy-3-[(3-methoxybenzyl)amino]-1-(2,3,5,6-tetrafluorobenzyl)propyl]-5-methyl-$N^3,N^3$-dipropylisophthalamide |
| 1009 | $N^1$-((1S,2R)-1-(3,5-difluorobenzyl)-2-hydroxy-3-{[(1R,2S)-2-hydroxy-6-methoxy-2,3-dihydro-1H-inden-1-yl]amino}propyl)-5-methyl-$N^3,N^3$-dipropylisophthalamide |
| 1010 | $N^1$-((1S,2R)-1-(3,5-difluorobenzyl)-2-hydroxy-3-{[(1R,2S)-2-hydroxy-6-methoxy-2,3-dihydro-1H-inden-1-yl]amino}propyl)-$N^3,N^3$-dipropyl-1,3,5-benzenetricarboxamide |
| 1011 | $N^1$-((1S,2R)-1-(3,5-difluorobenzyl)-3-{[(1R,2S)-6-ethyl-2-hydroxy-2,3-dihydro-1H-inden-1-yl]amino}-2-hydroxypropyl)-5-methyl-$N^3,N^3$-dipropylisophthalamide |
| 1012 | $N^1$-((1S,2R)-1-(3,5-difluorobenzyl)-3-{[(1R,2S)-6-ethyl-2-hydroxy-2,3-dihydro-1H-inden-1-yl]amino}-2-hydroxypropyl)-$N^3,N^3$-dipropyl-1,3,5-benzenetricarboxamide |
| 1013 | $N^1$-{(1S,2R)-2-hydroxy-1-(1H-indol-5-ylmethyl)-3-[(3-methoxybenzyl)amino]propyl}-5-methyl-$N^3,N^3$-dipropylisophthalamide |
| 1014 | $N^1$-[(1S,2R)-3-[(3-ethylbenzyl)amino]-2-hydroxy-1-(1H-indol-5-ylmethyl)propyl]-5-methyl-$N^3,N^3$-dipropylisophthalamide |
| 1015 | $N^1$-[(1S,2R)-2-hydroxy-3-[(3-methoxybenzyl)amino]-1-(3-methylbenzyl)propyl]-5-methyl-$N^3,N^3$-dipropylisophthalamide |

| EXAMPLE | Substituted Amine (X) |
|---|---|
| 1016 | $N^1$-[(1S,2R)-2-hydroxy-3-[(3-methoxybenzyl)amino]-1-(3-methylbenzyl)propyl]-$N^3$,$N^3$-dipropyl-1,3,5-benzenetricarboxamide |
| 1017 | $N^1$-{(1S,2R)-2-hydroxy-3-[(3-methoxybenzyl)amino]-1-[3-(trifluoromethyl)benzyl]propyl}-5-methyl-$N^3$,$N^3$-dipropylisophthalamide |
| 1018 | $N^1$-{(1S,2R)-2-hydroxy-3-[(3-methoxybenzyl)amino]-1-[3-(trifluoromethyl)benzyl]propyl}-$N^3$,$N^3$-dipropyl-1,3,5-benzenetricarboxamide |
| 1019 | $N^1$-[(1S,2R)-2-hydroxy-3-[(3-methoxybenzyl)amino]-1-(2-pyridinylmethyl)propyl]-5-methyl-$N^3$,$N^3$-dipropylisophthalamide |
| 1020 | $N^1$-[(1S,2R)-2-hydroxy-3-[(3-methoxybenzyl)amino]-1-(2-pyridinylmethyl)propyl]-$N^3$,$N^3$-dipropyl-1,3,5-benzenetricarboxamide |
| 1021 | $N^1$-{(1S,2R)-1-[3-fluoro-5-(trifluoromethyl)benzyl]-2-hydroxy-3-[(3-methoxybenzyl)amino]propyl}-5-methyl-$N^3$,$N^3$-dipropylisophthalamide |
| 1022 | $N^1$-{(1S,2R)-1-[3-fluoro-5-(trifluoromethyl)benzyl]-2-hydroxy-3-[(3-methoxybenzyl)amino]propyl}-$N^3$,$N^3$-dipropyl-1,3,5-benzenetricarboxamide |
| 1023 | $N^1$-{(1S,2R)-2-hydroxy-3-[(3-methoxybenzyl)amino]-1-[3-(trifluoromethoxy)benzyl]propyl}-5-methyl-$N^3$,$N^3$-dipropylisophthalamide |
| 1024 | $N^1$-{(1S,2R)-2-hydroxy-3-[(3-methoxybenzyl)amino]-1-[3-(trifluoromethoxy)benzyl]propyl}-$N^3$,$N^3$-dipropyl-1,3,5-benzenetricarboxamide |
| 1025 | $N^1$-{(1S,2R)-2-hydroxy-1-(3-hydroxybenzyl)-3-[(3-methoxybenzyl)amino]propyl}-5-methyl-$N^3$,$N^3$-dipropylisophthalamide |
| 1026 | $N^1$-{(1S,2R)-2-hydroxy-1-(3-hydroxybenzyl)-3-[(3-methoxybenzyl)amino]propyl}-$N^3$,$N^3$-dipropyl-1,3,5-benzenetricarboxamide |
| 1027 | $N^1$-[(1S,2R)-2-hydroxy-3-[(3-methoxybenzyl)amino]-1-(4-methylbenzyl)propyl]-5-methyl-$N^3$,$N^3$-dipropylisophthalamide |
| 1028 | $N^1$-[(1S,2R)-2-hydroxy-3-[(3-methoxybenzyl)amino]-1-(4-methylbenzyl)propyl]-$N^3$,$N^3$-dipropyl-1,3,5-benzenetricarboxamide |
| 1029 | $N^1$-{(1S,2R)-1-(4-fluoro-3-methylbenzyl)-2-hydroxy-3-[(3-methoxybenzyl)amino]propyl}-5-methyl-$N^3$,$N^3$-dipropylisophthalamide |
| 1030 | $N^1$-{(1S,2R)-1-(4-fluoro-3-methylbenzyl)-2-hydroxy-3-[(3-methoxybenzyl)amino]propyl}-$N^3$,$N^3$-dipropyl-1,3,5-benzenetricarboxamide |
| 1031 | $N^1$-{(1S,2R)-1-(4-chlorobenzyl)-2-hydroxy-3-[(3-methoxybenzyl)amino]propyl}-5-methyl-$N^3$,$N^3$-dipropylisophthalamide |
| 1032 | $N^1$-{(1S,2R)-1-(4-chlorobenzyl)-2-hydroxy-3-[(3-methoxybenzyl)amino]propyl}-$N^3$,$N^3$-dipropyl-1,3,5-benzenetricarboxamide |
| 1033 | $N^1$-{(1S,2R)-2-hydroxy-1-(3-methoxybenzyl)-3-[(3-methoxybenzyl)amino]propyl}-5-methyl-$N^3$,$N^3$-dipropylisophthalamide |
| 1034 | $N^1$-{(1S,2R)-2-hydroxy-1-(3-methoxybenzyl)-3-[(3-methoxybenzyl)amino]propyl}-$N^3$,$N^3$-dipropyl-1,3,5-benzenetricarboxamide |
| 1035 | $N^1$-{(1S,2R)-2-hydroxy-1-(4-methoxybenzyl)-3-[(3-methoxybenzyl)amino]propyl}-5-methyl-$N^3$,$N^3$-dipropylisophthalamide |
| 1036 | $N^1$-{(1S,2R)-2-hydroxy-1-(4-methoxybenzyl)-3-[(3-methoxybenzyl)amino]propyl}-$N^3$,$N^3$-dipropyl-1,3,5-benzenetricarboxamide |
| 1037 | $N^1$-{(1S,2R)-1-(3-chloro-5-fluorobenzyl)-2-hydroxy-3-[(3-methoxybenzyl)amino]propyl}-5-methyl-$N^3$,$N^3$-dipropylisophthalamide |
| 1038 | $N^1$-{(1S,2R)-1-(3-chloro-5-fluorobenzyl)-2-hydroxy-3-[(3-methoxybenzyl)amino]propyl}-$N^3$,$N^3$-dipropyl-1,3,5-benzenetricarboxamide |
| 1039 | $N^1$-{(1S,2R)-1-(4-chloro-3-fluorobenzyl)-2-hydroxy-3-[(3-methoxybenzyl)amino]propyl}-5-methyl-$N^3$,$N^3$-dipropylisophthalamide |
| 1040 | $N^1$-{(1S,2R)-1-(4-chloro-3-fluorobenzyl)-2-hydroxy-3-[(3-methoxybenzyl)amino]propyl}-$N^3$,$N^3$-dipropyl-1,3,5-benzenetricarboxamide |
| 1041 | $N^1$-{(1S,2R)-1-(3,5-dichlorobenzyl)-2-hydroxy-3-[(3-methoxybenzyl)amino]propyl}-5-methyl-$N^3$,$N^3$-dipropylisophthalamide |
| 1042 | $N^1$-{(1S,2R)-1-(3,5-dichlorobenzyl)-2-hydroxy-3-[(3-methoxybenzyl)amino]propyl}-$N^3$,$N^3$-dipropyl-1,3,5-benzenetricarboxamide |
| 1043 | $N^1$-{(1S,2R)-1-[4-(dimethylamino)benzyl]-2-hydroxy-3-[(3-methoxybenzyl)amino]propyl}-5-methyl-$N^3$,$N^3$-dipropylisophthalamide |
| 1044 | $N^1$-{(1S,2R)-1-[4-(dimethylamino)benzyl]-2-hydroxy-3-[(3-methoxybenzyl)amino]propyl}-$N^3$,$N^3$-dipropyl-1,3,5-benzenetricarboxamide |
| 1045 | $N^1$-{(1S,2R)-1-(3-chlorobenzyl)-2-hydroxy-3-[(3-methoxybenzyl)amino]propyl}-5-methyl-$N^3$,$N^3$-dipropylisophthalamide |
| 1046 | $N^1$-{(1S,2R)-1-(3-chlorobenzyl)-2-hydroxy-3-[(3-methoxybenzyl)amino]propyl}-5-methyl-$N^3$,$N^3$-dipropylisophthalamide |
| 1047 | $N^1$-{(1S,2R)-1-(3-fluorobenzyl)-2-hydroxy-3-[(3-methoxybenzyl)amino]propyl}-5-methyl-$N^3$,$N^3$-dipropylisophthalamide |
| 1048 | $N^1$-{(1S,2R)-1-(3-fluorobenzyl)-2-hydroxy-3-[(3-methoxybenzyl)amino]propyl}-$N^3$,$N^3$-dipropyl-1,3,5-benzenetricarboxamide |
| 1049 | $N^1$-{(1S,2R)-2-hydroxy-1-(4-isopropylbenzyl)-3-[(3-methoxybenzyl)amino]propyl}-5-methyl-$N^3$,$N^3$-dipropylisophthalamide |
| 1050 | $N^1$-{(1S,2R)-2-hydroxy-1-(4-isopropylbenzyl)-3-[(3-methoxybenzyl)amino]propyl}-$N^3$,$N^3$-dipropyl-1,3,5-benzenetricarboxamide |
| 1051 | $N^1$-{(1S,2R)-2-hydroxy-3-[(3-methoxybenzyl)amino]-1-[(6-methoxy-2-pyridinyl)methyl]propyl}-5-methyl-$N^3$,$N^3$-dipropylisophthalamide |
| 1052 | $N^1$-{(1S,2R)-2-hydroxy-3-[(3-methoxybenzyl)amino]-1-[(6-methoxy-2-pyridinyl)methyl]propyl}-$N^3$,$N^3$-dipropyl-1,3,5-benzenetricarboxamide |
| 1053 | $N^1$-{(1S,2R)-2-hydroxy-3-[(3-methoxybenzyl)amino]-1-[(5-methyl-2-pyridinyl)methyl]propyl}-5-methyl-$N^3$,$N^3$-dipropylisophthalamide |
| 1054 | $N^1$-{(1S,2R)-2-hydroxy-3-[(3-methoxybenzyl)amino]-1-[(5-methyl-2-pyridinyl)methyl]propyl}-$N^3$,$N^3$-dipropyl-1,3,5-benzenetricarboxamide |

-continued

| EXAMPLE | Substituted Amine (X) |
|---|---|
| 1055 | $N^1$-{(1S,2R)-1-(3-fluoro-4-methylbenzyl)-2-hydroxy-3-[(3-methoxybenzyl)amino]propyl}-5-methyl-$N^3,N^3$-dipropylisophthalamide |
| 1056 | $N^1$-{(1S,2R)-1-(3-fluoro-4-methylbenzyl)-2-hydroxy-3-[(3-methoxybenzyl)amino]propyl}-$N^3,N^3$-dipropyl-1,3,5-benzenetricarboxamide |
| 1057 | $N^1$-{(1S,2R)-1-(3-fluoro-4-methoxybenzyl)-2-hydroxy-3-[(3-methoxybenzyl)amino]propyl}-5-methyl-$N^3,N^3$-dipropylisophthalamide |
| 1058 | $N^1$-{(1S,2R)-1-(3-fluoro-4-methoxybenzyl)-2-hydroxy-3-[(3-methoxybenzyl)amino]propyl}-$N^3,N^3$-dipropyl-1,3,5-benzenetricarboxamide |
| 1059 | $N^1$-[(1S,2R)-2-hydroxy-3-[(3-methoxybenzyl)amino]-1-(2-methoxy-5-methylbenzyl)propyl]-5-methyl-$N^3,N^3$-dipropylisophthalamide |
| 1060 | $N^1$-[(1S,2R)-2-hydroxy-3-[(3-methoxybenzyl)amino]-1-(2-methoxy-5-methylbenzyl)propyl]-$N^3,N^3$-dipropyl-1,3,5-benzenetricarboxamide |
| 1061 | $N^1$-[(1S,2R)-2-hydroxy-3-[(3-methoxybenzyl)amino]-1-(1,3-thiazol-2-ylmethyl)propyl]-5-methyl-$N^3,N^3$-dipropylisophthalamide |
| 1062 | $N^1$-[(1S,2R)-2-hydroxy-3-[(3-methoxybenzyl)amino]-1-(1,3-thiazol-2-ylmethyl)propyl]-$N^3,N^3$-dipropyl-1,3,5-benzenetricarboxamide |
| 1063 | $N^1$-{(1S,2R)-1-[(5-chloro-2-thienyl)methyl]-2-hydroxy-3-[(3-methoxybenzyl)amino]propyl}-5-methyl-$N^3,N^3$-dipropylisophthalamide |
| 1064 | $N^1$-{(1S,2R)-1-[(5-chloro-2-thienyl)methyl]-2-hydroxy-3-[(3-methoxybenzyl)amino]propyl}-$N^3,N^3$-dipropyl-1,3,5-benzenetricarboxamide |

Examples 1,065-1,155

Following the general procedure of CHART A and EXAMPLES 4-6, 321-327, 329-464, 466-527, 529-579, 597-619 and 633-708 and making non-critical variations, and using the appropriate amines (VIII) and amide forming agents (IX), the titled compounds are obtained.

| EXAMPLE | Substituted Amine (X) |
|---|---|
| 1,065 | N-{(1S,2R)-1-(3,5-difluorobenzyl)-3-[(3-ethylbenzyl)amino]-2-hydroxypropyl}-4-hydroxy-3-(1-pyrrolidinylcarbonyl)benzamide |
| 1,066 | N-{(1S,2R)-1-(3,5-difluorobenzyl)-3-[(3-ethylbenzyl)amino]-2-hydroxypropyl}-5-methyl-2-[(methylsulfonyl)amino]-1,3-thiazole-4-carboxamide |
| 1,067 | N-{(1S,2R)-1-(3,5-difluorobenzyl)-3-[(3-ethylbenzyl)amino]-2-hydroxypropyl}-2-[(methylsulfonyl)amino]-1,3-oxazole-4-carboxamide |
| 1,068 | N-{(1S,2R)-1-(3,5-difluorobenzyl)-3-[(3-ethylbenzyl)amino]-2-hydroxypropyl}-2-[(propylsulfonyl)amino]-1,3-thiazole-4-carboxamide |
| 1,069 | N-{(1S,2R)-1-(3,5-difluorobenzyl)-2-hydroxy-3-[(3-methoxybenzyl)amino]propyl}-4-hydroxy-3-(1-pyrrolidinylcarbonyl)benzamide |

-continued

| EXAMPLE | Substituted Amine (X) |
|---|---|
| 1,070 | N-{(1S,2R)-1-(3,5-difluorobenzyl)-2-hydroxy-3-[(3-methoxybenzyl)amino]propyl}-2-[(propylsulfonyl)amino]-1,3-thiazole-4-carboxamide |
| 1,071 | N-{(1S,2R)-1-benzyl-3-[(3-ethylbenzyl)amino]-2-hydroxypropyl}-2-[(methylsulfonyl)amino]-1,3-oxazole-4-carboxamide |
| 1,072 | N-((1S,2R)-1-(3,5-difluorobenzyl)-3-{[1-(3-ethylphenyl)cyclopropyl]amino}-2-hydroxypropyl)-2-[(methylsulfonyl)amino]-1,3-oxazole-4-carboxamide |
| 1,073 | N-((1S,2R)-1-(3,5-difluorobenzyl)-3-{[1-(3-ethylphenyl)-1-methylethyl]amino}-2-hydroxypropyl)-4-hydroxy-3-(1-pyrrolidinylcarbonyl)benzamide |
| 1,074 | N-((1S,2R)-1-(3,5-difluorobenzyl)-3-{[1-(3-ethylphenyl)-1-methylethyl]amino}-2-hydroxypropyl)-2-[(methylsulfonyl)amino]-1,3-oxazole-4-carboxamide |
| 1,075 | N-{(1S,2R)-1-benzyl-2-hydroxy-3-[(3-methoxybenzyl)amino]propyl}-2-[(methylsulfonyl)amino]-1,3-oxazole-4-carboxamide |
| 1,076 | N-((1S,2R)-1-(3,5-difluorobenzyl)-3-{[1-(3-ethylphenyl)-1-methylethyl]amino}-2-hydroxypropyl)-5-methyl-2-[(methylsulfonyl)amino]-1,3-oxazole-4-carboxamide |
| 1,077 | N-((1S,2R)-1-(3,5-difluorobenzyl)-3-{[1-(3-ethylphenyl)cyclopropyl]amino}-2-hydroxypropyl)-4-hydroxy-3-(1-pyrrolidinylcarbonyl)benzamide |
| 1,078 | N-{(1S,2R)-1-(3,5-difluorobenzyl)-3-[(3-ethynylbenzyl)amino]-2-hydroxypropyl}-2-[(methylsulfonyl)amino]-1,3-oxazole-4-carboxamide |
| 1,079 | N-{(1S,2R)-1-(3,5-difluorobenzyl)-2-hydroxy-3-[(3-methoxybenzyl)amino]propyl}-2-[(methylsulfonyl)amino]-1,3-oxazole-4-carboxamide |
| 1,080 | N-{(1S,2R)-1-(3,5-difluorobenzyl)-3-[(3-ethynylbenzyl)amino]-2-hydroxypropyl}-5-methyl-2-[(methylsulfonyl)amino]-1,3-oxazole-4-carboxamide |
| 1,081 | N-{(1S,2R)-1-(3,5-difluorobenzyl)-2-hydroxy-3-[(3-methoxybenzyl)amino]propyl}-4-hydroxy-3-(1-piperidinylcarbonyl)benzamide |
| 1,082 | N-{(1S,2R)-1-(3,5-difluorobenzyl)-2-hydroxy-3-[(3-iodobenzyl)amino]propyl}-4-[(methylsulfonyl)amino]-1,3-oxazole-2-carboxamide |
| 1,083 | N-{(1S,2R)-1-benzyl-2-hydroxy-3-[(3-iodobenzyl)amino]propyl}-2-[(methylsulfonyl)amino]-1,3-oxazole-4-carboxamide |
| 1,084 | N-{(1S,2R)-1-(3,5-difluorobenzyl)-2-hydroxy-3-[(3-iodobenzyl)amino]propyl}-5-methyl-4-[(methylsulfonyl)amino]-1,3-oxazole-2-carboxamide |
| 1,085 | N-{(1S,2R)-1-(3,5-difluorobenzyl)-3-[(3-ethylbenzyl)amino]-2-hydroxypropyl}-4-hydroxy-3-(1-piperidinylcarbonyl)benzamide |
| 1,086 | N-{(1S,2R)-1-(3,5-difluorobenzyl)-3-[(3-ethylbenzyl)amino]-2-hydroxypropyl}-4-[(methylsulfonyl)amino]-1,3-oxazole-2-carboxamide |
| 1,087 | N-{(1S,2R)-1-benzyl-2-hydroxy-3-[(3-iodobenzyl)amino]propyl}-5-methyl-2-[(methylsulfonyl)amino]-1,3-oxazole-4-carboxamide |

| EXAMPLE | Substituted Amine (X) |
|---|---|
| 1,088 | N-{(1S,2R)-1-(3,5-difluorobenzyl)-3-[(3-ethylbenzyl)amino]-2-hydroxypropyl}-5-methyl-4-[(methylsulfonyl)amino]-1,3-oxazole-2-carboxamide |
| 1,089 | N-{(1S,2R)-1-(3,5-difluorobenzyl)-3-[(3-ethylbenzyl)amino]-2-hydroxypropyl}-4-hydroxy-3-(4-morpholinylcarbonyl)benzamide |
| 1,090 | N-{(1S,2R)-1-(3,5-difluorobenzyl)-3-[(3-ethylbenzyl)amino]-2-hydroxypropyl}-4-[(ethylsulfonyl)amino]-1,3-oxazole-2-carboxamide |
| 1,091 | N-{(1S,2R)-1-(3,5-difluorobenzyl)-2-hydroxy-3-[(3-iodobenzyl)amino]propyl}-5-methyl-2-[(methylsulfonyl)amino]-1,3-oxazole-4-carboxamide |
| 1,092 | N-{(1S,2R)-1-(3,5-difluorobenzyl)-2-hydroxy-3-[(3-iodobenzyl)amino]propyl}-4-[(ethylsulfonyl)amino]-1,3-oxazole-2-carboxamide |
| 1,093 | N-{(1S,2R)-1-(3,5-difluorobenzyl)-3-[(3-ethylbenzyl)amino]-2-hydroxypropyl}-4-hydroxy-3-(4-morpholinylcarbonyl)benzamide |
| 1,094 | N-{(1S,2R)-1-(3,5-difluorobenzyl)-2-hydroxy-3-[(3-iodobenzyl)amino]propyl}-4-[(propylsulfonyl)amino]-1,3-oxazole-2-carboxamide |
| 1,095 | N-{(1S,2R)-1-(3,5-difluorobenzyl)-2-hydroxy-3-[(3-methoxybenzyl)amino]propyl}-5-methyl-2-[(methylsulfonyl)amino]-1,3-oxazole-4-carboxamide |
| 1,096 | N-{(1S,2R)-1-(3,5-difluorobenzyl)-2-hydroxy-3-[(3-iodobenzyl)amino]propyl}-4-[(methylsulfonyl)amino]-1,3-thiazole-2-carboxamide |
| 1,097 | N-{(1S,2R)-1-(3,5-difluorobenzyl)-2-hydroxy-3-[(3-methoxybenzyl)amino]propyl}-4-hydroxy-3-(1-piperazinylcarbonyl)benzamide |
| 1,098 | N-{(1S,2R)-1-(3,5-difluorobenzyl)-3-[(3-ethylbenzyl)amino]-2-hydroxypropyl}-4-[(methylsulfonyl)amino]-1,3-thiazole-2-carboxamide |
| 1,099 | N-{(1S,2R)-1-(3,5-difluorobenzyl)-3-[(3-ethylbenzyl)amino]-2-hydroxypropyl}-5-methyl-2-[(methylsulfonyl)amino]-1,3-oxazole-4-carboxamide |
| 1,100 | N-{(1S,2R)-1-(3,5-difluorobenzyl)-3-[(3-ethylbenzyl)amino]-2-hydroxypropyl}-2-[(methylsulfonyl)amino]-1,3-oxazole-5-carboxamide |
| 1,101 | N-{(1S,2R)-1-(3,5-difluorobenzyl)-3-[(3-ethylbenzyl)amino]-2-hydroxypropyl}-4-hydroxy-3-(1-piperazinylcarbonyl)benzamide |
| 1,102 | N-{(1S,2R)-1-(3,5-difluorobenzyl)-3-[(3-ethylbenzyl)amino]-2-hydroxypropyl}-4-methyl-2-[(methylsulfonyl)amino]-1,3-oxazole-5-carboxamide |
| 1,103 | $N^4$-{(1S,2R)-1-(3,5-difluorobenzyl)-3-[(3-ethylbenzyl)amino]-2-hydroxypropyl}-2-[(methylsulfonyl)amino]-1,3-oxazole-4,5-dicarboxamide |
| 1,104 | N-{(1S,2R)-1-(3,5-difluorobenzyl)-2-hydroxy-3-[(3-iodobenzyl)amino]propyl}-2-[(methylsulfonyl)amino]-1,3-oxazole-5-carboxamide |
| 1,105 | $N^1$-{(1S,2R)-1-(3,5-difluorobenzyl)-3-[(3-ethylbenzyl)amino]-2-hydroxypropyl}-4-hydroxy-$N^3$-methylisophthalamide |
| 1,106 | N-{(1S,2R)-1-(3,5-difluorobenzyl)-2-hydroxy-3-[(3-iodobenzyl)amino]propyl}-4-methyl-2-[(methylsulfonyl)amino]-1,3-oxazole-5-carboxamide |
| 1,107 | N-{(1S,2R)-1-(3,5-difluorobenzyl)-3-[(3-ethylbenzyl)amino]-2-hydroxypropyl}-2-[(ethylsulfonyl)amino]-1,3-oxazole-4-carboxamide |
| 1,108 | N-{(1S,2R)-1-(3,5-difluorobenzyl)-2-hydroxy-3-[(3-iodobenzyl)amino]propyl}-5-[(methylsulfonyl)amino]-1,3-oxazole-2-carboxamide |
| 1,109 | $N^1$-{(1S,2R)-1-(3,5-difluorobenzyl)-2-hydroxy-3-[(3-methoxybenzyl)amino]propyl}-4-hydroxy-$N^3$-methylisophthalamide |
| 1,110 | N-{(1S,2R)-1-(3,5-difluorobenzyl)-2-hydroxy-3-[(3-iodobenzyl)amino]propyl}-4-methyl-5-[(methylsulfonyl)amino]-1,3-oxazole-2-carboxamide |
| 1,111 | N-{(1S,2R)-1-(3,5-difluorobenzyl)-2-hydroxy-3-[(3-methoxybenzyl)amino]propyl}-2-[(ethylsulfonyl)amino]-1,3-oxazole-4-carboxamide |
| 1,112 | N-{(1S,2R)-1-(3,5-difluorobenzyl)-3-[(3-ethylbenzyl)amino]-2-hydroxypropyl}-4-methyl-5-[(methylsulfonyl)amino]-1,3-oxazole-2-carboxamide |
| 1,113 | $N^1$-{(1S,2R)-1-(3,5-difluorobenzyl)-2-hydroxy-3-[(3-methoxybenzyl)amino]propyl}-$N^3$-ethyl-4-hydroxyisophthalamide |
| 1,114 | N-{(1S,2R)-1-(3,5-difluorobenzyl)-3-[(3-ethylbenzyl)amino]-2-hydroxypropyl}-5-[(methylsulfonyl)amino]-1,3-oxazole-2-carboxamide |
| 1,115 | N-{(1S,2R)-1-(3,5-difluorobenzyl)-2-hydroxy-3-[(3-iodobenzyl)amino]propyl}-2-[(ethylsulfonyl)amino]-1,3-oxazole-4-carboxamide |
| 1,116 | N-{(1S,2R)-1-(3,5-difluorobenzyl)-3-[(3-ethylbenzyl)amino]-2-hydroxypropyl}-5-[(methylsulfonyl)amino]-3-isoxazolecarboxamide |
| 1,117 | $N^1$-{(1S,2R)-1-(3,5-difluorobenzyl)-3-[(3-ethylbenzyl)amino]-2-hydroxypropyl}-$N^3$-ethyl-4-hydroxyisophthalamide |
| 1,118 | N-{(1S,2R)-1-(3,5-difluorobenzyl)-2-hydroxy-3-[(3-iodobenzyl)amino]propyl}-5-[(methylsulfonyl)amino]-3-isoxazolecarboxamide |
| 1,119 | N-{(1S,2R)-1-(3,5-difluorobenzyl)-2-hydroxy-3-[(3-iodobenzyl)amino]propyl}-2-[(propylsulfonyl)amino]-1,3-oxazole-4-carboxamide |
| 1,120 | N-{(1S,2R)-1-(3,5-difluorobenzyl)-2-hydroxy-3-[(3-iodobenzyl)amino]propyl}-3-[(methylsulfonyl)amino]-5-isoxazolecarboxamide |
| 1,121 | $N^1$-{(1S,2R)-1-(3,5-difluorobenzyl)-2-hydroxy-3-[(3-iodobenzyl)amino]propyl}-$N^3$-ethyl-4-hydroxyisophthalamide |
| 1,122 | N-{(1S,2R)-1-(3,5-difluorobenzyl)-3-[(3-ethylbenzyl)amino]-2-hydroxypropyl}-3-[(methylsulfonyl)amino]-5-isoxazolecarboxamide |
| 1,123 | N-{(1S,2R)-1-(3,5-difluorobenzyl)-2-hydroxy-3-[(3-methoxybenzyl)amino]propyl}-2-[(propylsulfonyl)amino]-1,3-oxazole-4-carboxamide |
| 1,124 | N-{(1S,2R)-1-(3,5-difluorobenzyl)-2-hydroxy-3-[(3-iodobenzyl)amino]propyl}-5-(hydroxymethyl)-2-[(methylsulfonyl)amino]-1,3-oxazole-4-carboxamide |

| EXAMPLE | Substituted Amine (X) |
|---|---|
| 1,125 | N³-(cyclopropylmethyl)-N¹-{(1S,2R)-1-(3,5-difluorobenzyl)-2-hydroxy-3-[(3-iodobenzyl)amino]propyl}-4-hydroxyisophthalamide |
| 1,126 | 5-cyclopropyl-N-{(1S,2R)-1-(3,5-difluorobenzyl)-2-hydroxy-3-[(3-iodobenzyl)amino]propyl}-2-[(methylsulfonyl)amino]-1,3-oxazole-4-carboxamide |
| 1,127 | N-{(1S,2R)-1-(3,5-difluorobenzyl)-3-[(3-ethylbenzyl)amino]-2-hydroxypropyl}-2-[(propylsulfonyl)amino]-1,3-oxazole-4-carboxamide |
| 1,128 | N-{(1S,2R)-1-(3,5-difluorobenzyl)-2-hydroxy-3-[(3-iodobenzyl)amino]propyl}-5-isopropyl-2-[(methylsulfonyl)amino]-1,3-oxazole-4-carboxamide |
| 1,129 | N³-(cyclopropylmethyl)-N¹-{(1S,2R)-1-(3,5-difluorobenzyl)-3-[(3-ethylbenzyl)amino]-2-hydroxypropyl}-4-hydroxyisophthalamide |
| 1,130 | N-[(1S,2R)-1-(3,5-difluorobenzyl)-2-hydroxy-3-(isopentylamino)propyl]-2-[(methylsulfonyl)amino]-1,3-oxazole-4-carboxamide |
| 1,131 | N-{(1S,2R)-1-(3,5-difluorobenzyl)-3-[(3-ethylbenzyl)amino]-2-hydroxypropyl}-5-methyl-2-[(propylsulfonyl)amino]-1,3-oxazole-4-carboxamide |
| 1,132 | N-[(1S,2R)-3-(cyclopropylamino)-1-(3,5-difluorobenzyl)-2-hydroxypropyl]-2-[(methylsulfonyl)amino]-1,3-oxazole-4-carboxamide |
| 1,133 | N-[(1S,2R)-3-[(3-ethylbenzyl)amino]-2-hydroxy-1-(4-hydroxybenzyl)propyl]-2-[(methylsulfonyl)amino]-1,3-oxazole-4-carboxamide |
| 1,134 | N¹-{(1S,2R)-1-(3,5-difluorobenzyl)-3-[(3-ethylbenzyl)amino]-2-hydroxypropyl}-4-hydroxy-N³-isobutylisophthalamide |
| 1,135 | 2-{[(cyclopropylmethyl)sulfonyl]amino}-N-{(1S,2R)-1-(3,5-difluorobenzyl)-3-[(3-ethylbenzyl)amino]-2-hydroxypropyl}-1,3-oxazole-4-carboxamide |
| 1,136 | N¹-{(1S,2R)-1-(3,5-difluorobenzyl)-3-[(3-ethylbenzyl)amino]-2-hydroxypropyl}-4-hydroxy-N³-isobutyl-N³-methylisophthalamide |
| 1,137 | N-{(1S,2R)-1-(3,5-difluorobenzyl)-3-[(3-ethylbenzyl)amino]-2-hydroxypropyl}-2-[(isobutylsulfonyl)amino]-1,3-oxazole-4-carboxamide |
| 1,138 | N3-(cyclopropylmethyl)-N¹-{(1S,2R)-1-(3,5-difluorobenzyl)-3-[(3-ethylbenzyl)amino]-2-hydroxypropyl}-4-hydroxy-N³-methylisophthalamide |
| 1,139 | N-{(1S,2R)-1-(3,5-difluorobenzyl)-2-hydroxy-3-[(3-methoxybenzyl)amino]propyl}-2-[(isobutylsulfonyl)amino]-1,3-oxazole-4-carboxamide |
| 1,140 | N¹-{(1S,2R)-1-(3,5-difluorobenzyl)-3-[(3-ethylbenzyl)amino]-2-hydroxypropyl}-4-hydroxy-N³-methyl-N³-propylisophthalamide |
| 1,141 | N-{(1S,2R)-1-(3,5-difluorobenzyl)-2-hydroxy-3-[(3-iodobenzyl)amino]propyl}-2-[(isobutylsulfonyl)amino]-1,3-oxazole-4-carboxamide |
| 1,142 | N¹-{(1S,2R)-1-(3,5-difluorobenzyl)-2-hydroxy-3-[(3-methoxybenzyl)amino]propyl}-4-hydroxy-N³-methyl-N³-propylisophthalamide |
| 1,143 | N-{(1S,2R)-1-(3,5-difluorobenzyl)-2-hydroxy-3-[(3-iodobenzyl)amino]propyl}-2-[(phenylsulfonyl)amino]-1,3-oxazole-4-carboxamide |
| 1,144 | N¹-{(1S,2R)-1-(3,5-difluorobenzyl)-2-hydroxy-3-[(3-methoxybenzyl)amino]propyl}-N3-ethyl-4-hydroxy-N³-propylisophthalamide |
| 1,145 | N-{(1S,2R)-1-(3,5-difluorobenzyl)-2-hydroxy-3-[(3-iodobenzyl)amino]propyl}-2-{[(4-methylphenyl)sulfonyl]amino}-1,3-oxazole-4-carboxamide |
| 1,146 | N¹-{(1S,2R)-1-(3,5-difluorobenzyl)-3-[(3-ethylbenzyl)amino]-2-hydroxypropyl}-N3-ethyl-4-hydroxy-N³-propylisophthalamide |
| 1,147 | N-{(1S,2R)-1-(3,5-difluorobenzyl)-3-[(3-ethylbenzyl)amino]-2-hydroxypropyl}-2-{[(4-methylphenyl)sulfonyl]amino}-1,3-oxazole-4-carboxamide |
| 1,148 | N-{(1S,2R)-1-(3,5-difluorobenzyl)-3-[(3-ethylbenzyl)amino]-2-hydroxypropyl}-2-[(phenylsulfonyl)amino]-1,3-oxazole-4-carboxamide |
| 1,149 | N¹-{(1S,2R)-1-(3,5-difluorobenzyl)-3-[(3-ethylbenzyl)amino]-2-hydroxypropyl}-4-hydroxy-N³,N³-dipropylisophthalamide |
| 1,150 | N-{(1S,2R)-1-(3,5-difluorobenzyl)-3-[(3-ethylbenzyl)amino]-2-hydroxypropyl}-2-[methyl(methylsulfonyl)amino]-1,3-oxazole-4-carboxamide |
| 1,151 | N¹-{(1S,2R)-1-(3,5-difluorobenzyl)-2-hydroxy-3-[(3-methoxybenzyl)amino]propyl}-4-hydroxy-N³,N³-dipropylisophthalamide |
| 1,152 | N-{(1S,2R)-1-(3,5-difluorobenzyl)-2-hydroxy-3-[(3-iodobenzyl)amino]propyl}-2-[methyl(methylsulfonyl)amino]-1,3-oxazole-4-carboxamide |
| 1,153 | N¹-{(1S,2R)-1-(3,5-difluorobenzyl)-2-hydroxy-3-[(3-iodobenzyl)amino]propyl}-4-hydroxy-N³,N³-dipropylisophthalamide |
| 1,154 | N-{(1S,2R)-1-(3,5-difluorobenzyl)-2-hydroxy-3-[(3-iodobenzyl)amino]propyl}-2-[(methylsulfonyl)amino]-1,3-thiazole-4-carboxamide |
| 1,155 | N-{(1S,2R)-1-(3,5-difluorobenzyl)-3-[(3-ethylbenzyl)amino]-2-hydroxypropyl}-2-[(methylsulfonyl)amino]-1,3-thiazole-4-carboxamide |

Examples 1,156-1,214

Following the general procedure of CHART A and EXAMPLES 4-6, 321-327, 329-464, 466-527, 529-579, 597-619 and 633-708 and making non-critical variations, and using the appropriate amines (VIII) and amide forming agents (IX), the titled compounds are obtained.

| EXAMPLE | Substituted Amine (X) | MH+ |
|---|---|---|
| 1,156 | N-{(1S,2R)-1-benzyl-2-hydroxy-3-[(3-methoxybenzyl)amino]propyl}-3-methyl-5-[propionyl(propyl)amino]benzamide | 532.5 |
| 1,157 | N-{(1S,2R)-1-benzyl-2-hydroxy-3-[(3-methoxybenzyl)amino]propyl}-1-butyl-1H-indole-5-carboxamide | Anal. Found: C = 73.58; H = 7.44; N = 8.24. |
| 1,159 | N-{(1S,2R)-1-benzyl-2-hydroxy-3-[(3-methoxybenzyl)amino]propyl}-3-[butyl(propionyl)amino]-5-methylbenzamide | 546.3 |
| 1,160 | N-{(1S,2R)-1-benzyl-2-hydroxy-3-[(3-methoxybenzyl)amino]propyl}-4-methyl-1-propyl-1H-indole-6-carboxamide | 500.3 |
| 1,161 | N-{(1S,2R)-1-benzyl-2-hydroxy-3-[(3-methoxybenzyl)amino]propyl}-1-(1-propylbutyl)-1H-indole-6-carboxamide | 542.2 |
| 1,162 | $N^1$-((1S,2R)-1-benzyl-2-hydroxy-3-{[(2-oxo-2,3-dihydro-1,3-benzoxazol-6-yl)methyl]amino}propyl)-5-methyl-$N^3,N^3$-dipropylisophthalamide | 573.3 |
| 1,163 | $N^1$-{(1S,2R)-1-(3,5-difluorobenzyl)-3-[(3-ethylbenzyl)amino]-2-hydroxypropyl}-$N^3,N^3$-dipropyl-5-{[(trifluoromethyl)sulfonyl]amino}isophthalamide | 713.0 |
| 1,164 | 3-[({(1S,2R)-1-benzyl-2-hydroxy-3-[(3-methoxybenzyl)amino]propyl}amino)carbonyl]-5-[(dipropylamino)carbonyl]benzoic acid | 576.1 |
| 1,165 | $N^1$-{(1S,2R)-1-(3,5-difluorobenzyl)-3-[(3-ethylbenzyl)amino]-2-hydroxypropyl}-$N^3,N^3$-dipropyl-5-prop-1-ynylisophthalamide | 604.4 |
| 1,166 | N-{(1S,2R)-1-benzyl-2-hydroxy-3-[(3-methoxybenzyl)amino]propyl}-2-(dipropylamino)isonicotinamide | HRMS = 505.3176 |
| 1,167 | $N^1$-{(1S,2R)-1-(3,5-difluorobenzyl)-3-[(3-ethylbenzyl)amino]-2-hydroxypropyl}-5-[(methylsulfonyl)amino]-$N^3,N^3$-dipropylisophthalamide | |
| 1,168 | $N^1$-{(1S,2R)-1-(3,5-difluorobenzyl)-3-[(3-ethylbenzyl)amino]-2-hydroxypropyl}-5-[(ethylsulfonyl)amino]-$N^3,N^3$-dipropylisophthalamide | |
| 1,169 | $N^1$-{(1S,2R)-1-(3,5-difluorobenzyl)-3-[(3-ethylbenzyl)amino]-2-hydroxypropyl}-$N^3,N^3$-dipropyl-5-[(propylsulfonyl)amino]isophthalamide | |
| 1,170 | $N^1$-{(1S,2R)-1-(3,5-difluorobenzyl)-3-[(3-ethylbenzyl)amino]-2-hydroxypropyl}-5-[(isopropylsulfonyl)amino]-$N^3,N^3$-dipropylisophthalamide | |
| 1,171 | $N^1$-{(1S,2R)-1-(3,5-difluorobenzyl)-3-[(3-ethylbenzyl)amino]-2-hydroxypropyl}-5-[(isobutylsulfonyl)amino]-$N^3,N^3$-dipropylisophthalamide | |
| 1,172 | $N^1$-{(1S,2R)-1-(3,5-difluorobenzyl)-3-[(3-ethylbenzyl)amino]-2-hydroxypropyl}-$N^3,N^3$-dipropyl-5-[(thien-2-ylsulfonyl)amino]isophthalamide | |
| 1,173 | $N^1$-{(1S,2R)-1-(3,5-difluorobenzyl)-3-[(3-ethylbenzyl)amino]-2-hydroxypropyl}-5-[(2-furylsulfonyl)amino]-$N^3,N^3$-dipropylisophthalamide | |
| 1,174 | $N^1$-{(1S,2R)-1-(3,5-difluorobenzyl)-3-[(3-ethylbenzyl)amino]-2-hydroxypropyl}-$N^3,N^3$-dipropyl-5-[(1,3-thiazol-5-ylsulfonyl)amino]isophthalamide | |
| 1,175 | $N^1$-{(1S,2R)-1-(3,5-difluorobenzyl)-3-[(3-ethylbenzyl)amino]-2-hydroxypropyl}-5-[(1,3-oxazol-5- | |

-continued

| EXAMPLE | Substituted Amine (X) | MH+ |
|---|---|---|
| | ylsulfonyl)amino]-N$^3$,N$^3$-dipropylisophthalamide | |
| 1,176 | N$^1$-{(1S,2R)-1-(3,5-difluorobenzyl)-3-[(3-ethylbenzyl)amino]-2-hydroxypropyl}-5-[(1,3-oxazol-4-ylsulfonyl)amino]-N$^3$,N$^3$-dipropylisophthalamide | |
| 1,177 | N$^1$-{(1S,2R)-1-(3,5-difluorobenzyl)-3-[(3-ethylbenzyl)amino]-2-hydroxypropyl}-N$^3$,N$^3$-dipropyl-5-[(1,3-thiazol-4-ylsulfonyl)amino]isophthalamide | |
| 1,178 | N$^1$-{(1S,2R)-1-(3,5-difluorobenzyl)-3-[(3-ethylbenzyl)amino]-2-hydroxypropyl}-5-{[(1-methyl-1H-imidazol-4-yl)sulfonyl]amino}-N$^3$,N$^3$-dipropylisophthalamide | |
| 1,179 | N$^1$-{(1S,2R)-1-(3,5-difluorobenzyl)-3-[(3-ethylbenzyl)amino]-2-hydroxypropyl}-5-[(phenylsulfonyl)amino]-N$^3$,N$^3$-dipropylisophthalamide | |
| 1,180 | 5-{[(5-cyanopyridin-2-yl)sulfonyl]amino}-N$^1$-{(1S,2R)-1-(3,5-difluorobenzyl)-3-[(3-ethylbenzyl)amino]-2-hydroxypropyl}-N$^3$,N$^3$-dipropylisophthalamide | |
| 1,181 | N$^1$-{(1S,2R)-1-(3,5-difluorobenzyl)-3-[(3-ethylbenzyl)amino]-2-hydroxypropyl}-N$^3$,N$^3$-dipropyl-5-({[5-(trifluoromethyl)pyridin-2-yl]sulfonyl}amino)isophthalamide | |
| 1,182 | N-{(1S,2R)-1-(3,5-difluorobenzyl)-3-[(3-ethylbenzyl)amino]-2-hydroxypropyl}-3-{[(1-methyl-1H-imidazol-4-yl)sulfonyl]amino}benzamide | |
| 1,183 | N-{(1S,2R)-1-(3,5-difluorobenzyl)-3-[(3-ethylbenzyl)amino]-2-hydroxypropyl}-3-({[5-(trifluoromethyl)pyridin-2-yl]sulfonyl}amino)benzamide | |
| 1,184 | 3-{[(5-cyanopyridin-2-yl)sulfonyl]amino}-N-{(1S,2R)-1-(3,5-difluorobenzyl)-3-[(3-ethylbenzyl)amino]-2-hydroxypropyl}benzamide | |
| 1,185 | N-{(1S,2R)-1-(3,5-difluorobenzyl)-3-[(3-ethylbenzyl)amino]-2-hydroxypropyl}-3-[(phenylsulfonyl)amino]benzamide | |
| 1,186 | N-{(1S,2R)-1-(3,5-difluorobenzyl)-3-[(3-ethylbenzyl)amino]-2-hydroxypropyl}-3-[(methylsulfonyl)amino]benzamide | |
| 1,187 | N-{(1S,2R)-1-(3,5-difluorobenzyl)-3-[(3-ethylbenzyl)amino]-2-hydroxypropyl}-3-[(ethylsulfonyl)amino]benzamide | |
| 1,188 | N-{(1S,2R)-1-(3,5-difluorobenzyl)-3-[(3-ethylbenzyl)amino]-2-hydroxypropyl}-3-[(propylsulfonyl)amino]benzamide | |
| 1,189 | N-{(1S,2R)-1-(3,5-difluorobenzyl)-3-[(3-ethylbenzyl)amino]-2-hydroxypropyl}-3-[(isobutylsulfonyl)amino]benzamide | |
| 1,190 | N-{(1S,2R)-1-(3,5-difluorobenzyl)-3-[(3-ethylbenzyl)amino]-2-hydroxypropyl}-3-[(isopropylsulfonyl)amino]benzamide | |
| 1,191 | N-{(1S,2R)-1-(3,5-difluorobenzyl)-3-[(3-ethylbenzyl)amino]-2-hydroxypropyl}-3-{[(1-ethylpropyl)sulfonyl]amino}benzamide | |
| 1,192 | 3-[(cyclohexylsulfonyl)amino]-N-{(1S,2R)-1-(3,5-difluorobenzyl)-3-[(3- | |

| EXAMPLE | Substituted Amine (X) | MH+ |
|---|---|---|
| | ethylbenzyl)amino]-2-hydroxypropyl}benzamide | |
| 1,193 | N-{(1S,2R)-1-(3,5-difluorobenzyl)-3-[(3-ethylbenzyl)amino]-2-hydroxypropyl}-3-{[(1-propylbutyl)sulfonyl]amino}benzamide | |
| 1,194 | N-{(1S,2R)-1-(3,5-difluorobenzyl)-3-[(3-ethylbenzyl)amino]-2-hydroxypropyl}-3-[(thien-2-ylsulfonyl)amino]benzamide | |
| 1,195 | N-{(1S,2R)-1-(3,5-difluorobenzyl)-3-[(3-ethylbenzyl)amino]-2-hydroxypropyl}-3-[(2-furylsulfonyl)amino]benzamide | |
| 1,196 | N-{(1S,2R)-1-(3,5-difluorobenzyl)-3-[(3-ethylbenzyl)amino]-2-hydroxypropyl}-3-[(isoxazol-5-ylsulfonyl)amino]benzamide | |
| 1,197 | N-{(1S,2R)-1-(3,5-difluorobenzyl)-3-[(3-ethylbenzyl)amino]-2-hydroxypropyl}-3-[(isoxazol-3-ylsulfonyl)amino]benzamide | |
| 1,198 | N-{(1S,2R)-1-(3,5-difluorobenzyl)-3-[(3-ethylbenzyl)amino]-2-hydroxypropyl}-3-[(3-furylsulfonyl)amino]benzamide | |
| 1,199 | N-{(1S,2R)-1-(3,5-difluorobenzyl)-3-[(3-ethylbenzyl)amino]-2-hydroxypropyl}-3-[(thien-3-ylsulfonyl)amino]benzamide | |
| 1,200 | N-{(1S,2R)-1-(3,5-difluorobenzyl)-3-[(3-ethylbenzyl)amino]-2-hydroxypropyl}-3-[(1,3-thiazol-4-ylsulfonyl)amino]benzamide | |
| 1,201 | N-{(1S,2R)-1-(3,5-difluorobenzyl)-3-[(3-ethylbenzyl)amino]-2-hydroxypropyl}-3-[(1,3-thiazol-5-ylsulfonyl)amino]benzamide | |
| 1,202 | N-{(1S,2R)-1-(3,5-difluorobenzyl)-3-[(3-ethylbenzyl)amino]-2-hydroxypropyl}-3-[(1,3-thiazol-2-ylsulfonyl)amino]benzamide | |
| 1,203 | $N^1$-[(1S,2R)-1-(3,5-difluorobenzyl)-2-hydroxy-3-(isopentylamino)propyl]-$N^3,N^3$-dipropyl-5-{[(trifluoromethyl)sulfonyl]amino}isophthalamide | |
| 1,204 | $N^1$-[(1S,2R)-3-amino-1-(3,5-difluorobenzyl)-2-hydroxypropyl]-$N^3,N^3$-dipropyl-5-{[(trifluoromethyl)sulfonyl]amino}isophthalamide | |
| 1,205 | $N^1$-[(1S,2R)-3-amino-1-(3,5-difluorobenzyl)-2-hydroxypropyl]-5-[(methylsulfonyl)amino]-$N^3,N^3$-dipropylisophthalamide | |
| 1,206 | $N^1$-[(1S,2R)-1-(3,5-difluorobenzyl)-2-hydroxy-3-(isopentylamino)propyl]-5-[(methylsulfonyl)amino]-$N^3,N^3$-dipropylisophthalamide | |
| 1,207 | $N^1$-(tert-butyl)-$N^3$-{(1S,2R)-1-(3,5-difluorobenzyl)-3-[(3-ethylbenzyl)amino]-2-hydroxypropyl}isophthalamide | |
| 1,208 | $N^1$-(tert-butyl)-$N^3$-{(1S,2R)-1-(3,5-difluorobenzyl)-3-[(3-ethylbenzyl)amino]-2-hydroxypropyl}-5-methylisophthalamide | |
| 1,209 | 5-bromo-$N^1$-(tert-butyl)-$N^3$-{(1S,2R)-1-(3,5-difluorobenzyl)-3-[(3-ethylbenzyl)amino]-2-hydroxypropyl}isophthalamide | |
| 1,210 | 3-tert-butoxy-N-{(1S,2R)-1-(3,5-difluorobenzyl)-3-[(3-ethylbenzyl)amino]-2-hydroxypropyl}benzamide | |
| 1,211 | 3-tert-butoxy-N-{(1S,2R)-1-(3,5-difluorobenzyl)-3-[(3- | |

| EXAMPLE | Substituted Amine (X) | MH+ |
|---|---|---|
| 1,212 | ethylbenzyl)amino]-2-hydroxypropyl}-5-methylbenzamide N-{(1S,2R)-1-(3,5-difluorobenzyl)-3-[(3-ethylbenzyl)amino]-2-hydroxypropyl}-3-{[(trifluoromethyl)sulfonyl]amino}benzamide | |
| 1,213 | N-{(1S,2R)-1-(3,5-difluorobenzyl)-3-[(3-ethylbenzyl)amino]-2-hydroxypropyl}-3-(trifluoromethoxy)benzamide | |
| 1,214 | N-{(1S,2R)-1-(3,5-difluorobenzyl)-3-[(3-ethylbenzyl)amino]-2-hydroxypropyl}-3-methyl-5-(trifluoromethoxy)benzamide | |

Examples 1,215-1,259

Following the general procedure of CHART A and EXAMPLES 4-6, 321-327, 329-464, 466-527, 529-579, 597-619 and 633-708 and making non-critical variations, and using the appropriate amines (VIII) and amide forming agents (IX), the titled compounds are obtained.

| EXAMPLE | Substituted Amine (X) | [M + H]+ |
|---|---|---|
| 1,215 | N-{(1S,2R)-1-(3,5-difluorobenzyl)-2-hydroxy-3-[(3-iodobenzyl)amino]propyl}-2-hydroxy-2-(4-methylphenyl)acetamide | 581.4 |
| 1,216 | N1-{(1S,2R)-1-(3,5-difluorobenzyl)-2-hydroxy-3-[(3-iodobenzyl)amino]propyl}-4-hydroxy-N3-methylisophthalamide | 610.4 |
| 1,217 | N-{(1S,2R)-1-(3,5-difluorobenzyl)-2-hydroxy-3-[(3-iodobenzyl)amino]propyl}-2-hydroxy-2-(4-methoxy-3-nitrophenyl)acetamide | 642.4 |
| 1,218 | 5-(aminosulfonyl)-N-{(1S,2R)-1-(3,5-difluorobenzyl)-2-hydroxy-3-[(3-iodobenzyl)amino]propyl}-2-methoxybenzamide | 646.5 |
| 1,219 | N-{(1S,2R)-1-(3,5-difluorobenzyl)-2-hydroxy-3-[(3-iodobenzyl)amino]propyl}-4-hydroxy-3-(pyrrolidin-1-ylcarbonyl)benzamide | 650.5 |
| 1,220 | N-{(1S,2R)-1-(3,5-difluorobenzyl)-2-hydroxy-3-[(3-iodobenzyl)amino]propyl}-2-[(methylsulfonyl)amino]-1,3-oxazole-4-carboxamide | 621.4 |
| 1,221 | N$^1$-{(1S,2R)-1-(3,5-difluorobenzyl)-2-hydroxy-3-[(3-methoxybenzyl)amino]propyl}-5-(3,5-dimethylisoxazol-4-yl)-N$^3$,N$^3$-dipropylisophthalamide | 663.4 |
| 1,222 | N$^1$-{(1S,2R)-1-(3,5-difluorobenzyl)-2-hydroxy-3-[(3-methoxybenzyl)amino]propyl}-N$^3$,N$^3$-dipropyl-5-(1,3-thiazol-2-yl)isophthalamide | 651.4 |
| 1,223 | 3-(cyclohexylcarbonyl)-N-{(1S,2R)-1-(3,5-difluorobenzyl)-2-hydroxy-3-[(3-methoxybenzyl)amino]propyl}-5-methylbenzamide | 565.4 |
| 1,224 | N$^1$-{(1S,2R)-1-(3,5-difluorobenzyl)-2-hydroxy-3-[(3-methoxybenzyl)amino]propyl}-5-methyl-N$^3$-propylisophthalamide | 540.4 |
| 1,225 | 3-[cyclohexyl(hydroxy)methyl]-N-{(1S,2R)-1-(3,5-difluorobenzyl)-2-hydroxy-3-[(3-methoxybenzyl)amino]propyl}-5-methylbenzamide | 567.4 |

| EXAMPLE | Substituted Amine (X) | [M + H]+ |
|---|---|---|
| 1,226 | N$^1$-{(1S,2R)-1-(3,5-difluorobenzyl)-3-[(3-ethylbenzyl)amino]-2-hydroxypropyl}-5-(4-methyl-1,3-oxazol-2-yl)-N$^3$,N$^3$-dipropylisophthalamide | 647.5 |
| 1,227 | N$^3$-{(1S,2R)-1-(3,5-difluorobenzyl)-3-[(3-ethylbenzyl)amino]-2-hydroxypropyl}-N$^5$,N$^5$-dipropylpyridine-3,5-dicarboxamide | 567 |
| 1,228 | N$^1$-((1S,2R)-1-(3,5-difluorobenzyl)-2-hydroxy-3-{[(3-isobutyl-1,2,4-oxadiazol-5-yl)methyl]amino}propyl)-5-methyl-N$^3$,N$^3$-dipropylisophthalamide | 600 |
| 1,229 | N$^3$-{(1S,2R)-1-(3,5-difluorobenzyl)-3-[(3-ethynylbenzyl)amino]-2-hydroxypropyl}-N$^5$,N$^5$-dipropylpyridine-3,5-dicarboxamide | 563 |
| 1,230 | N$^3$-{(1S,2R)-1-(3,5-difluorobenzyl)-2-hydroxy-3-[(3-isopropylbenzyl)amino]propyl}-N$^5$,N$^5$-dipropylpyridine-3,5-dicarboxamide | 581 |
| 1,231 | N$^1$-[(1S,2R)-3-{[(1-acetylpiperidin-4-yl)amino]-1-(3,5-difluorobenzyl)-2-hydroxypropyl]-5-methyl-N$^3$,N$^3$-dipropylisophthalamide | 587 |
| 1,232 | N$^1$-{(1S,2R)-1-(3,5-difluorobenzyl)-2-hydroxy-3-[(3-pent-1-ynylbenzyl)amino]propyl}-5-methyl-N$^3$,N$^3$-dipropylisophthalamide | 618 |
| 1,233 | N$^1$-((1S,2R)-1-(3,5-difluorobenzyl)-2-hydroxy-3-{[3-(4-hydroxybut-1-ynyl)benzyl]amino}propyl)-5-methyl-N$^3$,N$^3$-dipropylisophthalamide | 620 |
| 1,234 | 1-{3-[({(1S,2R)-1-(3,5-difluorobenzyl)-3-[(3-ethylbenzyl)amino]-2-hydroxypropyl}amino)carbonyl]-5-methylbenzoyl}-L-prolinamide | 593 |
| 1,235 | N$^1$-{(1S,2R)-1-(3,5-difluorobenzyl)-3-[(3-ethylbenzyl)amino]-2-hydroxypropyl}-N$^3$-isopropyl-5-methylisophthalamide | 538 |
| 1,236 | N$^1$-{(1S,2R)-1-(3,5-difluorobenzyl)-3-[(3-ethylbenzyl)amino]-2-hydroxypropyl}-N$^3$-ethyl-N$^3$,5-dimethylisophthalamide | 538 |
| 1,237 | N$^1$-{(1S,2R)-1-(3,5-difluorobenzyl)-3-[(3-ethylbenzyl)amino]-2-hydroxypropyl}-N$^3$,5-dimethyl-N$^3$-prop-2-ynylisophthalamide | 548 |
| 1,238 | N$^1$-{(1S,2R)-1-(3,5-difluorobenzyl)-3-[(3-ethylbenzyl)amino]-2-hydroxypropyl}-N$^3$-isobutyl-5-methylisophthalamide | 552 |
| 1,239 | N$^1$-(sec-butyl)-N$^3$-{(1S,2R)-1-(3,5-difluorobenzyl)-3-[(3- | 552 |

-continued

| EXAMPLE | Substituted Amine (X) | [M + H]+ |
|---|---|---|
| 1,240 | ethylbenzyl)amino]-2-hydroxypropyl}-5-methylisophthalamide | |
| | $N^1$-butyl-$N^3$-{(1S,2R)-1-(3,5-difluorobenzyl)-3-[(3-ethylbenzyl)amino]-2-hydroxypropyl}-5-methylisophthalamide | 552 |
| 1,241 | $N^1$-{(1S,2R)-1-(3,5-difluorobenzyl)-3-[(3-ethylbenzyl)amino]-2-hydroxypropyl}-$N^3$,$N^3$-diethyl-5-methylisophthalamide | 552 |
| 1,242 | $N^1$-{(1S,2R)-1-(3,5-difluorobenzyl)-3-[(3-ethylbenzyl)amino]-2-hydroxypropyl}-$N^3$,5-dimethyl-$N^3$-propylisophthalamide | 552 |
| 1,243 | $N^1$-{(1S,2R)-1-(3,5-difluorobenzyl)-3-[(3-ethylbenzyl)amino]-2-hydroxypropyl}-$N^3$-isopropyl-$N^3$,5-dimethylisophthalamide | 552 |
| 1,244 | $N^1$-butyl-$N^3$-{(1S,2R)-1-(3,5-difluorobenzyl)-3-[(3-ethylbenzyl)amino]-2-hydroxypropyl}-$N^1$,5-dimethylisophthalamide | 566 |
| 1,245 | $N^1$-{(1S,2R)-1-(3,5-difluorobenzyl)-3-[(3-ethylbenzyl)amino]-2-hydroxypropyl}-$N^3$-isobutyl-$N^3$,5-dimethylisophthalamide | 566 |
| 1,246 | $N^1$-{(1S,2R)-1-(3,5-difluorobenzyl)-3-[(3-ethylbenzyl)amino]-2-hydroxypropyl}-$N^3$-ethyl-5-methyl-$N^3$-propylisophthalamide | 566 |
| 1,247 | $N^1$-{(1S,2R)-1-(3,5-difluorobenzyl)-3-[(3-ethylbenzyl)amino]-2-hydroxypropyl}-$N^3$-ethyl-$N^3$-isopropyl-5-methylisophthalamide | 566 |
| 1,248 | $N^1$,$N^1$-diallyl-$N^3$-{(1S,2R)-1-(3,5-difluorobenzyl)-3-[(3-ethylbenzyl)amino]-2-hydroxypropyl}-5-methylisophthalamide | 576 |
| 1,249 | 3-(azepan-1-ylcarbonyl)-N-{(1S,2R)-1-(3,5-difluorobenzyl)-3-[(3-ethylbenzyl)amino]-2-hydroxypropyl}-5-methylbenzamide | 578 |
| 1,250 | N-{(1S,2R)-1-(3,5-difluorobenzyl)-3-[(3-ethylbenzyl)amino]-2-hydroxypropyl}-3-[(4-hydroxypiperidin-1-yl)carbonyl]-5-methylbenzamide | 580 |
| 1,251 | N-{(1S,2R)-1-(3,5-difluorobenzyl)-3-[(3-ethylbenzyl)amino]-2-hydroxypropyl}-3-[(3-hydroxypiperidin-1-yl)carbonyl]-5-methylbenzamide | 580 |
| 1,252 | $N^1$-{(1S,2R)-1-(3,5-difluorobenzyl)-3-[(3-ethylbenzyl)amino]-2-hydroxypropyl}-$N^3$,$N^3$-diisopropyl-5-methylisophthalamide | 580 |
| 1,253 | $N^1$-butyl-$N^3$-{(1S,2R)-1-(3,5-difluorobenzyl)-3-[(3-ethylbenzyl)amino]-2-hydroxypropyl}-$N^1$-ethyl-5-methylisophthalamide | 580 |
| 1,254 | $N^1$-(cyclopropylmethyl)-$N^3$-{(1S,2R)-1-(3,5-difluorobenzyl)-3-[(3-ethylbenzyl)amino]-2-hydroxypropyl}-5-methyl-$N^1$-propylisophthalamide | 592 |
| 1,255 | 1-{3-[({(1S,2R)-1-(3,5-difluorobenzyl)-3-[(3-ethylbenzyl)amino]-2-hydroxypropyl}amino)carbonyl]-5-methylbenzoyl}-D-prolinamide | 593 |
| 1,256 | $N^1$-cyclohexyl-$N^3$-{(1S,2R)-1-(3,5-difluorobenzyl)-3-[(3-ethylbenzyl)amino]-2-hydroxypropyl}-$N^1$,5-dimethylisophthalamide | 592 |
| 1,257 | $N^1$-((1S,2R)-1-(3,5-difluorobenzyl)-2-hydroxy-3-{[1-(3-methylphenyl)cyclopropyl]amino}propyl)-5-methyl-$N^3$,$N^3$-dipropylisophthalamide | 592 |
| 1,258 | $N^3$-[(1S,2R)-1-(3,5-difluorobenzyl)-2-hydroxy-3-(1,2,3,4-tetrahydronaphthalen-1-ylamino)propyl]- | 579 |

-continued

| EXAMPLE | Substituted Amine (X) | [M + H]+ |
|---|---|---|
| 1,259 | $N^5$,$N^5$-diisopropylpyridine-3,5-dicarboxamide N-{(1S,2R)-1-(3,5-difluorobenzyl)-3-[(3-ethylbenzyl)amino]-2-hydroxypropyl}-3-{[(trifluoromethyl)sulfonyl]amino}benzamide | 586.1 |

Following the procedures described above and those in international patent application WO 99/33815 (Published Jul. 8, 1999), the following prodrug compounds are made. WO 99/33815 is herein incorporated by reference in its entirety.

Example 1260

1-[(benzylamino)methyl]-3-(3,5-difluorophenyl)-2-({3-[(dipropylamino)carbonyl]benzoyl}amino)propyl 4-nitrophenyl carbonate (1260 Y)

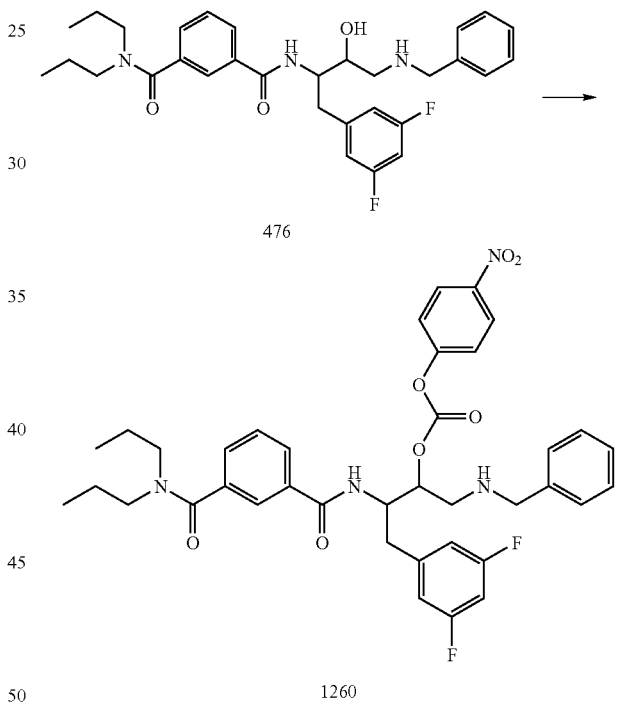

476 is first protected by methods well known in the art, as discussed above. For example, 476 is protected with t-butoxycarbonyl by treating the compound with di-tert-butyl dicarbonate in the presence of triethylamine, 4-(dimethylamino)pyridine (DMAP) and methylene chloride. A mixture of 3.7 mMol of protected 476 and 16 nMol of di-p-nitrophenyl carbonate in 10 ml of dimethylformamide is treated at 25° C. with 4 mMol of P4-phosphazene base (Fluka, 1M in hexane). The mixture is stirred for 6 h at 25° C. until all of the starting alcohol is consumed. The reaction mixture is partitioned between ethyl acetate and 1N hydrochloric acid. The organic layer is washed with 1N sodium hydroxide and brine, dried over magnesium sulfate and concentrated in vacuo. Titration with dichloromethane gives protected 1260. Deprotection of protected 1260 is conducted by methods well known in the art, as discussed above. For example, protected 1260 is treated with trifluoroacetic acid to yield 1260.

Example 1261

1-[(benzylamino)methyl]-3-(3,5-difluorophenyl)-2-({3-[(dipropylamino)carbonyl]benzoyl}amino)propyl 4-methylpiperazine-1-carboxylate (1261 Y)

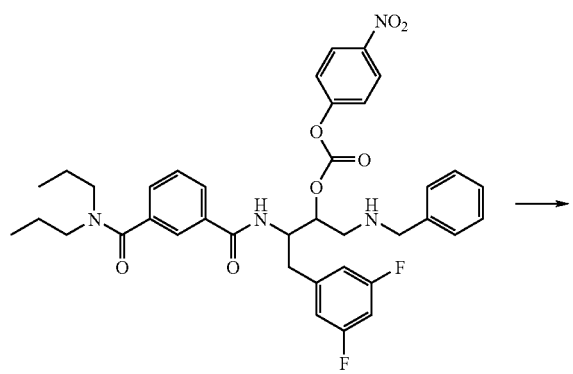

1260

1261

To 0.286 mM of protected 1260 dissolved in THF is added 1.14 mM of 1-methyl-piperazine and the mixture is stirred overnight at room temperature. All the solvents are then evaporated and the solid residue partitioned between EtOAc and water. The volatiles are removed and the residue is treated with 1:1 TFA/DCM over 30 min at room temperature to remove the Boc protecting groups, yielding product 1261.

Examples 1262-1267

Following the general procedure of EXAMPLE 1261 but using the reagents of Column A instead of 1-methyl-piperazine, prodrug (Y) of Column B is obtained.

| EX. | COL. A | COL. B; Compound Y |
|---|---|---|
| 1262 | N,N-dimethylamino-ethanol | 1-[(benzylamino)methyl]-3-(3,5-difluorophenyl)-2-({3-[(dipropylamino)carbonyl]benzoyl}amino)propyl 2-(dimethylamino)ethyl carbonate |
| 1263 | N-acetyl-ethylenediamine | 1-[(benzylamino)methyl]-3-(3,5-difluorophenyl)-2-({3-[(dipropylamino)carbonyl]benzoyl}amino)propyl 2-(acetylamino)ethylcarbamate |
| 1264 | Mono-N-Boc-piperazine | 1-[(benzylamino)methyl]-3-(3,5-difluorophenyl)-2-({3-[(dipropylamino)carbonyl]benzoyl}amino)propyl piperazine-1-carboxylate |
| 1265 | Mono-N-Boc-ethylenediamine | 1-[(benzylamino)methyl]-3-(3,5-difluorophenyl)-2-({3-[(dipropylamino)carbonyl]benzoyl}amino)propyl 2-aminoethylcarbamate |
| 1266 | 1,3-diamino-3-N-Boc-propane | 1-[(benzylamino)methyl]-3-(3,5-difluorophenyl)-2-({3-[(dipropylamino)carbonyl]benzoyl}amino)propyl 3-aminopropylcarbamate |
| 1267 | (3R)-(+)-3-Boc-aminopyrrolidine | 1-[(benzylamino)methyl]-3-(3,5-difluorophenyl)-2-({3-[(dipropylamino)carbonyl]benzoyl}amino)propyl (3R)-3-aminopyrrolidine-1-carboxylate |

Example 1268

1-[(benzylamino)methyl]-3-(3,5-difluorophenyl)-2-({3-[(dipropylamino)carbonyl]benzoyl}amino)propyl O-benzyl-L-tyrosinate

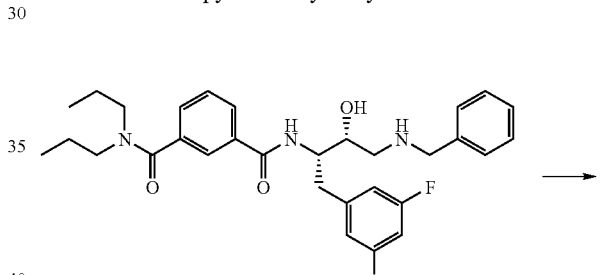

476

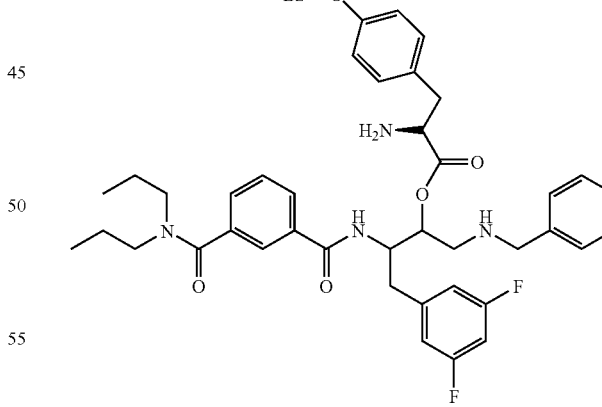

1268

476 is protected as described above. To 0.37 mM of protected 476 dissolved in CH$_2$Cl$_2$ is added 0.41 mM of N-CBz-O-Benzyl-L-tyrosine followed by 1.12 mM of DCC (dicyclohexylcarbodiimide), followed by 0.23 mM of DMAP. The reaction is stirred at rt for 24 hr. Precipitates are removed by filtration. The filtrate is then concentrated in vacuo. The product is deprotected as described above and purified by methods well known in the art to give 1268.

Examples 1269-1275

Following the general procedure of EXAMPLE 1268 but using the reagents of Column A instead of N-CBz-O-Benzyl-L-tyrosine, compound (Y) of Column B is obtained.

| EX. | COL. A | COL. B; Compound Y |
|---|---|---|
| 1269 | L-tyrosine | 1-[(benzylamino)methyl]-3-(3,5-difluorophenyl)-2-({3-[(dipropylamino)carbonyl]benzoyl}amino)-propyl L-tyrosinate |
| 1270 | 3-Methoxy-propionic acid | 1-[(benzylamino)methyl]-3-(3,5-difluorophenyl)-2-({3-[(dipropylamino)carbonyl]benzoyl}amino)-propyl 3-methoxypropanoate |
| 1271 | (2-Hydroxy-ethoxy)-acetic acid | 1-[(benzylamino)methyl]-3-(3,5-difluorophenyl)-2-({3-[(dipropylamino)carbonyl]benzoyl}amino)-propyl (2-hydroxyethoxy)acetate |
| 1272 | D-lysine | 1-[(benzylamino)methyl]-3-(3,5-difluorophenyl)-2-({3-[(dipropylamino)carbonyl]benzoyl}amino)-propyl D-lysinate |
| 1273 | [2-(2-Methoxy-ethoxy)-ethoxy]-acetic acid | 1-[(benzylamino)methyl]-3-(3,5-difluorophenyl)-2-({3-[(dipropylamino)carbonyl]benzoyl}amino)-propyl [2-(2-methoxyethoxy)ethoxy]acetate |
| 1274 | {2-[(2-Dimethylamino-ethyl)-methyl-amino]-ethoxy}-acetic acid | 1-[(benzylamino)methyl]-3-(3,5-difluorophenyl)-2-({3-[(dipropylamino)carbonyl]benzoyl}amino)-propyl {2-[[2-(dimethylamino)ethyl]-(methyl)amino]ethoxy}acetate |
| 1275 | (4-Methyl-piperazin-1-yl)-acetic acid | 1-[(benzylamino)methyl]-3-(3,5-difluorophenyl)-2-({3-[(dipropylamino)carbonyl]benzoyl}amino)-propyl (4-methylpiperazin-1-yl)acetate |

Following the general procedures outlined above and making non-critical variations, the following compounds (Y) are obtained.

(1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl (4-methylpiperazin-1-yl)acetate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl 4-methylpiperazine-1-carboxylate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl piperazine-1-carboxylate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl {2-[[2-(dimethylamino)ethyl](methyl)amino]ethoxy}acetate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl (2-methoxyethoxy)acetate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl L-tyrosinate, (1R, 2S)-3-(3,5-difluorophenyl)-2-{(3-[(dipropylamino)carbonyl]-5-methylbenzoyl}-amino)-1-{[(3-pent-1-ynylbenzyl)amino]methyl}propyl (3R)-3-aminopyrrolidine-1-carboxylate, (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl tetrahydrofuran-3-yl carbonate, N'-[(1S, 2R)-1-benzyl-3-(cyclohexylamino)-2-hydroxypropyl]-N,N-dipropylisophthalamide, (1R, 2S)-1-[(cyclohexylamino)methyl]-2-({3-[(dipropylamino)carbonyl]benzoyl}-amino)-3-phenylpropyl 4-methylpiperazine-1-carboxylate, (1R,2S)-1-[(cyclohexylamino)methyl]-2-({3-[(dipropylamino)carbonyl]benzoyl}-amino)-3-phenylpropyl piperazine-1-carboxylate, (1R,2S)-1-[(cyclohexylamino)methyl]-2-({3-[(dipropylamino)carbonyl]benzoyl}-amino)-3-phenylpropyl {2-[[2-(dimethylamino)ethyl](methyl)amino]ethoxy}acetate, (1R,2S)-1-[(cyclohexylamino)methyl]-2-({3-[(dipropylamino)carbonyl]benzoyl}-amino)-3-phenylpropyl (2-methoxyethoxy)acetate, (1R,2S)-1-[(cyclohexylamino)methyl]-2-({3-[(dipropylamino)carbonyl]benzoyl}-amino)-3-phenylpropyl L-tyrosinate, (1R,2S)-1-[(cyclohexylamino)methyl]-2-({3-[(dipropylamino)carbonyl]benzoyl}-amino)-3-phenylpropyl (3R)-3-aminopyrrolidine-1-carboxylate, (1R,2S)-1-[(cyclohexylamino)methyl]-2-({3-[(dipropylamino)carbonyl]benzoyl}-amino)-3-phenylpropyl tetrahydrofuran-3-yl carbonate.

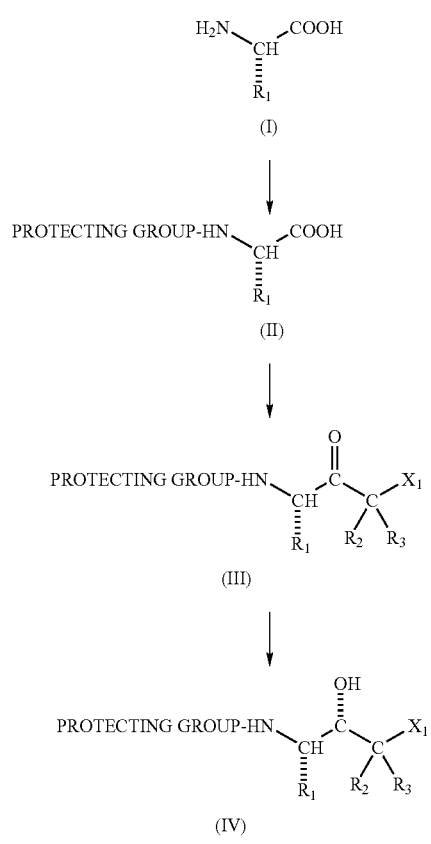

CHART A

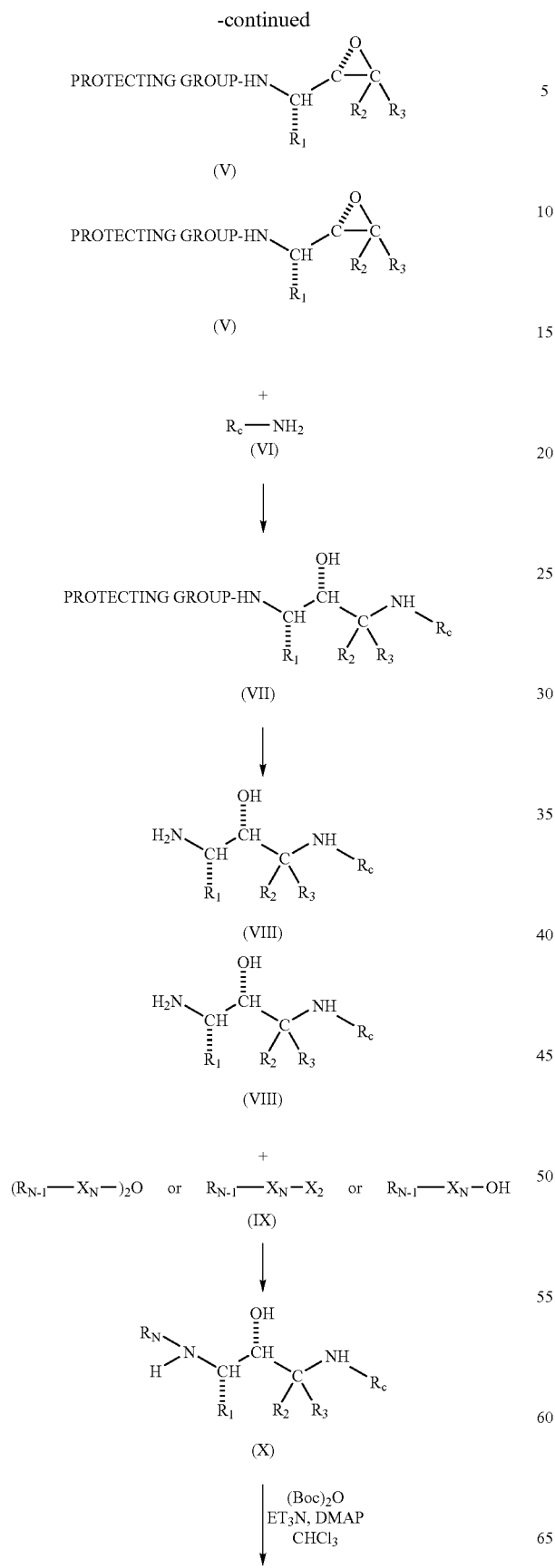
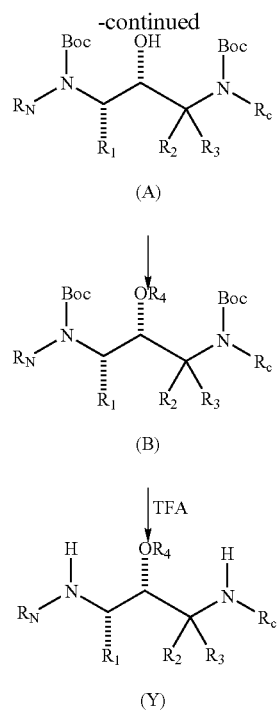
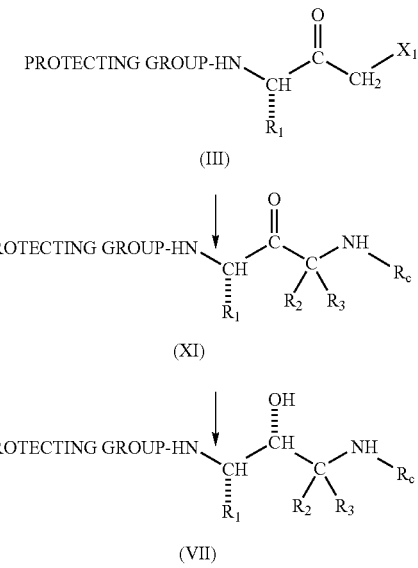
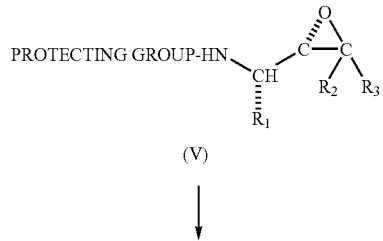

223
-continued
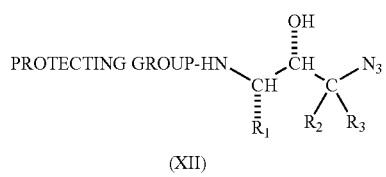
(XII)
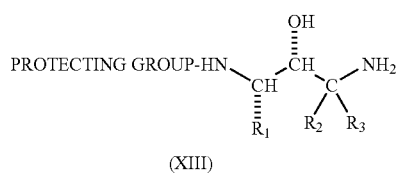
(XIII)
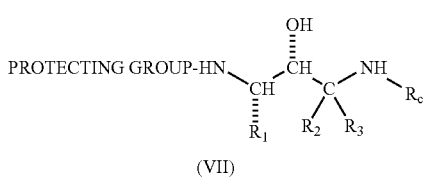
(VII)
CHART D
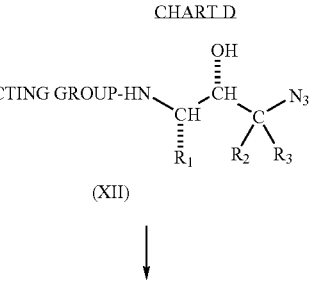
(XII)
224
-continued
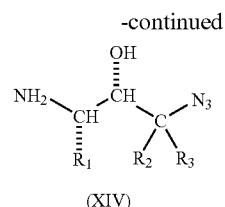
(XIV)
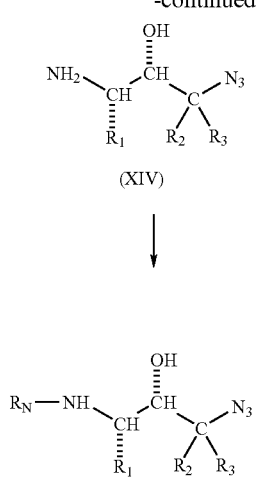
(XV)
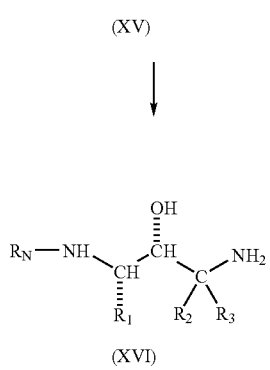
(XVI)
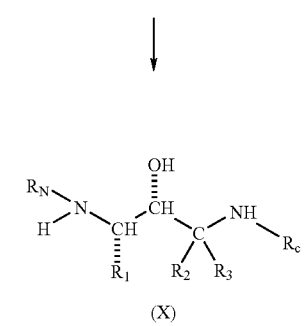
(X)
CHART E
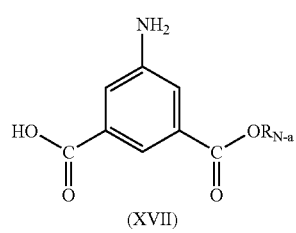
(XVII)

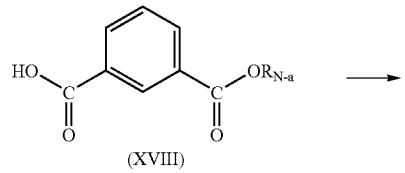
(XVIII)
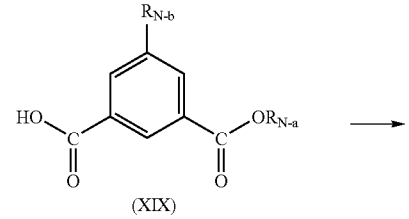
(XIX)
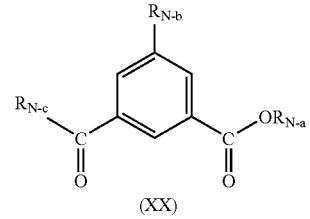
(XX)
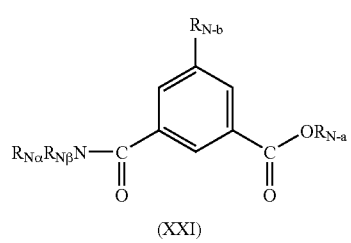
(XXI)
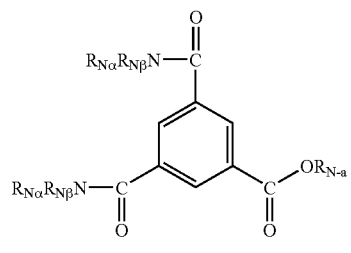
(XXII)
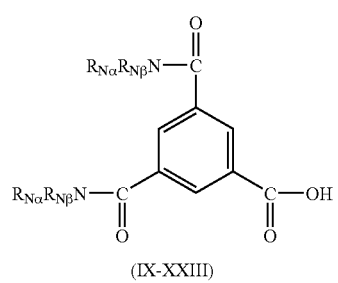
(IX-XXIII)

CHART F
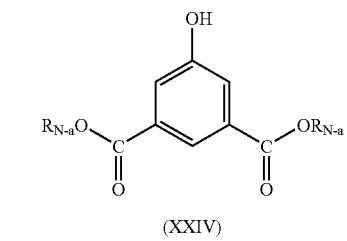
(XXIV)
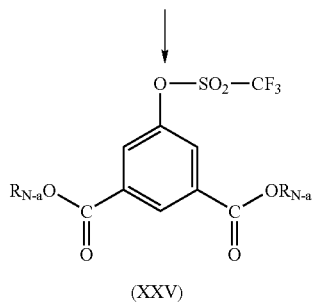
(XXV)
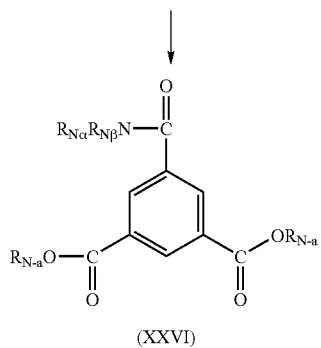
(XXVI)
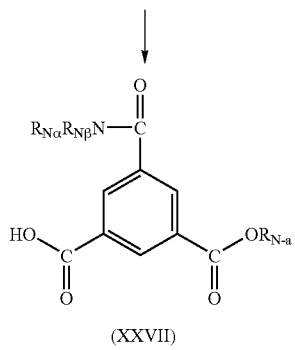
(XXVII)
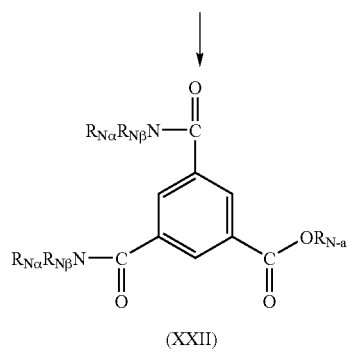
(XXII)
CHART G
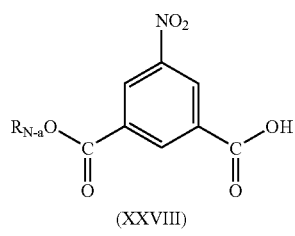
(XXVIII)
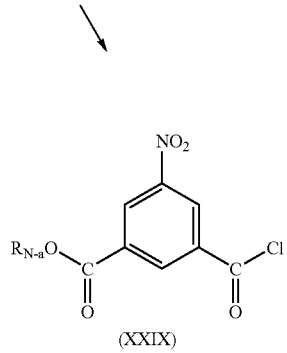
(XXIX)
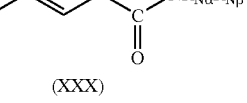
(XXX)
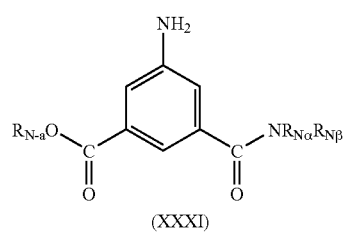
(XXXI)
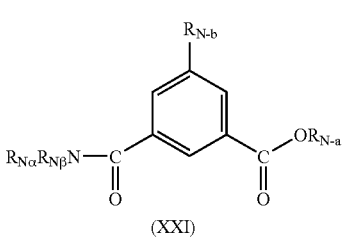
(XXI)

CHART H
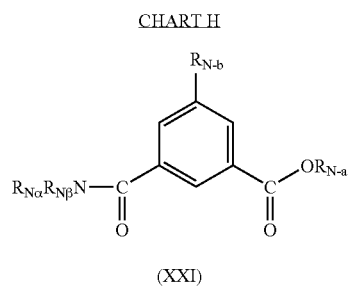
(XXI)
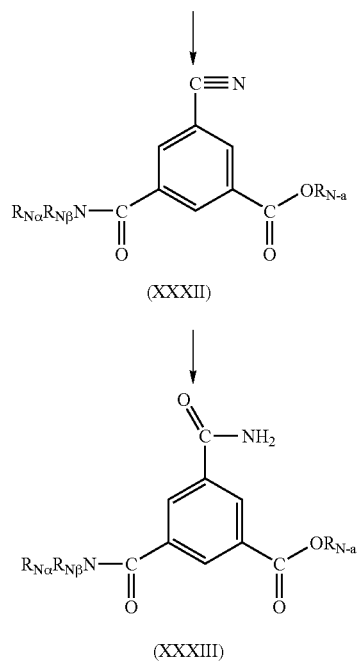
CHART I
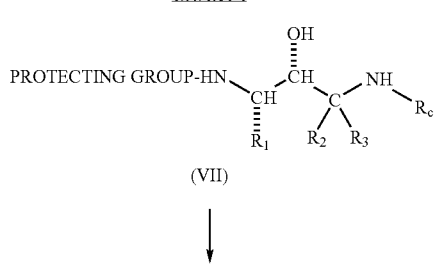
(VII)
-continued
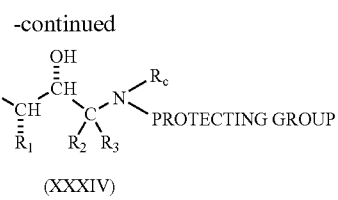
(XXXIV)
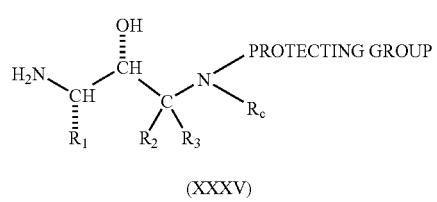
(XXXV)
+
$(R_N\!\!-\!\!)_2O$ or $R_N\!\!-\!\!X_2$ or $R_N\!\!-\!\!OH$
(IX)
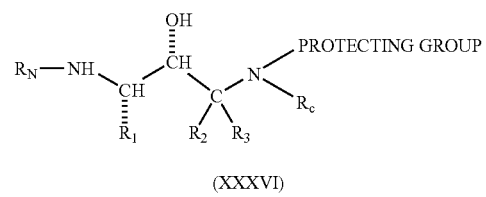
(XXXVI)
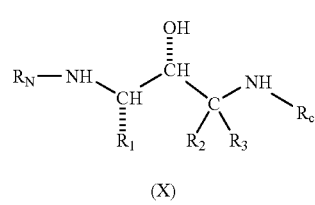
(X)
CHART J
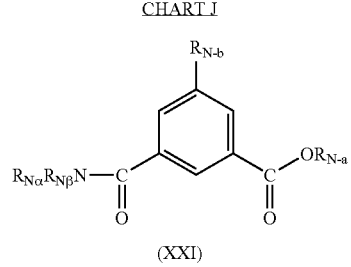
(XXI)

231
-continued
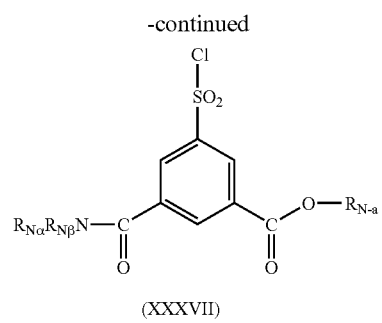
(XXXVII)
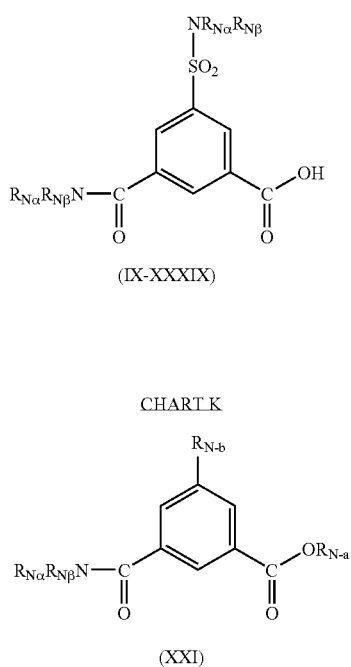
(XXXVIII)
(IX-XXXIX)
CHART K
(XXI)
232
-continued
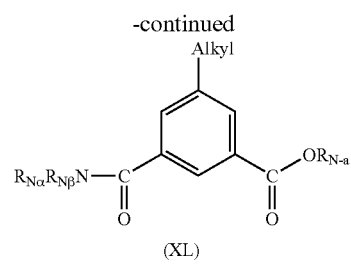
(XL)
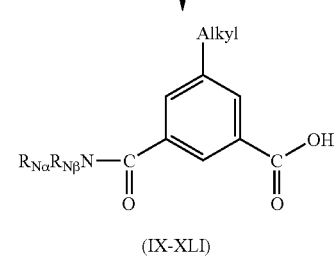
(IX-XLI)
CHART L
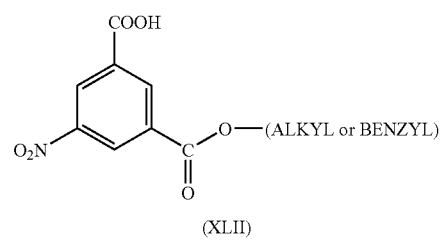
(XLII)
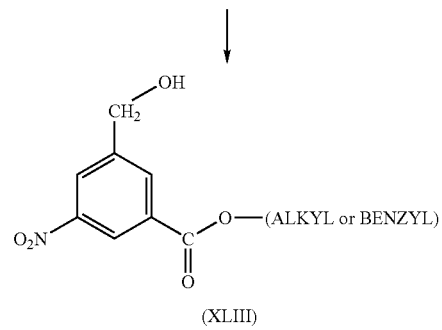
(XLIII)
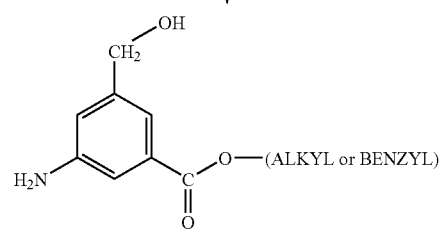
(XLIV)

-continued
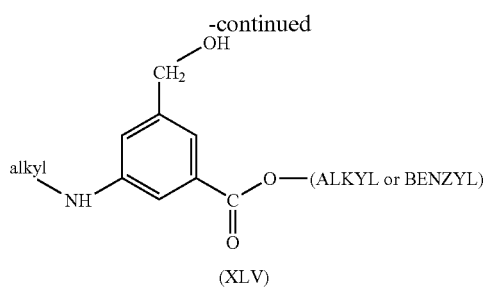
(XLV)
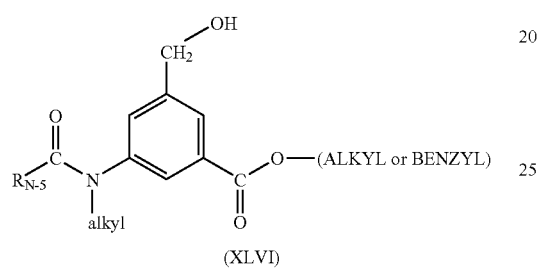
(XLVI)
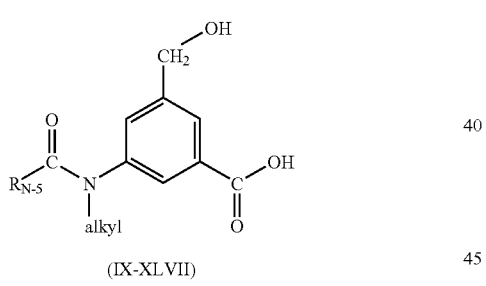
(IX-XLVII)
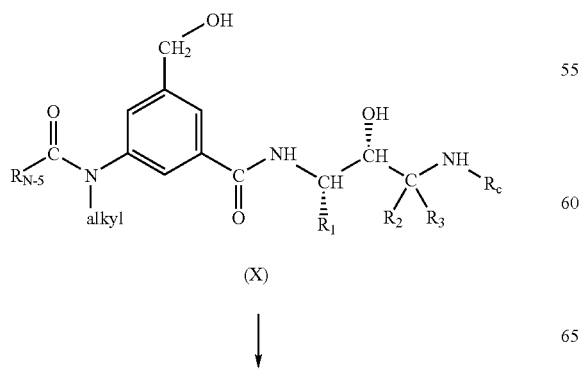
(X)
-continued
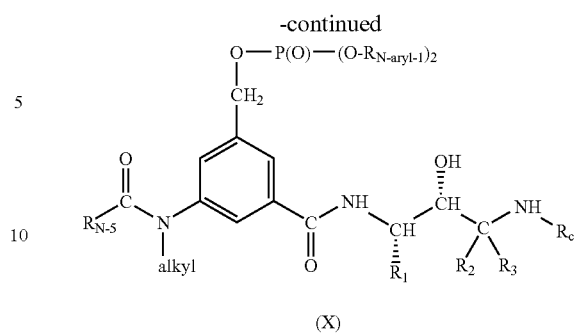
(X)
CHART M
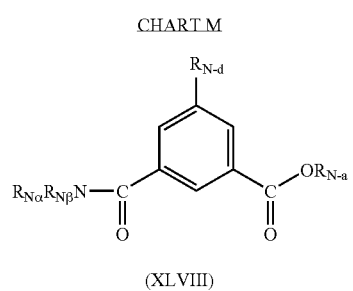
(XLVIII)
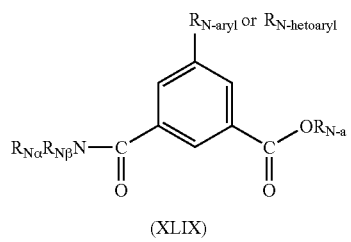
(XLIX)
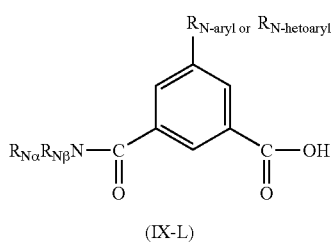
(IX-L)

235
CHART N
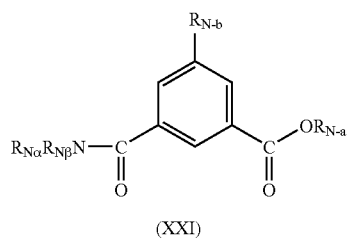
(XXI)
↓
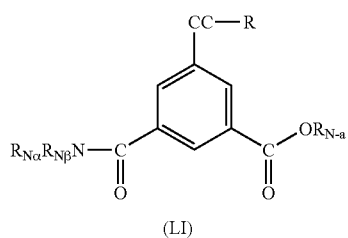
(LI)
↓
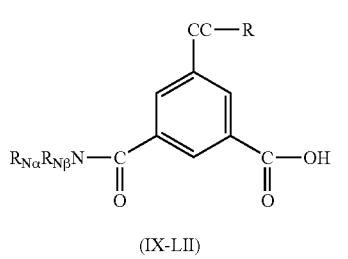
(IX-LII)
↓
CHART O
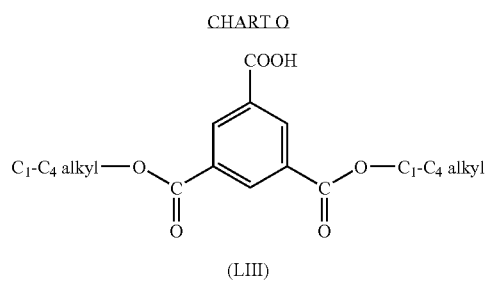
(LIII)
↓
236
-continued
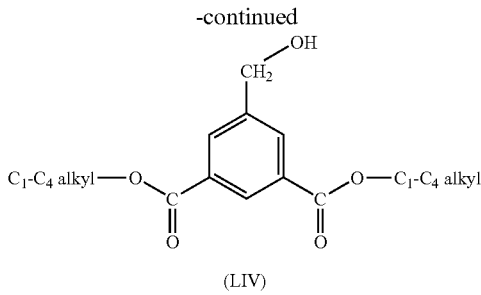
(LIV)
↓
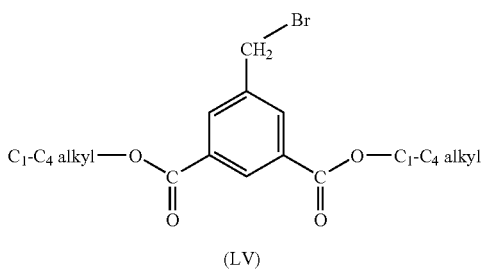
(LV)
↓
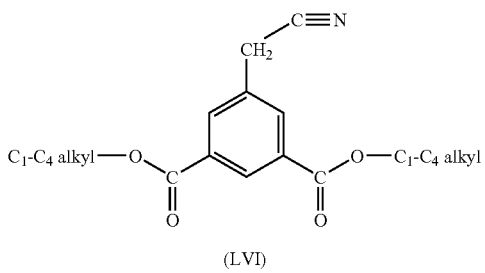
(LVI)
↓
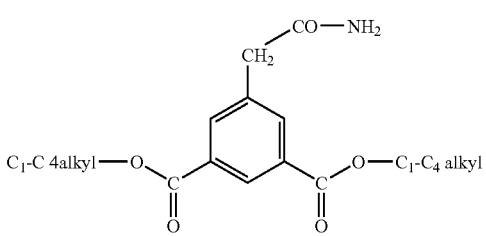
(LVII)
↓

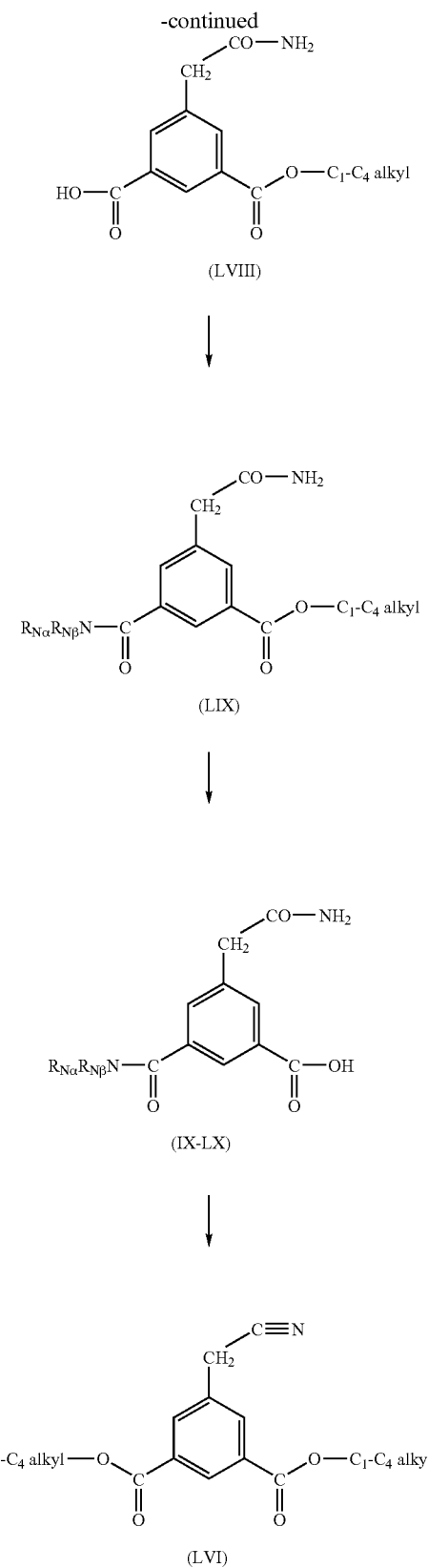
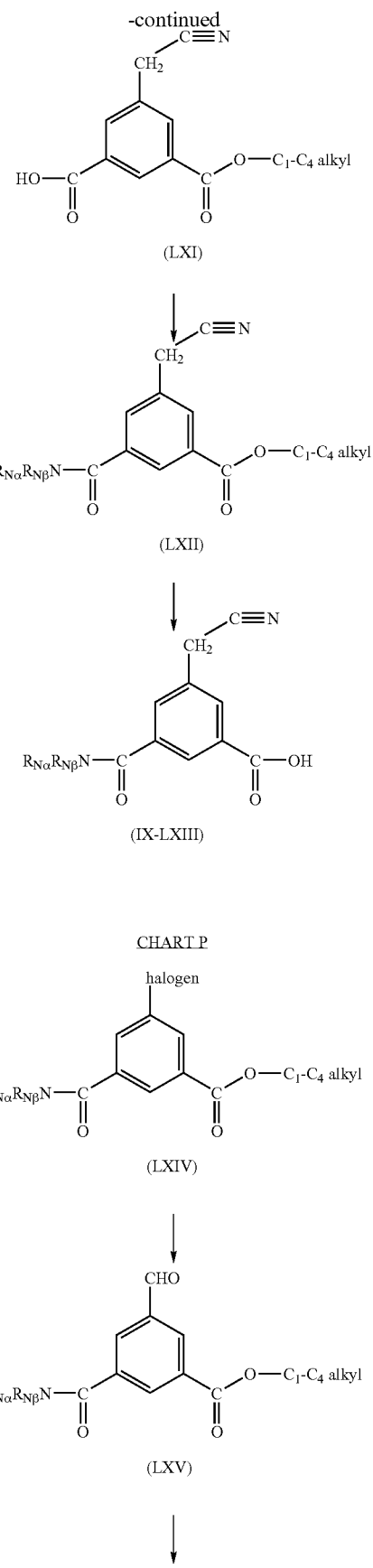

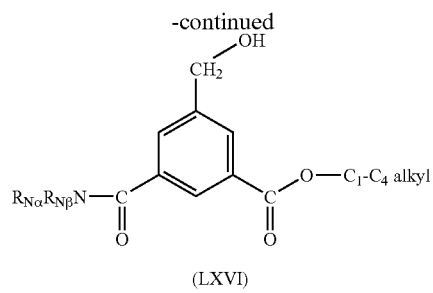
(LXVI)
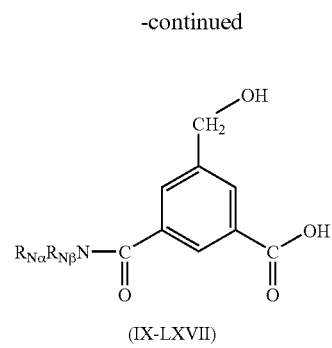
(IX-LXVII)
CHART Q
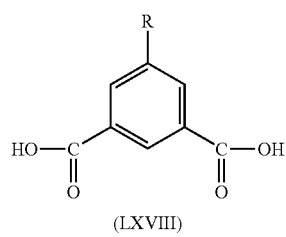
(LXVIII)
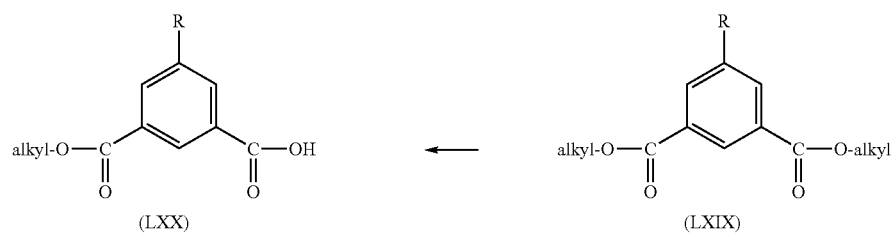
(LXX)  (LXIX)
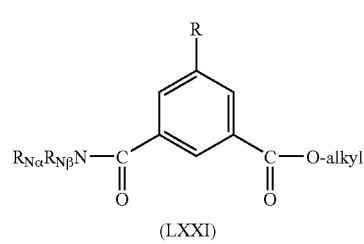
(LXXI)

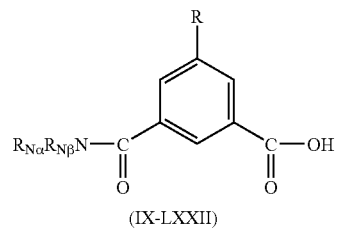
(IX-LXXII)
CHART R
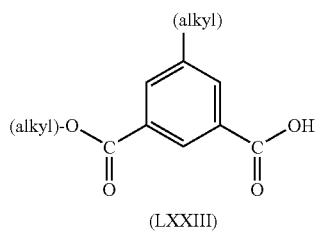
(LXXIII)
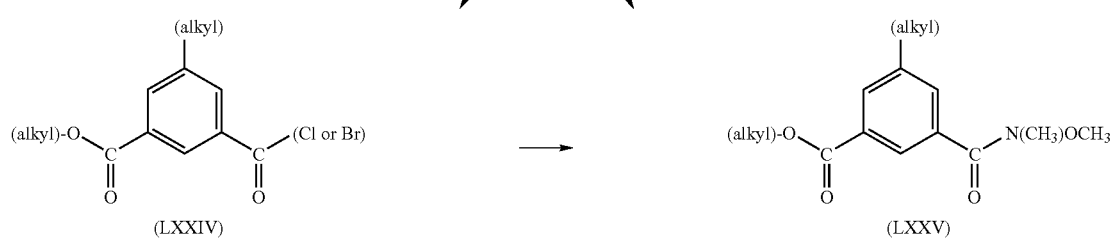
or
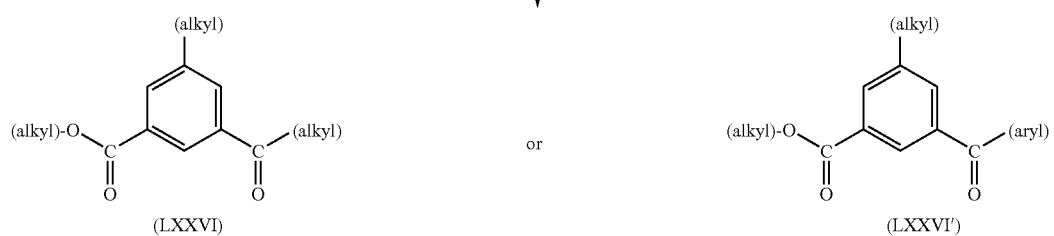
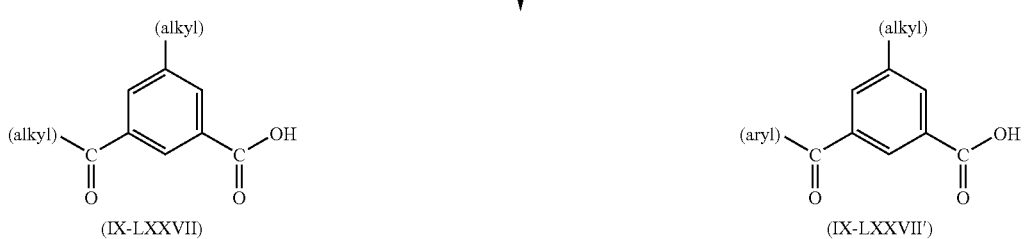

Chart S
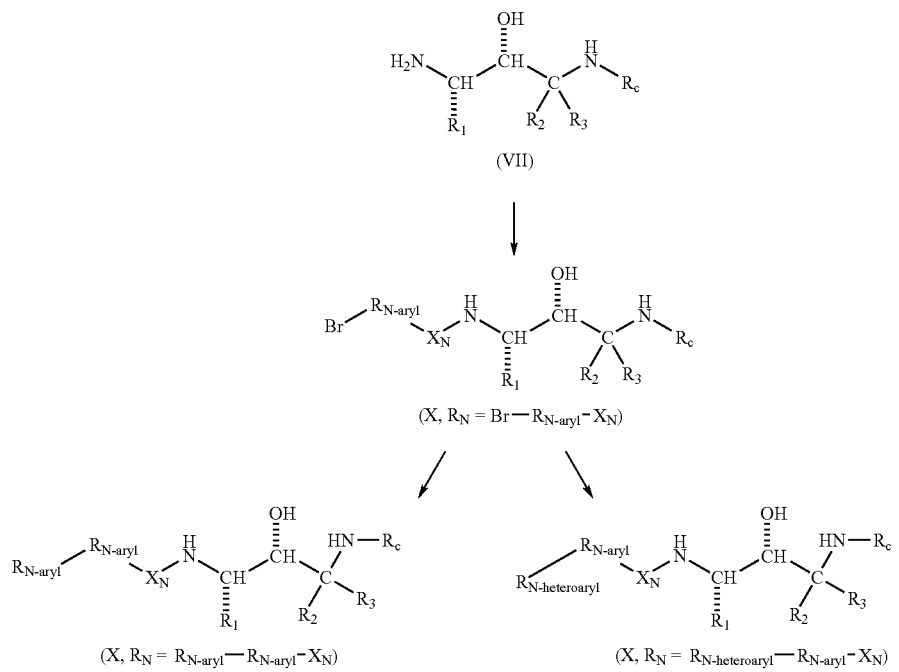
CHART T
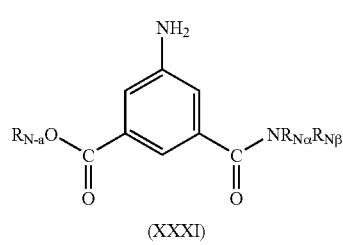
(XXXI)
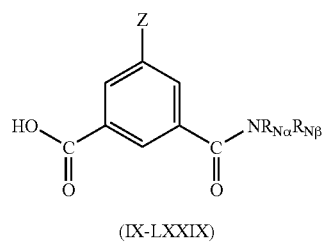
(LXXVIII)
-continued
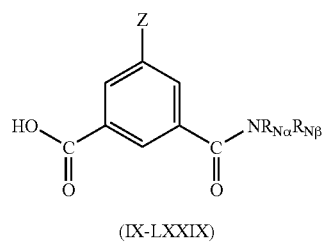
(IX-LXXIX)
CHART U
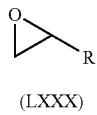
(LXXX)
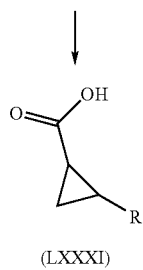
(LXXXI)

245
-continued
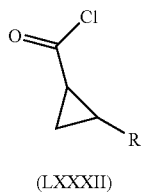
(LXXXII)
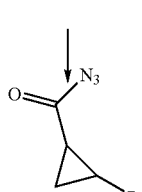
(LXXXIII)
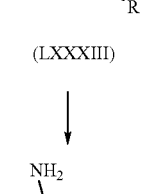
(LXXXIV)
CHART V
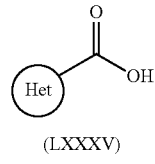 → 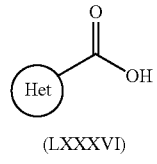
(LXXXV)          (LXXXVI)
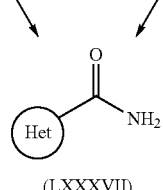
(LXXXVII)
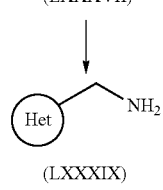
(LXXXIX)
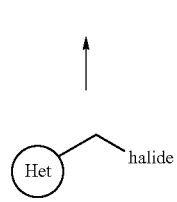
(LXXXVIII)
Het = Heteroaryl
246
CHART W
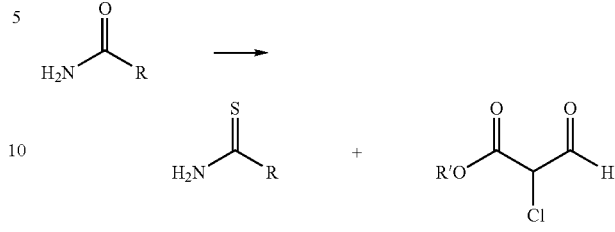
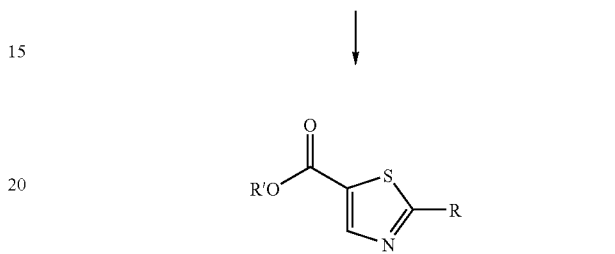
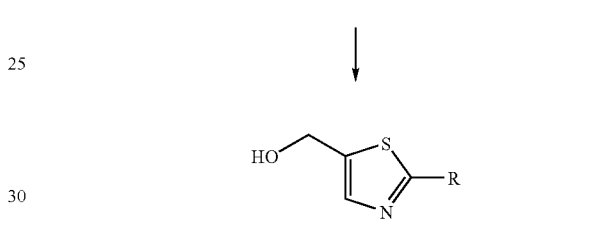
(XC)
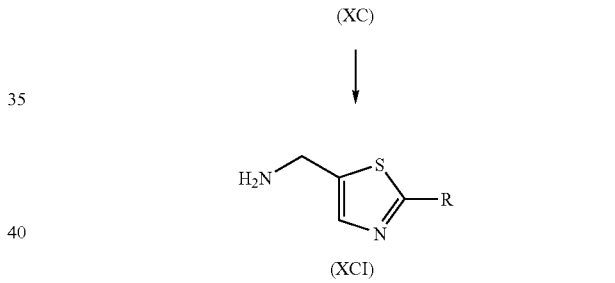
(XCI)
CHART X
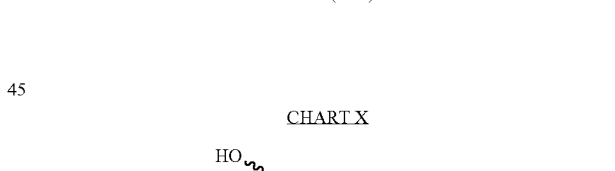
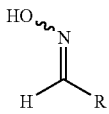
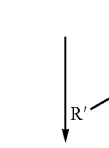
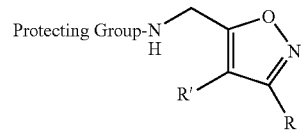

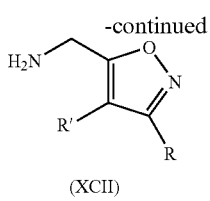

(XCII)

CHART Y

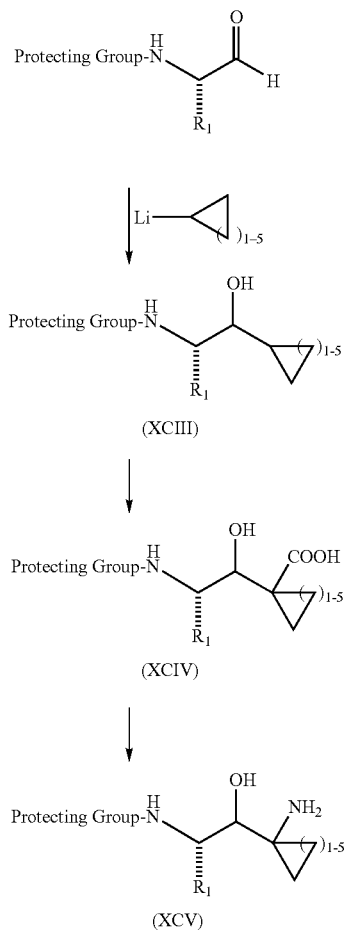

BIOLOGICAL EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et.al, 1999, Nature 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20-millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hours incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
Biotin-SEVNL-DAEFRC[oregon green]KK                              [SEQ ID NO: 1]

Biotin-SEVKM-DAEFRC[oregon green]KK                              [SEQ ID NO: 2]

Biotin-GLNIKTEEISEISY-EVEFRC[oregon green]KK                     [SEQ ID NO: 3]

Biotin-ADRGLTTRPGSGLTNIKTEEISEVNL-DAEFRC [oregon green]KK        [SEQ ID NO: 4]

Biotin-FVNQHLCoxGSHLVEALY-LVCoxGERGFFYTPKAC [oregon green]KK     [SEQ ID NO: 5]
```

The enzyme (0.1 nanomolar) and test compounds (0.001-100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, preferred compounds of the invention exhibit an $IC_{50}$ of less than 50 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:
(biotin)CGGADRGLTTRPGSGLTNIKTEEISEVNLDAEF [SEQ ID NO: 6]
The P26-P1 standard has the sequence:
(biotin)CGGADRGLTTRPGSGLTNIKTEEISEVNL [SEQ ID NO: 7].
Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, Nature 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, *Nature* 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

While this invention has been described with respect to various specific examples and embodiments, it is to be understood that the invention is not limited thereby and should only be construed by interpretation of the scope of the appended claims.

What is claimed is:

1. A compound of the formula:

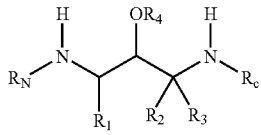

or a pharmaceutically acceptable salt thereof, where $R_1$ is:

—$(CH_2)_{n1}$—$(R_{1\text{-}aryl})$ where $n_1$ is one and where $R_{1\text{-}aryl}$ is phenyl optionally substituted with one, two, three or four of ring:

(A) $C_1$-$C_6$ alkyl optionally substituted with one, two or three substituents selected from the group consisting of $C_1$-$C_3$ alkyl, —F, —Cl, —Br, —I, —OH, —SH, —$NR_{1\text{-}a}R_{1\text{-}b}$ where $R_{1\text{-}a}$ and $R_{1\text{-}b}$ are as defined above, —C≡N, —$CF_3$, $C_1$-$C_3$ alkoxy, (B) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl, (C) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl, (D) —F, Cl, —Br and —I, (F) —$C_1$-$C_6$ alkoxy optionally substituted with one, two or three —F, (G) —$NR_{N\text{-}2}R_{N\text{-}3}$ where $R_{N\text{-}2}$ and $R_{N\text{-}3}$ are as defined below, (H) —OH, (I) —C≡N, (J) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are —H or $C_1$-$C_6$ alkyl, (K) —CO—($C_1$-$C_4$ alkyl), (L) —$SO_2$—$NR_{1\text{-}a}R_{1\text{-}b}$ where $R_{1\text{-}a}$ and $R_{1\text{-}b}$ are as defined above, (M) —CO—$NR_{1\text{-}a}R_{1\text{-}b}$ where $R_{1\text{-}a}$ and $R_{1\text{-}b}$ are as defined above, or (N) —$SO_2$—($C_1$-$C_4$ alkyl), where $R_2$ is —H;

where $R_3$ is —H;

where $R_N$ is $R_{N\text{-}1}$—$X_N$—, where $X_N$ is —CO—, where $R_{N\text{-}1}$ is $R_{N\text{-}aryl}$, where $R_{N\text{-}aryl}$ is phenyl substituted with one of —$(CH_2)_{0\text{-}4}$—CO—$NR_{N\text{-}2}R_{N\text{-}3}$ where $R_{N\text{-}2}$ and $R_{N\text{-}3}$ are independently $C_1$-$C_6$ alkyl and optionally substituted with one or two of (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1\text{-}a}R_{1\text{-}b}$ where $R_{1\text{-}a}$ and $R_{1\text{-}b}$ are as defined above, (2) —OH, (3) —$NO_2$, (4) —F, —Cl, —Br, —I, (5) —CO—OH, (6) —C≡N, (7) —$(CH_2)_{0\text{-}4}$—CO—$NR_{N\text{-}2}R_{N\text{-}3}$ where $R_{N\text{-}2}$ and $R_{N\text{-}3}$ are independently the same or different and are selected from the group consisting of:

(a) —H, (b) —$C_1$-$C_6$ alkyl; optionally substituted with one substitutent selected from the group consisting of:

(i) —OH, (ii) —$NH_2$, (c) —$C_1$-$C_6$ alkyl optionally substituted with one to three —F, —Cl, —Br, —I, (d) —$C_3$-$C_7$ cycloalkyl, (e) —($C_1$-$C_2$ alkyl)-($C_3$-$C_7$ cycloalkyl), (f) —($C_1$-$C_6$ alkyl)-O—($C_1$-$C_3$ alkyl), (g) —$C_2$-$C_6$ alkenyl with one or two double bonds, (h) —$C_2$-$C_6$ alkynyl with one or two triple bonds, (i) —$C_1$-$C_6$ alkyl chain with one double bond and one triple bond, (8) —$(CH_2)_{0-4}$—CO—($C_1$-$C_{12}$ alkyl),
(9) —$(CH_2)_{0-4}$—CO—($C_2$-$C_{12}$ alkenyl with one, two or three double bonds),
(10) —$(CH_2)_{0-4}$—CO—($C_2$-$C_{12}$ alkynyl with one, two or three triple bonds),
(11) —$(CH_2)_{0-4}$—CO—($C_3$-$C_7$ cycloalkyl), or
(15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of $C_1$-$C_6$ alkyl, where $R_C$ is:
—$(CR_{C-x}R_{C-y})_{0-4}$—$R_{C-aryl}$ where $R_{C-x}$ and $R_{C-y}$ are independently —H, and
$R_{C-aryl}$ is defined the same as $R_{N-aryl}$ is defined above in connection with the definition of $R_N$;

where $R_4$ is:

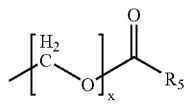

where x is 0 or 1 and $R_5$ is H or is:
(I) $R_{P-1}$ wherein $R_{P-1}$ is selected from the group consisting of:
(A) —Y—$R_{P-aryl}$ where Y is absent or is oxygen, and $R_{P-aryl}$ is phenyl, 1-naphthyl, 2-naphthyl, tetralinyl, indanyl, or 6,7,8,9-tetrahydro-5H-benzo[a]cycloheptenyl, optionally substituted with one, two or three of the following substituents which can be the same or different and are:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$ where $R_{1-a}$ and $R_{1-b}$ are independently —H or $C_1$-$C_6$ alkyl,
(2) —OH,
(3) —$NO_2$,
(4) —F, —Cl, —Br, —I,
(5) —CO—OH,
(6) —C≡N,
(7) —$(CH_2)_{0-4}$—CO—$NR_{P-2}R_{P-3}$ where $R_{P-2}$ and $R_{P-3}$ are the same or different and are selected from the group consisting of:
(a) —H,
(b) —$C_1$-$C_6$ alkyl optionally substituted with one substituent selected from the group consisting of:
(i) —OH, and
(ii) —$NH_2$,
(c) —$C_1$-$C_6$ alkyl optionally substituted with one to three —F, —Cl, —Br, or —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double bonds,
(h) —$C_2$-$C_6$ alkynyl with one or two triple bonds,
(i) —$C_1$-$C_6$ alkyl chain with one double bond and one triple bond,
(j) —$R_{P-aryl}$ where —$R_{P-aryl}$ is defined above,
(k) —$R_{P-heteroaryl}$ where $R_{P-heteroaryl}$ is defined below, and
(l) —C(O)$C_1$-$C_6$ alkyl,
(8) —$(CH_2)_{0-4}$—CO—($C_1$-$C_{12}$ alkyl),
(9) —$(CH_2)_{0-4}$—CO—($C_2$-$C_{12}$) alkenyl with one, two or three double bonds,
(10) —$(CH_2)_{0-4}$—CO—($C_2$-$C_{12}$) alkynyl with one, two or three triple bonds,
(11) —$(CH_2)_{0-4}$—CO—($C_3$-$C_7$ cycloalkyl),
(12) —$(CH_2)_{0-4}$—CO—$R_{P-aryl}$ where $R_{P-aryl}$ is as defined above,
(13) —$(CH_2)_{0-4}$—CO—$R_{P-heteroaryl}$ where $R_{P-heteroaryl}$ is as defined below,
(14) —$(CH_2)_{0-4}$—CO—$R_{P-heterocycle}$ where $R_{P-heterocycle}$ is selected from the group consisting of:
(A) morpholinyl,
(B) thiomorpholinyl,
(C) thiomorpholinyl S-oxide,
(D) thiomorpholinyl S,S-dioxide,
(E) piperazinyl,
(F) homopiperazinyl,
(G) pyrrolidinyl,
(H) pyrrolinyl,
(I) tetrahydropyranyl,
(J) piperidinyl,
(K) tetrahydrofuranyl,
(L) tetrahythiophenyl,
(M) homopiperidinyl,
(N) imidazolidine,
(O) imidazolidine dione, and
(P) dithiane,
where the $R_{P-heterocycle}$ group is bonded by any atom of the parent $R_{P-heterocycle}$ group substituted by hydrogen such that the new bond to the $R_{P-heterocycle}$ group replaces the hydrogen atom and its bond, where heterocycle is optionally substituted with one thru four:
(1) $C_1$-$C_6$ alkyl optionally substituted with one, two or three substituents selected from the group consisting of $C_1$-$C_3$ alkyl, —F, —Cl, —Br, —I, —OH, —SH, —O—CO—($C_1$-$C_6$ alkyl), —$NR_{1-a}R_{1-b}$ where $R_{1-a}$ and $R_{1-b}$ are as defined above, —C≡N, —$CF_3$, and $C_1$-$C_3$ alkoxy,
(2) $C_2$-$C_6$ alkenyl with one or two double bonds,
(3) $C_2$-$C_6$ alkynyl with one or two triple bonds,
(4) —F, Cl, —Br and —I,
(5) $C_1$-$C_6$ alkoxy,
(6) —O—$C_1$-$C_6$ alkyl optionally substituted with one thru three —F,
(7) —$NR_{P-2}R_{P-3}$ where $R_{P-2}$ and $R_{P-3}$ are as defined above,
(8) —OH,
(9) —C≡N,
(10) $C_3$-$C_7$ cycloalkyl,
(11) —CO—($C_1$-$C_4$ alkyl),
(12) —$SO_2$—$NR_{1-a}R_{1-b}$ where $R_{1-a}$ and $R_{1-b}$ are as defined above,
(13) —CO—$NR_{1-a}R_{1-b}$ where $R_{1-a}$ and $R_{1-b}$ are as defined above,
(14) —$SO_2$—($C_1$-$C_4$ alkyl);
(15) =O; or
(16) —O—CO—($C_1$-$C_6$ alkyl);
(15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl,

(16) —$(CH_2)_{0-4}$—CO—O—$R_{N-5}$ where $R_{N-5}$ is selected from the group consisting of:
  (a) $C_1$-$C_6$ alkyl,
  (b) —$(CH_2)_{0-2}$ ($R_{P-aryl}$) where $R_{P-aryl}$ is as defined above,
  (c) $C_2$-$C_6$ alkenyl containing one or two double bonds,
  (d) $C_2$-$C_6$ alkynyl containing one or two triple bonds,
  (e) $C_3$-$C_7$ cycloalkyl, and
  (f) —$(CH_2)_{0-2}$—($R_{P-heteroaryl}$) where $R_{P-heteroaryl}$ is as defined below,

(17) —$(CH_2)_{0-4}$—$SO_2$—$NR_{P-2}R_{P-3}$ where $R_{P-2}$ and $R_{P-3}$ are as defined above,

(18) —$(CH_2)_{0-4}$—SO—($C_1$-$C_8$ alkyl),

(19) —$(CH_2)_{0-4}$—$SO_2$—($C_1$—$C_{12}$ alkyl),

(20) —$(CH_2)_{0-4}$—$SO_2$—($C_3$-$C_7$ cycloalkyl),

(21) —$(CH_2)_{0-4}$—N(H or $R_{N-5}$)—CO—O—$R_{N-5}$ where $R_{N-5}$ can be the same or different and is as defined above,

(22) —$(CH_2)_{0-4}$—N(H or $R_{N-5}$)—CO—N ($R_{N-5}$) 2, where $R_{N-5}$ can be the same or different and is as defined above,

(23) —$(CH_2)_{0-4}$—N—CS—N ($R_{N-5}$)$_2$, where $R_{N-5}$ can be the same or different and is as defined above,

(24) —$(CH_2)_{0-4}$—N(—H or $R_{N-5}$)—CO—$R_{P-2}$ where $R_{N-5}$ and $R_{P-2}$ can be the same or different and are as defined above,

(25) —$(CH_2)_{0-4}$—$NR_{P-2}R_{P-3}$ where $R_{P-2}$ and $R_{P-3}$ can be the same or different and are as defined above,

(26) —$(CH_2)_{0-4}$-$R_{N-4}$ where $R_{N-4}$ is as defined above,

(27) —$(CH_2)_{0-4}$—O—CO—($C_1$-$C_6$ alkyl),

(28) —$(CH_2)_{0-4}$—O—P(O)—($OR_{N-aryl-1}$)$_2$ where $R_{N-aryl-1}$ is —H or $C_1$-$C_4$ alkyl,

(29) —$(CH_2)_{0-4}$—O—CO—N($R_{N-5}$)$_2$ where $R_{N-5}$ is as defined above,

(30) —$(CH_2)_{0-4}$—O—CS—N ($R_{N-5}$)$_2$ where $R_{N-5}$ is as defined above,

(31) —$(CH_2)_{0-4}$—O—($R_{N-5}$)$_2$ where $R_{N-5}$ is as defined above,

(32) —$(CH_2)_{0-4}$—O—($R_{N-5}$)$_2$—COOH where $R_{N-5}$ is as defined above,

(33) —$(CH_2)_{0-4}$—S—($R_{N-5}$)$_2$ where $R_{N-5}$ is as defined above,

(34) —$(CH_2)_{0-4}$—O—($C_1$-$C_6$ alkyl optionally substituted with one, two, three, four, or five of: —F),

(35) $C_3$-$C_7$ cycloalkyl,

(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$ where $R_{1-a}$ and $R_{1-b}$ are as defined above,

(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$ where $R_{1-a}$ and $R_{1-b}$ are as defined above,

(38) —$(CH_2)_{0-4}$—N(—H or $R_{N-5}$)—$SO_2$-$R_{P-2}$ where $R_{N-5}$ and $R_{P-2}$ can be the same of different and are as described above, or

(39) —$(CH_2)_{0-4}$—$C_3$-$C_7$ cycloalkyl, (B) —Y—$R_{P-heteroaryl}$ where Y is absent or is oxygen, and $R_{P-heteroaryl}$ is selected from the group consisting of:
(A) pyridinyl,
(B) pyrimidinyl,
(C) quinolinyl,
(F) benzothienyl,
(G) indolyl,
(H) indolinyl,
(I) pryidazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) beta-carbolinyl,
(PP) isochromanyl,
(QQ) chromanyl,
(SS) tetrahydroisoquinolinyl,
(TT) isoindolinyl,
(UU) isobenzotetrahydrofuranyl,
(VV) isobenzotetrahydrothienyl,
(WW) isobenzothienyl,
(XX) benzoxazolyl,
(YY) pyridopyridinyl,
(ZZ) benzotetrahydrofuranyl,
(AAA) benzotetrahydrothienyl,
(BBB) purinyl,
(CCC) benzodioxolyl,
(DDD) triazinyl,
(EEE) phenoxazinyl,
(FFF) phenothiazinyl,
(GGG) pteridinyl,
(HHH) benzothiazolyl,
(III) imidazopyridinyl,
(JJJ) imidazothiazolyl,
(KKK) dihydrobenzisoxazinyl,
(LLL) benzisoxazinyl,
(MMM) benzoxazinyl,
(NNN) dihydrobenzisothiazinyl,
(OOO) benzopyranyl,
(PPP) benzothiopyranyl,
(QQQ) coumarinyl, (RRR) isocoumarinyl,
(SSS) chromonyl,
(TTT) chromanonyl, and
(UUU) pyridinyl-N-oxide,
where the $R_{P\text{-}heteroaryl}$ group is bonded by any atom of the parent $R_{P\text{-}heteroaryl}$ group substituted by hydrogen such that the new bond to the $R_{P\text{-}heteroaryl}$ group replaces the hydrogen atom and its bond, where heteroaryl is optionally substituted with one, two, three, or four of:
  (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above,
  (2) —OH,
  (3) —NO$_2$,
  (4) —F, —Cl, —Br, —I,
  (5) —CO—OH,
  (6) —C≡N,
  (7) —(CH$_2$)$_{0\text{-}4}$—CO—NR$_{P\text{-}2}$R$_{P\text{-}3}$ where $R_{P\text{-}2}$ and $R_{P\text{-}3}$ are the same or different and are selected from the group consisting of:
    (a) —H,
    (b) —C$_1$-C$_6$ alkyl optionally substituted with one substituent selected from the group consisting of:
      (i) —OH, and
      (ii) —NH$_2$,
    (c) —C$_1$-C$_6$ alkyl optionally substituted with one to three —F, —Cl, —Br, or —I,
    (d) —C$_3$-C$_7$ cycloalkyl,
    (e) —(C$_1$-C$_2$ alkyl)-(C$_3$-C$_7$ cycloalkyl),
    (f) —(C$_1$-C$_6$ alkyl)-O—(C$_1$-C$_3$ alkyl),
    (g) —C$_2$-C$_6$ alkenyl with one or two double bonds,
    (h) —C$_2$-C$_6$ alkynyl with one or two triple bonds,
    (i) —C$_1$-C$_6$ alkyl chain with one double bond and one triple bond,
    (j) —R$_{P\text{-}aryl}$ where $R_{P\text{-}aryl}$ is as defined above, and
    (k) —R$_{P\text{-}heteroaryl}$ where $R_{P\text{-}heteroaryl}$ is as defined above,
  (8) —(CH$_2$)$_{0\text{-}4}$—CO—(C$_1$-C$_{12}$ alkyl),
  (9) —(CH$_2$)$_{0\text{-}4}$—CO—(C$_2$-C$_{12}$ alkenyl with one, two or three double bonds),
  (10) —(CH$_2$)$_{0\text{-}4}$—CO—(C$_2$-C$_{12}$ alkynyl with one, two or three triple bonds),
  (11) —(CH$_2$)$_{0\text{-}4}$—CO—(C$_3$-C$_7$ cycloalkyl),
  (12) —(CH$_2$)$_{0\text{-}4}$—CO—R$_{P\text{-}aryl}$ where $R_{P\text{-}aryl}$ is as defined above,
  (13) —(CH$_2$)$_{0\text{-}4}$—CO—R$_{P\text{-}heteroaryl}$ where $R_{P\text{-}heteroaryl}$ is as defined above,
  (14) —(CH$_2$)$_{0\text{-}4}$—CO—R$_{P\text{-}heterocycle}$ where $R_{P\text{-}heterocycle}$ is as defined above,
  (15) —(CH$_2$)$_{0\text{-}4}$—CO—R$_{N\text{-}4}$ where $R_{N\text{-}4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl,
  (16) —(CH$_2$)$_{0\text{-}4}$—CO—O—R$_{N\text{-}5}$ where $R_{N\text{-}5}$ is selected from the group consisting of:
    (a) $C_1$-$C_6$ alkyl,
    (b) —(CH$_2$)$_{0\text{-}2}$—(R$_{P\text{-}aryl}$) where $R_{P\text{-}aryl}$ is as defined above,
    (c) $C_2$-$C_6$ alkenyl containing one or two double bonds,
    (d) $C_2$-$C_6$ alkynyl containing one or two triple bonds,
    (e) $C_3$-$C_7$ cycloalkyl, and
    (f) —(CH$_2$)$_{0\text{-}2}$—(R$_{P\text{-}heteroaryl}$) where $R_{P\text{-}heteroaryl}$ is as defined above,
  (17) —(CH$_2$)$_{0\text{-}4}$—SO$_2$—NR$_{P\text{-}2}$R$_{P\text{-}3}$ where $R_{P\text{-}2}$ and $R_{P\text{-}3}$ are as defined above,
  (18) —(CH$_2$)$_{0\text{-}4}$—SO—(C$_1$-C$_8$ alkyl),
  (19) —(CH$_2$)$_{0\text{-}4}$—SO$_2$—(C$_1$-C$_{12}$ alkyl),
  (20) —(CH$_2$)$_{0\text{-}4}$—SO$_2$—(C$_3$-C$_7$ cycloalkyl),
  (21) —(CH$_2$)$_{0\text{-}4}$—N(H or R$_{N\text{-}5}$)—CO—O—R$_{N\text{-}5}$ where $R_{N\text{-}5}$ can be the same or different and is as defined above,
  (22) —(CH$_2$)$_{0\text{-}4}$—N(H or R$_{N\text{-}5}$)—CO—N(R$_{N\text{-}5}$)$_2$, where $R_{N\text{-}5}$ can be the same or different and is as defined above,
  (23) —(CH$_2$)$_{0\text{-}4}$—N—CS—N(R$_{N\text{-}5}$)$_2$, where $R_{N\text{-}5}$ can be the same or different and is as defined above,
  (24) —(CH$_2$)$_{0\text{-}4}$—N(—H or R$_{N\text{-}5}$)—CO—R$_{P\text{-}2}$ where $R_{N\text{-}5}$ and $R_{P\text{-}2}$ can be the same or different and are as defined above,
  (25) —(CH$_2$)$_{0\text{-}4}$—NR$_{P\text{-}2}$R$_{P\text{-}3}$ where $R_{P\text{-}2}$ and $R_{P\text{-}3}$ can be the same or different and are as defined above,
  (26) —(CH$_2$)$_{0\text{-}4}$—R$_{N\text{-}4}$ where $R_{N\text{-}4}$ is as defined above,
  (27) —(CH$_2$)$_{0\text{-}4}$—O—CO—(C$_1$-C$_6$ alkyl),
  (28) —(CH$_2$)$_{0\text{-}4}$—O—P(O)—(OR$_{N\text{-}aryl\text{-}1}$)$_2$ where $R_{N\text{-}aryl\text{-}1}$ is —H or $C_1$-$C_4$ alkyl,
  (29) —(CH$_2$)$_{0\text{-}4}$—O—CO—N(R$_{N\text{-}5}$)$_2$ where $R_{N\text{-}5}$ is as defined above,
  (30) —(CH$_2$)$_{0\text{-}4}$—O—CS—N(R$_{N\text{-}5}$)$_2$ where $R_{N\text{-}5}$ is as defined above,
  (31) —(CH$_2$)$_{0\text{-}4}$—O—(R$_{N\text{-}5}$)$_2$ where $R_{N\text{-}5}$ is as defined above,
  (32) —(CH$_2$)$_{0\text{-}4}$—O—(R$_{N\text{-}5}$)$_2$—COOH where $R_{N\text{-}5}$ is as defined above,
  (33) —(CH$_2$)$_{0\text{-}4}$—S—(R$_{N\text{-}5}$)$_2$ where $R_{N\text{-}5}$ is as defined above,
  (34) —(CH$_2$)$_{0\text{-}4}$—O—(C$_1$-C$_6$ alkyl optionally substituted with one, two, three, four, or five of: —F),
  (35) $C_3$-$C_7$ cycloalkyl,
  (36) $C_2$-$C_6$ alkenyl with one or two double bonds optionally substituted with $C_1$-$C_3$ alkyl, —F, —Cl, —Br, —I, —OH, —SH, —C≡N, —CF$_3$, $C_1$-$C_3$ alkoxy, —NR$_{1\text{-}a}$R$_{1\text{-}b}$ where $R_{1\text{-}a}$ and $R_{1\text{-}b}$ are as defined above,
  (37) $C_2$-$C_6$ alkynyl with one or two triple bonds optionally substituted with $C_1$-$C_3$ alkyl, —F, —Cl, —Br, —I, —OH, —SH, —C≡N, —CF$_3$, $C_1$-$C_3$ alkoxy, —NR$_{1\text{-}a}$R$_{1\text{-}b}$ where $R_{1\text{-}a}$ and $R_{1\text{-}b}$ are as defined above,
  (38) —(CH$_2$)$_{0\text{-}4}$—N(—H or R$_{N\text{-}5}$)—SO$_2$—R$_{P\text{-}2}$ where $R_{N\text{-}5}$ and $R_{P\text{-}2}$ can be the same of different and are as described above, or
  (39) —(CH$_2$)$_{0\text{-}4}$—C$_3$-C$_7$ cycloalkyl,
(C) $R_{P\text{-}aryl}$—W—$R_{P\text{-}aryl}$,
(D) $R_{P\text{-}aryl}$—W—$R_{P\text{-}heteroaryl}$,
(E) $R_{P\text{-}aryl}$—W—$R_{P\text{-}heterocycle}$,
(F) $R_{P\text{-}heteroaryl}$—W—$R_{P\text{-}aryl}$,
(G) $R_{P\text{-}heteroaryl}$—W—$R_{P\text{-}heteroaryl}$,
(H) $R_{P\text{-}heteroaryl}$—W—$R_{P\text{-}heterocycle}$,
(I) $R_{P\text{-}heterocycle}$—W—$R_{P\text{-}aryl}$,
(J) $R_{P\text{-}heterocycle}$—W—$R_{P\text{-}heteroaryl}$,
(K) $R_{P\text{-}heterocycle}$—W—$R_{P\text{-}heterocycle}$, where W is (1) —(CH$_2$)$_{0-4}$—,
(2) —O—,
(3) —S(O)$_{0-2}$—,
(4) —N(R$_{N-5}$)— where R$_{N-5}$ is as defined above;
(5) —CO—; or
(6) —O—(CH$_2$)$_{1-4}$—, and (L) —Y—R$_{P\text{-}heterocycle}$ where Y is absent or is oxygen, and R$_{P\text{-}heterocycle}$ is defined above;

(II) —(C$_1$-C$_{10}$ alkyl) where alkyl is optionally substituted with one, two, or three substituents selected from the group consisting of:
(A) —OH,
(B) —C$_1$-C$_6$ alkoxy,
(C) —C$_1$-C$_6$ thioalkoxy,
(D) —CO—O—R$_{N-8}$ where R$_{N-8}$ is —H, C$_1$-C$_6$ alkyl, phenyl or benzyl,
(E) —CO—NR$_{P-2}$R$_{P-3}$ where R$_{P-2}$ and R$_{P-3}$ are the same or different and are as defined above,
(F) —CO—R$_{N-4}$ where R$_{N-4}$ is as defined above,
(G) —SO$_2$—(C$_1$-C$_8$ alkyl),
(H) —SO$_2$—NR$_{P-2}$R$_{P-3}$ where R$_{P-2}$ and R$_{P-3}$ are the same or different and are as defined above,
(I) —NH—CO—(C$_1$-C$_6$ alkyl),
(J) —NH—CO—O—R$_{N-8}$ where R$_{N-8}$ is as defined above,
(K) —NR$_{P-2}$R$_{P-3}$ where R$_{P-2}$ and R$_{P-3}$ are the same or different and are as defined above,
(L) —R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—(C$_1$-C$_6$ alkyl) optionally substituted with one, two, or three of —F, —Cl, —Br, —I,
(Q) —NH—SO$_2$—(C$_1$-C$_6$ alkyl), and
(R) —F, —Cl, (III) —X-T-(C$_1$-C$_6$ alkyl) where X is absent or is C$_1$-C$_6$ alkyl, T is oxygen or is NR$_{P-2}$, and where alkyl is optionally substituted with one, two, or three substituents selected from the group consisting of:
(A) —OH,
(B) —C$_1$-C$_6$ alkoxy,
(C) —C$_1$-C$_6$ thioalkoxy,
(D) —CO—O—R$_{N-8}$ where R$_{N-8}$ is —H, C$_1$-C$_6$ alkyl, phenyl, or benzyl,
(E) —CO—NR$_{P-2}$R$_{P-3}$ where R$_{P-2}$ and R$_{P-3}$ are the same or different and are as defined above,
(F) —CO—R$_{N-4}$ where R$_{N-4}$ is as defined above,
(G) —SO$_2$—(C$_1$-C$_8$ alkyl),
(H) —SO$_2$—NR$_{P-2}$R$_{P-3}$ where R$_{P-2}$ and R$_{P-3}$ are the same or different and are as defined above,
(I) —NH—CO—(C$_1$-C$_6$ alkyl)
(J) —NH—CO—O—R$_{N-8}$ where R$_{N-8}$ is as defined above,
(K) —NR$_{P-2}$R$_{P-3}$ where R$_{P-2}$ and R$_{P-3}$ are the same or different and are as defined above,
(L) —R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—(C$_1$-C$_6$) alkyl optionally substituted with one, two, or three of —F, —Cl, —Br, —I,
(Q) —NH—SO$_2$—(C$_1$-C$_6$ alkyl),
(R) —F, —Cl,
(S) —O—R$_{P\text{-}aryl}$,
(T) —O—R$_{P\text{-}heteroaryl}$, and
(U) —O—R$_{P\text{-}hetrocycle}$;

(IV) —(C$_1$-C$_6$ alkyl)-Z-(C$_1$-C$_6$ alkyl) where Z is S or O, and alkyl is optionally substituted with one, two, or three substituents selected from the group consisting of:
(A) —OH,
(B) —C$_1$-C$_6$ alkoxy,
(C) —C$_1$-C$_6$ thioalkoxy,
(D) —CO—O—R$_{N-8}$ where R$_{N-8}$ is as defined above,
(E) —CO—NR$_{P-2}$R$_{P-3}$ where R$_{P-2}$ and R$_{P-3}$ are the same or different and are as defined above,
(F) —CO—R$_{N-4}$ where R$_{N-4}$ is as defined above,
(G) —SO$_2$—(C$_1$-C$_8$ alkyl),
(H) —SO$_2$—NR$_{P-2}$R$_{P-3}$ where R$_{P-2}$ and R$_{P-3}$ are the same or different and are as defined above,
(I) —NH—CO—(C$_1$-C$_6$ alkyl),
(J) —NH—CO—O—R$_{N-8}$ where R$_{N-8}$ is as defined above,
(K) —NR$_{P-2}$R$_{P-3}$ where R$_{P-2}$ and R$_{P-3}$ are the same or different and are as defined above,
(L) —R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—(C$_1$-C$_6$) alkyl optionally substituted with one, two, or three of —F, —Cl, —Br, —I,
(Q) —NH—SO$_2$—(C$_1$-C$_6$ alkyl), and
(R) —F, —Cl, (V) —CH (—(CH$_2$)$_{0-2}$—O—R$_{N-10}$)—(CH$_2$)$_{0-2}$—R$_{P\text{-}aryl}$/R$_{P\text{-}heteroaryl}$) where R$_{P\text{-}aryl}$ and R$_{P\text{-}heteroaryl}$ are as defined above, where R$_{N-10}$ is selected from the group consisting of:
(A) —H,
(B) C$_1$-C$_6$ alkyl,
(C) C$_3$-C$_7$ cycloalkyl,
(D) C$_2$-C$_6$ alkenyl with one double bond,
(E) C$_2$-C$_6$ alkynyl with one triple bond,
(F) R$_{P\text{-}aryl}$ where R$_{P\text{-}aryl}$ is as defined above, and
(G) R$_{P\text{-}heteroaryl}$ where R$_{P\text{-}heteroaryl}$ is as defined above, (VI) —(C$_3$-C$_8$ cycloalkyl) where cycloalkyl is optionally substituted with one or two substituents selected from the group consisting of:
(A) —(CH$_2$)$_{0-4}$—OH,
(B) —(CH$_2$)$_{0-4}$-C$_1$-C$_6$ alkoxy,
(C) —(CH$_2$)$_{0-4}$-C$_1$-C$_6$ thioalkoxy,
(D) —(CH$_2$)$_{0-4}$—CO—O—R$_{N-8}$ where R$_{N-8}$ is —H, C$_1$-C$_6$ alkyl, phenyl or benzyl,
(E) —(CH$_2$)$_{0-4}$—CO—NR$_{P-2}$R$_{P-3}$ where R$_{P-2}$ and R$_{P-3}$ are the same or different and are as defined above,
(F) —(CH$_2$)$_{0-4}$—CO—R$_{N-4}$ where R$_{N-4}$ is as defined above,
(G) —(CH$_2$)$_{0-4}$—SO$_2$—(C$_1$-C$_8$ alkyl),
(H) —(CH$_2$)$_{0-4}$—SO$_2$—NR$_{P-2}$R$_{P-3}$ where R$_{P-2}$ and R$_{P-3}$ are the same or different and are as defined above,
(I) —(CH$_2$)$_{0-4}$—NH—CO—(C$_1$-C$_6$ alkyl),
(J) —NH—CO—O—R$_{N-8}$ where R$_{N-8}$ is as defined above,
(K) —(CH$_2$)$_{0-4}$—NR$_{P-2}$R$_{P-3}$ where R$_{P-2}$ and R$_{P-3}$ are the same or different and are as defined above,
(L) —(CH$_2$)$_{0-4}$—R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—C$_1$-C$_6$ alkyl optionally substituted with one, two, or three of: —F, —Cl, —Br, or —I, (Q) —NH—SO$_2$—(C$_1$-C$_6$ alkyl), and
(R) —F, —Cl;
(VII) —(CR$_{P-x}$R$_{P-y}$)$_{0-4}$—R$_{P-1}$ where R$_{P-1}$ is as defined above and each of R$_{P-x}$ and R$_{P-y}$ are independently any combination of:
(A) —H,
(B) C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, —COOH, —COO (C$_1$-C$_6$ alkyl), —CONR$_{1a}$R$_{1b}$ and —NR$_{1-a}$R$_{1-b}$ where R$_{1-a}$ and R$_{1-b}$ are —H or C$_1$-C$_6$ alkyl,
(C) —CH$_2$—S—(C$_1$-C$_6$ alkyl),
(D) —CH$_2$—CH$_2$—S—(C$_1$-C$_6$ alkyl),
(E) C$_2$-C$_6$ alkenyl with one or two double bonds,
(F) C$_2$-C$_6$ alkynyl with one or two triple bonds,
(G) —(CH$_2$)$_{n1}$—(R$_{P\text{-}aryl}$) where n$_1$ is zero or one, where R$_{P\text{-}aryl}$ is as defined above,
(H) —(CH$_2$)$_{n1}$—(R$_{P\text{-}heteroaryl}$) where n$_1$ and R$_{P\text{-}heteroaryl}$ are as defined above, or
(I) —(CH$_2$)$_{n1}$—(R$_{P\text{-}heterocycle}$) where n$_1$ and R$_{P\text{-}heterocycle}$ are as defined above,
(J) —(CH$_2$)$_{0-3}$—(C$_3$-C$_7$) cycloalkyl where cycloalkyl can be optionally substituted with one, two or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, —CO—OH, —CO—O—(C$_1$-C$_4$ alkyl), and —NR$_{1-a}$R$_{1-b}$ where R$_{1-a}$ and R$_{1-b}$ are as defined above,
(K) F, Cl, Br or I, or
(L) —NR$_{P-2}$;
or R$_{P-x}$ and R$_{P-y}$ are taken together with the carbon to which they are attached to form a carbocycle of three thru seven carbon atoms, optionally where one carbon atom is replaced by a heteroatom selected from the group consisting of —O—, —S—, —SO$_2$—, and —NR$_{P-2}$—;
(VIII) —(C$_1$-C$_6$ alkyl)-Z-(C$_1$-C$_6$ alkyl)-T-(C$_1$-C$_6$ alkyl)- wherein Z is S or O, T is O or NR$_{P-2}$, and alkyl is optionally substituted with one, two, or three substituents selected from the group consisting of:
(A) —OH,
(B) —C$_1$-C$_6$ alkoxy,
(C) —C$_1$-C$_6$ thioalkoxy,
(D) —CO—O—R$_{N-8}$ where R$_{N-8}$ is as defined above,
(E) —CO—NR$_{P-2}$R$_{P-3}$ where R$_{P-2}$ and R$_{P-3}$ are the same or different and are as defined above,
(F) —CO—R$_{N-4}$ where R$_{N-4}$ is as defined above,
(G) —SO$_2$—(C$_1$-C$_8$ alkyl),
(H) —SO$_2$—NR$_{P-2}$R$_{P-3}$ where R$_{P-2}$ and R$_{P-3}$ are the same or different and are as defined above,
(I) —NH—CO—(C$_1$-C$_6$ alkyl),
(J) —NH—CO—O—R$_{N-8}$ where R$_{N-8}$ is as defined above,
(K) —NR$_{P-2}$R$_{P-3}$ where R$_{P-2}$ and R$_{P-3}$ are the same or different and are as defined above,
(L) —R$_{N-4}$ where R$_{N-4}$ is as defined above,
(M) —O—CO—(C$_1$-C$_6$ alkyl),
(N) —O—CO—NR$_{N-8}$R$_{N-8}$ where the R$_{N-8}$s are the same or different and are as defined above,
(O) —O—(C$_1$-C$_5$ alkyl)-COOH,
(P) —O—(C$_1$-C$_6$ alkyl) optionally substituted with one, two, or three of —F, —Cl, —Br, or —I,
(Q) —NH—SO$_2$—(C$_1$-C$_6$ alkyl), and
(R) —F, or —Cl.

2. A compound or salt according to claim 1 wherein R$_4$ is

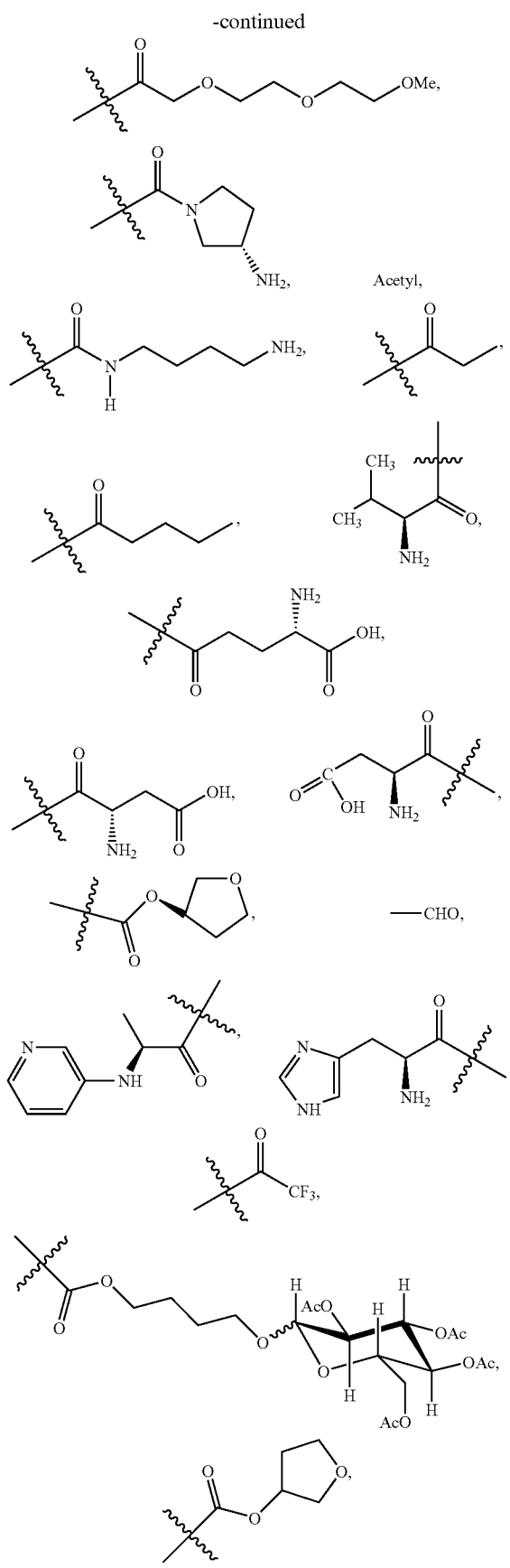
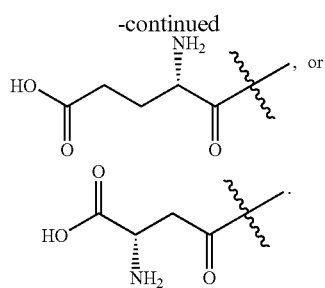

3. A compound or salt according to claim 1 selected from the group consisting of 1-[(benzylamino)methyl]-3-(3,5-difluorophenyl)-2-({3-[(dipropylamino)carbonyl]benzoyl}amino)propyl 4-nitrophenyl carbonate, 1-[(benzylamino)methyl]-3-(3,5-difluorophenyl)-2-({3-[(dipropylamino)carbonyl]benzoyl}amino)propyl 4-methylpiperazine-1-carboxylate, 1-[(benzylamino)methyl]-3-(3,5-difluorophenyl)-72-({3-[(dipropylamino)carbonyl]benzoyl}amino)-propyl 2-(dimethylamino)ethyl carbonate, 1-[(benzylamino)methyl]-3-(3,5-difluorophenyl)-2-({3-[(dipropylamino)carbonyl]benzoyl}amino)-propyl 2-(acetylamino)ethylcarbamate, 1-[(benzylamino)methyl]-3-(3,5-difluorophenyl)-2-({3-[(dipropylamino)carbonyl]benzoyl}amino)-propyl piperazine-1-carboxylate, 1-[(benzylamino)methyl]-3-(3,5-difluorophenyl)-2-({3-[(dipropylamino)carbonyl]benzoyl}amino)-propyl 2-aminoethylcarbamate, 1-[(benzylamino)methyl]-3-(3,5-difluorophenyl)-2-({3-[(dipropylamino)carbonyl]benzoyl}amino)-propyl 3-aminopropylcarbamate, 1-[(benzylamino)methyl]-3-(3,5-difluorophenyl)-2-({3-[(dipropylamino)carbonyl]benzoyl}amino)-propyl (3R)-3-aminopyrrolidine-1-carboxylate, 1-[(benzylamino)methyl]-3-(3,5-difluorophenyl)-2-({3-[(dipropylamino)carbonyl]benzoyl}amino)propyl O-benzyl-L-tyrosinate, 1-[(benzylamino)methyl]-3-(3,5-difluorophenyl)-2-({3-[(dipropylamino)carbonyl]benzoyl}amino)-propyl L-tyrosinate, 1-[(benzylamino)methyl]-3-(3,5-difluorophenyl)-2-({3-[(dipropylamino)carbonyl]benzoyl}amino)-propyl 3-methoxypropanoate, 1-[(benzylamino)methyl]-3-(3,5-difluorophenyl)-2-({3-[(dipropylamino)carbonyl]benzoyl}amino)-propyl (2-hydroxyethoxy)acetate, 1-[(benzylamino)methyl]-3-(3,5-difluorophenyl)-2-({3-[(dipropylamino)carbonyl]benzoyl}amino)-propyl D-lysinate, 1-[(benzylamino)methyl]-3-(3,5-difluorophenyl)-2-({3-[(dipropylamino)carbonyl]benzoyl}amino)-propyl [2-(2-methoxyethoxy)ethoxy]acetate, 1-[(benzylamino)methyl]-3-(3,5-difluorophenyl)-2-({3-[(dipropylamino)carbonyl]benzoyl}amino)-propyl {2-[[2-(dimethylamino)ethyl]-(methyl)amino]ethoxy}acetate, 1-[(benzylamino)methyl]-3-(3,5-difluorophenyl)-2-({3-[(dipropylamino)carbonyl]benzoyl}amino)-propyl (4-methylpiperazin-1-yl)acetate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl (4-methylpiperazin-1-yl)acetate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl 4-methylpiperazine-1-carboxylate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl piperazine-1-carboxylate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl {2-[[2-(dimethylamino)ethyl](methyl)amino]ethoxy}acetate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl (2-methoxyethoxy)acetate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl L-tyrosinate, (1R, 2S)-3-(3,5-difluorophenyl)-2-({3-[(dipropylamino)carbonyl]-5-methylbenzoyl}-amino)-1-{[(3-pent-1-ynylbenzyl)amino]methyl}propyl (3R)-3-aminopyrrolidine-1-carboxylate, or (1R,2S)-3-(3,5-difluorophenyl)-2-({3-[(dipropylamino)carbonyl]-5-methylbenzoyl}-amino)-1-{[(3-pent-1-ynylbenzyl)amino]methyl}propyl tetrahydrofuran-3-yl carbonate.

4. A method for the treatment of Alzheimer's disease, mild cognitive impairment Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, diffuse Lewy body type of Alzheimer's disease comprising administration of a therapeutically effective amount of a compound or a pharmaceutically acceptable salt to a patient in need thereof, wherein the compound or salt is of the formula:

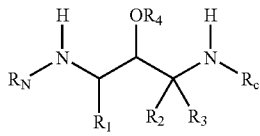

where $R_1$ is:
—$(CH_2)_{n1}$—$(R_{1-aryl})$ where $n_1$ is one and where $R_{1-aryl}$ is phenyl optionally substituted with one, two, three or four of:
(A) $C_1$-$C_6$ alkyl optionally substituted with one, two or three substituents selected from the group consisting of $C_1$-$C_3$ alkyl, —F, —Cl, —Br, —I, —OH, —SH, —$NR_{1-a}R_{1-b}$ where $R_{1-a}$ and $R_{1-b}$ are as defined above, —C≡N, —$CF_3$, $C_1$-$C_3$ alkoxy,
(B) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl,
(C) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl,
(D) —F;, CL, —Br and —I,
(F) —$C_1$-$C_6$ alkoxy optionally substituted with one, two or three —F,
(G) —$NR_{N-2}R_{N-3}$ where $R_{N-2}$ and $R_{N-3}$ are as defined below,
(H) —OH,
(I) —C≡N,
(J) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl,
(K) —CO—($C_1$-$C_4$ alkyl),
(L) —$SO_2$—$NR_{1-a}R_{1-b}$ where $R_{1-a}$ and $R_{1-b}$ are as defined above,
(M) —CO—$NR_{1-a}R_{1-b}$ where $R_{1-a}$ and $R_{1-b}$ are as defined above,
(N) —$SO_2$—($C_1$-$C_4$ alkyl),
where $R_2$ is —H;
where $R_3$ is —H;
where $R_N$ is
$R_{N-1}$—$X_N$—, where $X_N$ is —CO—,
where $R_{N-1}$ is $R_{N-aryl}$, where $R_{N-aryl}$ is phenyl substituted with one of —$(CH_2)_{0-4}$—$NR_{N-2}R_{N-3}$ where $R_{N-2}$ and $R_{N-3}$ are independently $C_1$-$C_6$ alkyl and optionally substituted with one or two of
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1-a}R_{1-b}$ where $R_{1-a}$ and $R_{1-b}$ are as defined above,
(2) —OH,
(3) —$NO_2$,
(4) —F, —Cl, —Br, —I,
(5) —CO—OH,
—C≡N,
—$(CH_2)_{0-4}$—CO—$NR_{N-2}R_{N-3}$ where $R_{N-2}$ and $R_{N-3}$ are independently the same or different and are selected from the group consisting of:
(a) —H,
(b) —$C_1$-$C_6$ alkyl; optionally substituted with one substituent selected from the group consisting of:
(i) —OH,
(ii) —$NH_2$,
(c) —$C_1$-$C_6$ alkyl optionally substituted with one to three —F, —Cl, —Br, —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O-($C_1$-$C_3$ alkyl),
(g) —($C_2$-$C_6$ alkenyl with one or two double bonds,
(h) —($C_2$-$C_6$ alkynyl with one or two triple bonds,
(i) —($C_1$-$C_6$ alkyl chain with one double bond and one triple bond,
(8) —$(CH_2)_{0-4}$—CO—($C_1$-$C_{12}$ alkyl),
(9) —$(CH_2)_{0-4}$—CO—($C_1$-$C_{12}$ alkenyl with one, two or three double bonds),
(10) —$(CH_2)_{0-4}$—CO—($C_1$-$C_{12}$ alkynyl with one, two or three triple bonds),
(11) —$(CH_2)_{0-4}$—CO—($C_1$-$C_{12}$ cycloalkyl), or
(15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl, where $R_C$ is:
—$(CR_{C-x}R_{C-y})_{0-4}$—$R_{C-aryl}$ where $R_{C-x}$ and $R_{C-y}$ are independently —H,
$R_{C-aryl}$ is defined the same as $R_{N-aryl}$ is defined above in connection with the definition of $R_N$; and where $R_4$ is:

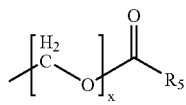

where x is 0 or 1 and $R_5$ is H or is:
(I) $R_{P-1}$ wherein $R_{P-1}$ is selected from the group consisting of:
  (A) -Y-$R_{P-aryl}$ where Y is absent or is oxygen, and $R_{R-aryl}$ is phenyl, 1-naphthyl, 2-naphthyl, tetralinyl, indanyl, or 6,7,8,9-tetrahydro-5H-benzo[a]cycloheptenyl, optionally substituted with one, two or three of the following substituents which can be the same or different and are:
    (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$ where $R_{1-a}$ and $R_{1-b}$ are independently —H or $C_1$-$C_6$ alkyl,
    (2) —OH,
    (3) —$NO_2$,
    (4) —F, —Cl, —Br, —I,
    (5) —CO—OH,
    (6) —CO≡N,
    (7) —$(CH_2)_{0-4}$—CO—$NR_{P-2}R_{P-3}$ where $R_{P-2}$ and $R_{P-3}$ are the same or different and are selected from the group consisting of:
      (a) —H,
      (b) —$C_1$-$C_6$ alkyl optionally substituted with one substituent selected the group consisting of:
        (i) —OH, and
        (ii) —$NH_2$,
      (c) —$C_1$-$C_6$ alkyl optionally substituted with one to three —F, —Cl, —Br, or —I,
      (d) —$C_3$-$C_7$ cycloalkyl,
      (e) —($C_1$-$C_2$ alkyl)-($C_3$-$C_7$ alkyl),
      (f) —($C_1$-$C_6$ alkyl)-O-($C_1$-$C_3$ alkyl),
      (g) —$C_2$-$C_6$ alkenyl with one or two double bonds,
      (h) —$C_2$-$C_6$ alkynyl with one or two triple bonds,
      (i) —$C_1$-$C_6$ alkyl chain with one double bond and one triple bond,
      (j) —$R_{P-aryl}$ where —$R_{P-aryl}$ is defined above,
      (l) —$R_{P-heteroaryl}$ where —$R_{P-heteroaryl}$ is defined below, and
    (8) —$(CH_2)_{0-4}$—CO—($C_1$-$C_{12}$ alkyl),
    (9) —$(CH_2)_{0-4}$—CO—($C_1$-$C_{12}$) alkenyl with one, two or three double bonds,
    (10) —$(CH_2)_{0-4}$—CO—($C_1$-$C_{12}$) alkynyl with one, two or three triple bonds,
    (11) —$(CH_2)_{0-4}$—CO—($C_3$-$C_7$ cycloalkyl),
    (12) —$(CH_2)_{0-4}$—CO—$R_{P-aryl}$ where $R_{P-aryl}$ is as defined above,
    (13) —$(CH_2)_{0-4}$—CO—$R_{P-heteroaryl}$ where $R_{P-heteroaryl}$ us as defined below,
    (14) —$(CH_2)_{0-4}$—CO—$R_{P-heteroaryl}$ where $R_{P-heteroaryl}$ is selected from the group consisting of:
      (A) morpholinyl,
      (B) thiomorpholinyl,
      (C) thiomorpholinyl S-oxide,
      (D) thiomorpholinyl S,S-dioxide,
      (E) piperazinyl,
      (F) homopiperazinyl,
      (G) pyrrolidinyl,
      (H) pyrrolinyl,
      (I) tetrahydropyranyl,
      (J) piperidinyl,
      (K) tetrahydrofuranyl,
      (L) tetrahydrophenyl,
      (M) homopiperidinyl,
      (N) imidazolidine,
      (O) imidazolidine dione, and
      (P) dithiane,
    where the $R_{P-heteroaryl}$ group is bonded by any atom of the parent $R_{P-heteroaryl}$ group substituted by hydrogen such that the new bond to the $R_{P-heteroaryl}$ group replaces the hydrogen atom and its bond, where heterocycle is optionally substituted with one thru four:
      (1) $C_1$-$C_6$ alkyl optionally substituted with one, two or three substituents selected from the group consisting of $C_1$-$C_3$ alkyl, —F, —Cl, —Br, —OH, —SH, —O—CO—($C_1$-$C_6$ alkyl), —$NR_{1-a}R_{1-b}$ where $R_{1-a}$ and $R_{1-b}$ are as defined above, —C≡N, —$CF_3$, and $C_1$-$C_3$ alkoxy,
      (2) $C_2$-$C_6$ alkenyl with one or two double bonds,
      (3) $C_2$-$C_6$ alkynyl with one or two triple bonds,
      (4) —F, Cl, —Br and —I,
      (5) $C_1$-$C_6$ alkoxy,
      (6) —O—$C_1$-$C_6$ alkyl optionally substituted with one thru three —F,
      (7) —$NR_{P-2}R_{P-3}$ where $R_{P-2}$ and $R_{P-3}$ are as defined above,
      (8) —OH,
      (9) —C≡N,
      (10) $C_3$-$C_7$ cycloalkyl,
      (11) —CO—($C_1$-$C_4$ alkyl),
      (12) —$SO_2$—$NR_{1-a}R_{1-b}$ where $R_{1-a}$ and $R_{1-b}$ are as defined above,
      (13) —CO—$NR_{1-a}R_{1-b}$ where $R_{1-a}$ and $R_{1-b}$ are as defined above,
      (14) —$SO_2$—($C_1$-$C_4$ alkyl),
      (15) =O; or
      (16) —O—CO—($C_1$-$C_6$ alkyl),
    (15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl,
    (16) —$(CH_2)_{0-4}$—CO—$R_{N-5}$ where $R_{N-5}$ is selected from the group consisting of:
      (a) $C_1$-$C_6$ alkyl,
      (b) (12) —$(CH_2)_{0-2}$—CO—$R_{P-aryl}$ where $R_{P-aryl}$ is as defined above,
      (c) $C_2$-$C_6$ alkenyl containing one or two double bonds, (d) $C_2$-$C_6$ alkynyl containing one or two triple bonds,
(e) $C_3$-$C_7$ cycloalkyl, and
(f) —$(CH_2)_{0-2}$—$(R_{P\text{-}heteroaryl})$ where $R_{P\text{-}heteroaryl}$ is as defined below,
(17) —$(CH_2)_{0-4}$—$SO_2$—$NR_{P\text{-}2}R_{P\text{-}3}$ where $R_{P\text{-}2}$ and $R_{P\text{-}3}$ are as defined above,
(18) —$(CH_2)_{0-4}$—SO—$(C_1$-$C_8$ alkyl),
(19) —$(CH_2)_{0-4}$—$SO_2$—$(C_1$-$C_{12}$ alkyl),
(20) —$(CH_2)_{0-4}$—SO—$(C_3$-$C_7$ cycloalkyl),
(21) —$(CH_2)_{0-4}$—N(H or $R_{N\text{-}5}$)—CO—O—$R_{N\text{-}5}$ where $R_{N\text{-}5}$ can be the same or different and is as defined above,
(22) —$(CH_2)_{0-4}$—N(H or $R_{N\text{-}5}$)—CO—$N(R_{N\text{-}5})_2$, where $R_{N\text{-}5}$ can be the same or different and is as defined above,
(23) —$(CH_2)_{0-4}$—N—CS—$N(R_{N\text{-}5})_2$, where $R_{N\text{-}5}$ can be the same or different and is as defined above,
(24) —$(CH_2)_{0-4}$—N(—H or $R_{N\text{-}5}$)—CO—$R_{P\text{-}2}$ where $R_{N\text{-}5}$ and $R_{P\text{-}2}$ can be the same or different and are as defined above,
(25) —$(CH_2)_{0-4}$—$NR_{P\text{-}2}R_{P\text{-}3}$ where $R_{P\text{-}2}$ and $R_{P\text{-}3}$ can be the same or different and are as defined above,
(26) —$(CH_2)_{0-4}$—$R_{N\text{-}4}$ where $R_{N\text{-}4}$ is as defined above,
(27) —$(CH_2)_{0-4}$—O—CO—$(C_1$-$C_6$ alkyl),
(28) —$(CH_2)_{0-4}$—O—P(O)—$(OR_{N\text{-}aryl\text{-}1})_2$ where $R_{N\text{-}aryl\text{-}1}$ is —H or $C_1$-$C_4$ alkyl,
(29) —$(CH_2)_{0-4}$—O—CO—$N(R_{N\text{-}5})_2$ where $R_{N\text{-}5}$ is as defined above,
(30) —$(CH_2)_{0-4}$—O—CS—$N(R_{N\text{-}5})_2$ where $R_{N\text{-}5}$ is as defined above,
(31) —$(CH_2)_{0-4}$—O—$(R_{N\text{-}5})_2$ where $R_{N\text{-}5}$ is as defined above,
(32) —$(CH_2)_{0-4}$—O—$(R_{N\text{-}5})_2$—COOH where $R_{N\text{-}5}$ is as defined above,
(33) —$(CH_2)_{0-4}$—S—$(R_{N\text{-}5})_2$ where $R_{N\text{-}5}$ is as defined above,
(34) —$(CH_2)_{0-4}$—O—$(C_1$-$C_6$ alkyl optionally substituted with one, two, three, four, or five of: —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above,
(38) —$(CH_2)_{0-4}$—N(—H or $R_{N\text{-}5}$)—$SO_2$—$R_{P\text{-}2}$ where $R_{N\text{-}5}$ and $R_{P\text{-}2}$ can be the same or different and are as defined above, or
(39) —$(CH_2)_{0-4}$—$C_3$-$C_7$ cycloalkyl, (B) -Y-$R_{P\text{-}heteroaryl}$ where Y is absent or is oxygen and $R_{P\text{-}heteroaryl}$ is selected from the group consisting of:
(A) pyridinyl,
(B) pyrimidinyl,
(C) quinolinyl,
(F) benzothienyl,
(G) indolyl,
(H) indolinyl,
(I) pryidazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) beta-carbolinyl,
(PP) isochromanyl,
(QQ) chromanyl,
(SS) tetrahydroisoquinolinyl,
(TT) isoindolinyl,
(UU) isobenzotetrahydrofuranyl,
(VV) isobenzotetrahydrothienyl,
(WW) isobenzothienyl,
(XX) benzoxazolyl,
(YY) pyridopyridinyl,
(ZZ) benzotetrahydrofuranyl,
(AAA) benzotetrahydrothienyl,
(BBB) purinyl,
(CCC) benzodioxolyl,
(DDD) triazinyl,
(EEE) phenoxazinyl,
(FFF) phenothiazinyl,
(GGG) pteridinyl,
(HHH) benzothiazolyl,
(III) imidazopyridinyl,
(JJJ) imidazothiazolyl,
(KKK) dihydrobenzisoxazinyl,
(LLL) benzisoxazinyl,
(MMM) benzoxazinyl,
(NNN) dihydrobenzisothiazinyl,
(OOO) benzopyranyl,
(PPP) benzothiopyranyl,
(QQQ) coumarinyl,
(RRR) isocoumarinyl,
(SSS) chromonyl,
(TTT) chromanonyl, and
(UUU) pyridinyl-N-oxide,
where the $R_{P\text{-}heteroaryl}$ group is bonded by any atom of the parent $R_{P\text{-}heteroaryl}$ group substituted by hydrogen such that the new bond to the $R_{P\text{-}heteroaryl}$ group replaces the hydrogen atom and its bond, where heteroaryl is optionally substituted with one, two, three, or four of:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$ where R$_{1-a}$ and R$_{1-b}$ are as defined above,
(2) —OH,
(3) —NO$_2$,
(4) —F, —Cl, —Br, —I,
(5) —CO—OH,
(6) —≡N,
(7) —(CH$_2$)$_{0-4}$—CO—NR$_{P-2}$R$_{P-3}$ where R$_{P-2}$ and R$_{P-3}$ are the same or different and are selected from the group consisting of:
(a) —H,
(b) —$C_1$-$C_6$ alkyl optionally substituted with one substituent selected from the group consisting of:
(i) —OH, and
(ii) —NH$_2$,
(c) —$C_1$-$C_6$ alkyl optionally substituted with one to three —F, —Cl, —Br, or —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double bonds,
(h) —$C_2$-$C_6$ alkynyl with one or two triple bonds,
(i) —$C_1$-$C_6$ alkyl chain with one double bond and one triple bond,
(j) —R$_{P-aryl}$ where R$_{P-aryl}$ is as defined above, and
(k) —R$_{P-heteroaryl}$ where —R$_{P-heteroaryl}$ is as defined above,
(8) —(CH$_2$)$_{0-4}$—CO—($C_1$-$C_{12}$ alkyl),
(9) —(CH$_2$)$_{0-4}$—CO—($C_1$-$C_{12}$ alkenyl with one, two or three double bonds),
(10) —(CH$_2$)$_{0-4}$—CO—($C_1$-$C_{12}$ alkynyl with one, two or three triple bonds),
(11) —(CH$_2$)$_{0-4}$—CO—($C_3$-$C_7$ cycloalkyl),
(12) —(CH$_2$)$_{0-4}$—CO—R$_{P-aryl}$ where R$_{P-aryl}$ is as defined above,
(13) —(CH$_2$)$_{0-4}$—CO—R$_{P-heteroaryl}$ where R$_{P-heteroaryl}$ is as defined above,
(14) —(CH$_2$)$_{0-4}$—CO—R$_{P-heterocycle}$ where R$_{P-heterocycle}$ is as defined above,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —(CH$_2$)$_{0-4}$—CO—R$_{N-5}$ where R$_{N-5}$ is selected from the group consisting of:
(a) $C_1$-$C_6$ alkyl,
(b) (12) —(CH$_2$)$_{0-2}$—CO—(R$_{P-aryl}$) where R$_{P-aryl}$ is as defined above,
(c) $C_2$-$C_6$ alkenyl containing one or two double bonds,
(d) $C_2$-$C_6$ alkynyl containing one or two triple bonds,
(e) $C_3$-$C_7$ cycloalkyl, and
(f) —(CH$_2$)$_{0-2}$—(R$_{P-heteroaryl}$) where R$_{P-heteroaryl}$ is as defined below,
(17) —(CH$_2$)$_{0-4}$—SO$_2$—NR$_{P-2}$R$_{P-3}$ where R$_{P-2}$ and R$_{P-3}$ are as defined above,
(18) —(CH$_2$)$_{0-4}$—SO—($C_1$-$C_8$ alkyl),
(19) —(CH$_2$)$_{0-4}$—SO$_2$—($C_1$-$C_{12}$ alkyl),
(20) —(CH$_2$)$_{0-4}$—SO—($C_3$-$C_7$ cycloalkyl),
(21) —(CH$_2$)$_{0-4}$—N(H or R$_{N-5}$)—CO—O—R$_{N-5}$ where R$_{N-5}$ can be the same or different and is as defined above,
(22) —(CH$_2$)$_{0-4}$—N(H or R$_{N-5}$)—CO—N(R$_{N-5}$)$_2$, where R$_{N-5}$ can be the same or different and is as defined above,
(23) —(CH$_2$)$_{0-4}$—N—CS—N(R$_{N-5}$)$_2$, where R$_{N-5}$ can be the same or different and is as defined above,
(24) —(CH$_2$)$_{0-4}$—N(—H or R$_{N-5}$)—CO—R$_{P-2}$ where R$_{N-5}$ and R$_{P-2}$ can be the same or different and are as defined above,
(25) —(CH$_2$)$_{0-4}$—NR$_{P-2}$R$_{P-3}$ where R$_{P-2}$ and R$_{P-3}$ can be the same or different and are as defined above,
(26) —(CH$_2$)$_{0-4}$—R$_{N-4}$ where R$_{N-4}$ is as defined above,
(27) —(CH$_2$)$_{0-4}$—O—CO—($C_1$-$C_6$ alkyl),
(28) —(CH$_2$)$_{0-4}$—O—P(O)—(OR$_{N-aryl-1}$)$_2$ where R$_{N-aryl-1}$ is —H or $C_1$-$C_4$ alkyl,
(29) —(CH$_2$)$_{0-4}$—O—CO—N(R$_{N-5}$)$_2$ where R$_{N-5}$ is as defined above,
(30) —(CH$_2$)$_{0-4}$—O—CS—N(R$_{N-5}$)$_2$ where R$_{N-5}$ is as defined above,
(31) —(CH$_2$)$_{0-4}$—O—(R$_{N-5}$)$_2$ where R$_{N-5}$ is as defined above,
(32) —(CH$_2$)$_{0-4}$—O—(R$_{N-5}$)$_2$—COOH where R$_{N-5}$ is as defined above,
(33) —(CH$_2$)$_{0-4}$—S—(R$_{N-5}$)$_2$ where R$_{N-5}$ is as defined above,
(34) —(CH$_2$)$_{0-4}$—O—($C_1$-$C_6$ alkyl optionally substituted with one, two, three, four, or five of: —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$ where R$_{1-a}$ and R$_{1-b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$ where R$_{1-a}$ and R$_{1-b}$ are as defined above,
(38) —(CH$_2$)$_{0-4}$—N(—H or R$_{N-5}$)—SO$_2$—R$_{P-2}$ where R$_{N-5}$ and R$_{P-2}$ can be the same or different and are as described above, or
(39) —(CH$_2$)$_{0-4}$—$C_3$-$C_7$ cycloalkyl,
(C) R$_{P-aryl}$-W—R$_{P-aryl}$,
(D) R$_{P-aryl}$-W—R$_{P-heteroaryl}$,
(E) R$_{P-aryl}$-W—R$_{P-heterocycle}$,
(F) R$_{P-heteroaryl}$-W—R$_{P-aryl}$,
(G) R$_{P-heteroaryl}$-W—R$_{P-heteroaryl}$,
(H) R$_{P-heteroaryl}$-W—R$_{P-heterocycle}$,
(I) R$_{P-heterocycle}$-W—R$_{P-aryl}$,
(J) R$_{P-heterocycle}$-W—R$_{P-heteroaryl}$,
(K) R$_{P-heterocycle}$-W—R$_{P-heterocycle}$,
where W is
(1) —(CH2)$_{0-4}$—,
—O—,
—S(O)$_{0-2}$—,
—N(R$_{N-5}$)— where R$_{N-5}$ is as defined above;
—CO—; or
—O—(CH$_2$)$_{1-4}$—, and
(L) -Y-R$_{P-heterocycle}$ where Y is absent or is oxygen, and R$_{P-heterocycle}$ is defined above;
(II) —($C_1$-$C_{10}$ alkyl) where alkyl is optionally substituted with one, two, or three substituents selected from the group consisting of:

(A) —OH,
(B) —$C_1$-$C_6$ alkoxy,
(C) —$C_1$-$C_6$ thioalkoxy,
(D) —CO—O—$R_{N-8}$ where $R_{N-8}$ is —H, $C_1$-$C_6$ alkyl, phenyl, or benzyl,
(E) —CO—$NR_{P-2}R_{P-3}$ where $R_{P-2}$ and $R_{P-3}$ are the same or different and are as defined above,
(F) —CO—$R_{N-4}$ where $R_{N-4}$ is as defined above,
(G) —$SO_2$—($C_1$-$C_8$ alkyl),
(H) —$SO_2$—$NR_{P-2}R_{P-3}$ where $R_{P-2}$ and $R_{P-3}$ are the same or different and are as defined above,
(I) —NH—CO—($C_1$-$C_6$ alkyl),
(J) —NH—CO—O—$R_{N-8}$ where $R_{N-8}$ is as defined above,
(K) —$NR_{P-2}R_{P-3}$ where $R_{P-2}$ and $R_{P-3}$ are the same or different and are as defined above,
(L) —$R_{N-4}$ where $R_{N-4}$ is as defined above,
(M) —O—CO—($C_1$-$C_6$ alkyl),
(N) —O—CO—$NR_{N-8}R_{N-8}$ where the $R_{N-8}$s are the same or different and are as defined above,
(O) —O—($C_1$-$C_5$ alkyl)-COOH,
(P) —O—($C_1$-$C_6$ alkyl) optionally substituted with one, two, or three of —F, —Cl, —Br, —I,
(Q) —NH—$SO_2$—($C_1$-$C_6$ alkyl), and
(R) —F, or —Cl, (III) -X-T-($C_1$-$C_6$ alkyl) where X is absent or is $C_1$-$C_6$ alkyl, T is oxygen or is $NR_{P-2}$, and where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N-8}$ where $R_{N-8}$ is —H, $C_1$-$C_6$ alkyl, phenyl, or benzyl,
(E) —CO—$NR_{P-2}R_{P-3}$ where $R_{P-2}$ and $R_{P-3}$ are the same or different and are as defined above,
(F) —CO—$R_{N-4}$ where $R_{N-4}$ is as defined above,
(G) —$SO_2$—($C_1$-$C_8$ alkyl),
(H) —$SO_2$—$NR_{P-2}R_{P-3}$ where $R_{P-2}$ and $R_{P-3}$ are the same or different and are as defined above,
(I) —NH—CO—($C_1$-$C_6$ alkyl),
(J) —NH—CO—O—$R_{N-8}$ where $R_{N-8}$ is as defined above,
(K) —$NR_{P-2}R_{P-3}$ where $R_{P-2}$ and $R_{P-3}$ are the same or different and are as defined above,
(L) —$R_{N-4}$ where $R_{N-4}$ is as defined above,
(M) —O—CO—($C_1$-$C_6$ alkyl),
(N) —O—CO—$NR_{N-8}R_{N-8}$ where the $R_{N-8}$s are the same or different and are as defined above,
(O) —O—($C_1$-$C_5$ alkyl)-COOH,
(P) —O—($C_1$-$C_6$ alkyl) optionally substituted with one, two, or three of —F, —Cl, —Br, —I,
(Q) —NH—$SO_2$—($C_1$-$C_6$ alkyl),
(R) —F, or —Cl,
(S) —O—$R_{P-aryl}$,
(T) —O—$R_{P-heteroaryl}$, and
(U) —O—$R_{P-hetrocycle}$, (IV) —($C_1$-$C_6$alkyl)-Z-($C_1$-$C_6$ alkyl) where Z is S or O, and alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N-8}$ where $R_{N-8}$ is as defined above,
(E) —CO—$NR_{P-2}R_{P-3}$ where $R_{P-2}$ and $R_{P-3}$ are the same or different and are as defined above,
(F) —CO—$R_{N-4}$ where $R_{N-4}$ is as defined above,
(G) —$SO_2$—($C_1$-$C_8$ alkyl),
(H) —$SO_2$—$NR_{P-2}R_{P-3}$ where $R_{P-2}$ and $R_{P-3}$ are the same or different and are as defined above,
(I) —NH—CO—($C_1$-$C_6$ alkyl),
(J) —NH—CO—O—$R_{N-8}$ where $R_{N-8}$ is as defined above,
(K) —$NR_{P-2}R_{P-3}$ where $R_{P-2}$ and $R_{P-3}$ are the same or different and are as defined above,
(L) —$R_{N-4}$ where $R_{N-4}$ is as defined above,
(M) —O—CO—($C_1$-$C_6$ alkyl),
(N) —O—CO—$NR_{N-8}R_{N-8}$ where the $R_{N-8}$s are the same or different and are as defined above,
(O) —O—($C_1$-$C_5$ alkyl)-COOH,
(P) —O—($C_1$-$C_6$ alkyl) optionally substituted with one, two, or three of —F, —Cl, —Br, —I,
(Q) —NH—$SO_2$—($C_1$-$C_6$ alkyl), and
(R) —F, or —Cl, (V) —CH(—$(CH_2)_{0-2}$—O—$R_{N-10}$)—$(CH_2)_{0-2}$—$R_{P-aryl}$/$R_{P-heteroaryl}$ where $R_{P-aryl}$ and $R_{P-heteroaryl}$ are as defined above, where $R_{N-10}$ is selected from the group consisting of:
(A) —H,
(B) $C_1$-$C_6$ alkyl,
(C) $C_3$-$C_7$ cycloalkyl,
(D) $C_2$-$C_6$ alkenyl with one double bond,
(E) $C_2$-$C_6$ alkynyl with one triple bond,
(F) $R_{P-aryl}$ where $R_{P-aryl}$ is as defined above, and
(G) $R_{P-heteroaryl}$ where $R_{P-heteroaryl}$ is as defined above, (VI) —($C_3$-$C_8$ cycloalkyl) where cycloalkyl is optionally substituted with one or two substituents selected from the group consisting of:
(A) —$(CH_2)_{0-4}$—OH,
(B) —$(CH_2)_{0-4}$-$C_1$-$C_6$ alkoxy,
(C) —$(CH_2)_{0-4}$-$C_1$-$C_6$ thioalkoxy,
(D) —$(CH_2)_{0-4}$—CO—O—$R_{N-8}$ where $R_{N-8}$ is —H, $C_1$-$C_6$ alkyl, phenyl or benzyl,
(E) —$(CH_2)_{0-4}$—CO—$NR_{P-2}R_{P-3}$ where $R_{P-2}$ and $R_{P-3}$ are the same or different and are as defined above,
(F) —$(CH_2)_{0-4}$—CO—$R_{N-4}$ where $R_{N-4}$ is as defined above,
(G) —$(CH_2)_{0-4}$—$SO_2$—($C_1$-$C_8$ alkyl),
(H) —$(CH_2)_{0-4}$—$SO_2$—$NR_{P-2}R_{P-3}$ where $R_{P-2}$ and $R_{P-3}$ are the same or different and are as defined above,
(I) —$(CH_2)_{0-4}$—NH—CO—($C_1$-$C_6$ alkyl),
(J) —NH—CO—O—$R_{N-8}$ where $R_{N-8}$ is as defined above,
(K) —$(CH_2)_{0-4}$—$NR_{P-2}R_{P-3}$ where $R_{P-2}$ and $R_{P-3}$ are the same or different and are as defined above,
(L) —$(CH_2)_{0-4}$—$R_{N-4}$ where $R_{N-4}$ is as defined above,
(M) —O—CO—($C_1$-$C_6$ alkyl),
(N) —O—CO—$NR_{N-8}R_{N-8}$ where the $R_{N-8}$s are the same or different and are as defined above,
(O) —O—($C_1$-$C_5$ alkyl)-COOH,
(P) —O—$C_1$-$C_6$ alkyl optionally substituted with one, two, or three of: —F, —Cl, —Br, or —I,
(Q) —NH—$SO_2$—($C_1$-$C_6$ alkyl), and
(R) —F, —Cl;

(VII) —$(CR_{P-x}R_{P-y})_{0-4}$—$R_{P-1\ where\ RP-1}$ is as defined above and each of $R_{P-x}$ and $R_{P-y}$ are independently any combination of:
(A) —H,
(B) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, —COOH, —COO($C_1$-$C_6$ alkyl), —CONR$_{1a}$R$_{1b}$ and —NR$_{1-a}$R$_{1-b}$ where R$_{1-a}$ and R$_{1-b}$ are —H or $C_1$-$C_6$ alkyl, (C) —CH$_2$—S—($C_1$-$C_6$ alkyl),
(D) —CH$_2$—CH$_2$—S—($C_1$-$C_6$ alkyl),
(E) $C_2$-$C_6$ alkenyl with one or two double bonds,
(F) $C_2$-$C_6$ alkynyl with one or two triple bonds,
(G) —(CH$_2$)$_{n1}$—(R$_{P\text{-}aryl}$) where n$_1$ is zero or one, where R$_{P\text{-}aryl}$ is as defined above,
(H) —(CH$_2$)$_{n1}$—(R$_{P\text{-}heteroaryl}$) where n$_1$ and R$_{P\text{-}heteroaryl}$ are as defined above, or
(I) —(CH$_2$)$_{n1}$—(R$_{P\text{-}heterocycle}$) where n$_1$ and R$_{P\text{-}heterocycle}$ are as defined above,
(J) —(CH$_2$)$_{0\text{-}3}$—($C_3$-$C_7$) cycloalkyl where cycloalkyl can be optionally substituted with one, two or three substituents selected from the group consisting of $C_1$-$C_3$ alkyl, —F, —Cl, —Br, —I, —OH, —SH, —C≡N, —CF$_3$, $C_1$-$C_6$ alkoxy, —O-phenyl, —CO—OH, —CO—O—($C_1$-$C_4$ alkyl), and —NR$_{1-a}$R$_{1-b}$ where R$_{1-a}$ and R$_{1-b}$ are as defined above,
(K) F, Cl, Br or I, or
(L) —NR$_{P\text{-}2}$;

or R$_{P\text{-}x}$ and R$_{P\text{-}y}$ are taken together with the carbon to which they are attached to form a carbocycle of three thru seven carbon atoms, optionally where one carbon atom is replaced by a heteroatom selected from the group consisting of —O—, —S—, —SO$_2$—, and —NR$_{P\text{-}2}$—;

(VIII) —($C_1$-$C_6$ alkyl)-Z-($C_1$-$C_6$ alkyl)-T-($C_1$-$C_6$ alkyl)- wherein Z is S or O, T is O or NR$_{P\text{-}2}$, and alkyl is optionally substituted with one, two, or three substituents selected from the group consisting of:

(A) —OH,
(B) —$C_1$-$C_6$ alkoxy,
(C) —$C_1$-$C_6$ thioalkoxy,
(D) —CO—O—R$_{N\text{-}8}$ where R$_{N\text{-}8}$ is as defined above,
(E) —CO—NR$_{P\text{-}2}$R$_{P\text{-}3}$ where R$_{P\text{-}2}$ and R$_{P\text{-}3}$ are the same or different and are as defined above,
(F) —CO—R$_{N\text{-}4}$ where R$_{N\text{-}4}$ is as defined above,
(G) —SO$_2$—($C_1$-$C_8$ alkyl),
(H) —SO$_2$—NR$_{P\text{-}2}$R$_{P\text{-}3}$ where R$_{P\text{-}2}$ and R$_{P\text{-}3}$ are the same or different and are as defined above,
(I) —NH—CO—($C_1$-$C_6$ alkyl),
(J) —NH—CO—O—R$_{N\text{-}8}$ where R$_{N\text{-}8}$ is as defined above,
(K) —NR$_{P\text{-}2}$R$_{P\text{-}3}$ where R$_{P\text{-}2}$ and R$_{P\text{-}3}$ are the same or different and are as defined above,
(L) —R$_{N\text{-}4}$ where R$_{N\text{-}4}$ is as defined above,
(M) —O—CO—($C_1$-$C_6$ alkyl),
(N) —O—CO—NR$_{N\text{-}8}$R$_{N\text{-}8}$ where the R$_{N\text{-}8}$s are the same or different and are as defined above,
(O) —O—($C_1$-$C_5$ alkyl)-COOH,
(P) —O—($C_1$-$C_6$ alkyl) optionally substituted with one, two, or three of —F, —Cl, —Br, or —I,
(Q) —NH—SO$_2$—($C_1$-$C_6$ alkyl), and
(R) —F, or —Cl.

5. A method of treatment as in claim 4, wherein the patient is a human.

6. A method of treatment according to claim 4, wherein the disease is dementia.

7. A compound according to claim 1, wherein R$_1$ is 3,5-difluorobenzyl.

* * * * *